US012616713B2

(12) United States Patent
Wu et al.

(10) Patent No.: US 12,616,713 B2
(45) Date of Patent: May 5, 2026

(54) METHODS FOR ENHANCING VASCULAR DENSITY

(71) Applicant: Metro International Biotech, LLC, Worcester, MA (US)

(72) Inventors: Lindsay Edward Wu, Coogee (AU); David Andrew Sinclair, Chestnut Hill, MA (US); Abhirup Das, Eastlakes (AU)

(73) Assignee: Metro International Biotech, LLC, Worcester, MA (US)

( * ) Notice: Subject to any disclaimer, the term of this patent is extended or adjusted under 35 U.S.C. 154(b) by 110 days.

(21) Appl. No.: 18/157,510

(22) Filed: Jan. 20, 2023

(65) Prior Publication Data

US 2023/0149437 A1 May 18, 2023

Related U.S. Application Data

(63) Continuation of application No. 16/471,653, filed as application No. PCT/AU2017/051435 on Dec. 21, 2017, now abandoned.

(30) Foreign Application Priority Data

Dec. 21, 2016 (AU) ................................ 2016905310

(51) Int. Cl.

| | |
|---|---|
| ***A61K 31/7084*** | (2006.01) |
| ***A61K 9/00*** | (2006.01) |
| ***A61K 31/706*** | (2006.01) |
| ***A61K 33/04*** | (2006.01) |
| ***A61P 9/14*** | (2006.01) |
| ***C12N 15/113*** | (2010.01) |
| ***C12N 15/87*** | (2006.01) |

(52) U.S. Cl.

CPC ........ *A61K 31/7084* (2013.01); *A61K 9/0053* (2013.01); *A61K 31/706* (2013.01); *A61K 33/04* (2013.01); *A61P 9/14* (2018.01); *C12N 15/1137* (2013.01); *C12N 15/87* (2013.01); *C12N 2310/14* (2013.01); *C12N 2310/141* (2013.01); *C12N 2710/10043* (2013.01); *C12N 2740/15043* (2013.01)

(58) Field of Classification Search

CPC ...... A61K 31/7084; A61K 31/706; A61P 9/14

See application file for complete search history.

(56) References Cited

U.S. PATENT DOCUMENTS

| | | | |
|---|---|---|---|
| 3,201,389 | A | 8/1965 | Fujimoto et al. |
| 3,451,997 | A | 6/1969 | Fujimoto et al. |
| 4,411,995 | A | 10/1983 | Whitesides et al. |
| 7,560,442 | B2 | 7/2009 | Susilo |
| 7,776,326 | B2 | 8/2010 | Milbrandt et al. |
| 7,977,049 | B2 | 7/2011 | Sinclair et al. |
| 8,481,711 | B2 | 7/2013 | Kaminishi et al. |
| 9,169,209 | B2 | 10/2015 | Bair et al. |
| 9,295,688 | B2 | 3/2016 | Milbrandt et al. |
| 9,458,172 | B2 | 10/2016 | Bair et al. |
| 9,676,721 | B2 | 6/2017 | Bair et al. |
| 9,822,129 | B2 | 11/2017 | Bair et al. |
| 9,855,289 | B2 | 1/2018 | Normington et al. |
| 9,861,651 | B2 | 1/2018 | Brown et al. |
| 9,919,003 | B2 | 3/2018 | Normington et al. |
| 9,975,915 | B1 | 5/2018 | Migaud et al. |
| 10,000,519 | B2 | 6/2018 | Migaud et al. |
| 10,214,552 | B2 | 2/2019 | Fu et al. |
| 10,233,208 | B1 | 3/2019 | Carr et al. |
| 10,392,415 | B2 | 8/2019 | Livingston et al. |
| 10,392,416 | B2 | 8/2019 | Livingston et al. |
| 10,548,913 | B2 | 2/2020 | Normington et al. |
| 10,618,927 | B1 | 4/2020 | Szczepankiewicz et al. |
| 11,059,847 | B2 | 7/2021 | Livingston et al. |
| 11,180,521 | B2 | 11/2021 | Kremsky et al. |
| 11,464,796 | B2 | 10/2022 | Normington et al. |
| 11,787,830 | B2 | 10/2023 | Kremsky et al. |
| 11,878,027 | B2 | 1/2024 | Normington et al. |
| 11,939,348 | B2 | 3/2024 | Szczepankiewicz et al. |
| 11,952,396 | B1 | 4/2024 | Kremsky et al. |
| 12,391,721 | B2 | 8/2025 | Livingston et al. |
| 2004/0224039 | A1 | 11/2004 | Brucker |
| 2006/0002914 | A1* | 1/2006 | Milbrandt ............... A61P 39/00 424/94.5 |

(Continued)

FOREIGN PATENT DOCUMENTS

| | | |
|---|---|---|
| CN | 101497638 A | 8/2009 |
| CN | 101601679 B | 8/2011 |

(Continued)

OTHER PUBLICATIONS

"Extended European Search Report corresponding to European Application No. 17883855.3 dated Dec. 15, 2020".

"Non-antioxidant function of resveratrol", Vitamins 90:286-289 (2016).

"Office Action corresponding to Chinese Application No. 20178006403.4 issued Dec. 29, 2022".

"Office Action corresponding to Chinese Application No. 201780086403.4 dated Apr. 6, 2022".

"Office Action corresponding to Japanese Application No. 2019-533084 dated Jun. 27, 2022".

"Office Action corresponding to Japanese Application No. 2019-533084 dated Mar. 30, 2023".

(Continued)

*Primary Examiner* — George W Kosturko

(74) *Attorney, Agent, or Firm* — Foley Hoag LLP; David P. Halstead; Tesia V. Chciuk

(57) ABSTRACT

The present invention relates to methods of increasing vascular density and/or blood flow in tissue of a subject, and to increasing exercise capacity of a subject, the methods include administering to a subject an effective amount of an agent that elevates SIRTI activity in endothelial cells of the subject, the invention further includes administering an NAD+ agonist or NAD+ precursor to a subject to increase vascular density and/or blood flow. The invention includes compositions comprising the said agent.

25 Claims, 68 Drawing Sheets

Specification includes a Sequence Listing.

(56) References Cited

U.S. PATENT DOCUMENTS

| | | | |
|---|---|---|---|
| 2007/0037809 | A1 | 2/2007 | Nunes et al. |
| 2007/0149466 | A1 | 6/2007 | Milburn et al. |
| 2008/0318892 | A1 | 12/2008 | Pickering et al. |
| 2009/0143376 | A1 | 6/2009 | Milburn et al. |
| 2010/0047177 | A1 | 2/2010 | Milbrandt et al. |
| 2012/0107888 | A1 | 5/2012 | Schmalisch et al. |
| 2012/0328526 | A1 | 12/2012 | Kristian |
| 2013/0102771 | A1 | 4/2013 | Kaminishi et al. |
| 2013/0273034 | A1 | 10/2013 | Bair et al. |
| 2013/0295051 | A1 | 11/2013 | Bair et al. |
| 2014/0221319 | A1 | 8/2014 | Sinclair et al. |
| 2014/0275057 | A1 | 9/2014 | Bair et al. |
| 2014/0294805 | A1 | 10/2014 | Bair et al. |
| 2015/0104384 | A1 | 4/2015 | Bair et al. |
| 2015/0132280 | A1 | 5/2015 | Lopez et al. |
| 2015/0175621 | A1 | 6/2015 | Bair et al. |
| 2015/0258052 | A1 | 9/2015 | Evans et al. |
| 2016/0002266 | A1 | 1/2016 | Bair et al. |
| 2016/0022712 | A1 | 1/2016 | Imai et al. |
| 2016/0038613 | A1 | 2/2016 | Kaspar et al. |
| 2016/0168184 | A1 | 6/2016 | Migaud et al. |
| 2016/0287621 | A1 | 10/2016 | Sinclair et al. |
| 2016/0333041 | A1 | 11/2016 | Fu et al. |
| 2016/0355514 | A1 | 12/2016 | Bair et al. |
| 2016/0355539 | A1* | 12/2016 | Migaud .................... C07H 1/04 |
| 2017/0066724 | A1 | 3/2017 | Evans et al. |
| 2017/0182076 | A1 | 6/2017 | Alvarez et al. |
| 2017/0189433 | A1 | 7/2017 | Szczepankiewicz et al. |
| 2017/0204131 | A1 | 7/2017 | Szczepankiewicz et al. |
| 2017/0210774 | A1 | 7/2017 | Carlson et al. |
| 2017/0216262 | A1 | 8/2017 | Bair et al. |
| 2017/0267709 | A1 | 9/2017 | Migaud et al. |
| 2017/0304338 | A1 | 10/2017 | Dellinger et al. |
| 2017/0368039 | A1 | 12/2017 | Kenneth et al. |
| 2018/0030079 | A1 | 2/2018 | Carlson et al. |
| 2018/0051253 | A1 | 2/2018 | Chen |
| 2018/0086783 | A1 | 3/2018 | Carlson et al. |
| 2018/0104248 | A1 | 4/2018 | Lopez et al. |
| 2018/0134743 | A1 | 5/2018 | Migaud et al. |
| 2018/0147227 | A1 | 5/2018 | Normington et al. |
| 2018/0162895 | A1 | 6/2018 | Fu et al. |
| 2018/0186824 | A1 | 7/2018 | Migaud et al. |
| 2018/0228824 | A1 | 8/2018 | Yoshino et al. |
| 2019/0328761 | A1 | 10/2019 | Wu et al. |
| 2020/0031860 | A1 | 1/2020 | Sauve |
| 2020/0157136 | A1 | 5/2020 | Livingston et al. |
| 2020/0181188 | A1 | 6/2020 | Rhonemus et al. |
| 2020/0352966 | A1 | 11/2020 | Normington et al. |
| 2020/0368198 | A1 | 11/2020 | Wu et al. |
| 2021/0030908 | A1 | 2/2021 | Mason |
| 2022/0098229 | A1 | 3/2022 | Livingston et al. |
| 2022/0144880 | A1 | 5/2022 | Szczepankiewicz et al. |
| 2023/0158053 | A1 | 5/2023 | Normington et al. |
| 2023/0210746 | A1 | 7/2023 | Bermond et al. |
| 2023/0257412 | A1 | 8/2023 | Kremsky et al. |
| 2024/0109932 | A1 | 4/2024 | Kremsky et al. |
| 2024/0350523 | A1 | 10/2024 | Normington et al. |

FOREIGN PATENT DOCUMENTS

| | | | | |
|---|---|---|---|---|
| CN | 102876759 | A | 1/2013 | |
| CN | 104367587 | B | 6/2018 | |
| JP | S41-12737 | B2 | 7/1966 | |
| JP | S41-15179 | B2 | 8/1996 | |
| JP | 2007063167 | A * | 3/2007 | |
| JP | 2008501343 | A | 1/2008 | |
| WO | WO-2006/072809 | A2 | 7/2006 | |
| WO | WO-2006094235 | A1 * | 9/2006 | .............. A61P 21/00 |
| WO | WO-2007124447 | A2 * | 11/2007 | ............. A61K 31/00 |
| WO | WO-2010/135520 | A1 | 11/2010 | |
| WO | 2011130595 | A2 | 10/2011 | |
| WO | WO-2012/004917 | A1 | 1/2012 | |
| WO | WO-2012/031196 | A1 | 3/2012 | |
| WO | WO-2012/031197 | A1 | 3/2012 | |
| WO | WO-2012/031199 | A1 | 3/2012 | |
| WO | WO-2012/094343 | A1 | 7/2012 | |
| WO | 2012114204 | A2 | 8/2012 | |
| WO | WO-2012/150952 | A1 | 11/2012 | |
| WO | WO-2013/085555 | A2 | 6/2013 | |
| WO | WO-2013/127266 | A1 | 9/2013 | |
| WO | WO-2013/127267 | A1 | 9/2013 | |
| WO | WO-2013/127268 | A1 | 9/2013 | |
| WO | WO-2013/127269 | A1 | 9/2013 | |
| WO | WO-2013/130943 | A1 | 9/2013 | |
| WO | 2014059034 | A2 | 4/2014 | |
| WO | WO-2014/074715 | A1 | 5/2014 | |
| WO | WO-2014/111906 | A1 | 7/2014 | |
| WO | WO-2014/146044 | A1 | 9/2014 | |
| WO | WO-2015/014722 | A1 | 2/2015 | |
| WO | WO-2015/069860 | A1 | 5/2015 | |
| WO | WO-2015/073576 | A1 | 5/2015 | |
| WO | WO-2015070280 | A1 * | 5/2015 | ........... A61K 31/352 |
| WO | WO-2015/138969 | A1 | 9/2015 | |
| WO | 2015187649 | A1 | 12/2015 | |
| WO | WO-2015/186068 | A1 | 12/2015 | |
| WO | WO-2016/014927 | A2 | 1/2016 | |
| WO | 2016086088 | A2 | 6/2016 | |
| WO | WO-2016/086860 | A1 | 6/2016 | |
| WO | WO-2016093515 | A1 * | 6/2016 | ........... A23L 33/105 |
| WO | WO-2016/144660 | A1 | 9/2016 | |
| WO | WO-2016/196941 | A1 | 12/2016 | |
| WO | WO-2016/210232 | A1 | 12/2016 | |
| WO | WO-2017/022768 | A1 | 2/2017 | |
| WO | WO-2017/059249 | A1 | 4/2017 | |
| WO | WO-2017/062311 | A1 | 4/2017 | |
| WO | WO-2017/079195 | A1 | 5/2017 | |
| WO | WO-2017/110317 | A1 | 6/2017 | |
| WO | WO-2017/114796 | A1 | 7/2017 | |
| WO | WO-2017/145151 | A1 | 8/2017 | |
| WO | WO-2017/161165 | A1 | 9/2017 | |
| WO | WO-2017/185549 | A1 | 11/2017 | |
| WO | WO-2017/218580 | A1 | 12/2017 | |
| WO | WO-2018/023205 | A1 | 2/2018 | |
| WO | WO-2018/023207 | A1 | 2/2018 | |
| WO | WO-2018/023208 | A1 | 2/2018 | |
| WO | WO-2018/023209 | A1 | 2/2018 | |
| WO | WO-2018/023210 | A1 | 2/2018 | |
| WO | WO-2018/047715 | A1 | 3/2018 | |
| WO | WO-2018/047716 | A1 | 3/2018 | |
| WO | WO-2018/052019 | A1 | 3/2018 | |
| WO | WO-2018/052020 | A1 | 3/2018 | |
| WO | WO-2018/089830 | A1 | 5/2018 | |
| WO | WO-2018/120069 | A1 | 7/2018 | |
| WO | WO-2018/132833 | A1 | 7/2018 | |
| WO | WO-2018/143258 | A1 | 8/2018 | |
| WO | WO-2019/152416 | A1 | 8/2019 | |
| WO | WO-2020/072497 | A1 | 4/2020 | |
| WO | WO-2020/197882 | A1 | 10/2020 | |
| WO | WO-2022/251491 | A1 | 12/2022 | |

OTHER PUBLICATIONS

"Office Action corresponding to Japanese Application No. 2019-533084 dated Oct. 27, 2021".

"Office Action corresponding to Korean Application No. 10-2019-7021500 issued Feb. 28, 2023".

Chung, Sangwoon , et al., "Regulation of SIRT1 in cellular functions: Role of polyphenols", Archives of Biochemistry and Biophysics 501(1):79-90 (May 5, 2010).

Das, A , et al., "Nicotinamide mononucleotide, an NAD+ precursor, reverses age-associated decline in exercise capacity by increasing skeletal muscle capillary density in a Sirt1-dependent manner", AuPS(Australian Physiological Society) 2015 hobart Programme. 18P abstract (Nov. 29, 2015-Dec. 2).

Fan, Weiwei , et al., "Exercise Mimetics: Impact on Health and Performance", Cell Metabolism 25:242-247 (Feb. 7, 2017).

Hart, Nikolett , et al., "Resveratrol enhances exercise training responses in rats selectively bred for high running performace", Food and Chemical Toxicology 61:53-59 (2013).

Imai, Shin-Ichiro , et al., "NAD+ and Sirtuins in Aging and Disease", Trends Cell Biol 24(8):464-471 (Aug. 2014).

(56) References Cited

OTHER PUBLICATIONS

Koltai, Eric , et al., "Exercise alters SIRT1, SIRT6, NAD and NAMPT levels in skeletal muscle of aged rats", Mechanisms of Ageing and Development 131(1):21-28 (Nov. 12, 2009).
Novelle, Marta G, et al., "Resveratrol supplementation: Where are we now and where should we go?", Ageing Research Reviews 21:1-15 (2015).
Rechsteiner, Martin , et al., "The Biosynthesis and Turnover of Nicotinamide Adenine Dinucleotide in Enucleated Culture Cells", The Journal of Cellular Physiology 84(3):409-421 (Dec. 1, 1974).
Verdin, Eric , et al., "NAD+ in aging, metabolism, and neurodegeneration", Science 350(6265):1208-1213 (Dec. 4, 2015).
Vinciguerra, Manlio , et al., "SirT1 in muscle physiology and disease: lessons from mouse models", Disease Models & Mechanisms 3:298-303 (2010).
Zhao, Jun , et al., "SIRT1 and exercises", Chinese Journal of Gerontology, vol. 31, No. 5, published on May 4, 2011, pp. 906-910.
Bauer, "Pharmaceutical solids-the amorphous phase." Journal of Validation Technology 15.3 (2009): 63.
Extended European Search Report for EP Application No. 22812156.2 dated Apr. 14, 2025.
"International Search Report and Written Opinion for International Application No. PCT/AU2017/051435 mailed Mar. 6, 2018".
Arany, Zoltan , et al., "HIF-independent regulation of VEGF and angiogenesis by the transcriptional coactivator PGC-1alpha", Nature 451:1008-1012 (Feb. 2018).
Arbiser, Jack L, et al., "Overexpression of VEGF 121 in Immortalized Endothelial Cells Causes Conversion to Slowly Growing Angiosarcoma and High Lebel Expression of the VEGF Receptors VEGFR-1 and VEGFR-2 in Vivo", Am J Pathol, 156(4):1469-1476 (Apr. 2000).
Askew, Christopher D, et al., "Skeletal muscle phenotype is associated with exercise tolerance in patients with peripheral arterial disease", J Vasc Surg, 41(5):802-807 (2005).
Baker, Marianne , et al., "Use of the mouse aortic ring assay to study angiogenesis", Nat Protoc 7(1):89-104 (Dec. 22, 2011).
Baltgalvis, Kristen A, et al., "Exercise performance and peripheral vascular insufficiency improve with AMPK activation in high-fat diet-fed mice", Am J Physiol Heart Circ Physiol 306:H1128-H1145 (Feb. 21, 2014).
Bassel-Duby, Rhonda , et al., "Signaling Pathways in Skeletal Muscle Remodeling", Annu Rev Biochem 75:19-37 (Feb. 15, 2006).
Blanco, Raquel , et al., "VEGF and notch in tip and stalk cell selection", Cold Spring Harb Perspect Med 3: a006569 (2013).
Bogan, Katrina L, et al., "Nicotinic acid, nicotinamide, and nicotinamide roboside: A molecuar evaluation of NAD+ precursos vitamins in human nutrition", Annu Rev Nutr 28:115-130 (Apr. 22, 2008).
Booth, Frank W, et al., "Molecular and cellular adaptation of muscle in response to exercise: perspectives of various models", Physiol Rev 71(2):541-585 (Apr. 1991).
Borradaile, Nica M, et al., "Nicotinamide Phosphoribosyltransferase Imparts Human Endothelial Cells with Extended Replicative Lifespan and Enhanced Angiogenic Capacity in a High Glucose Environment", Aging Cells 8:100-112 (2009).
Braidy, Nady , et al., "Age related changes in NAD+ metabolism oxidative stress and sirt1 activity in wistar rats", PLoS One, 6(4):e19194 (Apr. 26, 2011).
Canto, Carles , et al., "The NAD+ Precursor Nicotinamide Riboside Enhances Oxidative Metabolism—and Protects against High-Fat Diet-Induced Obesity", Cell Metab, 15:838-847 (Jun. 6, 2012).
Cardus, Anna , et al., "SIRT6 protects human endothelial cells from DNA damage, telomere dysfunction, and senescence", Cardiovasc Res, 97:571-579 (2013).
Cebasek, V , et al., "A novel staining method for quantification and 3D visualisation of capillaries and muscle fibres", EurJ Histochem, 48(2):151-158 (Apr.-Jun. 2004).
Chalkiadaki, Angeliki , et al., "Muscle-specific SIRT1 Gain-of-Function Increases Slow-Twitch Fibers and Ameliorates Pathophysiology in a Mouse Model of Duchenne Muscular Dystrophy", PLoS Genet, 10(7):e1004490 (Jul. 17, 2014).
Chang, Linda , et al., "Notch activation promotes endothelial survival through a P13K-Slug axis", Microvasc Res, 89:80-85 (Jun. 3, 2013).
Chinsomboon, Jessica , et al., "The transcriptional coactivator PGC-1? mediates exercise-induced angiogenesis in skeletal muscle", Proc Natl Acad Sci, 106(50):21401-21406 (Dec. 15, 2009).
Costa, Carla , et al., "The endothelial-erectile dysfunction connection: An essential update", J Sex Med, 6:2390-2404 (2009).
De Souza, Natalie , "Primer: Genome editing with engineered nucleases", Nat Meth, 9(1):27 (Jan. 2012).
Dimmeler, Stefanie , et al., "Endothelial cell apoptosis in angiogenesis and vessel regression", Circulation Res, 87:434-439 (Aug. 3, 2000).
Duscha, Brian D, et al., "Capillary Density of Skeletal Muscle", J Am Coil Cardiol, 33(7):1956-1963 (Feb. 10, 1999).
Escande, Carlos , et al., "Flavonoid apigenin is an inhibitor of the NAD+ ase CD38", Diabetes, 62:1084-1093 (Apr. 2013).
Escudier, Bernard , et al., "Axitinib for the Management of Metastatic Renal Cell Carcinoma", Drugs R D 11 (2):113-126 (2011).
Firestein, Ron , et al., "The SIRT1 deacetylase suppresses intestinal tumorigenesis and colon cancer growth", PLoS One, 3(4):e2020 (Apr. 16, 2008).
Gomes, Ana P, et al., "Declining NAD+ induces a pseudohypoxic state disrupting nuclear-mitochondrial communication during aging", Cell, 155(7):1624-1638 (Dec. 19, 2013).
Grieger, Joshua C, et al., "Adeno-Associated Virus as a Gene Therapy Vector: Vector Development, Production and Clinical Applications", Advances in Biochemical Engineering/Biotechnology 99:119-145 (Oct. 25, 2005).
Guarani, Virginia , et al., "Acetylation-dependent regulation of endothelial notch signalling by the SIRT1 deacetylase,", Nature, 473(7346):234-238 (May 12, 2011).
Harasta, Anne E, et al., "Septal Glucagon-Like Peptide I Receptor Expression Determines Suppression of Cocaine-Induced Behavior", Neuropsychopharmacology, 40:1969-1978 (Mar. 4, 2015).
Hood, David A, "Plasticity in Skeletal, Cardiac, and Smooth Muscle", J Appl Physiol, 90:1137-1157 (2001).
Kolluru, Gopi Krishna, et al., "Endothelial Dysfunction and Diabetes: Effects on Angiogenesis, Vascular Remodeling, and Wound Healing", Int J Vasc Med, 918267, 1-30 (2012).
Koni, Pandelakis A, et al., "Conditional Vascular Cell Adhesion Molecule 1 Deletion in Mice: Impaired Lymphocyte Migration to Bone Marrow", J Exp Med, 193(6):741-753 (Mar. 19, 2001).
Korff, Thomas , et al., "Integration of Endothelial Cells in Multicellular Spheroids Prevents Apoptosis and Induces Differentiation", J Cell Biol, 143(5):1341-1352 (Nov. 30, 1998).
Kuznetsov, Andrey V, et al., "Analysis of mitochondrial function in situ in permeabilized muscle fibers, tissues and cells", Nat Protoc, 3(6):965-976 (May 15, 2008).
Lanza, Gaetano Antonio, et al., "Primary Coronary Microvascular Dysfunction", Circulation, 121:2317-2325 (2010).
Le Couteur, David G, et al., "A Vascular Theory of Aging", Journal of Gerontology, 65A(10):1025-1027 (Oct. 2010).
Limbourg, Anne , et al., "Evaluation of postnatal arteriogenesis and angiogenesis in a mouse model of hind-limb ischemia", Nat Protoc, 4(12):1737-1746 (Nov. 5, 2009).
Lin, Jiandie , et al., "Transcriptional co-activator PGC-1alpha drives the formation of slow-twitch muscle fibres", Nature, 418:797-801 (Aug. 15, 2002).
Massudi, Hassina , et al., "Age-Associated Changes in Oxidative Stress and NAD Metabolism in Human Tissue", PLoS One, 7(7):e42357 (Jul. 27, 2012).
McCormick, William F, "The Pathology of Vascular ("Arteriovenous") Malformations", J Neurosurg 24:807-816 (1966).
Mersmann, Nadine , et al., "Aspartoacylase-LacZ Knockin Mice: An Engineered Model of Canavan Disease", PLOS One, 6(5):e20336 (May 20, 2011).
Mitchell, Sarah J, et al., "The SIRT1 Activator SRT1720 Extends Lifespan and Improves Health of Mice Fed a Standard Diet", Cell Reports 6:836-843 (Mar. 13, 2014).

(56) References Cited

OTHER PUBLICATIONS

Morscher, Stefan, et al., "Semi-Quantitative Multispectral Optoacoustic Tomography (MSOT) for Volumetric PK Imaging of Gastric Emptying", Photoacoustics, 2:103-110 (Jun. 18, 2014).
Mouchiroud, Laurent , et al., "NAD+ metabolism, a therapeutic target for age-related metabolic disease", Crit Rev Biochem Mol Biol, 48(4):397-408 (2013).
Mouchiroud, Laurent , et al., "The NAD+/Sirtuin Pathway Modulates Longevity through Activation of Mitochondrial URP and FOXO Signaling", Cell, 154:430-441 (Jul. 18, 2013).
Muzumdar, Mandar Deepak, et al., "A Global Double-Fluorescent Cre Reporter Mouse", Genesis, 45:593-605 (Sep. 14, 2007).
Noseda, Michela , et al., "Notch Activation Induces Endothelial Cell Cycle Arrest and Participates in Contact Inhibition: Role of P21Cip1 Repression", Mob Cell Biol, 24(20):8813-8822 (Oct. 2004).
Dommen, Saji , et al., "Vascular Endothelial Growth Factor A (VEGF-A) Induces Endothelial and Cancer Cell Migration Through Direct Binding to Integrin alpha9beta1", J Biol Chem, 286(2):1083-1092 (Jan. 14, 2011).
Pearson, Kevin J, et al., "Resveratrol delays age-related deterioration and mimics transcriptional aspects of dietary restriction with out extending lifespan", Cell Metab, 8(2):157-168 (Aug. 2008).
Pette, Dirk , et al., "Myosin isoforms, muscle fiber types, and transitions", Microsc Res Tech, 50:500-509 (Apr. 2000).
Potente, Michael , et al., "Emerging roles of SIRT1 in vascular endothelial homeostasis", Cell Cycle 7 (14):2117-2122 (Jul. 15, 2008).
Potente, Michael , et al., "SIRTI Controls Endothelial Angiogenic Functions During Vascular Growth", Genes & Development 21:2644-2658 (Aug. 23, 2007).
Price, Nathan L, et al., "SIRT1 is required for AMPK activation and the beneficial effects of resveratrol on mitochondrial function", Cell Metab, 15(5):675-690 (May 2, 2012).
Prior, Steven J, et al., "Sacropenia is Associated with Lower Skeletal Muscle Capillarization and Exercise Capacity in Older Adults", J Gerontol A Biol Sci Med Sci, 71 (8):1096-1101 (Feb. 17, 2016).
Respress, Jonathan L, et al., "Transthoracic Echocardiography in Mice", Journal of Visualized Experiments 39: e1738 (May 28, 2010).
Rose, Peter , et al., "GYY4137, a Novel Water-Soluble, H25-Releasing Molecule", Methods in Enzymology, 554:143-167 (2015).
Ross, Jaime M, "Visualization of Mitochondrial Respiratory Function Using Cytochrome C Oxidase/Succinate Dehydrogenase (COX/SDH) Double-Labeling Histochemistry", J Vis Exp 57:e3266 (Nov. 23, 2011).
Rowe, Glenn C, et al., "Running Forward: New Frontiers in Endurance Exercise Biology", Circulation 129 (7):798-810 (Feb. 18, 2014).
Sauve, Anthony A, et al., "Sir2 Regulation by Nicotinamide Results from Switching Between Base Exchange and Deacetylation Chemistry", Biochemistry, 42(31):9249-9256 (Aug. 12, 2003).
Schwartz, Joan P, et al., "The Effect of Growth Conditions on NAD and NADH Concentrations and the NAD: NADH Ratio in Normal and Transformed Fibroblasts", J Biol Chem, 249(13):4138-4143 (Jul. 1974).
Smith, Julianne , et al., "A combinatorial approach to create artificial homing endonucleases cleaving—chosen sequences", Nucleic Acids Research, 34(22):e149 (Nov. 27, 2006).
Tan, Wenfang , et al., "Precision Editing of Large Animal Genomes", Adv Genet, 80:37-97 (2012).
Turner, Nigel , et al., "Enhancement of Muscle Mitochondrial Oxidative Capacity and Alterations in Insulin Action are Lipid Species Dependent", Diabetes, 58:2547-2554 (Nov. 2009).
Uddin, Golam M, et al., "Head to Head Comparison of Short-Term Treatment with the NAD+ Precursos Nicotinamide Mononucleotide (NMN) and 6 Weeks of Exercise in Obese Female Mice", Front Pharmacol, 7(258):1-11 (Aug. 19, 2016).
Urnov, Fyodor D, et al., "Genome editing with engineered zinc finger nucleases", Nat Rev Genet 11(9):636-646 (Sep. 2010).
Van Beijnum, Judy R, et al., "Isolation of endothelial cells from fresh tissues", Nat Protoc, 3(6):1085-1091 (Jun. 5, 2008).
Vasko, Radovan , et al., "Endothelial Sirtuin 1 Deficiency Perpetrates Nephrosclerosis through Downregulation of Matrix Metalloproteinase-14: Relevance to Fibrosis of Vascular Senescence", J Am Soc Nephrol, 25:276-291 (2014).
Wang, Pei , et al., "Intracellular NAMPT-NAD+-SIRT1 Cascade Improves Post-Ischaemic Vascular Repair by Modulating Notch Signalling in Endothelial Progenitors", Cardiovascular Research 104:477-488 (Oct. 23, 2014).
Wang, Gelin , et al., "P7C3 Neuroprotective Chemicals Function by Activating the Rate-Limiting Enzyme in NAD Salvage", Cell, 158(6):1324-1334 (Sep. 11, 2014).
Wei, Hao , et al., "Aortopathy in a Mouse Model of Marfan Syndrome is Not Mediated by Altered Transforming Growth Factor 13 Signaling", J Am Heart Assoc, 1-14 (2017).
Wen, Liang , et al., "Ca2+/Calmodulin-Dependent Protein Kinase Kinase Beta Phosphorylation of Sirtuin 1 in Endothelium is Atheroprotective", Proc Natl Acad Sci, 110:e2420-e2427 (Jun. 10, 2013).
Yamada, Kazuo , et al., "The simultaneous measurement of nicotinamide adenine dinucleotide and related compounds by liquid chromatography/electrospray ionization tandem mass spectrometry", Analytical Biochemistry, 352:282-285 (Mar. 9, 2006).
Yang, Guangdong , et al., "H2S and Blood Vessels: An Overview", P.K. Moore, M. Whiteman (eds.), Chemistry, Biochemistry and Pharmacology of Hydrogen Sulfide, Handbook of Experimental Pharmacology 230 (2015).
Yang, Guangdong , et al., "H2S and Blood Vessels: An Overview", P.K. Moore, M. Whiteman (eds.), H I Chemistry, Biochemistry and Pharmacology of Hydrogen Sulfide, Handbook of Experimental Pharmacology 230 pp. 85-110 (2015).
Yoshino, Jun , et al., "Nicotinamide mononucleotide, a key NAD intermediate, treats the pathophysiology of diet- and age-Induced diabetes in mice", Cell Metab, 14(4):528-536 (Oct. 5, 2011).
Zhang, Yuan , et al., "Hydrogen Sulfide, the Next Potent Preventive and Therapeutic Agent in Aging and Age-Associated Diseases", Molecular and Cellular Biology 33(6):1104-1113 (Mar. 2013).
Zhang, Yi , et al., "Liung endothelial HO-i targeting in vivo using lentiviral miRNA regulates apoptosis and autophagy during oxidant injury", FASEB J, 27:1-18 (Jun. 14, 2013).
Zhu, Chen-Tseh , et al., "A Hydrazine Coupled Cycling Assay Validates the Decrease in Redox Ratio Under Starvation in *Drosophilia*", PLoS One, 7(10):e47584 (Oct. 17, 2012).
ADP PubChem SID 134971804 deposited on Mar. 21, 2012.
Ahmadibeni et al., "Solid-Phase Synthesis of Symmetrical 5',5'-Dinucleoside Mono-, Di-, Tri-, and Tetraphosphodiesters," Organic Letters, 9(22): 4483-4486 (2007).
AMP PubChem SID 134970876 deposited on Mar. 21, 2012.
Anastasi et al., "New antiviral nucleoside prodrugs await application," *Current medicinal chemistry*, 10(18):1825-1843 (2003).
Asher et al., "SIRT1 Regulates Circadian Clock Gene Expression through PER2 Deacetylation," Cell, 134:317 (2008).
Atkinson et al., "Nicotinamide 6-Mercaptopurine Dinucleotide and Related Compounds: Potential Sources of 6-Mercaptopurine Nucleotide in Chemotherapy," Nature, 196: 35-36 (1962).
ATP PubChem SID 134972915 deposited on Mar. 21, 2012.
Barnea et al., "High-Fat Diet Delays and Fasting Advances the Circadian Expression of Adiponectin Signaling Components in Mouse Liver," Endicrinology 150:161 (2009).
Bauer, "Polymorphism-A Critical Consideration in Pharmaceutical Development, Manufacturing, and Stability," Journal of Validation of Technology, 14(5):15-23 (2008).
Bazzanini et al., "Synthetic approaches to a mononucleotide prodrug of cytarabine," Nucleosides, Nucleotides, and Nucleic Acids, 24(10-12):1635-1649 (2005).
Belenky et al., "Nicotinamide riboside promotes Sir2 silencing and extends lifespan via Nrk and Urh1/Pnp1/Meu1 pathways to NAD+," Cell, 129(3):473-484 (2007).
Berghaeuser et al., "A Simple Preparation of an Enzyme Reactor Producing Nicotinamidemononucleotide," Biotechnology Letters, 3(7): 339-344 (1981).

(56) References Cited

OTHER PUBLICATIONS

Bieganowski et al., "Discoveries of nicotinamide riboside as a nutrient and conserved NRK genes establish a preiss-handler independent route to NAD+ in fungi and humans," Cell, 117:495-502 (2004).
Bobeck et al., "Advances in nucleoside monophosphate prodrugs as anti-HCV agents," Antiviral Therapy—An Official Publication of the International Society for Antiviral Research, 15(7):935-950 (2010).
Bordone et al., "Calorie restriction, SIRT1 and metabolism: understanding longevity," Nat Rev Mol Cell Biol, 6:298-305 (2005).
Borradaile et al., "NAD+, Sirtuins, and Cardiovascular Disease," Current Pharmaceutical Design, 15(1):110-117 (2016).
Brittain et al., "X-Ray Diffraction of Pharmaceutical Materials," Profiles of Drug Substances, Excipients, and Related Methodology, 30:273-319 (2003).
Byrn et al., "Pharmaceutical solids: a strategic approach to regulatory considerations," Pharmaceut Res, 12(7):945-954 (1995).
Caira., Crystalline Polymorphism of Organic Compounds, Topics in Current Chemistry, 198: 163-208 (1998).
Cardiac Medications, Heart.org, http://www.heart.org/en/health-topics/heart-attack/treatment-of-a-heart-attack/cardiac-medications (2015).
CAS Registry No. 108273-23-0 (1987).
CAS Registry No. 108489-22-1 (1987).
CAS Registry No. 1094-61-7 (1984).
CAS Registry No. 150035-58-8 (1993).
CAS Registry No. 321-02-8.
CAS Registry No. 906748-40-1 (2006).
Cattaneo-Pangrazzi et al., "The novel heterodinucleoside dimer 5-FdU-NOAC is a potent cytotoxic drug and a p53-independent inducer of apoptosis in the androgen-independent human prostate cancer cell lines PC-3 and DU-145", The Prostate 45(1): 8-18 (2000).
Cayman Chemical, "Beta-Nicotinamide mononucleotide," Item No. 16411 Product Information (2014).
Cayman Chemical, "Beta-Nicotinamide Mononucleotide," Item No. 16411 Safety Data Sheet, Cayman Chemical (2015).
Chemical Cayman, "Nicotinic Acid Mononucleotide," Item No. 32883.
Cherney, "Osteoarthritis Medications List," Healthline, https://www.healthline.com/health/osteoarthritis/medications-list#nsaids (2016).
Cho et al., "Efficient synthesis of nucleoside aryloxy phosphoramidate prodrugs utilizing benzyloxycarbonyl protection," Tetrahedron, 67(30): 14 pages (2011).
Congiatu et al., "Novel potential anticancer naphthyl phosphoramidates of BVdU: separation of diastereoisomers and assignment of the absolute configuration of the phosphorus center," Journal of medicinal chemistry, 49(2): 452-455 (2006).
Corda et al., "Functional aspects of protein mono-ADP-ribosylation," EMBO J, 22(9):1953-1958 (2003).
Cross et al., "Rules for the Nomenclature of Organic Chemistry. Section E: Sterohemistry," Pure Appl Chem, 45(1):11-30, (1976).
Das et al., "Nicotinamide mononucleotide, an NAD+ precursor, reverses age-associated decline in exercise capacity byincreasing skeletal muscle capillary density in a Sirt1-dependent manner.": 2015 Hobart Programme, Nov. 29, 2015-Dec. 2, 2015, Abstract published: Nov. 2015.
Database Registry Chemical Abstracts, Database Accession No. 807266-77-9, CAS Registry No. 807266-77-9 (Jan. 2, 2005).
Dekker, Polymorphism in Pharmaceutical Solids, First Ed, pp. 184-208 (1999).
Dekker, Polymorphism in Pharmaceutical Solids, First Ed, pp. 7-8 (1999).
Diabetes Treatment, Drugs.com, https://www.drugs.com/diabetes-treatment.html (2018).
Dowden et al., "Chemical Synthesis of the Novel CA 2+ Messenger NAADP," Nucleosides, Nucleotides and Nucleic Acids, 24(5-7):513-518 (2005).
Eliseev et al., "Comparative study of antihypoxic properties of some nucleosides and nucleotides." *Pharmaceutical Chemistry Journal* 20.3 (1986): 160-162.
Erion et al., "Design, Synthesis, and Characterization of a Series of Cytochrome P450 3A-Activated Prodrugs (HepDirect Prodrugs) Useful for Targeting Phosph(on)ate-Based Drugs to the Liver," JACS Articles, 126: 5154-5163 (2004).
Extended European Search Report for EP Application No. 16833957.0 dated Dec. 21, 2018.
Extended European Search Report for EP Application No. 16852711.7 dated Feb. 11, 2019.
Extended European Search Report for EP Application No. 23197016.1 dated Oct. 18, 2023.
Fang et al., "Defective Mitophagy in XPA via PARP-1 Hyperactivation and NAD+/SIRT1 Reduction," Cell, 157(4):882-896 (2014).
Galli et al., "The Nicotinamide Phosphoribosyltransferase: A Molecular Link between Metabolism, Inflammation, and Cancer", Cancer Research, 70(1), pp. 8-11, 2010.
Garten et al., "Nampt: Linking NAD biology, metabolism, and cancer," Trends Endocrinol Metab, 20(3):130-138 (2009).
Gavande et al., "DNA repair targeted therapy: The past or future of cancer treatment?," Pharmacology & Therapeutics, 160:65-83 (2016).
Gockel et al., "Synthesis of an oligonucleotide with a nicotinamide mononucleotide residue and its molecular recognition in DNA helices," Organic & Biomolecular Chemistry, 13(41):10303-10309 (2015).
Guest et al., "Changes in Oxidative Damage, Inflammation and [NAD(H)] with Age in Cerebrospinal Fluid," PLOS One, 9(1):e85335 (2014).
Hardie, "Minireview: the AMP-activated protein kinase cascade: the key sensor of cellular energy status", *Endocrinology* 144(12): 5179-5183 (2003).
Harrison et al., "Inhibition of Platelet Aggregation and the Platelet Release Reaction by alpha, omega Diadenosine polyphosphates," FEBS Letts 54(1):57-60 (1975).
Hecker et al., "Prodrugs of Phosphates and Phosphonates," Journal of Medicinal Chemistry, 51(8):2328-2345 (2008).
Hirayama, Yuukikagoubutsu Kessyo sakusei Handbook—Genri to Know-how—(Handbook for Preparation of Crystals of Organic Compounds—Principle and Know-how—), Maruzen Co. Ltd., pp. 37-84 (2008).
Huang et al., "Metabolomics-driven identification of adenosine deaminase as therapeutic target in a mouse model of Parkinson's disease," Journal of Neurochemistry, 150: 282-295 (2019).
Imai et al., "Transcriptional silencing and longevity protein Sir2 is an NAD-dependent histone deacetylase," Nature, 403:795-800 (2000).
International Search Report and Written Opinion for International Application No. PCT/US2016/045855 dated Nov. 14, 2016.
International Search Report and Written Opinion for International Application No. PCT/US2016/054776 dated Jan. 25, 2017.
International Search Report and Written Opinion for International Application No. PCT/US2019/015672 dated May 15, 2019.
International Search Report and Written Opinion for International Application No. PCT/US2020/023318 dated Jun. 24, 2020.
International Search Report and Written Opinion for International Application No. PCT/US22/31124 dated Oct. 6, 2022.
Invitation to Pay Additional Fees for International Application No. PCT/US22/31124 dated Aug. 5, 2022.
Kamel et al., "Pharmaceutical significance of cellulose: A review", Express Polym Letters 2(11): 758-778 (2008).
Kohsaka et al., "high-Fat Diet Disrupts Behavioral and Molecular Circadian Rhythms in Mice," Cell Metab, 6:414 (2007).
Lee et al., "A Chemical Synthesis of Nicotinamide Adenine Dinucleotide (NAD+)," Chemical Communications (Cambridge), 8: 729-730 (1999).
Lee, "A practical guide to pharmaceutical polymorph screening & selection," Asian Journal of Pharmaceutical Science 9(4): 163-175 (2014).
Leisvuori et al. "5', 5'-Phosphodiesters and esterase labile triesters of 2'-C methylribonucleosides", ARKIVOC: Online Journal of Organic Chemistry (2012).

(56) References Cited

OTHER PUBLICATIONS

Lin et al., "Nicotinamide adenine dinucleotide, a metabolic regulator of transcription, longevity and disease," Curr Opin Cell Biol, 15:241-246 (2003).
Liu et al., "A Novel Preparation of Nicotinamide Mononucleotide," Nucleosides & Nucleotides, 13(5): 1215-1216 (1994).
Liu et al., "Enzymatic synthesis of polymers containing nicotinamide mononucleotide," Nucleic Acids Research, 23(18):3742 (1995).
Liu et al., "Synthesis of Phosphodiester-type Nicotinamide Adenine Dinucleotide Analogs," Tetrahedron, 65(40): 8378-8383 (2009).
Makarov et al., "Syntheses and chemical properties of B-nicotinamide riboside and its analogues and derivatives," Beilstein J Org Chem, 15: 401-430 (2019).
McGuigan et al., "Certain phosphoramidate derivatives of dideoxy uridine (ddU) are active against HIV and successfully by-pass thymidine kinase," FEBS Letters, 351: 11-14 (1994).
McGuigan et al., "Phosphorodiamidates as a Promising New Phosphate Prodrug Motif for Antiviral Drug Discovery: Application to Anti-HCV Agents," Journal of Medicinal Chemistry, 54: 8632-8645 (2011).
Medications for Dermatitis, Drugs.com, https://www.drugs.com/condition/dermatitis.html (2018).
Medications for Obesity, Drugs.com, https://www.drugs.com/condition/obesity.html (2018).
Medications for Peripheral Neuropathy, Drugs.com, https://www.drugs.com/condition/peripheral-neuropathy.html (2018).
Medications for Thrombotic/Thromboembolic Disorder, Drugs.com, https://www.drugs.com/condition/thrombotic-thromboembolic-disorder.html (2018).
Menissier de Murcia et al., "Functional Interaction between PARP-1 and PARP-2 in chromosome stability and embryonic development in mouse," EMBO J, 22(9):2255-2263 (2003).
Migaud et al., "Probing Aplysia californica Adenosine 5'-Diphosphate Ribosyl Cyclase for Substrate Binding Requirements: Design of Potent Inhibitors," Biochemistry, 38:9105-9114 (1999).
Mikhailopulo et al., "Synthesis of glycosides of nicotinamide and nicotinamide mononucleotide," Synthesis, 5:388-389 (1981).
Moazed, "Enzymatic activities of Sir2 and chromatin silencing," Curr Opin Cell Biol, 13(2):232-238 (2001).
Montgomery et al., "Synthesis of Potential Anticancer Agents. XXVIII. Simple Esters of 6-Mercaptopurine Ribonucleotide2," The Journal of Organic Chemistry, 26(6):1929-1933 (1961).
Moynihan et al., "Increased dosage of mammalian Sir2 in pancreatic β cells enhances glucose-stimulated insulin secretion in mice," Cell Metab, 2:105-117 (2005).
Nakahata et al., "The NAD+-Dependent Deacetylase SIRT1 Modulates CLOCK-Mediated Chromatin Remodeling and circadian Control," Cell, 134(2):329 (2008).
Nakai et al., Shin Seizaigaku (New Pharmacy), Nanzando Co. Ltd., 1st Edition, 2nd Printing, pp. 102-104, 217-236 (1984).
Nikiforov et al., "Pathways and Subcellular Compartmentation of NAD Biosynthesis in Human Cells," The Journal of Biological Chemistry, 286 (24): 21767-21778 (2011).
Park et al., "Nicotinamide Ribose 5'-0-[S-(3-Bromo-2-oxopropyl)] thiophosphate: A New Affinity Label for NMN Sites in Enzymes," Archives of Biochemistry and Biophysics, 303(2):483-488 (1993).
Pencina et al., "MIB-626, an Oral Formulation of a Microcrystalline Unique Polymorph of Beta-Nicotinamide Mononucleotide, Increases Circulating Nicotinamide Adenine Dinucleotide and its Metabolome in Middle-Aged and Older Adults", J Gerontol A Biol Sci Med Sci, 2023, vol. 78, No. 1, 90-96.
Pencina et al., "Nicotinamide Adenine Dinucleotide Augmentation in Overweight or Obese Middle-Aged and Older Adults: A Physiologic Study", The Journal of Clinical Endocrinology & Metabolism, Feb. 6, 2023, 00, pp. 1-13.
Pertusati et al., "Medicinal chemistry of nucleoside phosphonate prodrugs for antiviral therapy," Antivir Chem Chemother, 22(5):181-203 (2012).
Petrelli et al., "NMN/NaMN Adenylyltransferase (NMNAT) and NAD Kinase (NADK) Inhibitors: Chemistry and Potential Therapeutic Applications," Current Medicinal Chemistry, 18: 1973-1992 (2011).
Pfleiderer et al., "Zum Wirkungsmechanismus von Dehydrogenasen V. Uber die Bedeutung des Adenosindiphosphatrestes im Nicotinamid-Adenin-Dinucleotid," Biochimica et Biophysica Acta, 73:39-49 (1963).
Pfleiderer et al., "Zum Wirkungsmechanismus von Dehydrogenasen. Das Reaktionsverhalten von Pyridinnucleotiden (PN) und PN-Modellen mit Sulfit als nucleophilem Agens," Chemische Berichte, 93(12):3083-3099 (1960).
Picard et al., "Sirt1 promotes fat mobilization in white adipocytes by repressing PPAR-γ," Nature, 429:771-776 (2004).
Preitner et al., "The Orphan Nuclear Receptor REV-ERBa Controls Circadian Transcription within the Positive Limb of the Mammalian circadian Oscillator," Cell, 110:251 (2002).
PubChem SID: 347731451 "Substance Record 321-02-8" retrieved online <https://pubchem.ncbi.nlm.nih.gov/substance/347731451>: 6 pages (Create Date Oct. 23, 2017).
Puech et al., "Nucleotidic prodrugs of anti-HIV dideoxynucleosides", Bioorganic & medicinal chemistry letters 2(6): 603-606 (1992).
Rajman et al., "Therapeutic Potential of NAD-Boosting Molecules: The In Vivo Evidence," Cell Metabolism, 27(3): 529-547 (2018).
Ramsey et al., "Cicadian clock feedback cycle through NAMPT-mediated NAD+ biosynthesis," Science, 324(5927):651-654 (2009).
Redpath et al., "Nicotinamide Benzimidazolide Dinucleotides Non-Cyclisable Analogues of NAD+," Synlett, 25:2331-2336 (2014).
Riemschneider et al., "Zur Beeinflussung von Stoffwechselvorgangcn durch unphysiologische Verbindungen, IV: Nicotinylaminosaureester und Nucleosid-Deritvate," Insect repellent science, 41(3):99-106 (1976).
Rodgers et al., "Nutrient control of glucose homeostasis through a complex of PGC-1α and SIRT1," Nature, 434:113-118 (2005).
Rodionova et al., "Metabolic and bactericidal effects of targeted suppression of NadD and NadE enzymes in mycobacteria," mBio, 5(1):e00747-13 (2014).
Roskar et al., "Analytical Methods for Quantification of Drug Metabolites in Biological Samples," IntechOpen, Chapter 4:79-126 (2012).
Rudic et al., "BMAL1 and CLOCK, Two Essential Components of the Circadian Clock, Are Involved in Glucose Homeostasis," PLoS Biol, 2:e377 (2004).
Rutter et al., "Regulation of Clock and NPAS2 DNA Binding by the Redox State of NAD Cofactors," Science, 293(5529):510 (2001).
Sarma et al., "Investigations of Inter- and Intramolecular Interactions in Flavin-Adenine Dinucleotide by Proton Magnetic Resonance," Biochemistry, 7(12):4359-4367 (1968).
Sato et al., "A Functional Genomics Strategy Reveals Rora as a Component of the Mammalian Circadian Clock," Neuron, 43:527 (2004).
Sharma et al., "X-ray diffraction: a powerful method of characterizing nanomaterials," Recent Research in Science and Technology, 4:77-79 (2012).
Shioji, Kokei Seizai no Seizo Gijutsu (Manufacture Technology of Solid Tablet), CMC Publishing Co. Ltd., Popular Edition, 1st Printing, pp. 9-14 (2003).
Sleep Disorders: Medications for Circadian Rhythm Disorders, WebMD, https://www.webmd.com/sleep-disorders/circadian-rhythm-disorder-medications#1 (2018).
Smith et al., "A phylogenetically conserved NAD+-dependent protein decetylase activity in the Sir2 protein family," Proc Natl Acad Sci, 97(12):6658-6663 (2000).
Soto-Gamez et al., "Therapeytic interventions for aging: the case of cellular senescence," Drug Discovery Today, 22(5):786-795 (2017).
Stein et al., "Expression of nampt in hippocampal and cortical excitatory neurons is critical for cognitive function," J Neurosci, 34(17): 5800-5815 (2014).
Stein et al., "Scientific ablation on Nampt in adult neural stem cells recapitulates their functional defects during aging," EMBO J, 33(12):1321-1340 (2014).
Stieger et al., "7: Recrystallization of Active Pharmaceutical Ingredients," Crystallization—Science and Technology, 183-204 (2012).

(56) References Cited

OTHER PUBLICATIONS

Takada, "API form screening and selection in drug discovery stage", Pharm Stage, 6(10):20-25. (2007).
Takahashi et al., "The Genetics of Mammalian Circadian Order and Disorder: Implications for Physiology and Disease," Nat Rev Genet, 9(10):764 (2008).
The Chemical Society of Japan Ed., 4th Edition Jikken Kagaku Kouza 1 Kihon Sousa I (4th Edition Experimental Chemistry 1 Basic Operation I), Maruzen Co. Ltd., 2nd Printing, pp. 184-186 (1996).
Thorpe et al., "Lipoamide Dehydrogenase from Pig Heart. Pyridine Nucleotide Induced Changes in Monoalkylated Two-Electron Reduced Enzyme," Biochemistry, 20: 1507-1513 (1981).
Turek et al., "Obesity and Metabolic Syndrome in Circadian Clock Mutant Mice," Science, 308:1043 (2005).
United States Department of Health and Human Services. "Guidance for Industry Pyrogen and Endotoxin Testing: Questions and Answers," pp. 1-10 (2012).
United States Pharmacopeia General Chapter <151> Pyrogen Test, 2 pages.
Walt et al., "An Efficient Chemical and Enzymatic Synthesis of Nicotinamide Adenine Dinucleotide (NAD+)," Journal of the American Chemical Society, 106(1): 234-239 (1984).
Wang et al., "A local mechanism mediates NAD-dependent protection of axon degeneration," J Cell Biol, 170(3):349-355 (2005).
Wiemer et al., "Prodrugs of Phosphnates and Phosphates: Crossing the Membrane Barrier," Topics in Current Chemistry, 360:115-160 (2014).
Woenckhaus, "Synthesen und biochemische Eigenschaften wassertoffübertragender Coenzye modelle," Chemische Berichte, 97(9):2439-2446 (1964).
Wound Care Medications, GoodRx.com, https://www.goodrx.com/wound-care/drugs (2018).
Yamamoto et al., "Nicotinamide mononucleotide, an intermediate of NAD+ synthesis, protects the heart from ischemia and reperfusion", PloS one 9.6: e98972 (2014).
Yang et al., "NAD+-dependent Deacetylase SIRT3 Regulates Mitochondrial Protein Synthesis by Deacetylation of the Ribosomal Protein MRPL10," J Biol Chem, 285:7417-7429 (2010).
Ho et al., "Fertility protection during chemotherapy treatment by boosting the NAD (P)+ metabolome." EMBO Molecular Medicine 16 (2024): 2583-2618.
Pencina et al., "Nicotinamide adenine dinucleotide augmentation in overweight or obese middle-aged and older adults: a physiologic study." The Journal of Clinical Endocrinology & Metabolism 108 (2023): 1968-1980.
Pencina et al., "MIB-626, an oral formulation of a microcrystalline unique polymorph of β-nicotinamide mononucleotide, increases circulating nicotinamide adenine dinucleotide and its metabolome in middle-aged and older adults." The Journals of Gerontology: Series A 78 (2023): 90-96.
Pencina et al., "Oral MIB-626 (β Nicotinamide Mononucleotide) Safely Raises Blood Nicotinamide Adenine Dinucleotide Levels in Hospitalized Patients With COVID-19 and Acute Kidney Injury: A Randomized Controlled Trial." FASEB BioAdvances (2025): e70011.
Perry et al., "NAD+ precursors prolong survival and improve cardiac phenotypes in a mouse model of Friedreich's Ataxia." JCI Insight 9(16) (2024): e177152.
Sands et al., "Assessing colonic exposure, safety, and clinical activity of SRT2104, a novel oral SIRT1 activator, in patients with mild to moderate ulcerative colitis." Inflammatory Bowel Diseases 22(3) (2016): 607-614.
Valderrabano et al., "Dysregulated nicotinamide adenine dinucleotide metabolome in patients hospitalized with COVID-19." Aging Cell 23 (2024): e14326.
Van der Meer et al., "The selective sirtuin 1 activator SRT2104 reduces endotoxin-induced cytokine release and coagulation activation in humans." Critical Care Medicine 43(6) (2015): e199-e202.
Wikipedia, "SRT-2104." edited Jun. 29, 2025.

* cited by examiner

Quadriceps

B

A
Tissue weight/body weight (mg/g)
WT
ESTO
GA
QA
H
B
ESTO
WT
H&E (Quadriceps)
C
Relative mRNA levels
MHC:
I
IIa
IIb
IIx
D
Quadriceps
WT
ESTO
Complex II
Complex IV
Complex V
14-3-3
Relative protein levels
Complex:
II
IV
V
E
Blood glucose (mg/dL)
*

A
% annexin V staining
PBS
NMN
**
40
30
20
10
0
B
Scr siRNA
SIRT1 siRNA
PBS
NMN
C
Tubule branch points
*
Scr siRNA
SIRT1 siRNA
Total tubule length (μ)
x 10^3
**
15
10
5
0

A
Soleus
Vehicle NMN
nmoles $O_2$/min/ mg wet weight
Complex: I II IV
EDL
B
Vehicle NMN
Tissue weight (mg)
GA QA H
C
H&E (Quadriceps)
Vehicle
NMN
D
Vehicle NMN
Relative mRNA levels
MHC: I IIa IIb IIx
E
Vehicle NMN
# of beam breaks ($X_{amb}$)
$X10^3$
Light Dark
$VO_2$ (mL/kg/hr)
p=0.06
p=0.06

SEQUENCE LISTING

```
Sequence total quantity: 51
SEQ ID NO: 1           moltype = DNA  length = 1668
FEATURE                Location/Qualifiers
source                 1..1668
                       mol_type = unassigned DNA
                       organism = Homo sapiens
SEQUENCE: 1
atgattggca cagatcctcg aacaattctt aaagatttat tgccggaaac aatacctcca   60
cctgagttgg atgatatgac actgtggcag attgttatta atatcctttc agaaccacca   120
aaaaggaaaa aaagaaaaga tattaataca attgaagatg ctgtgaaatt actgcaagag   180
tgcaaaaaaa ttatagttct aactggagct ggggtgtctg tttcatgtgg aatacctgac   240
ttcaggtcaa gggatggtat ttatgctcgc cttgctgtag acttcccaga tcttccagat   300
cctcaagcga tgtttgatat tgaatatttc agaaaagatc caagaccatt cttcaagttt   360
gcaaaggaaa tatatcctgg acaattccag ccatctctct gtcacaaatt catagccttg   420
tcagataagg aaggaaaact acttcgcaac tatacccaga acatagacac gctggaacag   480
gttgcgggaa tccaaaggat aattcagtgt catggttcct ttgcaacagc atcttgcctg   540
atttgtaaat acaaagttga ctgtgaagct gtacgaggag ctctttttag tcaggtagtt   600
cctcgatgtc ctaggtgccc agctgatgaa ccgcttgcta tcatgaaacc agagattgtg   660
ttttttggtg aaaatttacc agaacagttt catagagcca tgaagtatga caaagatgaa   720
gttgacctcc tcattgttat tgggtcttcc ctcaaagtaa gaccagtagc actaattcca   780
agttccatac cccatgaagt gcctcagata ttaattaata gagaaccttt gcctcatctg   840
cattttgatg tagagcttct tggagactgt gatgtcataa ttaatgaatt gtgtcatagg   900
ttaggtggtg aatatgccaa actttgctgt aaccctgtaa agctttcaga aattactgaa   960
aaacctccac gaacacaaaa agaattggct tatttgtcag agttgccacc cacacctctt   1020
catgtttcag aagactcaag ttcaccagaa agaacttcac caccagattc ttcagtgatt   1080
gtcacacttt tagaccaagc agctaagagt aatgatgatt tagatgtgtc tgaatcaaaa   1140
ggttgtatgg aagaaaaacc acaggaagta caaacttcta ggaatgttga aagtattgct   1200
gaacagatgg aaaatccgga tttgaagaat gttggttcta gtactgggga gaaaaatgaa   1260
agaacttcag tggctggaac agtgagaaaa tgctggccta atagagtggc aaaggagcag   1320
attagtaggc ggcttgatgg taatcagtat ctgtttttgc caccaaatcg ttacattttc   1380
catggcgctg aggtatattc agactctgaa gatgacgtct tatcctctag ttcttgtggc   1440
agtaacagtg atagtgggac atgccagagt ccaagtttag aagaacccat ggaggatgaa   1500
agtgaaattg aagaattcta caatggctta gaagatgagc ctgatgttcc agagagagct   1560
ggaggagctg gatttgggac tgatggagat gatcaagagg caattaatga agctatatct   1620
gtgaaacagg aagtaacaga catgaactat ccatcaaaca aatcatag                1668

SEQ ID NO: 2           moltype = AA  length = 555
FEATURE                Location/Qualifiers
source                 1..555
                       mol_type = protein
                       organism = Homo sapiens
```

-continued

```
SEQUENCE: 2
MIGTDPRTIL KDLLPETIPP PELDDMTLWQ IVINILSEPP KRKKRKDINT IEDAVKLLQE  60
CKKIIVLTGA GVSVSCGIPD FRSRDGIYAR LAVDFPDLPD PQAMFDIEYF RKDPRPFFKF  120
AKEIYPGQFQ PSLCHKFIAL SDKEGKLLRN YTQNIDTLEQ VAGIQRIIQC HGSFATASCL  180
ICKYKVDCEA VRGALFSQVV PRCPRCPADE PLAIMKPEIV FFGENLPEQF HRAMKYDKDE  240
VDLLIVIGSS LKVRPVALIP SSIPHEVPQI LINREPLPHL HFDVELLGDC DVIINELCHR  300
LGGEYAKLCC NPVKLSEITE KPPRTQKELA YLSELPPTPL HVSEDSSSPE RTSPPDSSVI  360
VTLLDQAAKS NDDLDVSESK GCMEEKPQEV QTSRNVESIA EQMENPDLKN VGSSTGEKNE  420
RTSVAGTVRK CWPNRVAKEQ ISRRLDGNQY LFLPPNRYIF HGAEVYSDSE DDVLSSSSCG  480
SNSDSGTCQS PSLEEPMEDE SEIEEFYNGL EDEPDVPERA GGAGFGTDGD DQEAINEAIS  540
VKQEVTDMNY PSNKS                                                   555

SEQ ID NO: 3           moltype = AA  length = 576
FEATURE                Location/Qualifiers
source                 1..576
                       mol_type = protein
                       organism = Mus sp.
SEQUENCE: 3
MAAAAAAAAI GYRGPYTFVQ QHLMIGTDPR TILKDLLPET IPPPELDDMT LWQIVINILS  60
EPPKRKKRKD INTIEDAVKL LQECKKIIVL TGAGVSVSCG IPDFRSRDGI YARLAVDFPD  120
LPDPQAMFDI EYFRKDPRPF FKFAKEIYPG QFQPSLCHKF IALSDKEGKL LRNYTQNIDT  180
LEQVAGIQRI LQCHGSFATA SCLICKYKVD CEAVRGDIFN QVVPRCPRCP ADEPLAIMKP  240
EIVFFGENLP EQFHRAMKYD KDEVDLLIVI GSSLKVRPVA LIPSSIPHEV PQILINREPL  300
PHLHFDVELL GDCDVIINEL CHRLGGEYAK LCCNPVKLSE ITEKPPRPQK ELVHLSELPP  360
TPLHISEDSS SPERTVPQDS SVIATLVDQA TNNNVNDLEV SESSCVEEKP QEVQTSRNVE  420
NINVENPDFK AVGSSTADKN ERTSVAETVR KCWPNRLAKE QISKRLEGNQ YLFVPPNRYI  480
FHGAEVYSDS EDDVLSSSSC GSNSDSGTCQ SPSLEEPLED ESEIEEFYNG LEDDTERPEC  540
AGGSGFGADG GDQEVVNEAI ATRQELTDVN YPSDKS                            576

SEQ ID NO: 4           moltype = AA  length = 746
FEATURE                Location/Qualifiers
source                 1..746
                       mol_type = protein
                       organism = Felis catus
SEQUENCE: 4
MADEAALALQ PGGSPSAVVA EREAASPPAG EPLRKRPRRD CPGLGRSPGE PGGAAPEREV  60
PAATGGCPAA AAALWREAAA AGEEREAQAA TAGEGDNGPG LQGLTREPPP ADDFYDDDDD  120
DDDEGEEEEE AAAAAAIGYR DNLLFGDEII TNGFHSCESD EDDRASHASS SDWTPRPRIG  180
PYTFVQQHLM IGTDPRTILK DLLPETIPPP ELDDMTLWQI VINILSEPPK RKKRKDINTI  240
EDAVKLLQEC KKIIVLTGAG VSVSCGIPDF RSRDGIYARL AIDFPDLPDP QAMFDIEYFR  300
KDPRPFFKFA KEIYPGQFQP SLCHKFIALS DKEGKLLRNY TQNIDTLEQV AGIQRIIQCH  360
GSFATASCLI CKYKVDCEAV RGDIFNQVVP RCPRCPADEP LAIMKPEIVF FGENLPEQFH  420
RAMKYDKDEV DLLIVIGSSL KVRPVALIPS SIPHEVPQIL INREPLPHLH FDVELLGDCD  480
VIINELCHRL GGEYAKLCCN PVKLSEITEK PPRTQKELAH LSELPPTPLN ISEDSSSPER  540
TSPPDSSVIV TLLDQATKSN VNDPEVSEPR DHMEEKSQEG QNSTRNIESV TEQLGSPDSK  600
NVDSNTGEKN ERTSIAETVR KCWPARLAKE QISKRLDGNQ YLFLPPNRYI FHGAEVYSDS  660
EDDVLSSSSC GSNSDSGTCQ SPSLEEHLED ESEIEEFYNG LEDDADVNER AGGTGFGVDG  720
GDQEAVNEAI SVKQEATDIN YPSNKS                                       746

SEQ ID NO: 5           moltype = AA  length = 557
FEATURE                Location/Qualifiers
source                 1..557
                       mol_type = protein
                       organism = Canis lupus
                       note = Canis lupus familiaris
SEQUENCE: 5
MIGTDPRTIL KDLLPETIPP PELDDMTLWQ IVINILSEPP KRKKRKDINT IEDAVKLLQE  60
CKKIIVLTGA GVSVSCGIPD FRSRDGIYAR LAIDFPDLPD PQAMFDIEYF RKDPRPFFKF  120
AKEIYPGQFQ PSLCHKFIAL SDKEGKLLRN YTQNIDTLEQ VAGIQRIIQC HGSFATASCL  180
ICKYKVDCEA VRGDIFNQVV PRCPRCPADE PLAIMKPEIV FFGENLPEQF HRAMKYDKDE  240
VDLLIVIGSS LKVRPVALIP SSIPHEVPQI LINREPLPHL HFDVELLGDC DVIINELCHR  300
LGGEYAKLCC NPVKLSEITE KPPRTQKELA HLSELPPTPL NISEDSSSPE RTSPPDSSVI  360
VTLLDEATKS NVDDPGVSES RDCMEEKSQE GQNSIRNIES VTEHLESPDL KNVGCNTGEK  420
NERTSVADPV RKCWPARLAK EQISKRLDGN QYLFLPPNRY IFHGAEVYSD SEDDVLSSSS  480
CGSNSDSGTC QSPSLEEHLE DESEIEEFYN GLEDEADVNE RAGGTGFGID GGDQEAVNEA  540
ISMKQEATDT NYPSNKS                                                 557

SEQ ID NO: 6           moltype = AA  length = 491
FEATURE                Location/Qualifiers
source                 1..491
                       mol_type = protein
                       organism = Homo sapiens
SEQUENCE: 6
MNPAAEAEFN ILLATDSYKV THYKQYPPNT SKVYSYFECR EKKTENSKLR KVKYEETVFY  60
GLQYILNKYL KGKVVTKEKI QEAKDVYKEH FQDDVFNEKG WNYILEKYDG HLPIEIKAVP  120
EGFVIPRGNV LFTVENTDPE CYWLTNWIET ILVQSWYPIT VATNSREQKK ILAKYLLETS  180
GNLDGLEYKL HDFGYRGVSS QETAGIGASA HLVNFKGTDT VAGLALIKKY YGTKDPVPGY  240
SVPAAEHSTI TAWGKDHEKD AFEHIVTQFS SVPVSVVSDS YDIYNACEKI WGEDLRHLIV  300
SRSTQAPLII RPDSGNPLDT VLKVLEILGK KFPVTENSKG YKLLPPYLRV IQGDGVDINT  360
```

```
LQEIVEGMKQ KMWSIENIAF GSGGGLLQKL TRDLLNCSFK CSYVVTNGLG INVFKDPVAD  420
PNKRSKKGRL SLHRTPAGNF VTLEEGKGDL EEYGQDLLHT VFKNGKVTKS YSFDEIRKNA  480
QLNIELEAAH H                                                      491

SEQ ID NO: 7           moltype = AA  length = 491
FEATURE                Location/Qualifiers
source                 1..491
                       mol_type = protein
                       organism = Mus sp.
SEQUENCE: 7
MNAAAEAEFN ILLATDSYKV THYKQYPPNT SKVYSYFECR EKKTENSKVR KVKYEETVFY  60
GLQYILNKYL KGKVVTKEKI QEAKEVYREH FQDDVFNERG WNYILEKYDG HLPIEVKAVP  120
EGSVIPRGNV LFTVENTDPE CYWLTNWIET ILVQSWYPIT VATNSREQKK ILAKYLLETS  180
GNLDGLEYKL HDFGYRGVSS QETAGIGASA HLVNFKGTDT VAGIALIKKY YGTKDPVPGY  240
SVPAAEHSTI TAWGKDHEKD AFEHIVTQFS SVPVSVVSDS YDIYNACEKI WGEDLRHLIV  300
SRSTEAPLII RPDSGNPLDT VLKVLDILGK KFPVTENSKG YKLLPPYLRV IQGDGVDINT  360
LQEIVEGMKQ KKWSIENVSF GSGGALLQKL TRDLLNCSFK CSYVVTNGLG VNVFKDPVAD  420
PNKRSKKGRL SLHRTPAGNF VTLEEGKGDL EEYGHDLLHT VFKNGKVTKS YSFDEVRKNA  480
QLNIEQDVAP H                                                      491

SEQ ID NO: 8           moltype = AA  length = 529
FEATURE                Location/Qualifiers
source                 1..529
                       mol_type = protein
                       organism = Canis lupus
                       note = Canis lupus familiaris
SEQUENCE: 8
MTDSGCPAPR QPSARGRRPR RAPGCGGARS WRDPSGPRSA PARAAASPGP AGSSSAQVTH  60
YKQYPPNTSK VYSYFECREK KTENSKIKKV KYEETVFYGL QYILNKYLKG KVVTAEKIQE  120
AKEVYREHFQ DDVFNEKGWN YILEKYDGHL PIEIKAVPEG YVIPRGNVLF TVENTDPECY  180
WLTNWIETIL VQSWYPITVA TNSREQKKIL AKYLLETSGN LDGLEYKLHD FGYRGVSSQE  240
TAGIGASAHL VNFKGTDTVA GIAFVKKYYG TKDPVPGYSV PAAEHSTITA WGKDREKDAF  300
EHIVTQFSSV PVSVVSDSYD IYNACEKIWG EDLRHLILSR TTEAPLIIRP DSGNPLDTVL  360
KVLDILGKKF PITENSKGYK LLPPYLRVIQ GDGVDINTLQ EIVEGMKQKK WSIENIAFGS  420
GGALLQKLTR DLLNCSFKCS YVVTNGLGIN VFKDPVADPN KRSKKGRLSL HRTPAGNFVT  480
LEEGKGDLEE YGHDLLHTVF KNGKVTKSYS FDEIRKNAKL NIELEVAPH             529

SEQ ID NO: 9           moltype = AA  length = 279
FEATURE                Location/Qualifiers
source                 1..279
                       mol_type = protein
                       organism = Homo sapiens
SEQUENCE: 9
MENSEKTEVV LLACGSFNPI TNMHLRLFEL AKDYMNGTGR YTVVKGIISP VGDAYKKKGL  60
IPAYHRVIMA ELATKNSKWV EVDTWESLQK EWKETLKVLR HHQEKLEASD CDHQQNSPTL  120
ERPGRKRKWT ETQDSSQKKS LEPKTKAVPK VKLLCGADLL ESFAVPNLWK SEDITQIVAN  180
YGLICVTRAG NDAQKFIYES DVLWKHRSNI HVVNEWIAND ISSTKIRRAL RRGQSIRYLV  240
PDLVQEYIEK HNLYSSESED RNAGVILAPL QRNTAEAKT                        279

SEQ ID NO: 10          moltype = AA  length = 285
FEATURE                Location/Qualifiers
source                 1..285
                       mol_type = protein
                       organism = Mus sp.
SEQUENCE: 10
MDSSKKTEVV LLACGSFNPI TNMHLRLFEL AKDYMHATGK YSVIKGIISP VGDAYKKKGL  60
IPAHHRIIMA ELATKNSHWV EVDTWESLQK EWVETVKVLR YHQEKLATGS CSYPQSSPAL  120
EKPGRKRKWA DQKQDSSPQK PQEPKPTGVP KVKLLCGADL LESFSVPNLW KMEDITQIVA  180
NFGLICITRA GSDAQKFIYE SDVLWRHQSN IHLVNEWITN DISSTKIRRA LRRGQSIRYL  240
VPDLVQEYIE KHELYNTESE GRNAGVTLAP LQRNAAEAKH NHSTL                  285

SEQ ID NO: 11          moltype = AA  length = 279
FEATURE                Location/Qualifiers
source                 1..279
                       mol_type = protein
                       organism = Canis lupus
                       note = Canis lupus familiaris
SEQUENCE: 11
MENSKMEVVL LACGSFNPIT NMHLRLFELA KDYMNGTGKY KVIKGIISPV GDAYKKKGLI  60
SAHHRVIMAE LATKSSEWVE VDTWESLQKE WVETAKVLRH HQEKLEAGSC DHQQDSPVRG  120
RPGQKRKWAE QRQDFSQKKS LEPKTKDVPK VKLLCGADLL ESFGVPNLWK SEDITQIVGD  180
YGLVCITRAG NDAQKFIYES DALWQHRNNI HLVNEWITND ISSTKIRRAL RRGQSIRYLV  240
PDLVQEYIEK HDLYSCESEE RNVGVILAPL QRNTAEANS                        279

SEQ ID NO: 12          moltype = AA  length = 307
FEATURE                Location/Qualifiers
source                 1..307
                       mol_type = protein
                       organism = Homo sapiens
```

-continued

```
SEQUENCE: 12
MTETTKTHVI LLACGSFNPI TKGHIQMFER ARDYLHKTGR FIVIGGIVSP VHDSYGKQGL  60
VSSRHRLIMC QLAVQNSDWI RVDPWECYQD TWQTTCSVLE HHRDLMKRVT GCILSNVNTP  120
SMTPVIGQPQ NETPQPIYQN SNVATKPTAA KILGKVGESL SRICCVRPPV ERFTFVDENA  180
NLGTVMRYEE IELRILLLCG SDLLESFCIP GLWNEADMEV IVGDFGIVVV PRDAADTDRI  240
MNHSSILRKY KNNIMVVKDD INHPMSVVSS TKSRLALQHG DGHVVDYLSQ PVIDYILKSQ  300
LYINASG                                                            307

SEQ ID NO: 13          moltype = AA  length = 307
FEATURE                Location/Qualifiers
source                 1..307
                       mol_type = protein
                       organism = Mus sp.
SEQUENCE: 13
MTETTKTHVI LLACGSFNPI TKGHIQMFER ARDYLHKTGR FIVIGGIVSP VHDSYGKQGL  60
VSSRHRLIMC QLAVQNSDWI RVDPWECYQD TWQTTCSVLE HHRDLMKRVT GCILSNVNTP  120
SMTPVIGQPQ HENTQPIYQN SNVPTKPTAA KILGKVGESL SRICCVRPPV ERFTFVDENA  180
NLGTVMRYEE IELRILLLCG SDLLESFCIP GLWNEADMEV IVGDFGIVVV PRDAADTDRI  240
MNHSSILRKY KNNIMVVKDD INHPMSVVSS TKSRLALQHG DGHVVDYLSQ PVIDYILKSQ  300
LYINASG                                                            307

SEQ ID NO: 14          moltype = AA  length = 307
FEATURE                Location/Qualifiers
source                 1..307
                       mol_type = protein
                       organism = Canis lupus
                       note = Canis lupus familiaris
SEQUENCE: 14
MTETTKTHVI LLACGSFNPI TKGHIQMFER ARDYLHKTGR FIVIGGIVSP VHDSYGKQGL  60
VSSRHRLIMC QLAVQNSDWI RVDPWECYQD TWQTTCSVLE HHRDLMKRVT GCILSNVNTP  120
SMTPVIGQPQ NETPQPIYQN SNVSTKPTAA KILGKVGESL SRICCVRPPV ERFTFVDENA  180
NLGTVMRYEE IELRILLLCG SDLLESFCIP GLWNEADMEV IVGDFGIVVV PRDAADTDRI  240
MNHSSILRKY KNNIMVVKDD INHPMSVVSS TKSRLALQHG DGHVVDYLSQ PVIDYILKSQ  300
LYINASG                                                            307

SEQ ID NO: 15          moltype = AA  length = 142
FEATURE                Location/Qualifiers
source                 1..142
                       mol_type = protein
                       organism = Homo sapiens
SEQUENCE: 15
MEGPDHGKAL FSTPAAVPEL KLLCGADVLK TFQTPNLWKD AHIQEIVEKF GLVCVGRVGH  60
DPKGYIAESP ILRMHQHNIH LAKEPVQNEI SATYIRRALG QGQSVKYLIP DAVITYIKDH  120
GLYTKGSTWK GKSTQSTEGK TS                                           142

SEQ ID NO: 16          moltype = AA  length = 179
FEATURE                Location/Qualifiers
source                 1..179
                       mol_type = protein
                       organism = Mus sp.
SEQUENCE: 16
MARLALQTSD WIRVDPWESE QAQWMETVKV LRHHHRELLR SSAQMDGPDP SKTPSASAAL  60
PELKLLCGAD VLKTFQTPNL WKDTHIQEIV EKFGLVCVSR SGHDPERYIS DSPILQQFQH  120
NIHLAREPVL NEISATYVRK ALGQGQSVKY LLPEAVITYI RDQGLYINDG SWKGKGKTG   179

SEQ ID NO: 17          moltype = AA  length = 313
FEATURE                Location/Qualifiers
source                 1..313
                       mol_type = protein
                       organism = Canis lupus
                       note = Canis lupus familiaris
SEQUENCE: 17
MKSRIPVVLL ACGSFNPITN MHLRLFEVAR DHLHQTGWYF SLLSPVLVSR RQESLRSNLS  60
RKQTSSLCQD GGIGLYQVIG GIISPVNDNY RKKDLVSAHH RVAMARLALQ TSDWVRVDPW  120
ESEQVQWMET VKVLRTFLTQ MSRKTVQHHH SELLRSLPQT EGLDHGRAGS TARTAGPELK  180
LLCGADVLKT FQTPNLWKDA HIQEIVEKFG IVCVSRTGHN PKEYISGSPI LHRYRHNIHL  240
AREPVQNELS STYVRQALSQ GHSVKYLLPD AVIAYIKDHN LYTRDSSRKG SSTQRNEGKP  300
SWGEPAPPPR SSS                                                     313

SEQ ID NO: 18          moltype = DNA  length = 23
FEATURE                Location/Qualifiers
misc_feature           1..23
                       note = primer sequence
source                 1..23
                       mol_type = other DNA
                       organism = synthetic construct
SEQUENCE: 18
tagccttgtc agataaggaa gga                                          23
```

-continued

```
SEQ ID NO: 19          moltype = DNA  length = 22
FEATURE                Location/Qualifiers
misc_feature           1..22
                       note = primer sequence
source                 1..22
                       mol_type = other DNA
                       organism = synthetic construct
SEQUENCE: 19
acagcttcac agtcaacttt gt                                           22

SEQ ID NO: 20          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 20
tgtgacagag agatggctgg                                              20

SEQ ID NO: 21          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 21
atcttccaga tcctcaagcg                                              20

SEQ ID NO: 22          moltype = DNA  length = 20
FEATURE                Location/Qualifiers
source                 1..20
                       mol_type = other DNA
                       organism = synthetic construct
SEQUENCE: 22
agctgcgctg atagacatcc                                              20

SEQ ID NO: 23          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 23
ctacctccac catgccaagt                                              20

SEQ ID NO: 24          moltype = DNA  length = 22
FEATURE                Location/Qualifiers
misc_feature           1..22
                       note = primer sequence
source                 1..22
                       mol_type = other DNA
                       organism = synthetic construct
SEQUENCE: 24
ctgtaacgat gaagccctgg ag                                           22

SEQ ID NO: 25          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 25
tggtgaggtt tgatccgcat                                              20

SEQ ID NO: 26          moltype = DNA  length = 25
FEATURE                Location/Qualifiers
misc_feature           1..25
                       note = primer sequence
source                 1..25
                       mol_type = other DNA
                       organism = synthetic construct
SEQUENCE: 26
gccaactatg ctggagctga tgccc                                        25

SEQ ID NO: 27          moltype = DNA  length = 28
```

-continued

```
FEATURE                 Location/Qualifiers
misc_feature            1..28
                        note = primer sequence
source                  1..28
                        mol_type = other DNA
                        organism = synthetic construct
SEQUENCE: 27
ggtgcgtgga gcgcaagttt gtcataag                                      28

SEQ ID NO: 28           moltype = DNA  length = 24
FEATURE                 Location/Qualifiers
misc_feature            1..24
                        note = primer sequence
source                  1..24
                        mol_type = other DNA
                        organism = synthetic construct
SEQUENCE: 28
ggcacaaact gctgaagcag aggc                                          24

SEQ ID NO: 29           moltype = DNA  length = 25
FEATURE                 Location/Qualifiers
misc_feature            1..25
                        note = primer sequence
source                  1..25
                        mol_type = other DNA
                        organism = synthetic construct
SEQUENCE: 29
ggtgctcctg aggttggtca tcagc                                         25

SEQ ID NO: 30           moltype = DNA  length = 24
FEATURE                 Location/Qualifiers
misc_feature            1..24
                        note = primer sequence
source                  1..24
                        mol_type = other DNA
                        organism = synthetic construct
SEQUENCE: 30
gagctactgg atgccagtga gcgc                                          24

SEQ ID NO: 31           moltype = DNA  length = 24
FEATURE                 Location/Qualifiers
misc_feature            1..24
                        note = primer sequence
source                  1..24
                        mol_type = other DNA
                        organism = synthetic construct
SEQUENCE: 31
ctggacgatg tcttccatct ctcc                                          24

SEQ ID NO: 32           moltype = DNA  length = 30
FEATURE                 Location/Qualifiers
misc_feature            1..30
                        note = primer sequence
source                  1..30
                        mol_type = other DNA
                        organism = synthetic construct
SEQUENCE: 32
ggcagcagca gctgcggaag cagagtctgg                                    30

SEQ ID NO: 33           moltype = DNA  length = 26
FEATURE                 Location/Qualifiers
misc_feature            1..26
                        note = primer sequence
source                  1..26
                        mol_type = other DNA
                        organism = synthetic construct
SEQUENCE: 33
gagtgctcct cagattggtc attagc                                        26

SEQ ID NO: 34           moltype = DNA  length = 21
FEATURE                 Location/Qualifiers
misc_feature            1..21
                        note = primer sequence
source                  1..21
                        mol_type = other DNA
                        organism = synthetic construct
SEQUENCE: 34
gttaagcagt acagccccaa a                                             21
```

-continued

```
SEQ ID NO: 35          moltype = DNA  length = 23
FEATURE                Location/Qualifiers
source                 1..23
                       mol_type = other DNA
                       organism = synthetic construct
SEQUENCE: 35
agggcatatc caacaacaaa ctt                                              23

SEQ ID NO: 36          moltype = DNA  length = 21
FEATURE                Location/Qualifiers
misc_feature           1..21
                       note = primer sequence
source                 1..21
                       mol_type = other DNA
                       organism = synthetic construct
SEQUENCE: 36
aggtcggtgt gaacggattt g                                                21

SEQ ID NO: 37          moltype = DNA  length = 23
FEATURE                Location/Qualifiers
misc_feature           1..23
                       note = primer sequence
source                 1..23
                       mol_type = other DNA
                       organism = synthetic construct
SEQUENCE: 37
tgtagaccat gtagttgagg tca                                              23

SEQ ID NO: 38          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 38
aactgttggt ggcctgaatc                                                  20

SEQ ID NO: 39          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 39
aattctttgt gttgctgggg                                                  20

SEQ ID NO: 40          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 40
ttcaaggcag ctcggtaact                                                  20

SEQ ID NO: 41          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 41
gggcatttta cttccccaat                                                  20

SEQ ID NO: 42          moltype = DNA  length = 21
FEATURE                Location/Qualifiers
misc_feature           1..21
                       note = primer sequence
source                 1..21
                       mol_type = other DNA
                       organism = synthetic construct
SEQUENCE: 42
tcaacacgac accggataaa c                                                21

SEQ ID NO: 43          moltype = DNA  length = 21
```

-continued

```
FEATURE                Location/Qualifiers
misc_feature           1..21
                       note = primer sequence
source                 1..21
                       mol_type = other DNA
                       organism = synthetic construct
SEQUENCE: 43
gccgcgagct atctttcttc a                                                21

SEQ ID NO: 44          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 44
tcaacgtgaa ctcgttcggg                                                  20

SEQ ID NO: 45          moltype = DNA  length = 21
FEATURE                Location/Qualifiers
misc_feature           1..21
                       note = primer sequence
source                 1..21
                       mol_type = other DNA
                       organism = synthetic construct
SEQUENCE: 45
acttcgcctt ggtgatgaga t                                                21

SEQ ID NO: 46          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 46
gcaacagctc cttccacttc                                                  20

SEQ ID NO: 47          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 47
gcctcagaca ctttgaagcc                                                  20

SEQ ID NO: 48          moltype = DNA  length = 17
FEATURE                Location/Qualifiers
misc_feature           1..17
                       note = primer sequence
source                 1..17
                       mol_type = other DNA
                       organism = synthetic construct
SEQUENCE: 48
gttgtcgacg acgagcg                                                     17

SEQ ID NO: 49          moltype = DNA  length = 17
FEATURE                Location/Qualifiers
misc_feature           1..17
                       note = primer sequence
source                 1..17
                       mol_type = other DNA
                       organism = synthetic construct
SEQUENCE: 49
gcacagagcc tcgcctt                                                     17

SEQ ID NO: 50          moltype = DNA  length = 20
FEATURE                Location/Qualifiers
misc_feature           1..20
                       note = primer sequence
source                 1..20
                       mol_type = other DNA
                       organism = synthetic construct
SEQUENCE: 50
accctttcca aatcctcagc                                                  20
```

-continued

```
SEQ ID NO: 51           moltype = DNA  length = 17
FEATURE                 Location/Qualifiers
misc_feature            1..17
                        note = primer sequence
source                  1..17
                        mol_type = other DNA
                        organism = synthetic construct
SEQUENCE: 51
gttatggcga cccgcag                                                   17
```

METHODS FOR ENHANCING VASCULAR DENSITY

CROSS-REFERENCE TO RELATED APPLICATIONS

This application is a continuation of and claims priority to U.S. patent application Ser. No. 16/471,653, filed Jun. 20, 2019, which is a § 371 national phase application of PCT Application No. PCT/AU2017/051435 filed Dec. 21, 2017, which claims priority to Australian Application No. 2016905310 filed Dec. 21, 2016, the entire contents of each of which is incorporated by reference herein.

FIELD

The invention relates to method of increasing vascular density and/or blood flow in tissue of a subject, to increasing exercise capacity in a subject, and to a composition for increasing vascular density, and blood flow in tissue of a subject, and increasing exercise capacity of a subject.

The present application claims priority from Australian provisional application no. 2016905310, the entirety of which is incorporated herein by reference.

SEQUENCE LISTING

The instant application contains a Sequence Listing which has been submitted electronically in XML file format and is hereby incorporated by reference in its entirety. Said XML copy, created on Mar. 27, 2026, is named MBS-02802_SL.xml and is 66,499 bytes in size.

BACKGROUND

One of the most profound changes to the body as it ages is a decline in the number and function of endothelial cells (ECs) that line the vasculature. According to the Vascular Theory of Aging (Le Couteur and Lakatta, 2010), the progressive loss of vascular density is one of the major causes of aging and age-related diseases, manifesting in diverse ways, including cardiac infarction, stroke, exercise intolerance, erectile dysfunction, liver failure, osteoporosis, impaired wound healing, sarcopenia, dementia and frailty (Askew et al., 2005; Costa and Virag, 2009; Duscha et al., 1999; Kolluru et al., 2012; Lanza and Crea, 2010; McCormick, 1966; Prior et al., 2016). The performance of most organs and tissues is critically dependent on an abundant, fully functional microcapillary network that maintains a supply of oxygen, exchanges heat and various nutrients, and removes the waste products of metabolism.

Despite the importance of vascular density loss to human health and longevity, it is surprising how little is understood about its underlying causes. Exercise is currently the best way to delay the effects of aging on the microvasculature by promoting neovascularization in tissues, but almost nothing is known why tissues become desensitized to exercise with age (Bassel-Duby and Olson, 2006; Booth and Thomason, 1991; Hood, 2001).

Skeletal muscle is an ideal tissue to study the negative effects of aging on capillary maintenance and neovascularization in response to exercise. In young individuals, muscle performance is critically dependent upon an abundant, fully functional microcapillary network that maintains a supply of oxygen, exchanges heat and various nutrients, and removes the waste products of metabolism. For reasons that are unclear, there is an overall increase in the senescence and apoptosis of muscle endothelial cells with age, leading to blood vessel loss and decreased neovascularization of muscle in response to exercise. The result is reduced muscle mass (sarcopenia) and the steady decline in strength and endurance in the later decades of life, even with exercise. It would therefore be advantageous to increase vascular density and/or blood flow in aged subjects.

An increase in vascularisation would also be of benefit in subjects of any age seeking to increase vascular density and/or blood flow in muscle tissue to increase physical performance, or in subjects of any age suffering from conditions where an increase in vascular density and/or blood flow may be of benefit.

Despite their potential utility, only a few exercise-mimetic agents have been reported (e.g. resveratrol and PPARγ agonists), none of which are known to work by promoting neovascularization or muscle capillary density.

What is needed are methods for increasing vascular density and/or blood flow in tissue of subjects.

SUMMARY

The inventors have found that increasing Sirtuin 1 (SIRT1) activity or expression in endothelial cells of tissue, e.g. in skeletal muscle, results in an increase in vascular density in that tissue. The inventors have further found that subjects in which endothelial cell SIRT1 activity or expression is increased have increased exercise capacity.

Accordingly, a first aspect of the present invention provides a method of increasing vascular density and/or blood flow in tissue of a subject, the method comprising administering to the subject an effective amount of an agent which elevates SIRT1 activity or SIRT1 expression in endothelial cells of the subject.

An alternative first aspect provides an agent which elevates SIRT1 activity or SIRT1 expression in endothelial cells for use in increasing vascular density and/or blood flow in tissue of a subject, or use of an agent which elevates SIRT1 activity or SIRT1 expression in endothelial cells in the manufacture of a medicament for increasing vascular density and/or blood flow in tissue of a subject.

A second aspect provides a method of increasing the exercise capacity of a subject, the method comprising administering to the subject an effective amount of an agent which elevates SIRT1 activity or SIRT1 expression in endothelial cells of the subject.

An alternative second aspect provides an agent which elevates SIRT1 activity or SIRT1 expression in endothelial cells for use in increasing the exercise capacity of a subject, or use of an agent which elevates SIRT1 activity or SIRT1 expression in endothelial cells in the manufacture of a medicament for increasing exercise capacity of a subject.

A third aspect of the present invention provides a method of increasing vascular density and/or blood flow in tissue of a subject, the method comprising administering to the subject an effective amount of an $NAD^+$ agonist.

An alternative third aspect provides an $NAD^+$ agonist for use in increasing vascular density and/or blood flow in tissue of a subject, or use of an $NAD^+$ agonist in the manufacture of a medicament for increasing vascular density and/or blood flow in tissue of a subject.

A fourth aspect of the present invention provides a method of increasing exercise capacity of a subject, the method comprising administering to the subject an effective amount of an $NAD^+$ agonist.

An alternative fourth aspect provides an $NAD^+$ agonist for use in increasing exercise capacity of a subject, or use of an $NAD^+$ agonist in the manufacture of a medicament for increasing exercise capacity of a subject.

A fifth aspect of the present invention provides a method of increasing vascular density and/or blood flow in tissue of a subject, the method comprising administering to the subject an effective amount of an $NAD^+$ precursor.

An alternative fifth aspect provides an $NAD^+$ precursor for use in increasing vascular density and/or blood flow in tissue of a subject, or use of an $NAD^+$ precursor in the manufacture of a medicament for increasing vascular density and/or blood flow in tissue of a subject.

A sixth aspect of the present invention provides a method of increasing exercise capacity of a subject, the method comprising administering to the subject an effective amount of an $NAD^+$ precursor.

An alternative sixth aspect provides an $NAD^+$ precursor for use in increasing exercise capacity of a subject, or use of an $NAD^+$ precursor in the manufacture of a medicament for increasing exercise capacity of a subject.

A seventh aspect provides a method of increasing angiogenesis and/or neovascularisation in tissue of a subject, comprising administering to the subject an effective amount of an agent which elevates SIRT1 activity or SIRT1 expression in endothelial cells of the subject.

An alternative seventh aspect provides an agent which elevates SIRT1 activity or SIRT1 expression in endothelial cells for use in increasing angiogenesis and/or neovascularisation in tissue of a subject, or use of an agent which elevates SIRT1 activity or SIRT1 expression in endothelial cells in the manufacture of a medicament for increasing angiogenesis and/or neovascularisation in tissue of the subject.

A eighth aspect of the present invention provides a method of increasing angiogenesis and/or neovascularisation in tissue of a subject, the method comprising administering to the subject an effective amount of an $NAD^+$ agonist.

An alternative eighth aspect provides an $NAD^+$ agonist for use in increasing angiogenesis and/or neovascularisation in tissue of a subject, or use of an $NAD^+$ agonist in the manufacture of a medicament for increasing angiogenesis and/or neovascularisation in tissue of a subject.

A ninth aspect of the present invention provides a method of increasing angiogenesis and/or neovascularisation in tissue of a subject, the method comprising administering to the subject an effective amount of an $NAD^+$ precursor.

An alternative ninth aspect provides an $NAD^+$ precursor for use in increasing angiogenesis and/or neovascularisation in tissue of a subject, or use of an $NAD^+$ precursor in the manufacture of a medicament for increasing angiogenesis and/or neovascularisation in tissue of a subject.

A tenth aspect provides a method of increasing vascular density and/or blood flow in tissue of a subject, comprising:

(a) subjecting the subject to exercise training over an exercise training period; and (b) administering to the subject an effective amount of an agent which elevates SIRT1 activity or SIRT1 expression in endothelial cells of the subject before and/or during the exercise training period.

An alternative tenth aspect provides an agent which elevates SIRT1 activity or SIRT1 expression in endothelial cells of the subject for use in increasing vascular density and/or blood flow in tissue of a subject, wherein: (a) the subject is subjected to exercise training over an exercise training period; and (b) the agent is administered before and/or during the exercise training period; or use of an agent which elevates SIRT1 activity or SIRT1 expression in endothelial cells of the subject in the manufacture of a medicament for increasing vascular density and/or blood flow in tissue of a subject wherein (a) the subject is subjected to exercise training over an exercise training period, and (b) the agent is administered before and/or during the exercise training period.

An eleventh aspect provides a method of increasing vascular density and/or blood flow in tissue of a subject, comprising: (a) subjecting the subject to exercise training over an exercise training period; and (b) administering to the subject an effective amount of an NAD+ agonist before and/or during the exercise training period.

An alternative eleventh aspect provides an $NAD^+$ agonist for use in increasing vascular density and/or blood flow in tissue of a subject, wherein (a) the subject is subjected to exercise training over an exercise training period; and (b) the $NAD^+$ agonist is administered before and/or during the exercise training period; or use of an $NAD^+$ agonist in the manufacture of a medicament for increasing vascular density and/or blood flow in tissue of a subject, wherein (a) the subject is subjected to exercise training over an exercise training period; and (b) the $NAD^+$ agonist is administered before and/or during the exercise training period.

A twelfth aspect provides a method of increasing exercise capacity in a subject, comprising: (a) subjecting the subject to exercise training over an exercise training period; and (b) administering to the subject an effective amount of an agent which elevates SIRT1 activity or SIRT1 expression in endothelial cells of the subject before and/or during the exercise training period.

An alternative twelfth aspect provides an agent which elevates SIRT1 activity or SIRT1 expression in endothelial cells of the subject for use in increasing exercise capacity of a subject, wherein: (a) the subject is subjected to exercise training over an exercise training period; and (b) the agent is administered before and/or during the exercise training period; or use of an agent which elevates SIRT1 activity or SIRT1 expression in endothelial cells of the subject in the manufacture of a medicament for increasing exercise capacity of a subject, wherein: (a) the subject is subjected to exercise training over an exercise training period; and (b) the agent is administered before and/or during the exercise training period.

A thirteenth aspect provides a method of increasing exercise capacity in a subject, comprising: (a) subjecting the subject to exercise training over an exercise training period; and (b) administering to the subject an effective amount of an $NAD^+$ agent before and/or during the exercise training period.

An alternative thirteenth aspect provides an $NAD^+$ agent for use in increasing exercise capacity of a subject, wherein: (a) the subject is subjected to exercise training over an exercise training period; and (b) the agent is administered before and/or during exercise training, or use of $NAD^+$ agent in the manufacture of a medicament for increasing exercise capacity of a subject, wherein: (a) the subject is subjected to exercise training over an exercise training period; and (b) the agent is administered before and/or during the exercise training period.

A fourteenth aspect provides a method of increasing vascular density and/or blood flow in tissue of a subject, comprising: (a) subjecting the subject to exercise training over an exercise training period; and (b) administering to the subject an effective amount of an NAD+ precursor before and/or during the exercise training period.

An alternative fourteenth aspect provides an $NAD^+$ precursor for use in increasing vascular density and/or blood flow in tissue of a subject, wherein: (a) the subject is subjected to exercise training over an exercise training period; and (b) the $NAD^+$ precursor is administered before and/or during the exercise training period; or use of an $NAD^+$ precursor in the manufacture of a medicament for increasing vascular density and/or blood flow in tissue of a subject, wherein: (a) the subject is subjected to exercise training over an exercise training period; and (b) the $NAD^+$ precursor is administered before and/or during exercise training.

A fifteenth aspect provides a method of increasing exercise capacity in a subject, comprising: (a) subjecting the subject to exercise training over an exercise training period; and (b) administering to the subject an effective amount of an NAD+ precursor before and/or during the exercise training period.

An alternative fifteenth aspect provides an $NAD^+$ precursor for use in increasing exercise capacity of a subject, wherein: (a) the subject is subjected to exercise training over an exercise training period; and (b) the $NAD^+$ precursor is administered before and/or during the exercise training period, or use of an $NAD^+$ precursor in the manufacture of a medicament for increasing exercise capacity of a subject, wherein: (a) the subject is subjected to exercise training over an exercise training period; and (b) the $NAD^+$ precursor is administered before and/or during exercise training.

A sixteenth aspect provides a method of treating or preventing vascular disease in a subject, comprising; (a) subjecting the subject to exercise training over an exercise training period; and (b) administering to the subject an effective amount of an agent which elevates SIRT1 activity or SIRT1 expression in endothelial cells of the subject before and/or during the exercise training period.

An alternative sixteenth aspect provides an agent which elevates SIRT1 activity or SIRT1 expression in endothelial cells of the subject for use in treating or preventing vascular disease in a subject, wherein: (a) the subject is subjected to exercise training over an exercise training period; and (b) the agent is administered before and/or during the exercise training period; or use of an agent which elevates SIRT1 activity or SIRT1 expression in endothelial cells of the subject in the manufacture of a medicament for treating or preventing vascular disease in a subject wherein: (a) the subject is subjected to exercise training over an exercise training period: and (b) the agent is administered before and/or during the exercise training period.

A seventeenth aspect provides a method of treating or preventing vascular disease in a subject, comprising: (a) subjecting the subject to exercise training over an exercise training period; and (b) administering to the subject an effective amount of an $NAD^+$ agonist before and/or during the exercise training period.

An alternative seventeenth aspect provides an $NAD^+$ agonist for use in treating or preventing vascular disease in a subject, wherein: (a) the subject is subjected to exercise training over an exercise training period; and (b) the $NAD^+$ agonist is administered before and/or during the exercise training period; or use of an $NAD^+$ agonist in the manufacture of a medicament for treating or preventing vascular disease in a subject wherein: (a) the subject is subjected to exercise training over an exercise training period; and (b) the $NAD^+$ agonist is administered before and/or during the exercise training period.

An eighteenth aspect provides a method of treating or preventing vascular disease in a subject, comprising: (a) subjecting the subject to exercise training over an exercise training period; and (b) administering to the subject an effective amount of an $NAD^+$ precursor before and/or during the exercise training period.

An alternative eighteenth aspect provides an $NAD^+$ precursor for use in treating or preventing vascular disease in a subject, wherein: (a) the subject is subjected to exercise training over an exercise training period; and (b) the $NAD^+$ agonist is administered before and/or during the exercise training period; or use of an $NAD^+$ precursor in the manufacture of a medicament for treating or preventing vascular disease in a subject wherein: (a) the subject is subjected to exercise training over an exercise training period; and (b) the $NAD^+$ agonist is administered before and/or during the exercise training period.

A nineteenth aspect provides a composition for increasing vascular density and/or blood flow in tissue of a subject, and/or increasing exercise capacity in a subject, comprising an $NAD^+$ agonist, and optionally a $H_2S$ precursor.

A twentieth aspect provides a composition for increasing vascular density and/or blood flow in tissue of a subject, and/or increasing exercise capacity in a subject, comprising an $NAD^+$ precursor, and optionally a $H_2S$ precursor.

A twenty first aspect provides a method of treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease, in a subject, comprising administering to the subject an effective amount of an agent which elevates SIRT1 activity or SIRT1 expression in endothelial cells of the subject.

An alternative twenty first aspect comprises an agent which elevates SIRT1 activity or SIRT1 expression in endothelial cells of the subject for use in treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease; or use of an agent which elevates SIRT1 activity or SIRT1 expression in endothelial cells of the subject in the manufacture of a medicament for treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease.

A twenty second aspect provides a method of treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease, in a subject, comprising administering to the subject an effective amount of an $NAD^+$ agonist.

An alternative twenty second aspect provides an $NAD^+$ agonist for use in treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease; or use of an $NAD^+$ agonist in the manufacture of a medicament for treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease.

A twenty third aspect provides a method of treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease, in a subject, comprising administering to the subject an effective amount of an $NAD^+$ precursor.

An alternative twenty third aspect provides an $NAD^+$ precursor for use in treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease; or use of an $NAD^+$ precursor in the manufacture of a medicament for treating or preventing a disease or condition selected from the group consisting of: coronary and/or peripheral arterial disease; ischaemia; ulcers; lung disease; pulmonary hypertension; frailty; sarcopenia; neurodegenerative disease, such as vascular dementia; stroke; haemorrhage; osteoporosis; heart disease; and vascular disease.

A twenty fourth aspect provides a method of increasing vascular density and/or blood flow in tissue of a subject having reduced mobility, comprising administering to the subject an effective amount of an agent which elevates SIRT1 activity or SIRT1 expression in endothelial cells of the subject.

An alternative twenty fourth aspect provides an agent which elevates SIRT1 activity or SIRT1 expression in endothelial cells for use in increasing vascular density and/or blood flow in tissue of a subject having reduced mobility, or use of an agent which elevates SIRT1 activity or SIRT1 expression in endothelial cells in the manufacture of a medicament for increasing vascular density and/or blood flow in tissue of a subject having reduced mobility.

A twenty fifth aspect provides a method of increasing exercise capacity in a subject having reduced mobility, comprising administering to the subject an effective amount of an agent which elevates SIRT1 activity or SIRT1 expression in endothelial cells of the subject.

An alternative twenty fifth aspect provides an agent which elevates SIRT1 activity or SIRT1 expression in endothelial cells for use in increasing exercise capacity in a subject having reduced mobility, or use of an agent which elevates SIRT1 activity or SIRT1 expression in endothelial cells in the manufacture of a medicament for increasing exercise capacity in a subject having reduced mobility.

A twenty sixth aspect provides a method of enhancing liver sinusoidal endothelial cell function in a subject, comprising administering to the subject an effective amount of an agent which elevates SIRT1 activity or SIRT1 expression in endothelial cells of the liver of the subject.

An alternative twenty sixth aspect provides an agent which elevates SIRT1 activity or SIRT1 expression in endothelial cells for use in enhancing liver sinusoidal endothelial cell function in a subject, or use of an agent which elevates SIRT1 activity or SIRT1 expression in endothelial cells in the manufacture of a medicament for enhancing liver sinusoidal endothelial cell function in a subject.

A twenty seventh aspect provides a method of enhancing the physical performance of a subject (e.g. a racing animal), comprising administering to the subject an effective amount of an agent which elevates SIRT1 activity or SIRT1 expression in endothelial cells of the animal.

An alternative twenty seventh aspect provides an agent which elevates SIRT1 activity or SIRT1 expression in endothelial cells for use in enhancing the physical performance of a subject, or use of an agent which elevates SIRT1 activity or SIRT1 expression in endothelial cells in the manufacture of a medicament for enhancing the physical performance of a subject.

A twenty eighth aspect provides a method of increasing endurance in a subject, comprising administering to the subject an effective amount of an agent which elevates SIRT1 activity or SIRT1 expression in endothelial cells of the subject.

An alternative twenty eighth aspect provides an agent which elevates SIRT1 activity or SIRT1 expression in endothelial cells for use in increasing endurance in a subject, or use of an agent which elevates SIRT1 activity or SIRT1 expression in endothelial cells in the manufacture of a medicament for increasing endurance in a subject.

A twenty ninth aspect provides a method of enhancing the effects of exercise in a subject, comprising administering to the subject an effective amount of an agent which elevates SIRT1 activity or SIRT1 expression in endothelial cells of the subject.

An alternative twenty ninth aspect provides an agent which elevates SIRT1 activity or SIRT1 expression in endothelial cells for use in enhancing the effects of exercise in a subject, or use of an agent which elevates SIRT1 activity or SIRT1 expression in endothelial cells in the manufacture of a medicament for enhancing the effects of exercise in a subject.

A thirtieth aspect provides method of improving vascular recovery in a subject following injury or immobilisation, comprising administering to the subject an effective amount of an agent which elevates SIRT1 activity or SIRT1 expression in endothelial cells of the subject.

An alternative thirtieth aspect provides an agent which elevates SIRT1 activity or SIRT1 expression in endothelial cells for use in improving vascular recovery in a subject following injury or immobilisation, or use of an agent which elevates SIRT1 activity or SIRT1 expression in endothelial cells in the manufacture of a medicament for improving vascular recovery in a subject following injury or immobilisation.

A thirty second aspect provides a method of enhancing benefits of physiotherapy in a subject, comprising administering to the subject an effective amount of an agent which elevates SIRT1 activity or SIRT1 expression in endothelial cells of the subject.

An alternative thirty second aspect provides an agent which elevates SIRT1 activity or SIRT1 expression in endothelial cells for use in enhancing benefits of physiotherapy in a subject, or use of an agent which elevates SIRT1 activity or SIRT1 expression in endothelial cells in the manufacture of a medicament for enhancing benefits of physiotherapy in a subject.

A thirty third aspect provides a method of enhancing blood flow to the eyes of a subject (e.g. to improve vision), comprising administering to the subject an effective amount of an agent which elevates SIRT1 activity or SIRT1 expression in endothelial cells of the subject.

An alternative thirty third aspect provides an agent which elevates SIRT1 activity or SIRT1 expression in endothelial cells for use in enhancing blood flow to the eyes of a subject, or use of an agent which elevates SIRT1 activity or SIRT1 expression in endothelial cells in the manufacture of a medicament for enhancing blood flow to the eyes of a subject.

A thirty fourth aspect provides a method of enhancing skin appearance of a subject, comprising administering to the subject an effective amount of an agent which elevates SIRT1 activity or SIRT1 expression in endothelial cells of the subject.

An alternative thirty fourth aspect provides an agent which elevates SIRT1 activity or SIRT1 expression in endothelial cells for use in enhancing skin appearance in a subject, or use of an agent which elevates SIRT1 activity or SIRT1 expression in endothelial cells in the manufacture of a medicament for enhancing skin appearance in a subject.

A thirty fifth aspect provides a method of enhancing meat production in an animal (e.g. in an immobile animal or in an animal having restrained movement), comprising administering to the animal an effective amount of an agent which elevates SIRT1 activity or SIRT1 expression in endothelial cells of the subject.

An alternative thirty fifth aspect provides an agent which elevates SIRT1 activity or SIRT1 expression in endothelial cells for use in enhancing meat production in an animal, or use of an agent which elevates SIRT1 activity or SIRT1 expression in endothelial cells in the manufacture of a medicament for enhancing meat production in an animal.

A thirty sixth aspect provides a method of:
- increasing vascular density in tissue of a subject having reduced mobility;
- increasing exercise capacity in subjects having reduced mobility;
- enhancing liver sinusoidal endothelial cell function in a subject;
- enhancing the physical performance of a subject;
- enhancing the effects of exercise in a subject;
- improving vascular recovery in a subject following injury or immobilisation;
- enhancing benefits of physiotherapy in a subject;
- increasing endurance in a subject;
- enhancing blood flow to the eyes of a subject;
- enhancing skin appearance of a subject; or
- enhancing meat production in an animal;
- comprising administering to the subject an effective amount of an $NAD^+$ agonist.

An alternative thirty sixth aspect provides an $NAD^+$ agonist for use in:
- increasing vascular density in tissue of a subject having reduced mobility;
- increasing exercise capacity in subjects having reduced mobility;
- enhancing liver sinusoidal endothelial cell function in a subject;
- enhancing the physical performance of a subject;
- enhancing the effects of exercise in a subject;
- improving vascular recovery in a subject following injury or immobilisation;
- enhancing benefits of physiotherapy in a subject;
- increasing endurance in a subject;
- enhancing blood flow to the eyes of a subject;
- enhancing skin appearance of a subject; or
- enhancing meat production in an animal;
- or
- use of an $NAD^+$ agonist in the manufacture of a medicament for:
- increasing vascular density in tissue of a subject having reduced mobility;
- increasing exercise capacity in subjects having reduced mobility;
- enhancing liver sinusoidal endothelial cell function in a subject;
- enhancing the physical performance of a subject;
- enhancing the effects of exercise in a subject;
- improving vascular recovery in a subject following injury or immobilisation;
- enhancing benefits of physiotherapy in a subject;
- increasing endurance in a subject;
- enhancing blood flow to the eyes of a subject;
- enhancing skin appearance of a subject; or
- enhancing meat production in an animal.

A thirty seventh aspect provides an exercise mimetic comprising an $NAD^+$ agonist, and optionally a $H_2S$ precursor.

A thirty eighth aspect provides a kit for increasing vascular density and/or blood flow in tissue of a subject, and/or for increasing exercise capacity of a subject, comprising an agent which elevates SIRT1 activity or SIRT1 expression in endothelial cells.

A thirty ninth aspect provides a kit for increasing vascular density and/or blood flow in tissue of a subject, and/or for increasing exercise capacity of a subject, comprising an NAD+ agonist.

A fortieth aspect provides a kit for increasing vascular density and/or blood flow in tissue of a subject, and/or for increasing exercise capacity of a subject, comprising an NAD+ precursor.

A forty first aspect provide a composition for increasing vascular density and/or blood flow in tissue of a subject, and/or increasing exercise capacity in a subject, comprising an agent which elevates SIRT1 activity or SIRT1 expression in endothelial cells of the subject, and optionally a $H_2S$ precursor.

A forty second aspect provides an exercise mimetic comprising an agent which elevates SIRT1 activity or SIRT1 expression in endothelial cells of a subject, and optionally a $H_2S$ precursor.

representative images of microvessel sprouts in aortic rings from (4× magnification) embedded in collagen matrix in which the aortic rings prepared from SIRT1-iKO and WT mice and stimulated with BSA or VEGF (30 ng/mL) for 7 days. (black bar=500 m). (D) graphs showing quantification of the number of sprouts per aortic ring, and the total area of sprouts originating from aortic rings (n=15) in aortic rings prepared in (C). Data are expressed as mean±SEM. *p<0.05, p<0.005, *p<0.0005, $^{\delta}$p<0.00005 by one-way ANOVA with Bonferroni's Multiple Comparisons Test.

Figure 22:
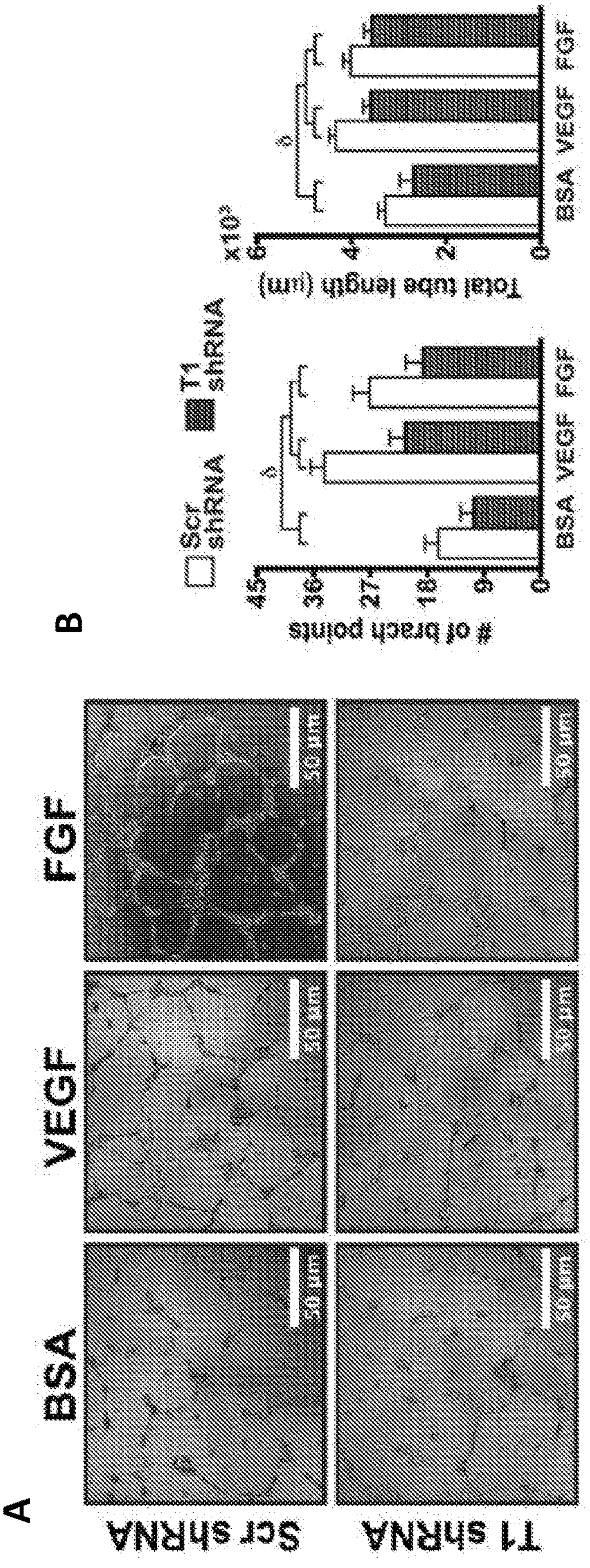
Figure 22:

FIG. 22 is (A) representative phase-contrast micrographs of tube networks (10× magnification) resulting from a tube formation assay using human aortic ECs (HAECs) infected with lentivirus expressing scrambled (Scr) or SIRT1 (T1) shRNA and assessed for tube networks on matrigel matrix in the presence of BSA (carrier), VEGF (25 ng/mL) or FGF (25 ng/mL). (white bar=50 μm) (B) graphs showing the number of tube branch points, and the total tube length per field of view (n=8) in tubes formed in the tube formation assay referred to in (A). (C) a graph showing number of migrated ECs per field of view (n=8) in a Transwell migration assay using HAECs expressing lentiviral-mediated Scr or T1 shRNAs seeded onto transwell inserts and simulated with BSA, VEGF (50 ng/mL) or FGF (50 ng/mL) for 24 hours. (D) a graph showing relative SIRT1 and VEGF mRNA levels in HUVECS transduced with non-targeting (NT) or SIRT1 (T1) siRNAs (n=3). (F) a graph showing quantification of VEGF protein levels in serum collected from 6-month old WT and ESKO mice (n=5). Data in are expressed as mean±SEM. *p<0.05, p<0.005, *p<0.0005, $^{\delta}$p<0.00005 one-way ANOVA with Bonferroni's Multiple Comparisons Test (B) and (C), or Student's t test (E).

Figure 23:
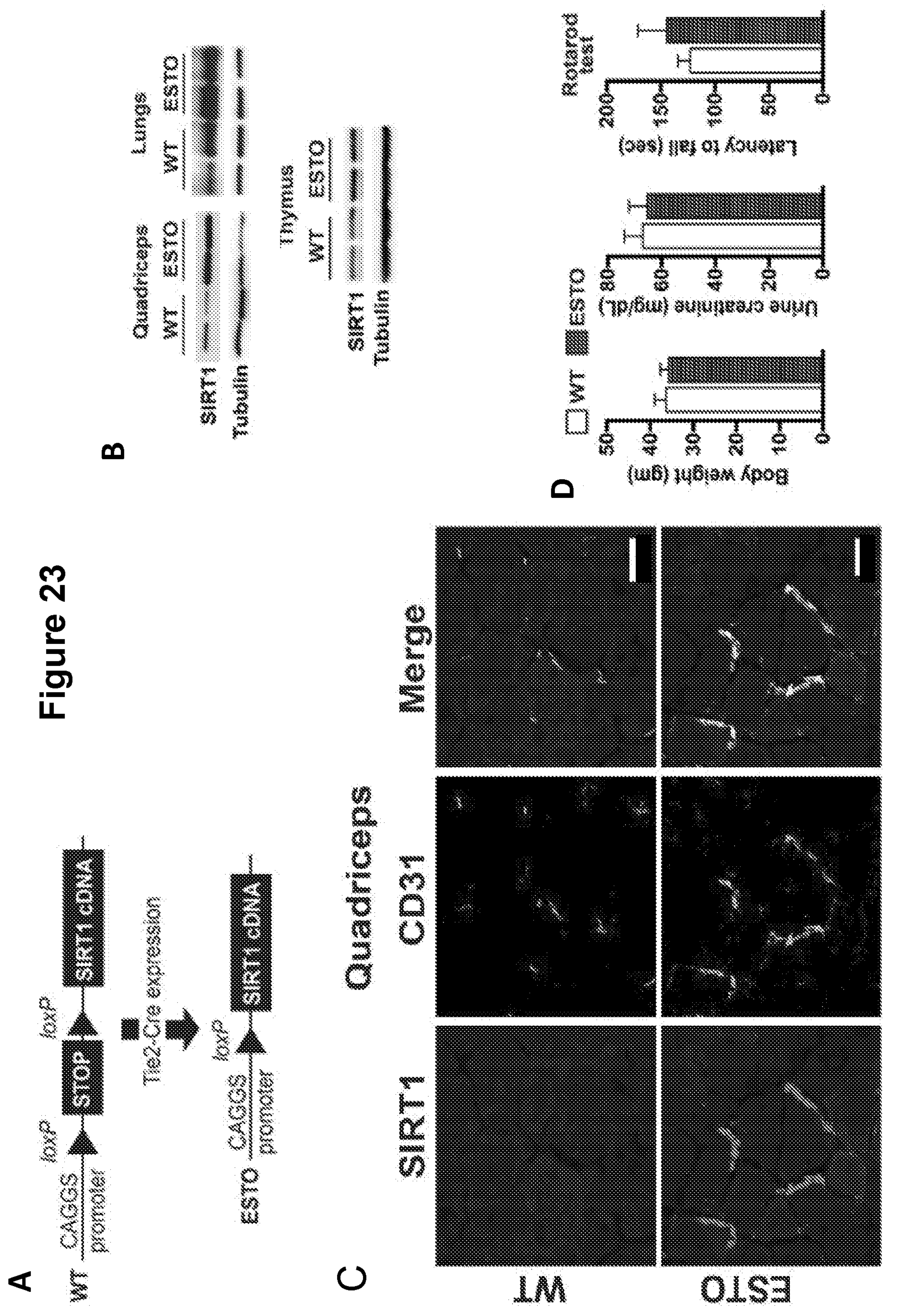

FIG. 23 is (A) a schematic diagram showing the strategy to generate EC-specific SIRT1 overexpression mouse (ESTO) by crossing a transgenic mouse that expresses Cre protein under the direction of EC-specific Tie2 promoter and WT (SIRT1STOP) mouse. SIRT1STOP mouse expresses a transgene in which SIRT1 has been cloned downstream of a constitutive CAGGS promoter followed by a transcriptional loxP-STOP-loxP cassette. (B) image of Western blots for SIRT1 protein in quadriceps, lung tissue and thymic tissue protein homogenates from endothelial-specific SIRT1 overexpressor (ESTO) and WT control mice showing the overexpression of SIRT1. Tubulin served as a loading control. (C) representative images of quadriceps muscle traverse cross sections (60× magnification) showing co-expression of SIRT1 and CD31 in muscle capillaries. Quadriceps muscle cross-sections from ESTO and WT mice were immunostained for SIRT1 and CD31 antibodies to show EC-specific overexpression of SIRT1. (white bar=30 μm) (D) graphs showing quantification of body weight, urine creatinine levels and rotarod performance showing time of latency to fall of 6-month old WT and ESTO mice (n=7).

Figure 24:
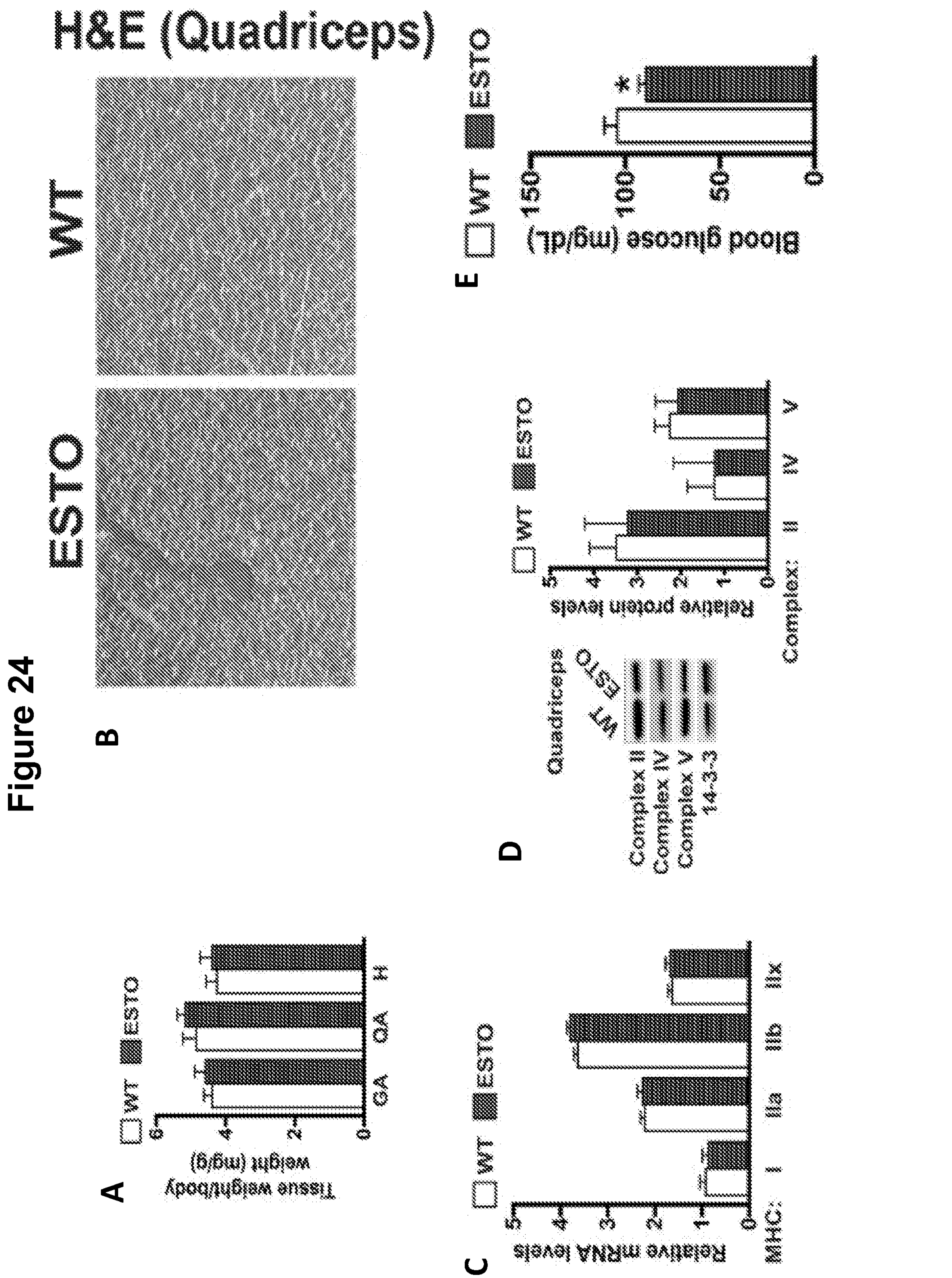

FIG. 24 is (A) a graph showing quantification of gastrocnemius (GA), quadriceps (QA) and heart (H) tissue weights normalized to body weights in 6-month old WT and ESTO mice (n=7). (B) representative H&E staining images of quadriceps muscles from 6-month old WT and ESTO mice. (C) a graph showing relative mRNA levels of myosin heavy chains I, IIA, IIB and IIX in gastrocnemius muscles from 6-month old WT and ESTO mice (n=10). (D) an image of Western blots for mitochondrial protein complexes II, IV and V in quadriceps tissue homogenates from 6-month old WT and ESTO mice (14-3-3 was used as loading control), and a graph showing relative quantifications of complexes II, IV and V is shown on the right (n=4). (E) a graph showing quantification of fasting blood glucose levels of 6-month old WT and ESTO mice (n=7).

Figure 25:
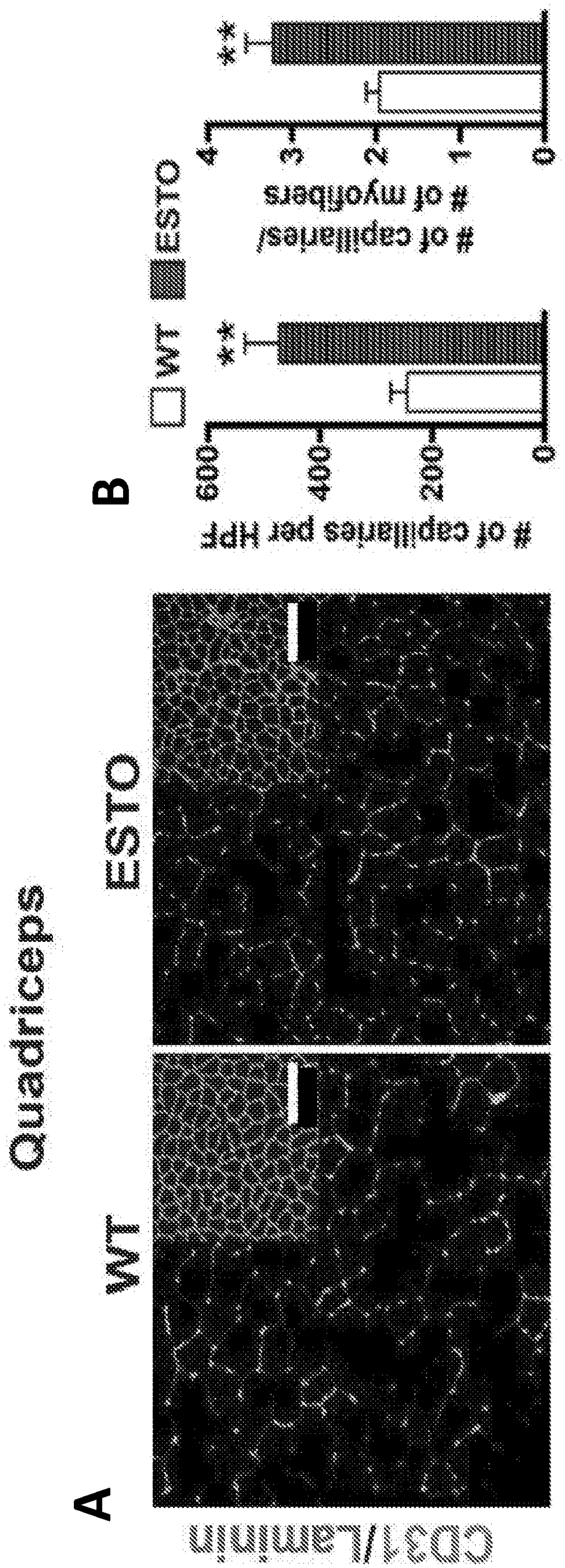
Figure 25:
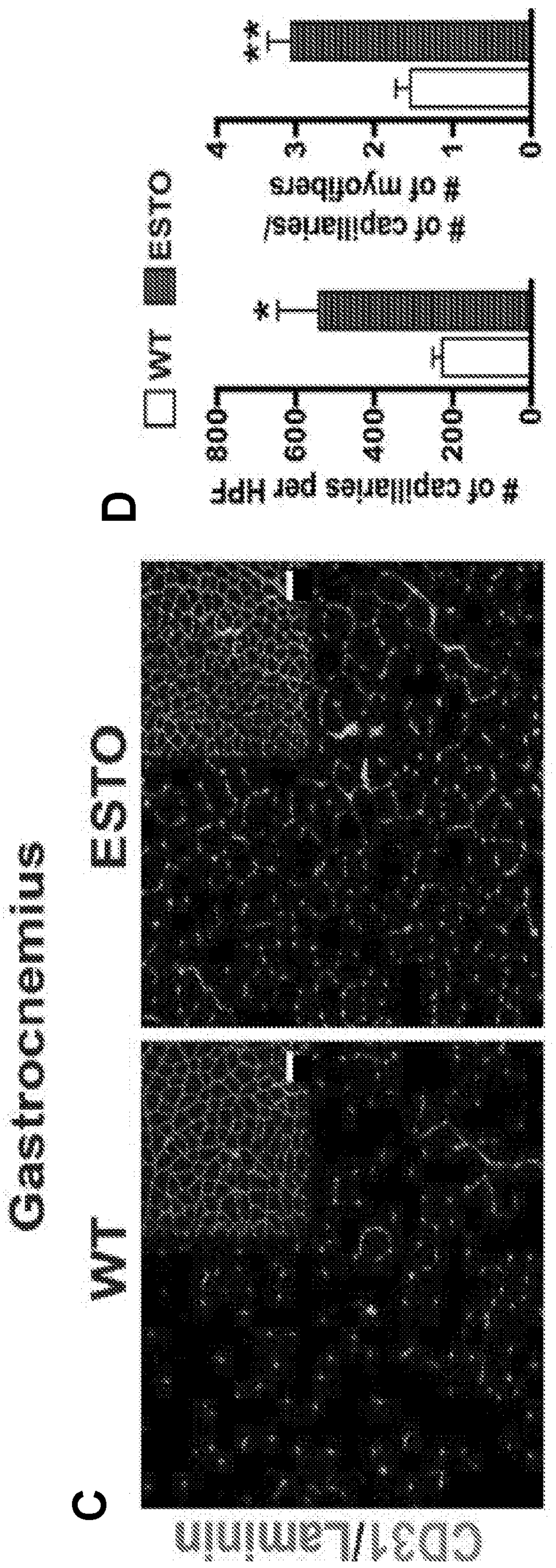

FIG. 25 is (A) representative images of capillaries (CD31) and stroma (laminin, inset) in quadriceps muscle cross-sections (20× magnification) from 6-month old WT and ESTO mice. (white bar=200 μm) (B) is graphs showing quantification of the number of capillaries per HPF, and the number of capillaries/the number of myofiber ratio per HPF (n=8) in the quadriceps tissue of WT and ESTO mice. (C) representative images of capillaries (CD31) and muscle stroma (laminin, inset) in gastrocnemius muscle cross-sections (20× magnification) from 6-month old WT and ESTO mice. (white bar=100 μm). (D) graphs showing quantification of the number of capillaries per HPF, and the number of capillaries/the number of myofiber ratio per HPF (n=8), in the gastrocnemius muscle tissue of WT and ESTO mice. Data in are expressed as mean±SEM. *p<0.05, **p<0.005, Student's t test.

Figure 26:
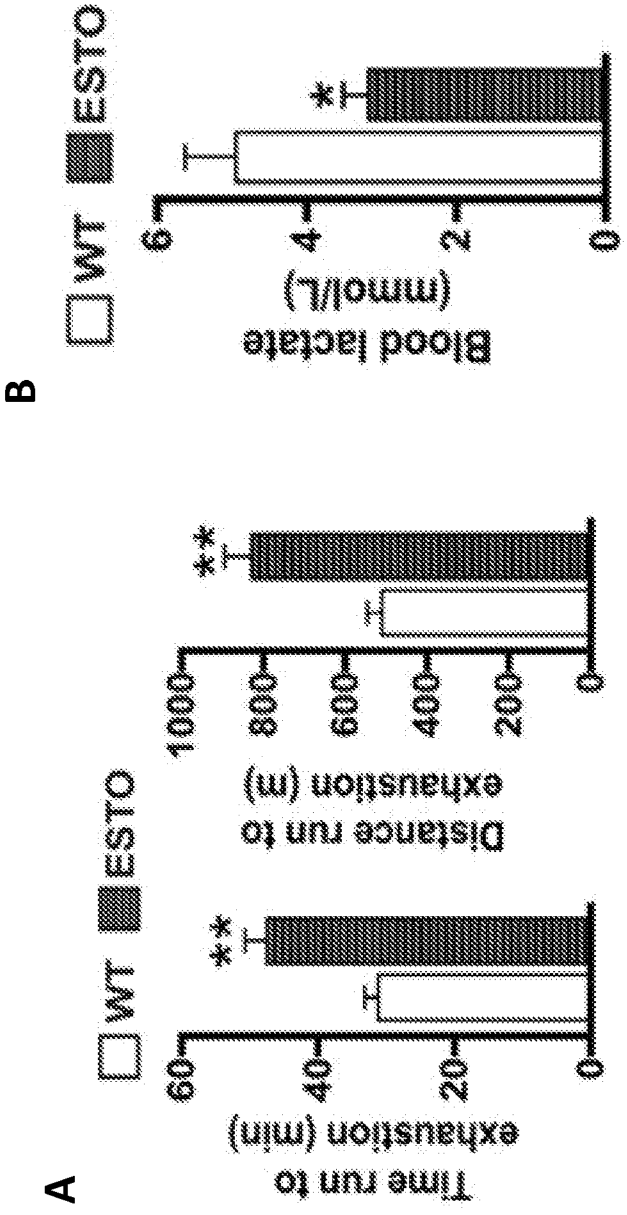

FIG. 26 is (A) graphs showing time run until exhaustion, and distance run until exhaustion, by 6-month old WT and ESTO mice in a high intensity treadmill exercise test (n=8). (B) a graph showing post-exercise blood lactate levels in 6-month old WT and ESTO mice (n=5). Data in are expressed as mean±SEM. *p<0.05, **p<0.005, by Student's t test.

Figure 27:
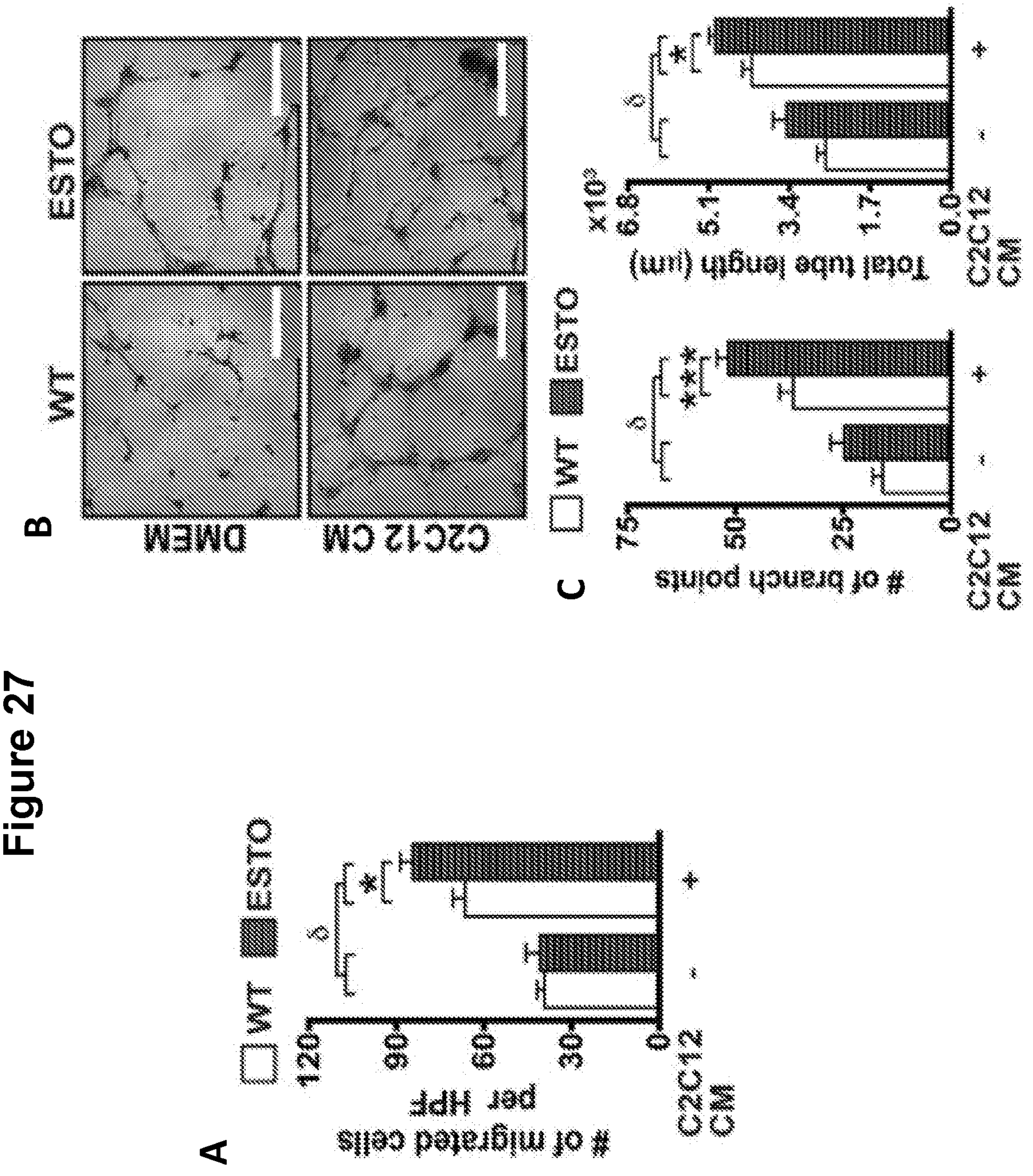

FIG. 27 is (A) a graph showing the number of migrated MLECs isolated from WT and ESTO mice+/−C2C12 CM per field of view (n=10) in a Transwell migration assay. (B) representative phase-contrast micrographs of tube networks (10× magnification) formed by WT and ESTO MLECs on matrigel matrix+/−C2C12 CM. (white bar=50 μm) (C) graphs showing quantification of the number of tube branch points and total tube length in tube networks formed by WT and ESTO MLECs on matrigel matrix+/−C2C12 CM referred to in (B), per field of view (n=8). Data is expressed as mean±SEM. *p<0.05, p<0.005, *p<0.0005, $^{\delta}$p<0.00005 by two-way ANOVA with Bonferroni's Multiple Comparisons Test.

Figure 28:
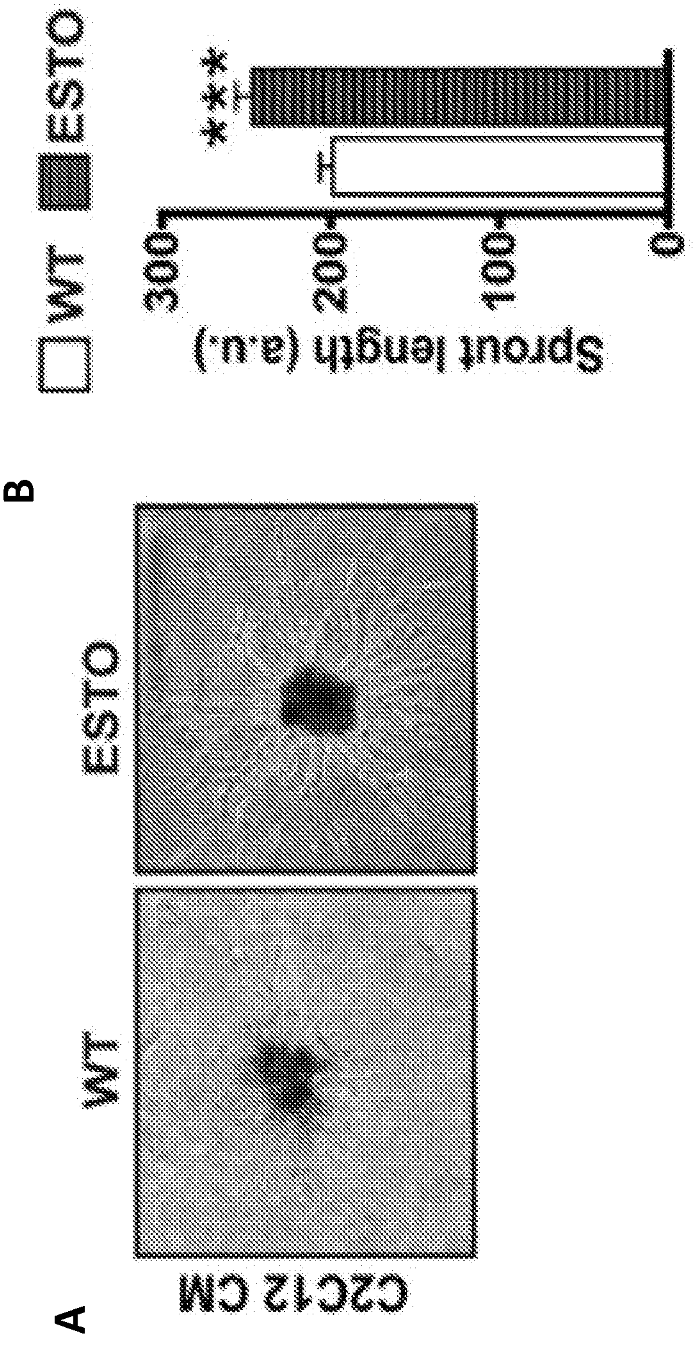

FIG. 28 is (A) representative phase-contrast micrographs of spheroids (10× magnification) from WT and ESTO MLECs treated with C2C12 CM. (B) a graph showing sprout length from WT and ESTO MLECs treated with C2C12 CM (n=8-9). Data is expressed as mean±SEM. ***p<0.0005 by Student's t test.

Figure 29:
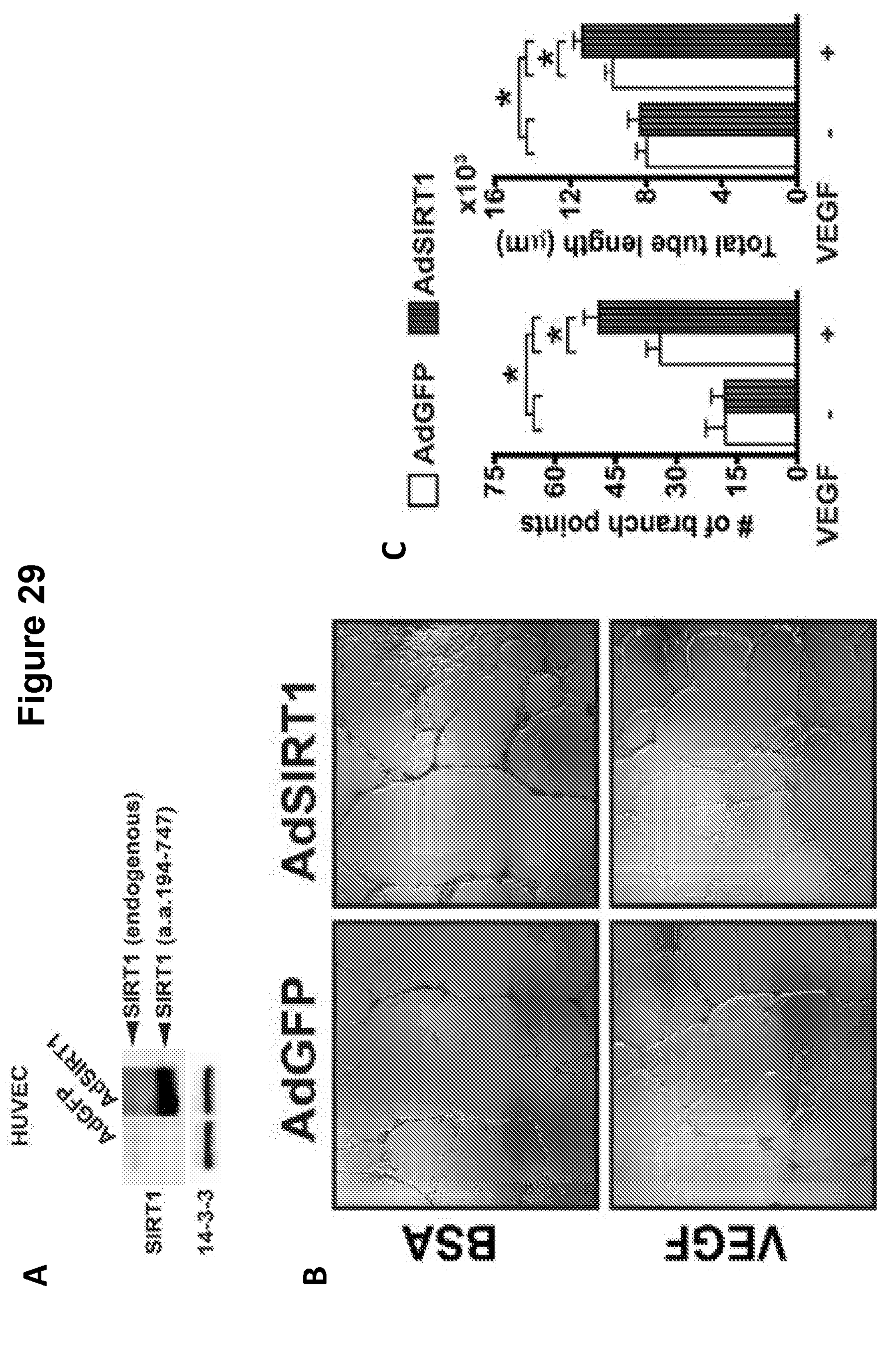

FIG. 29 is (A) an image of Western blots showing protein levels of SIRT1 in HUVECs infected with adenoviruses expressing GFP or SIRT1 (a.a.194-747). The overexpressed SIRT1 runs slightly below the endogenous SIRT1 in adeno-SIRT1 infected cells. 14-3-3 was used as a loading control. (B) representative images of phase-contrast micrographs of tube networks (10× magnification) formed by HUVECs infected with AdGFP or AdSIRT1, and treated with BSA or VEGF (30 ng/mL). (C) graphs showing the number of branch points and the total tube length per field of view in human umbilical vein ECs (HUVECs) infected with adenovirus expressing GFP (AdGFP) or SIRT1 (AdSIRT1) and assessed for tube networks+/−VEGF (30 ng/mL) (n=8-9). Data is expressed as mean±SEM. *p<0.05 by two-way ANOVA with Bonferroni's Multiple Comparisons Test.

Figure 30:
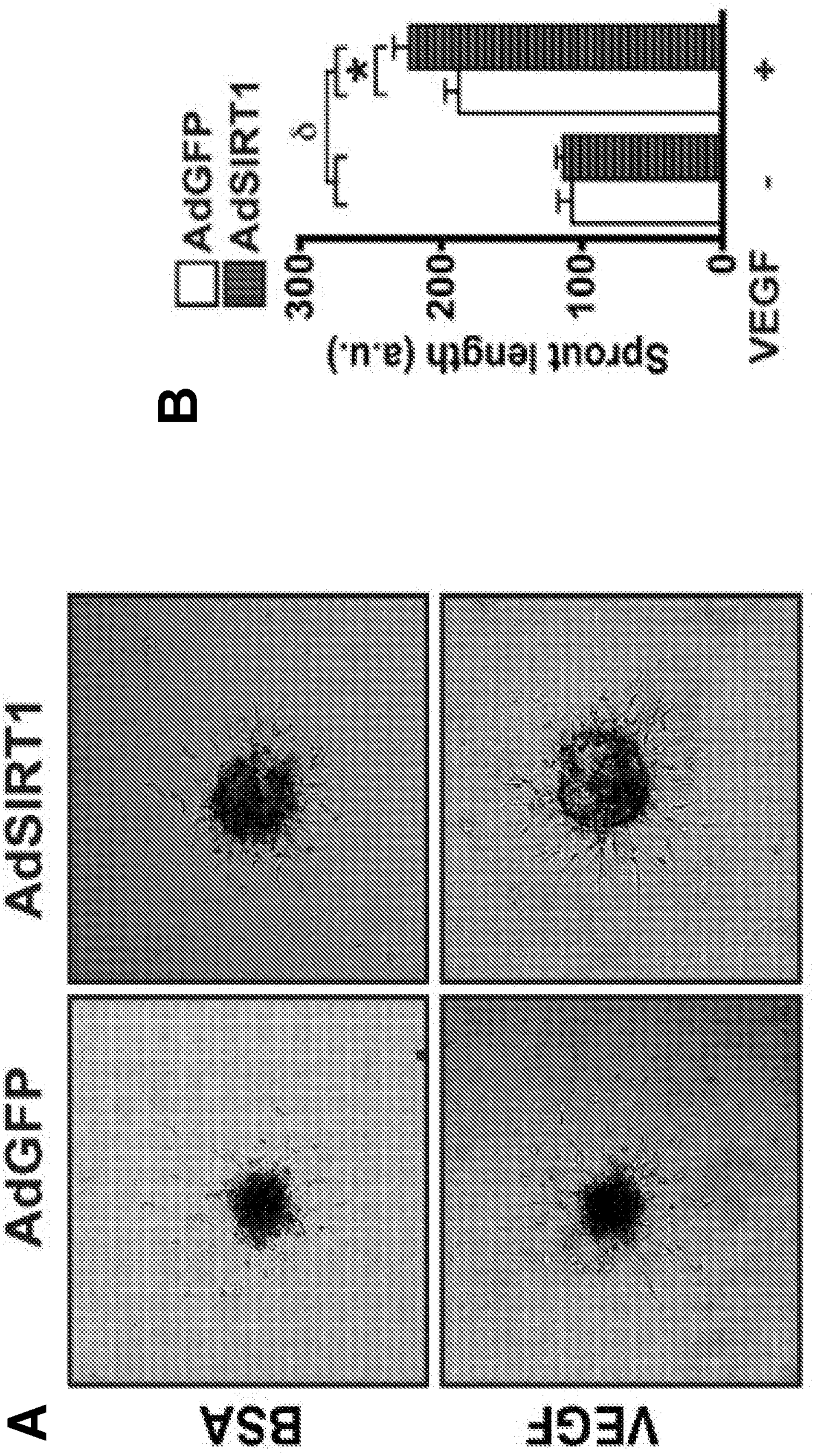

FIG. 30 is (A) representative phase-contrast micrographs of spheroids (10× magnification) formed from Ad-GFP or Ad-SIRT1 transduced HUVECs stimulated with VEGF (50 ng/mL). (B) a graph showing sprout length of spheroids from HAECs infected with Ad-GFP or Ad-SIRT1+/−VEGF (50 ng/mL) referred to in (A) (n=8). Data is expressed as mean±SEM. *$p<0.05$, $^{\delta}p<0.00005$ by two-way ANOVA with Bonferroni's Multiple Comparisons Test.

Figure 31:
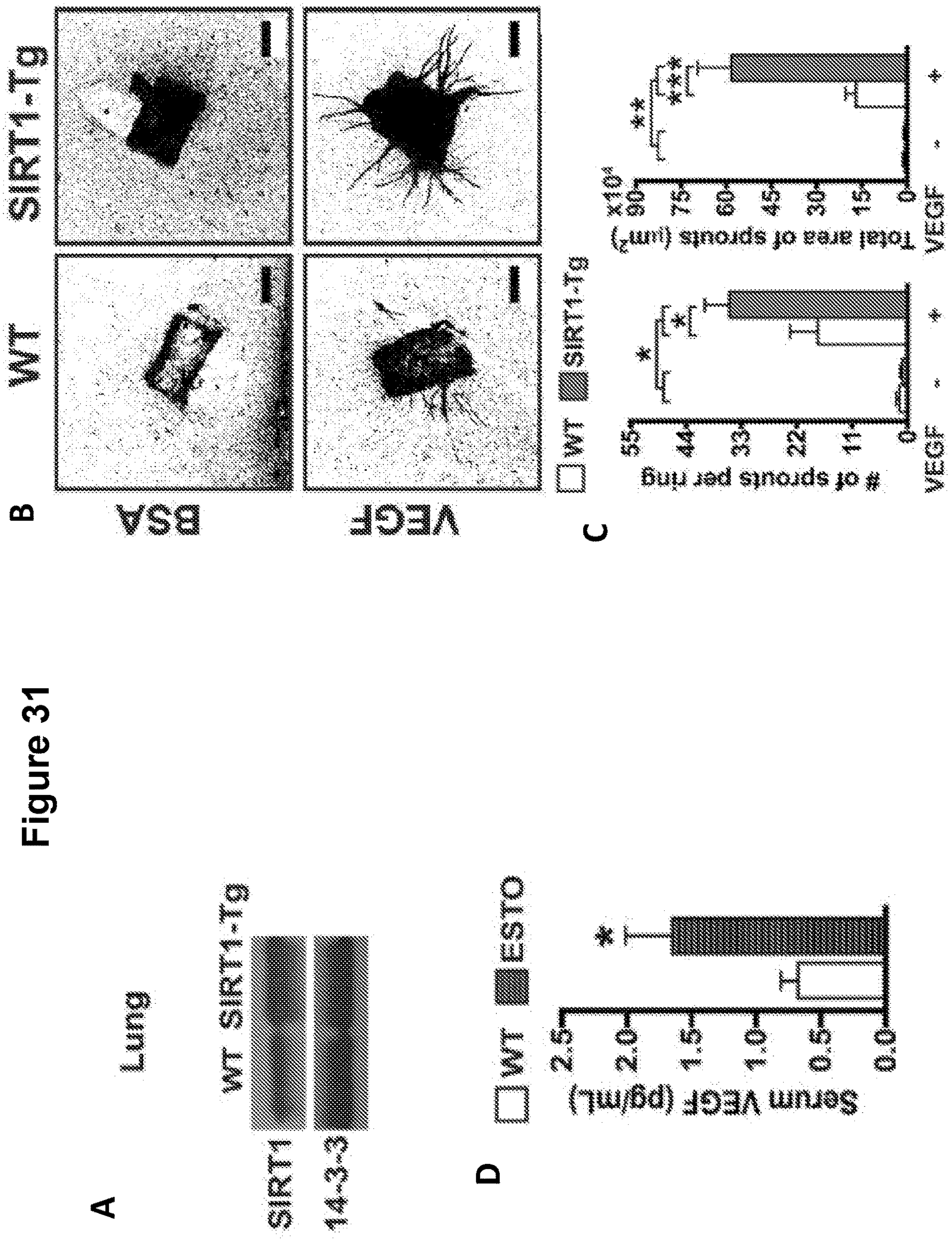

FIG. 31 is (A) an image of Western blots showing SIRT1 protein levels in lung tissue homogenates from WT and whole-body overexpressing SIRT1 transgenic (SIRT1-Tg) mice. 14-3-3 was used as a loading control. (B) representative images of microvessel sprouts in aortic rings (4× magnification) prepared from whole-body SIRT1 transgenic (SIRT1-Tg) and WT mice and treated with BSA or VEGF (30 ng/mL) in an aortic ring assay. Control condition was minimal growth factors (2.5% FBS) with almost no sprouting because of low factor stimulation. (black bar=500 μm). (C) a graph showing the number of sprouts per ring and total area of sprouts originating from aortic rings (n=15) in the aortic ring assay referred to in (B). Data is expressed as mean±SEM. *$p<0.05$, $p<0.005$, *$p<0.0005$, $^{\delta}p<0.00005$ by two-way ANOVA with Bonferroni's Multiple Comparisons Test. (D) a graph showing quantification of VEGF protein levels in serum collected from 6-month old WT and ESTO mice (n=5). Data are expressed as mean±SEM. *$p<0.05$, **$p<0.005$ by Student's t test (D) and two-way ANOVA with Bonferroni's Multiple Comparisons Test (C).

Figure 4:
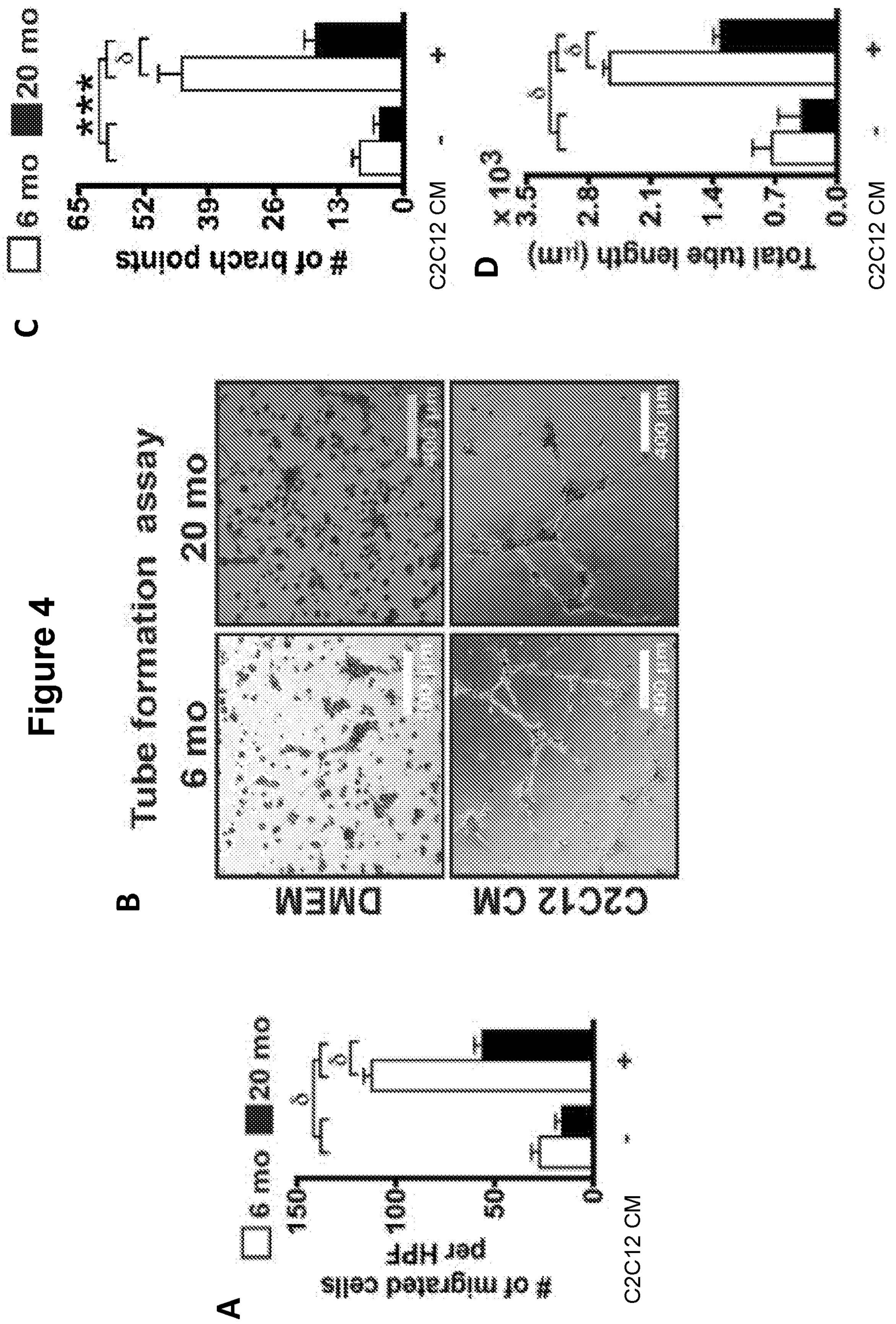
FIG. 4 is (A) a graph showing quantification of the number of migrated ECs treated with +/−C2C12 CM per HPF (n=10) following a transwell migration assay in which primary murine lung endothelial cells (MLECs) isolated from 6 and 20-month old mice were starved overnight and then seeded ($2.5\times10^4$ cells) onto a BD FluoroBlok transwell with 8 μm pore diameter, and conditioned media (CM) collected from C2C12 myotubes transduced with adenovirus expressing PGC-1α transgene added to the bottom chamber. After 24 hours, the migrated cells were fixed, stained with DAPI and then photographed (10× magnification) and counted; (B) representative images from phase-contrast micrographs of tube networks (10× magnification) resulting from a tube formation assay in which MLECs from 6 and 20-month old mice were seeded ($5\times10^4$ cells) onto growth factor depleted matrigel matrix and overlaid with C2C12 CM for 18 hours (white bar=400 μm); (C) is a graph showing quantification of the number of tube branch points +/−C2C12 CM per field of view (n=8) from the tube formation assay in (B); and (D) is a graph showing quantification of total tube length of capillary networks formed by MLECs from 6 and 20-month old mice treated with +/−C2C12 CM (n=8) in the tube formation assay referred to in (B). Data are expressed as mean±SEM. *$p<0.05$, $p<0.005$, *$p<0.0005$, $^{\delta}p<0.00005$ by two-way ANOVA with Bonferroni's Multiple Comparisons Test.
Figure 32:
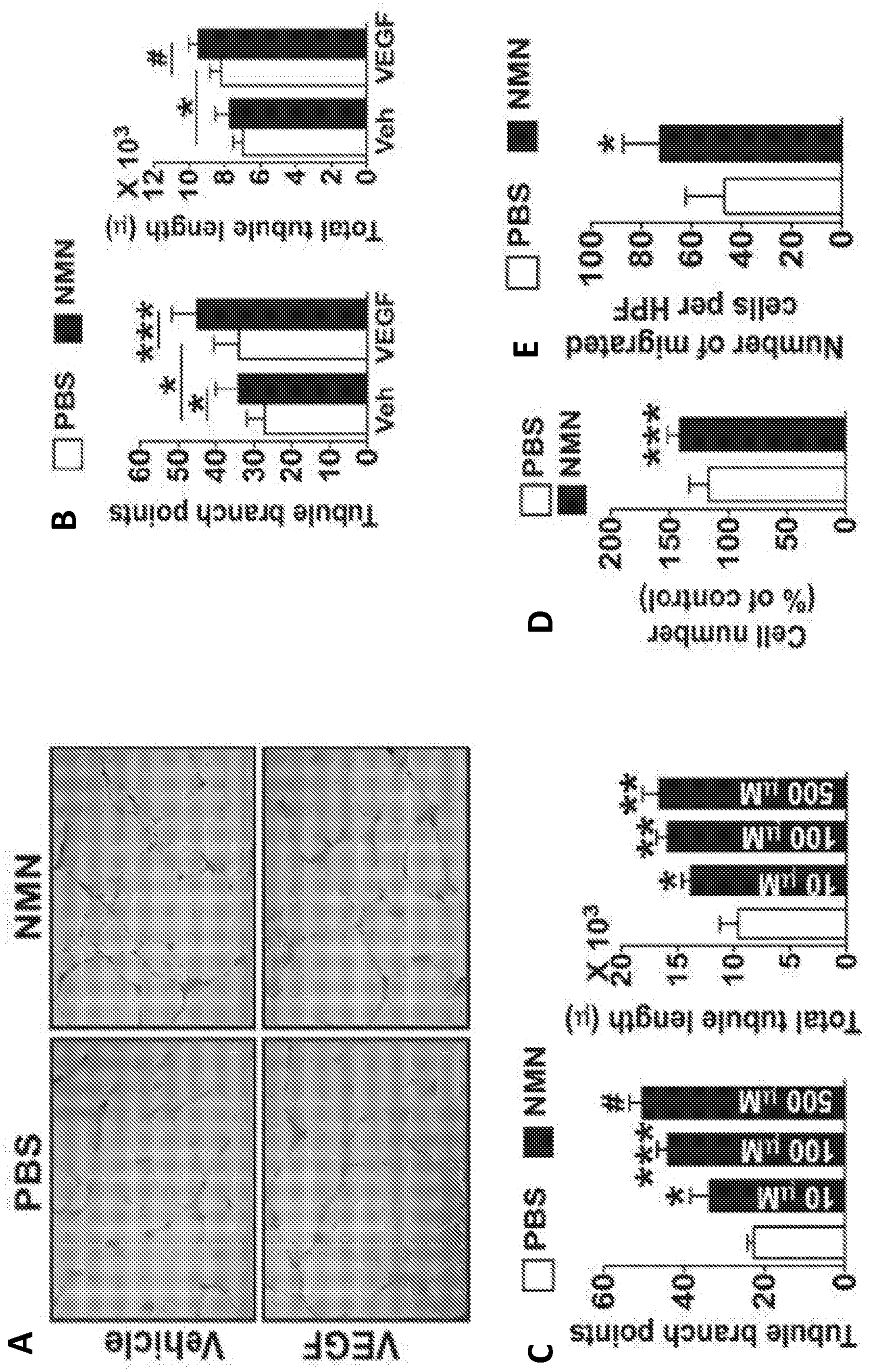

FIG. 32 is (A) representative bright field images (10× magnification) of tube networks formed by human aortic endothelial cells (HAECs) in the presence or absence of VEGF (30 ng/mL) and NMN. (B) graphs showing quantification of tube branch points and total tube length per field of view from tube networks formed in (A) (n=12). (C) graphs showing quantification of tube branch points and total tube length per field of view in the tube networks formed by HAECs treated with PBS or different doses of NMN (10 μM, 100 μM or 500 μM). (n=3, *$p<0.05$, *$p<0.0005$ and #$p<0.00005$ versus PBS). (D) a graph showing cell numbers after FIG. 4**B HUVECs were incubated with PBS or NMN (500 μM) for 48 h in complete growth medium. Cell number was determined using flow cytometry. (E) a graph showing results after HUVECs were subjected to a VEGF-mediated transwell migration assay in the presence of vehicle (PBS) or NMN (500 μM). The number of migrated cells per high power field was quantified (n=12).

Figure 33:
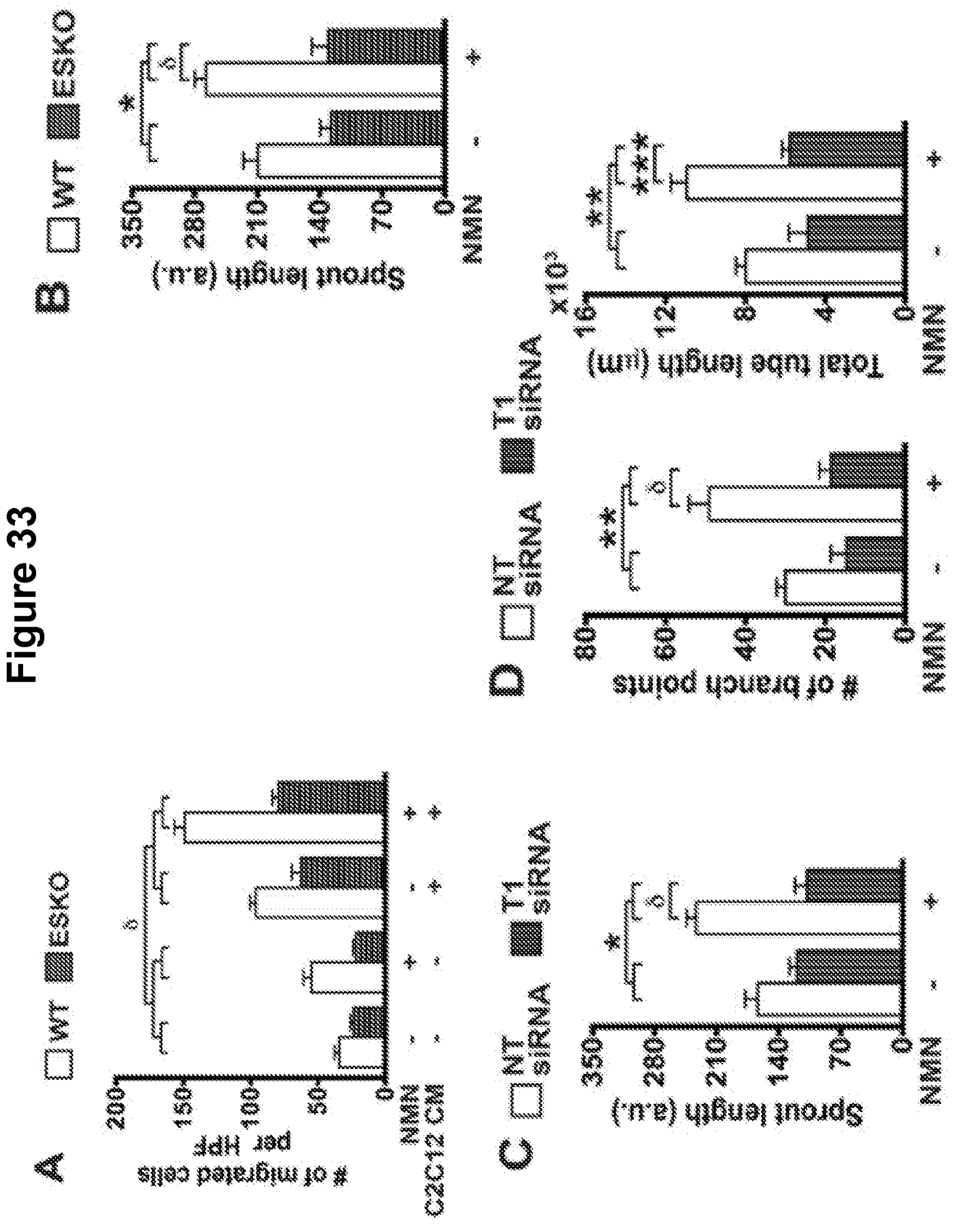

FIG. 33 is (A) a graph showing the number of migrated MLECs isolated from WT and ESKO mice+/−C2C12 CM and +/−NMN (0.5 mM) per field of view (n=12) in a transwell migration assay. (B) a graph showing sprout length of spheroids from WT and ESKO stimulated with C2C12 CM and +/−NMN (0.5 mM) (n=8). (C) a graph showing sprout length of spheroids from HAECs transduced with non-targeting (NT) or SIRT1 (T1) siRNAs and stimulated with VEGF (50 ng/mL) and +/−NMN (0.5 mM) (n=8). (D) graphs showing number of branch points, and total tube length, per field of view (n=13), in a tube formation assay using HAECs transfected with NT or T1 siRNAs and subjected to VGEF (30 ng/mL)-mediated tube formation+/−NMN (0.5 mM). Data are expressed as mean±SEM. *$p<0.05$, $p<0.005$, *$p<0.0005$, $^{\delta}p<0.00005$, two-way ANOVA with Bonferroni's Multiple.Comparisons Test.

Figure 34:
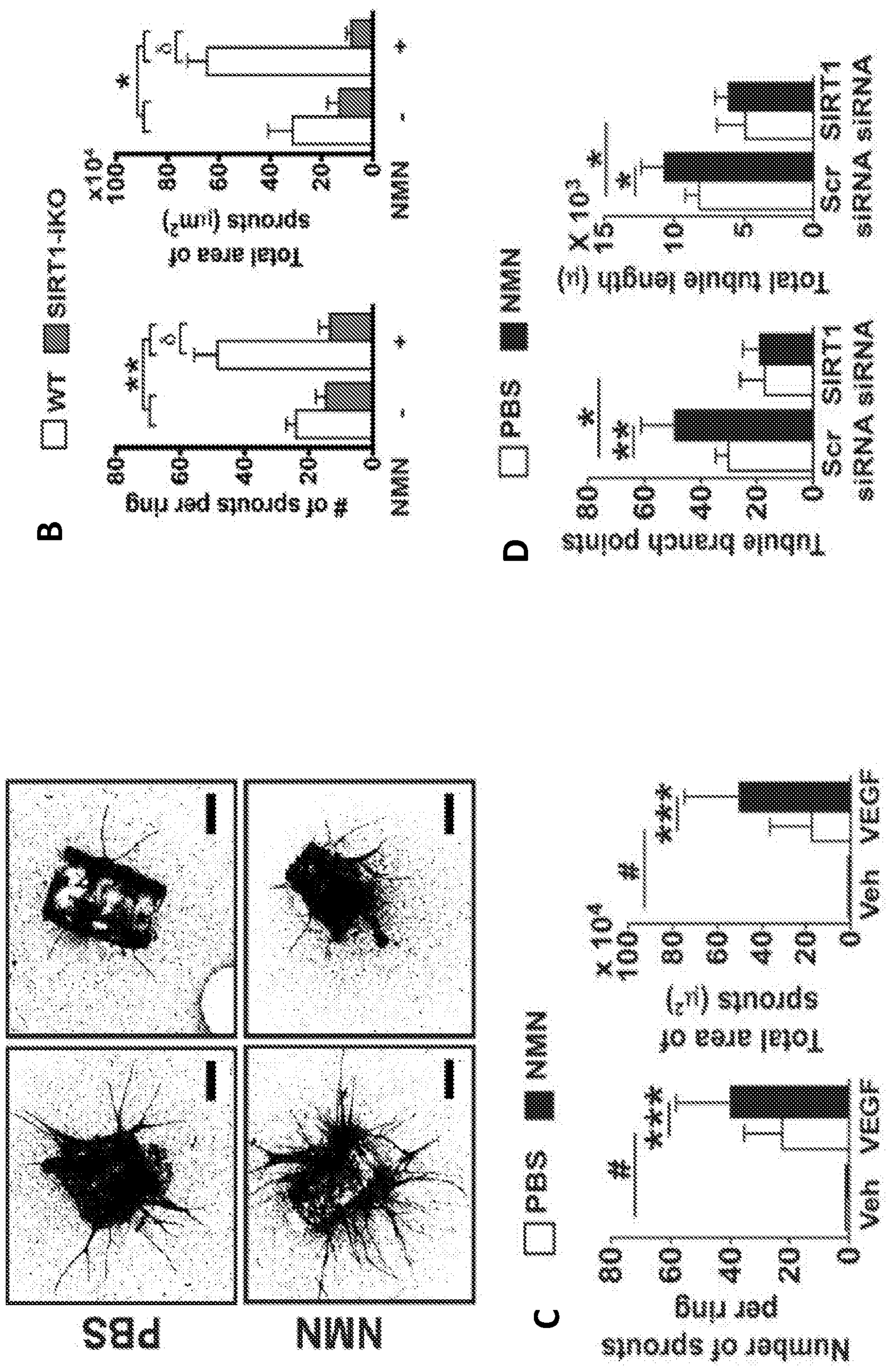

FIG. 34 is (A) is representative images of microvessel sprouts in aortic rings (4× magnification) prepared from WT and SIRT1-iKO mice stimulated VEGF (30 ng/mL)+/−NMN (0.5 mM) for 7 days. (black bar=500 μm). (B) is graphs showing number of sprouts per ring, and total area of sprouts originating from the aortic rings (n=15) prepared from WT and SIRT1-iKO (18-month old) mice subjected to VEGF (30 ng/mL)-mediated sprouting for 7 days+/−NMN (0.5 mM) as referred to in (A). (C) graphs showing quantification of the number and total area of sprouts originating from aortic rings prepared from 18-month old wild-type mice and treated with or without VEGF (30 ng/mL) for 7 days (n=15). (D) graphs showing HAECs transfected with Scr or SIRT1 siRNA and then subjected to VGEF-mediated tube formation with PBS or NMN (500 μM). Quantification of tube branch points and total tube length per field of view of the resulting tube networks are shown (n=12). Data are expressed as mean±SEM. *$p<0.05$, $p<0.005$, *$p<0.0005$, $^{\delta}p<0.00005$, two-way ANOVA with Bonferroni's Multiple.Comparisons Test.

Figure 35:
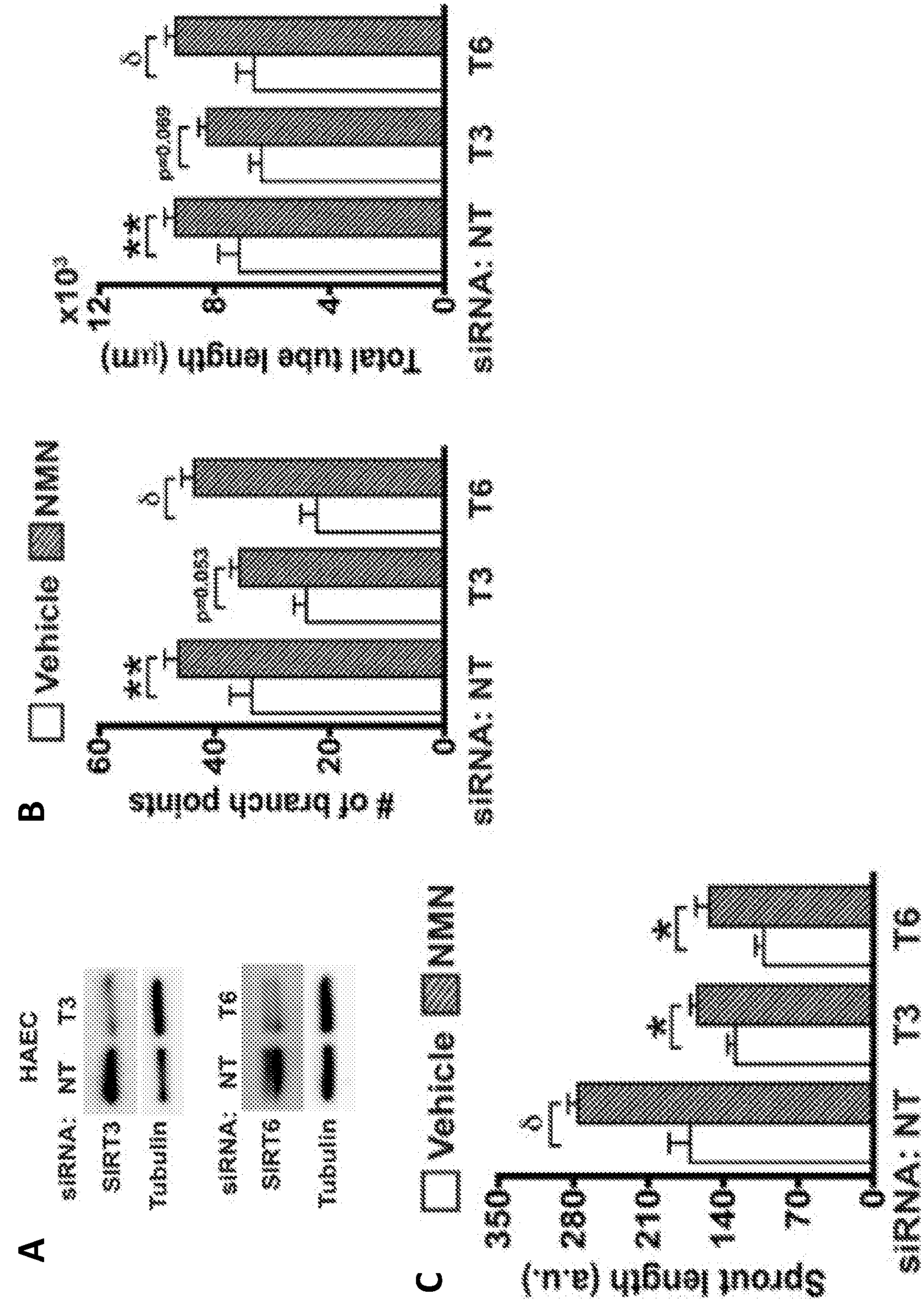

FIG. 35 is (A) images of Western blots showing SIRT3 and SIRT6 protein levels in HAECs transfected with NT, SIRT3 (T3) or SIRT6 (T6) siRNAs. Tubulin was used as a loading control. (B) graphs of quantification of number of tube branch points and total tube length per field of view (10× magnification) of the resulting tube networks formed by HAECs transfected with NT, T3 or T6 siRNAs under VEGF (30 ng/mL)+/−NMN (n=10-12). (C) a graph showing quantification of sprout length of spheroids from HAECs transfected with NT, T3 or T6 siRNAs and stimulated with VEGF+/−NMN (0.5 mM) (n=8). Data are expressed as mean±SEM. *$p<0.05$, $p<0.005$, *$p<0.0005$, $^{\delta}p<0.00005$, one-way ANOVA with Bonferroni's Multiple. Comparisons Test.

Figure 36:
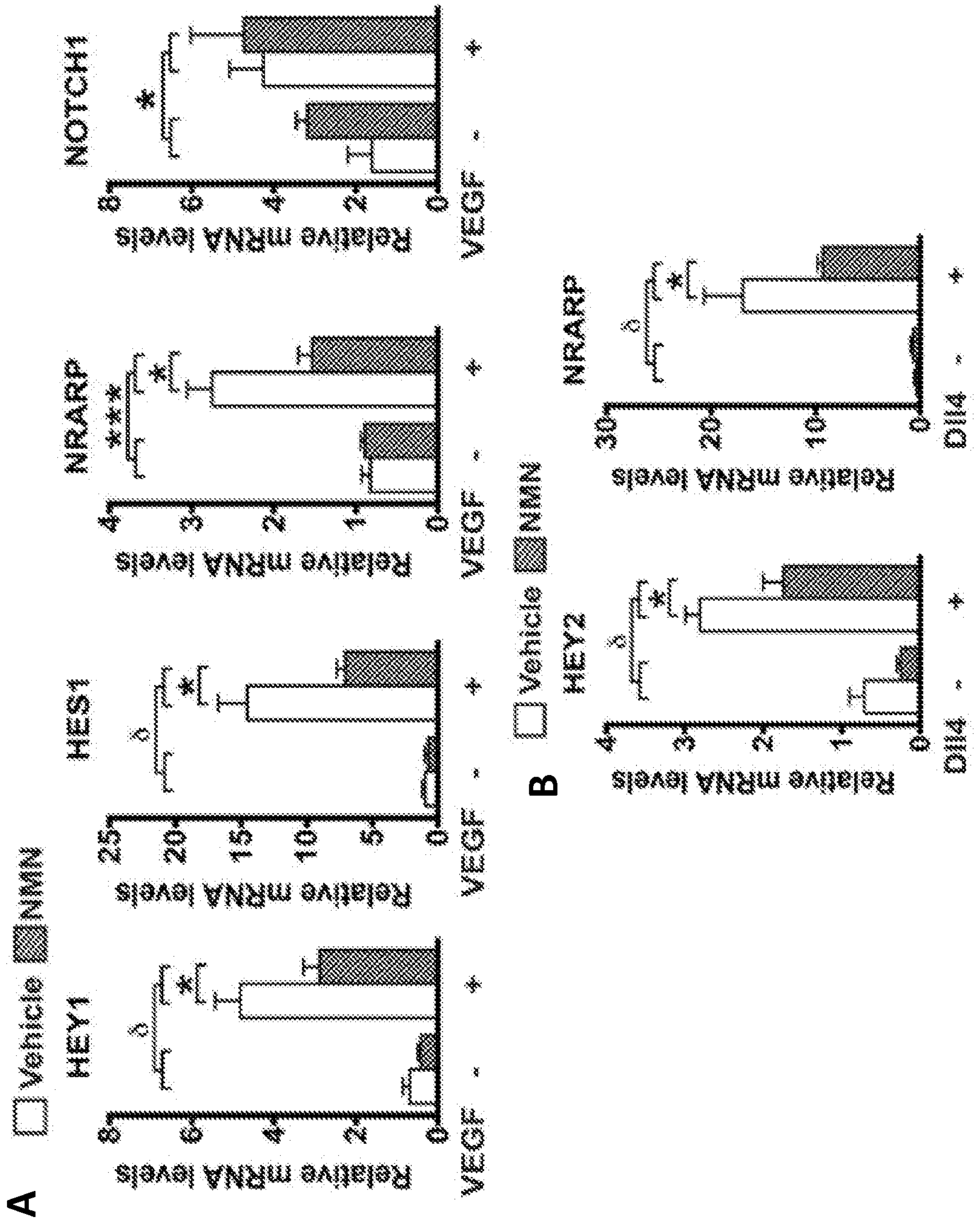
Figure 37:
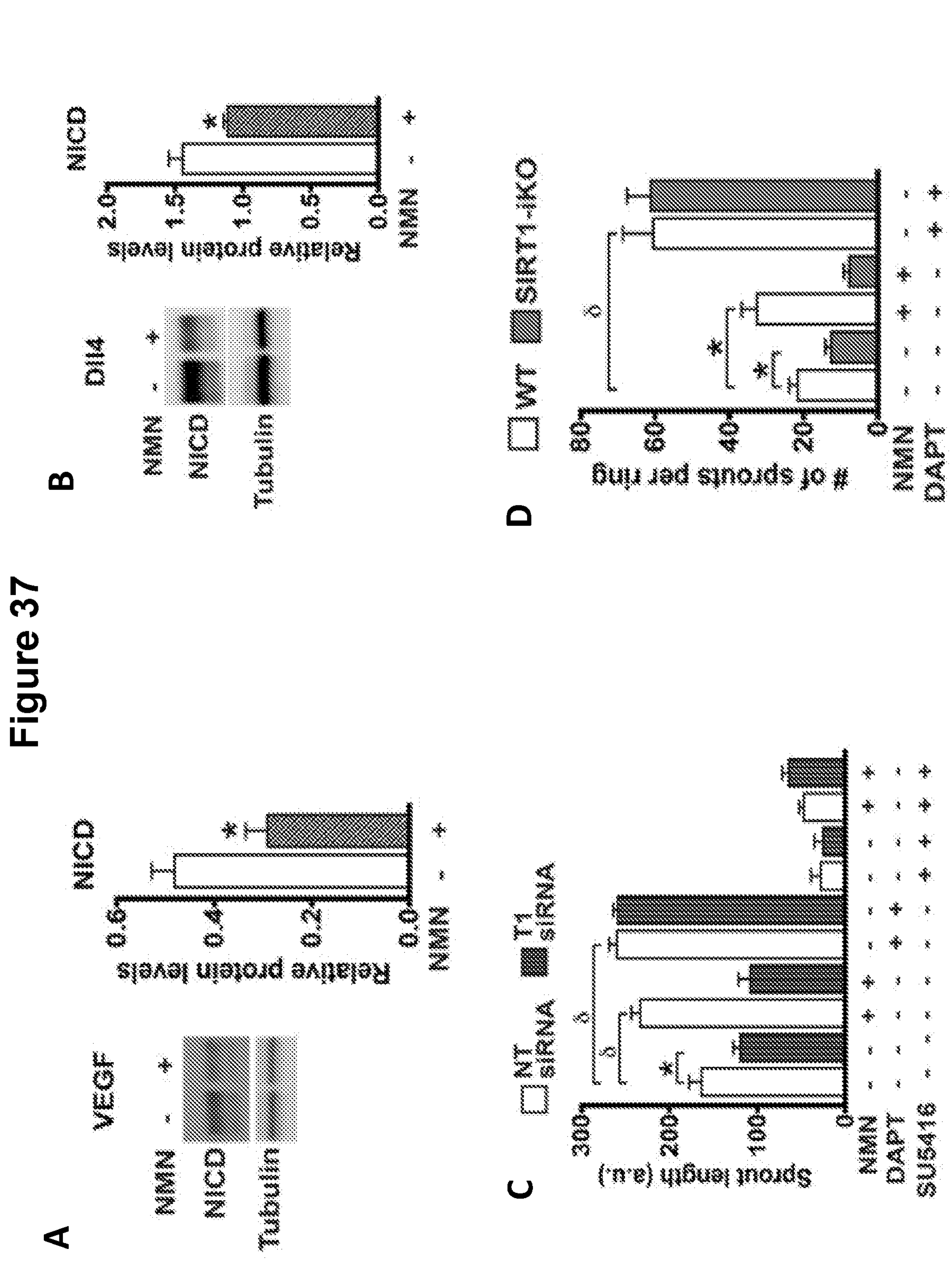

FIG. 36 is (A) graphs showing relative mRNA levels of Notch target genes HEY1, HES1 and NRARP and NOTCH1 from HAECs stimulated with VEGF (50 ng/mL)+/−NMN (0.5 mM) quantified by qPCR (n=4). (B) graphs showing relative mRNA levels of Notch target genes (HEY2 and NRARP) in Dll4-stimulated HAECs (n=3). Data are expressed as mean±SEM. *$p<0.05$, $p<0.005$, *$p<0.0005$, $^{\delta}p<0.00005$, two-way ANOVA with Bonferroni's Multiple.Comparisons Test FIG. 37 is (A) an image of Western blots showing the notch intracellular domain (NICD) protein levels in VEGF-stimulated HAECs+/−NMN (0.5 mM), and a graph showing the relative NICD levels on the right (n=3). (B) an image of Western blots showing the NICD protein levels in Dll4-stimulated HAECs+/−NMN (0.5 mM), and a graph showing relative NICD levels on the right (n=3). (C) a graph showing sprout length of spheroids from HAECs transduced with NT or T1 siRNAs and stimulated with VEGF (50 ng/mL)+/−NMN (0.5 mM), +/−DAPT (20 μM) and +/−SU5416 (10 μM) (n=8). DAPT (N—[N-(3,5-Difluorophenacetyl)-L-alanyl]-S-phenylglycine t-butyl ester): γ-secretase inhibitor, SU5416: VEGFR2 inhibitor. (D) a graph showing the number sprouts originating from aortic rings (n=13-15) in prepared from WT and SIRT1-iKO (18-month old) mice subjected to VEGF (30 ng/mL)-mediated sprouting for 7 days+/−NMN (0.5 mM) and +/−DAPT (20 μM). Data expressed as mean±SEM. *$p<0.05$, $p<0.005$, *$p<0.0005$, $^{\delta}p<0.00005$ by Student's t test (A), one-way (C and D) ANOVA with Bonferroni's Multiple Comparisons Test.

Figure 38:
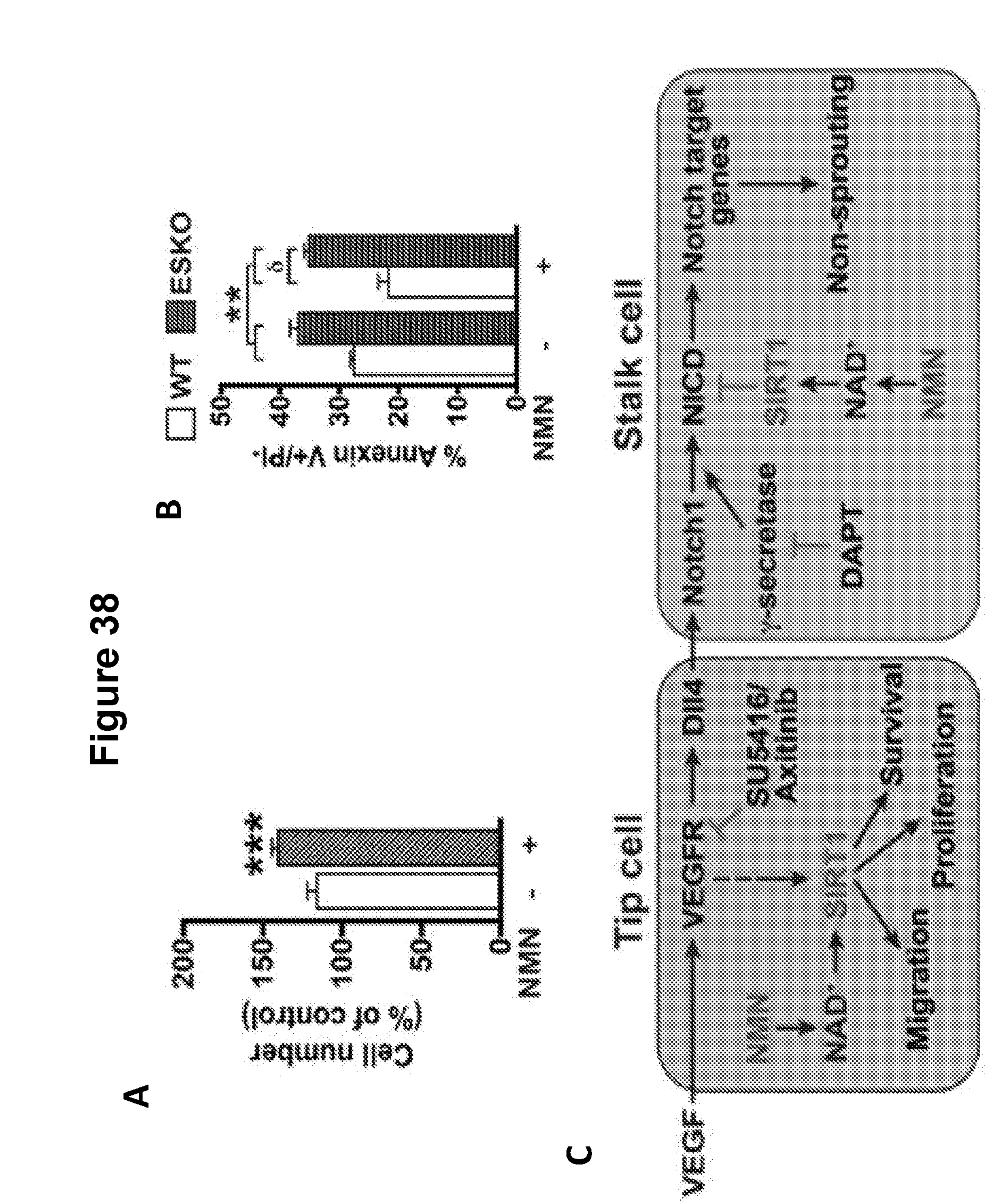

FIG. 38 is (A) a graph showing quantification of the relative cell number (n=12) of HUVECs incubated with PBS or NMN (0.5 mM) for 48 h in complete growth medium and cell number determined using flow cytometry. (B) a graph showing the number of apoptotic cells (Annexin V+/PI−) (n=12) when MLECs from WT and ESKO mice were serum-starved overnight, then assessed for apoptosis by Annexin V/PI staining and analyzed using flow cytometry. Data are expressed as mean±SEM. *$p<0.05$, $p<0.005$, *$p<0.0005$, $^{\delta}p<0.00005$ by Student's t test (A), or two-way (B) ANOVA with Bonferroni's Multiple Comparisons Tests. (C) a schematic diagram of a model of how SIRT1 promotes sprouting angiogenesis. VEGF stimulation during sprouting angiogenesis upregulates expression of Dll4 ligand in the tip cells, which in turn activates Notch signaling in the stalk cells. This interaction triggers proteolytic cleavage of Notch receptor by γ-secretase complex to release NICD from the cell membrane. NICD translocates to the nucleus and induces transcriptional gene activation. Activation of SIRT1 by NMN promotes migration, proliferation and survival in VEGF-stimulated ECs. In stalk cells NMN decreases the levels of NICD during VEGF/Dll4 stimulation and suppresses Notch target gene activation, thereby promoting sprouting.

Figure 39:
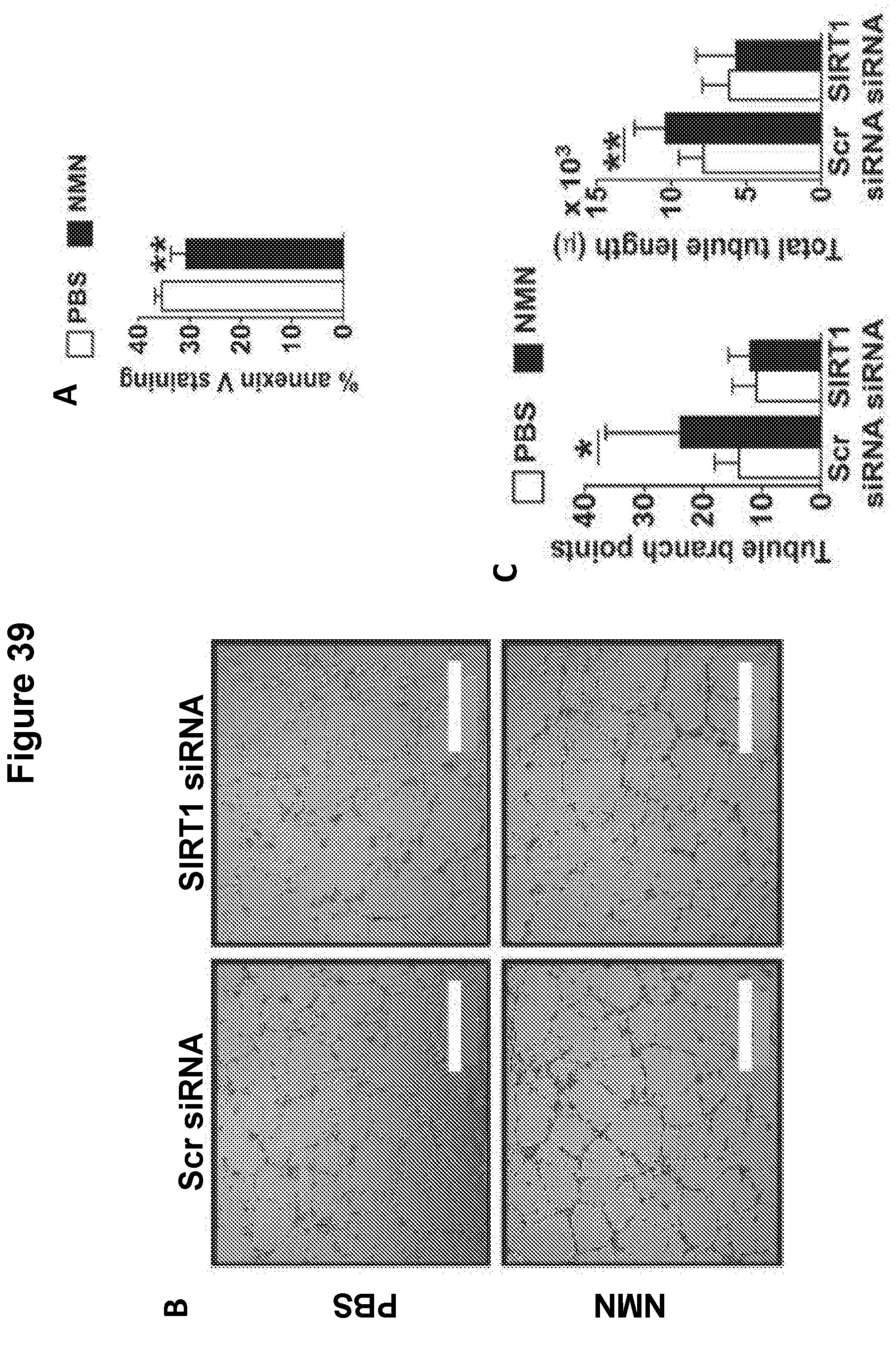

FIG. 39 is (A) a graph showing n annexin V staining in HUVECs pretreated with PBS or NMN (500 μM) for 6 h, followed by exposure to $H_2O_2$ (600 μM) for another 4 h. Annexin V staining was detected by flow cytometry (n=12). (B) representative bright field images (4× magnification) of tube networks formed from Scr or SIRT1 siRNA-transfected HUVECs exposed to $H_2O_2$ (150 μM) for 1 h and then subjected to VEGF-induced tube formation with PBS or NMN (500 μM) for 10 h. (white bar=500 μm) (C) graphs showing quantification of tube branch points, and total tube length per field of view from Scr or SIRT1 siRNA-transfected HUVECs exposed to $H_2O_2$ (150 μM) for 1 h and then subjected to VEGF-induced tube formation with PBS or NMN (500 μM) for 10 h (n=12). Data are expressed as mean±s. dev. *p<0.05, p<0.005, *p<0.005 and #p<0.00005 by Oneway ANOVA test.

Figure 40:
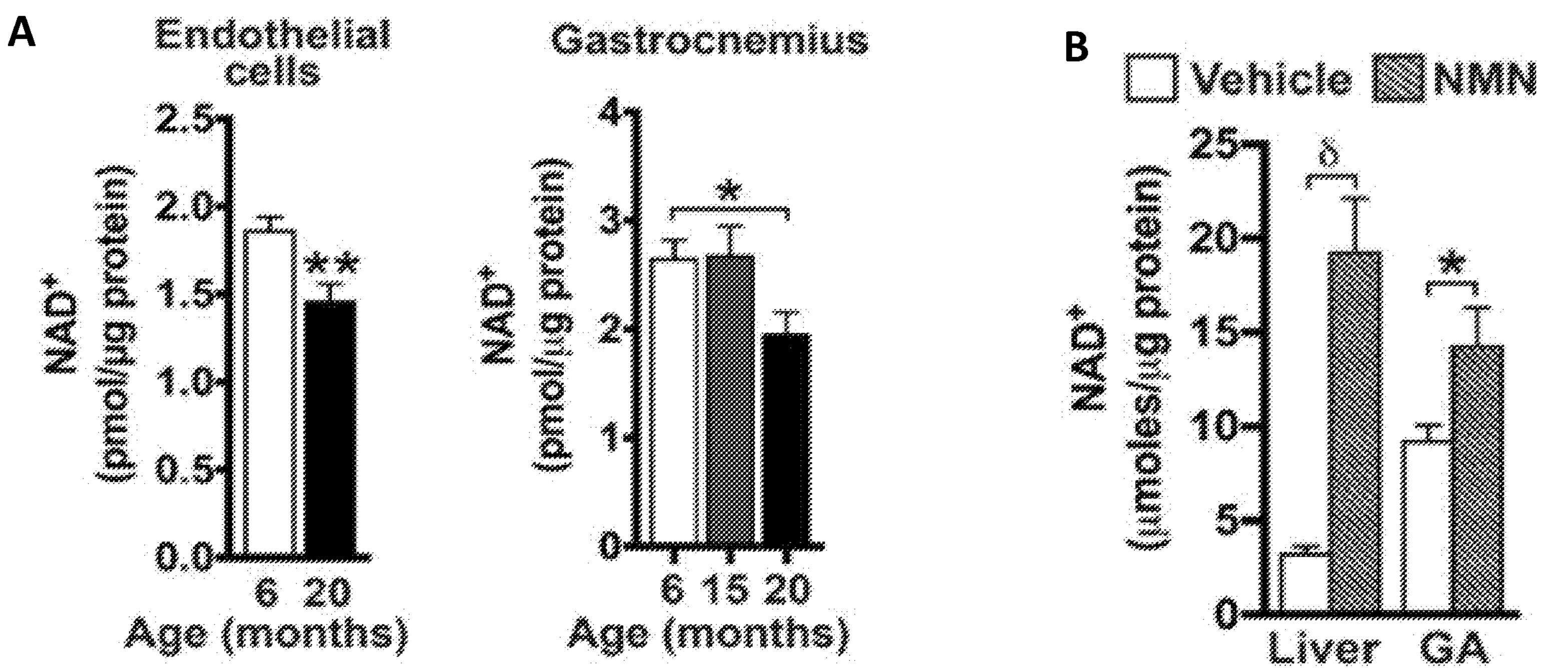

FIG. 40 is (A) graphs showing NAD+ levels in MLECs (n=6) and gastrocnemius muscles (n=10) isolated from 6, 15 (in the case of gastrocnemius) and 20-month old mice, normalized to total protein content. (B) a graph showing NAD+ levels in the liver and gastrocnemius muscle tissues from vehicle and NMN-treated mice (18-month old) normalized to the total protein content (n=12-14). Data are expressed as mean±s. dev. *p<0.05, p<0.005, *p<0.005 and #p<0.00005 by student's t test.

Figure 41:
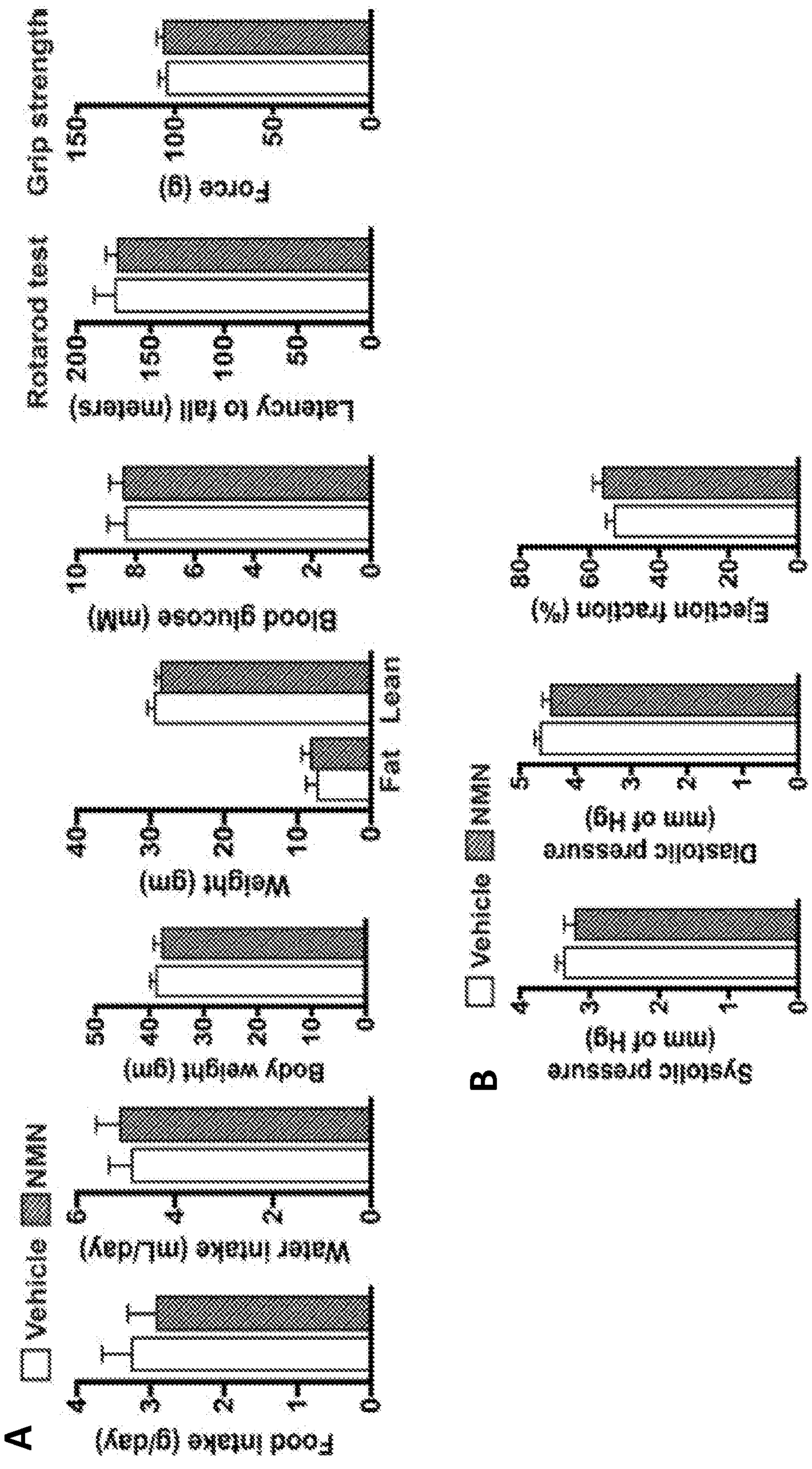

FIG. 41 is (A) graphs showing quantification of food intake, water consumption, body weights, lean mass, fat mass, fasting blood glucose, rotarod performance and grip strength of 20-month old vehicle and NMN-treated mice (n=10). (B) graphs showing cardiac function of 20-month old vehicle and NMN-treated mice measured using echocardiography (Vevo 2100). Quantifications of systolic and diastolic pressures, and ejection fraction are shown (n=10).

Figure 42:
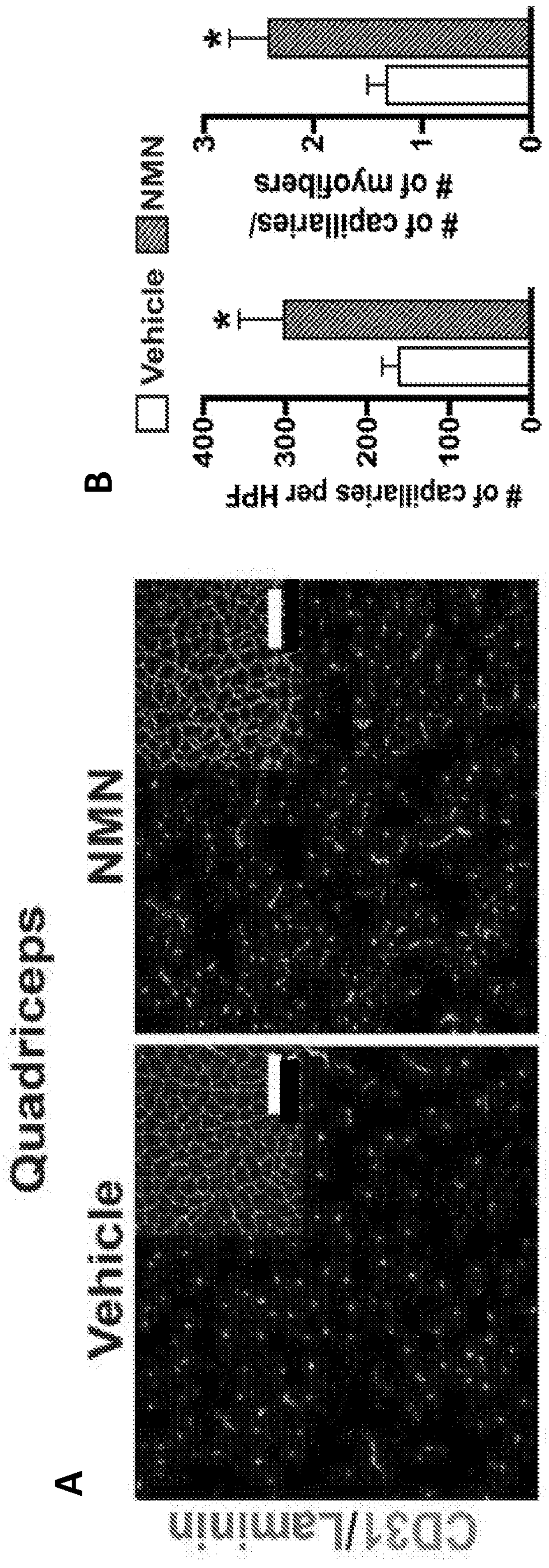
Figure 42:
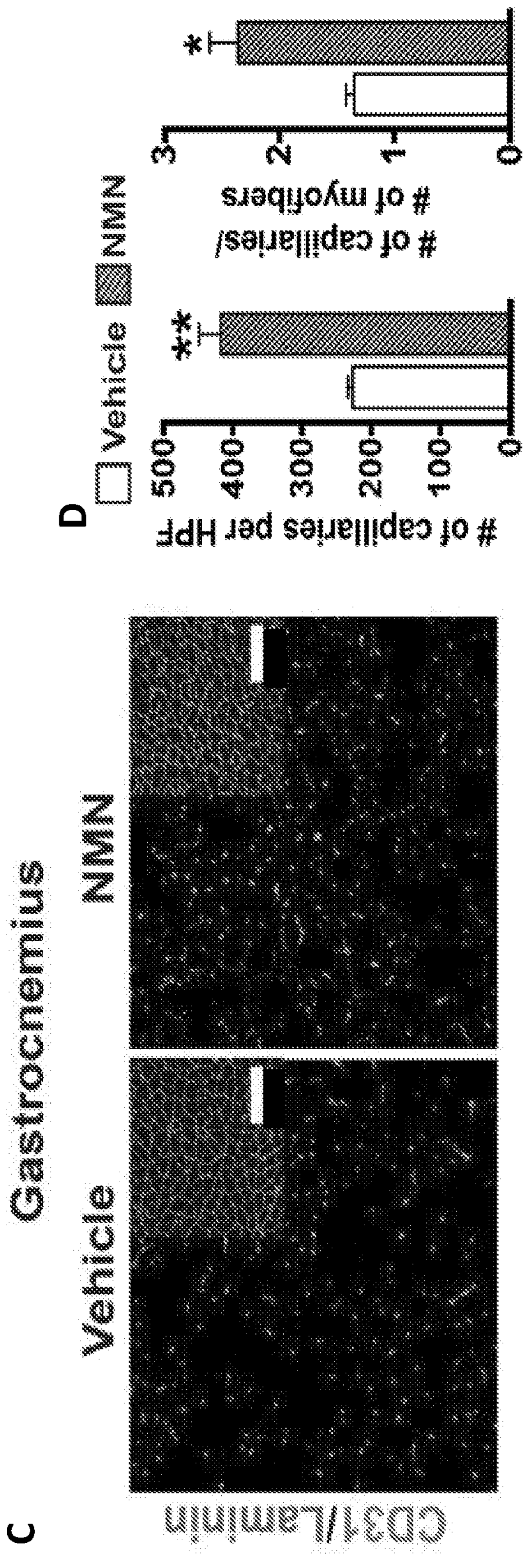

FIG. 42 is (A) representative images of capillaries (CD31) and stroma (laminin, inset) (20× magnification) in quadriceps muscle cross-sections from 20-month old vehicle and NMN (400 mg/kg/day)-treated mice. (white bar=200 μm). (B) is a graph showing number of capillaries per HPF, and number of capillaries/number of myofiber ratio per HPF (n=8), in quadriceps muscle cross-sections from 20-month old vehicle and NMN (400 mg/kg/day)-treated mice. (C) representative images of capillaries (CD31) and muscle stroma (laminin, inset) in gastrocnemius muscle cross-sections (20× magnification) from 20-month old vehicle and NMN-treated mice. (white bar=200 m) (D) graphs showing number of capillaries per HPF, and number of capillaries/number of myofiber ratio per HPF (n=8), in gastrocnemius muscle cross-sections from 20-month old vehicle and NMN (400 mg/kg/day)-treated mice. Data are expressed as mean±s. dev. *p<0.05, **p<0.005, by Student's t test.

Figure 43:
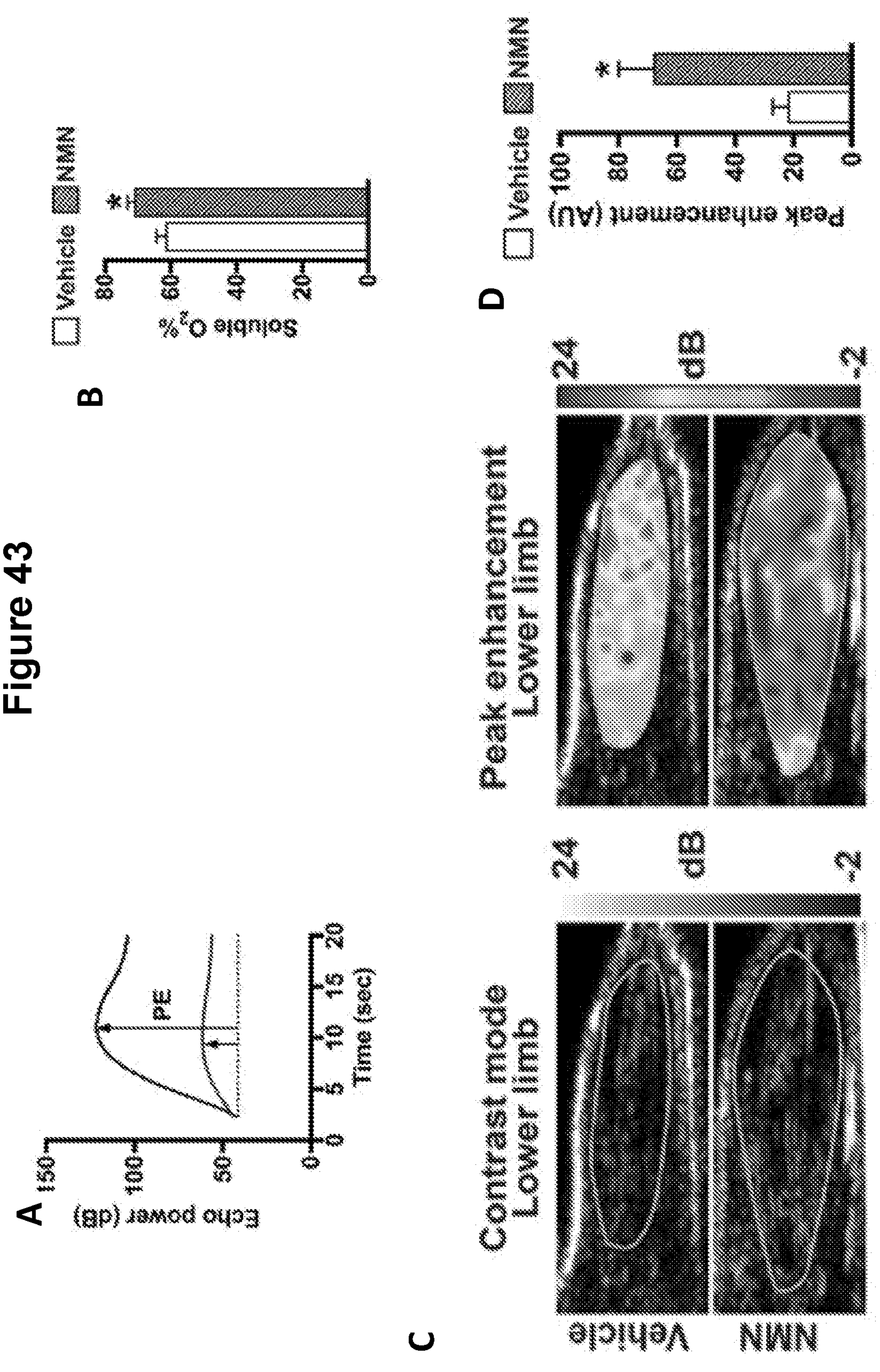

FIG. 43 is (A) a graph showing peak enhancement (PE) as measured using contrast-enhanced ultrasound. (B) a graph showing hindlimb soluble oxygen ($sO_2$) levels in the hindlimbs of vehicle and NMN-treated mice (20-month old) (n=13). (C) an image of representative contrast-mode and peak enhancement-mode ultrasound images of hindlimb skeletal muscle perfusion of 20-month old mice treated with or without NMN, measured using contrast-enhanced ultrasound (CEU) imaging. (D) a graph showing the average peak enhancement (PE), the maximum-minimum video intensity, an indicator of relative blood volume in the hindlimbs is shown (n=5). Data are expressed as mean±s. dev. *p<0.05 by Student's t test.

Figure 44:
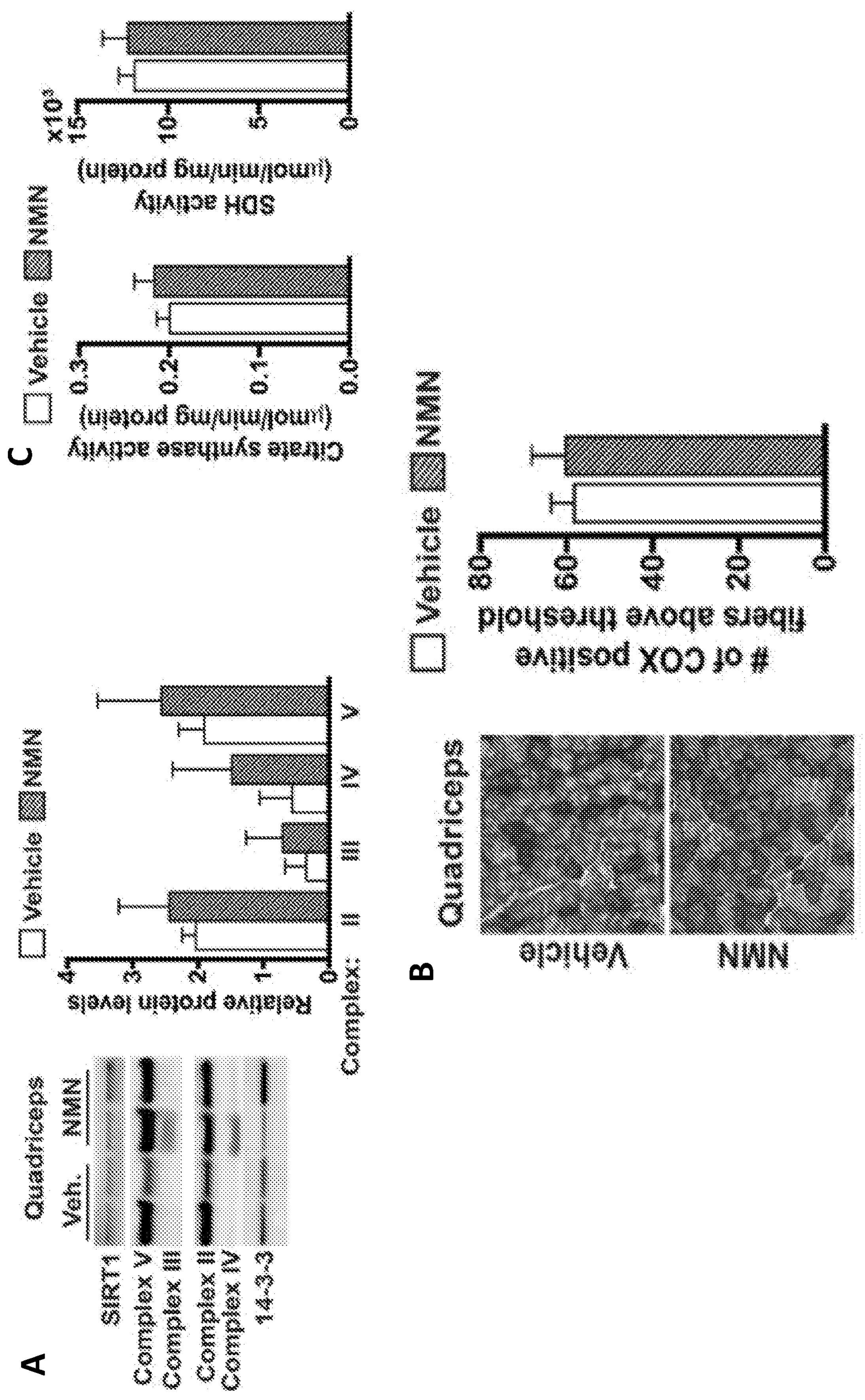

FIG. 44 is (A) an image of Western blots for SIRT1 and mitochondrial protein complexes II, III, IV and V in quadriceps tissue homogenates from 20-month old vehicle and NMN-treated mice (14-3-3 was used as loading control), and on the right, a graph of the relative quantifications of complexes II, III, IV and V are shown (n=4[). (B) representative COX staining images of quadriceps muscles from 20-month old vehicle and NMN-treated mice, and on the right, a graph showing quantification of number of COX positive fibers above a set threshold (n=4). (C) graphs showing mitochondrial capacity as assessed by determining citrate synthase and succinate dehydrogenase (SDH) activities in quadriceps tissue homogenates from 20-month old vehicle and NMN-treated mice (n=10).

Figure 45:
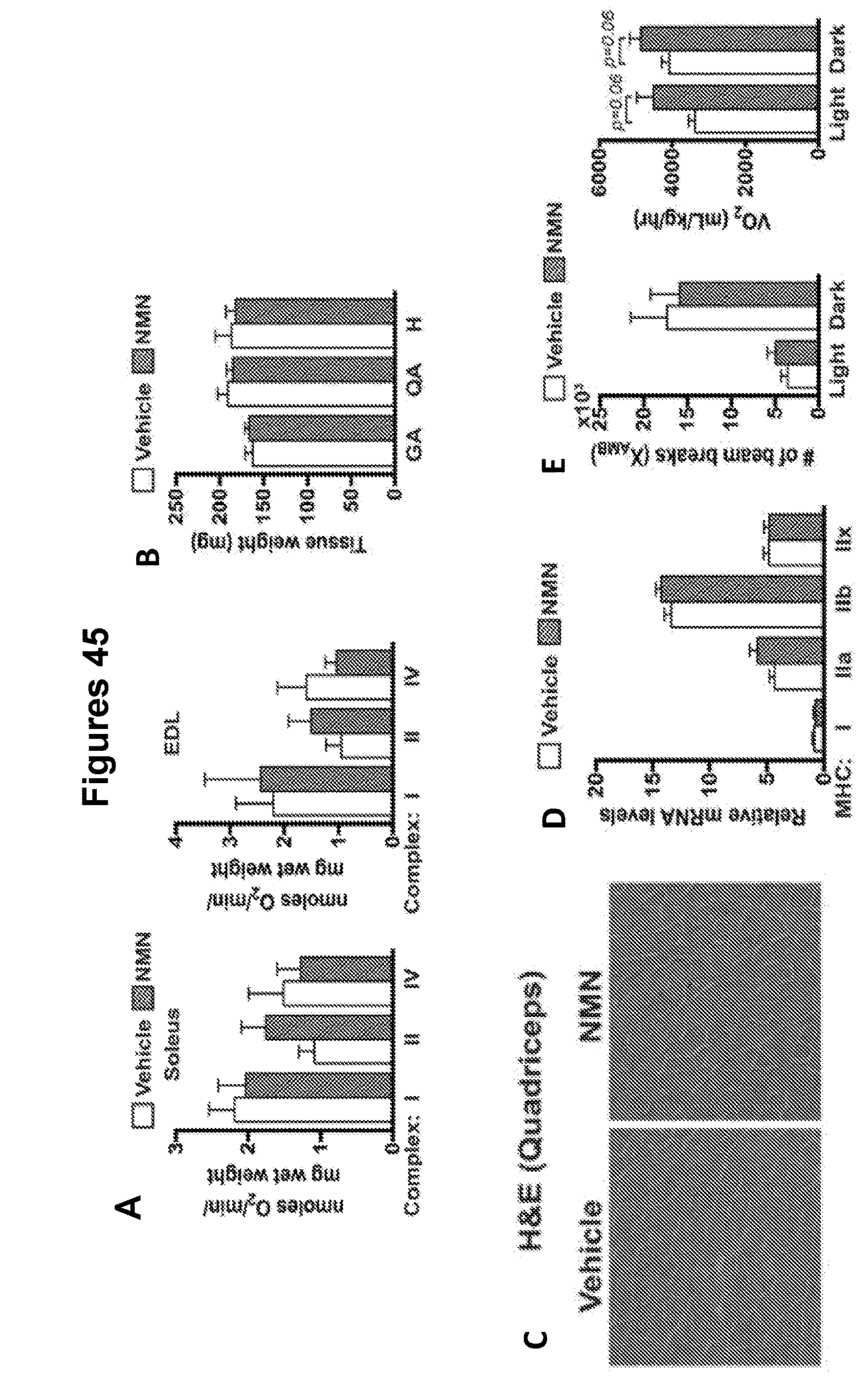

FIG. 45 is (A) graphs showing relative quantitations of oxygen consumption rates mediated through mitochondrial complexes I, II and IV in soleus and EDL permeabilised muscle fibers from 20-month old vehicle and NMN-treated mice were measured using a Clark electrode system (n=10). (B) a graph showing quantifications of gastrocnemius (GA), quadriceps (QA) and heart (H) tissue weights in 20-month old vehicle and NMN-treated mice (n=13). (C) representative H&E staining images of quadriceps muscles from 20-month old vehicle and NMN-treated mice. (D) a graph showing relative mRNA levels of myosin heavy chains I, IIA, IIB and IIX in gastrocnemius muscles from 20-month old vehicle and NMN-treated mice (n=13). (E) graphs showing locomotor activity (Xamb—successive beam breaks in the X-axis) and oxygen consumption rates (VO2) of 20-month old vehicle and NMN-treated mice measured using Oxymax-CLAMS system. Quantifications of Xamb and VO2 are presented (n=6). Data are expressed as mean±s. dev. p by Student's t test.

Figure 46:
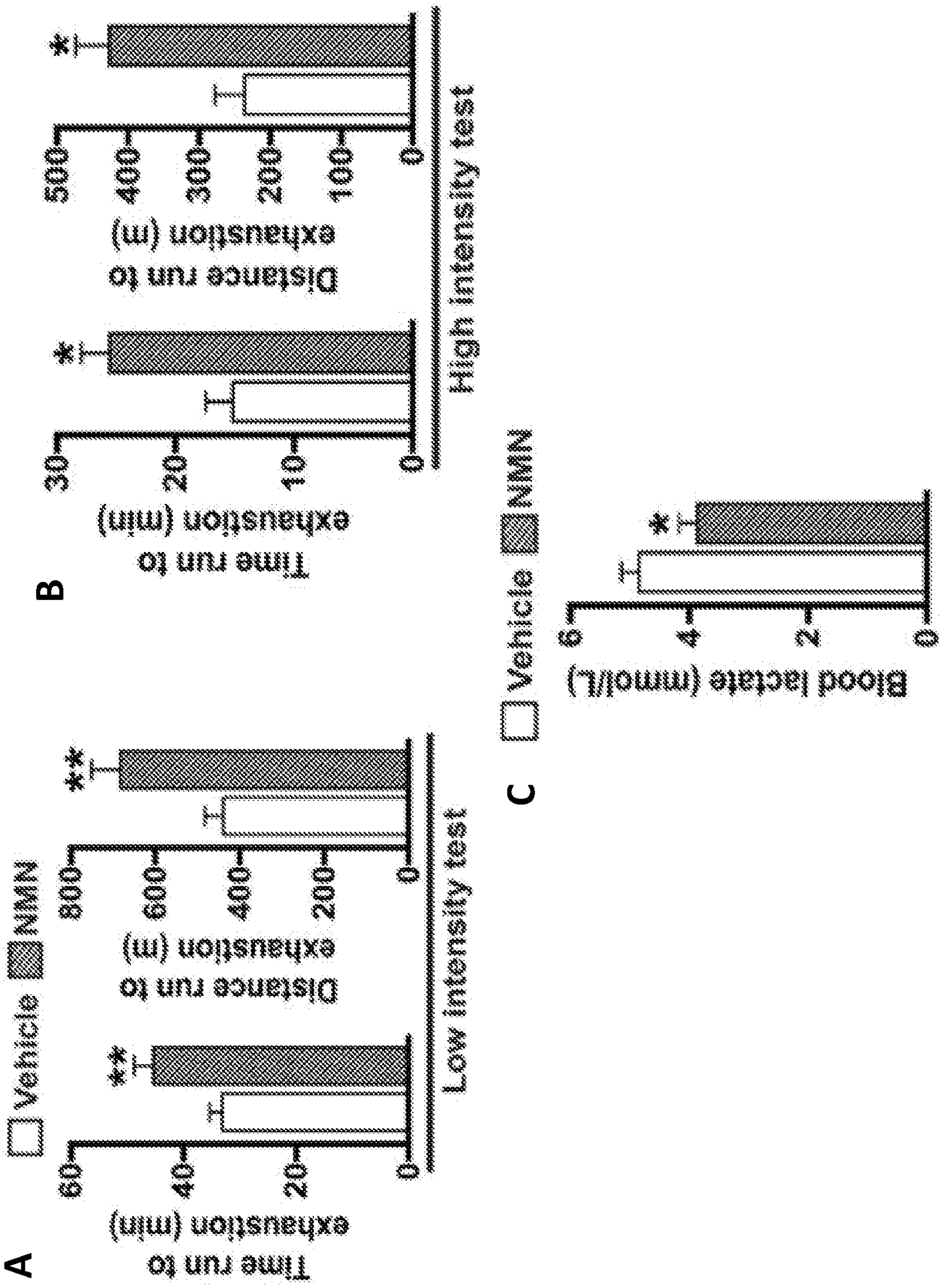

FIG. 46 is graphs showing time run until exhaustion, and distance run until exhaustion, by 20-month old vehicle and NMN-treated mice in (A) low and (B) high intensity treadmill exercise tests (n=13). (C) is a graph showing post-exercise blood lactate levels in 20-month old vehicle and NMN-treated mice (n=13). Data are expressed as mean±s. dev. *p<0.05, **p<0.005, by Student's t test.

Figure 47:
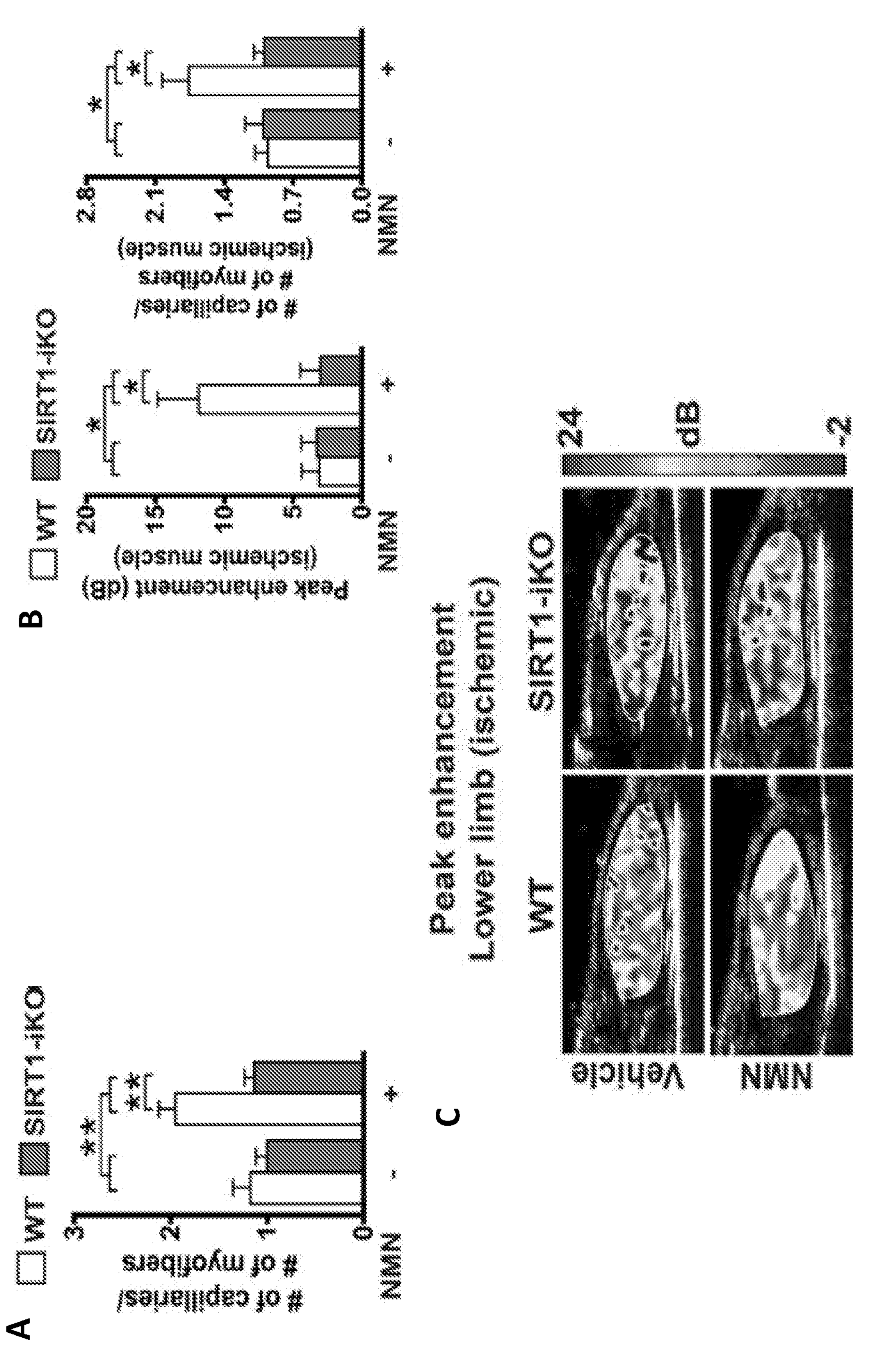

FIG. 47 is (A) a graph showing quantification of number of capillaries/number of myofiber ratio per HPF (20× magnification) (n=5) in in gastrocnemius muscle cross-sections of tamoxifen-fed SIRT1-iKO and WT (20-month old) mice on standard chow diet+/−NMN (400 mg/kg) for two months as determined by immunostaining. NMN treatment increased capillaries in WT mice but not in SIRT1-iKO mice. (B) graphs showing quantification of PE values and number of capillaries/number of myofiber ratio per HPF (20× magnification) (n=5) for ischemic limb in ischemic gastrocnemius muscle cross-sections (n=5) of tamoxifen-fed SIRT1-iKO and WT (8-month old) mice subjected to hindlimb ischemia+/−NMN (500 mg/kg/day) as determined, after 20 days, by CEU imaging and by immunostaining in gastrocnemius muscle cross-sections. (C) representative peak enhancement-mode ultrasound images of the ischemic hindlimbs of vehicle and NMN-treated mouse, measured 20 days after inducing hindlimb ischemia. Data expressed as mean±SEM. *p<0.05, **p<0.005, two-way ANOVA with Bonferroni's Multiple Comparisons Test.

Figure 48:
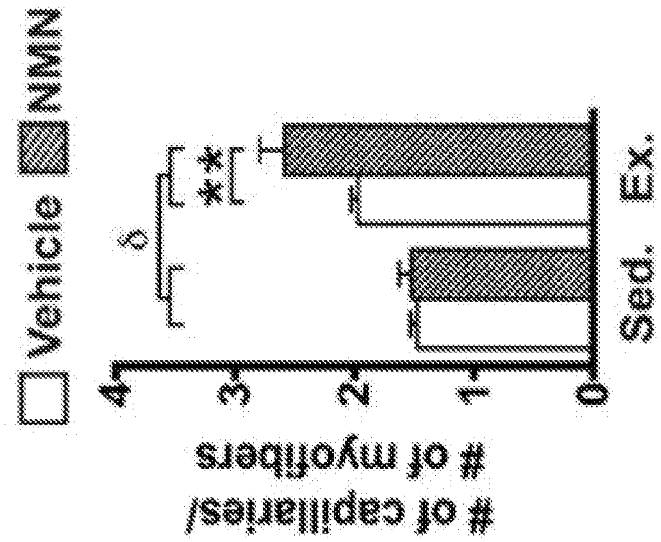

FIG. 48 is (A) is a graph showing capillary density in the quadriceps muscle cross-sections from 10-month old vehicle and NMN treated sedentary or exercised mice (n=5). WT C57BL/6J (10-month old) mice kept sedentary or trained for four weeks of treadmill exercise training (15 m/min for 30 min @ 5° inclination)+/−NMN (400 mg/kg/day). Capillaries and stroma in quadriceps muscle were immunostained with CD31 and laminin antibodies and capillary/myofiber ratio per HPF determined (n=5). Data expressed as mean±SEM. $^{\delta}$p<0.00005, **p<0.005, by two-way ANOVA with Bonferroni's Multiple Comparisons Test.

Figure 49:
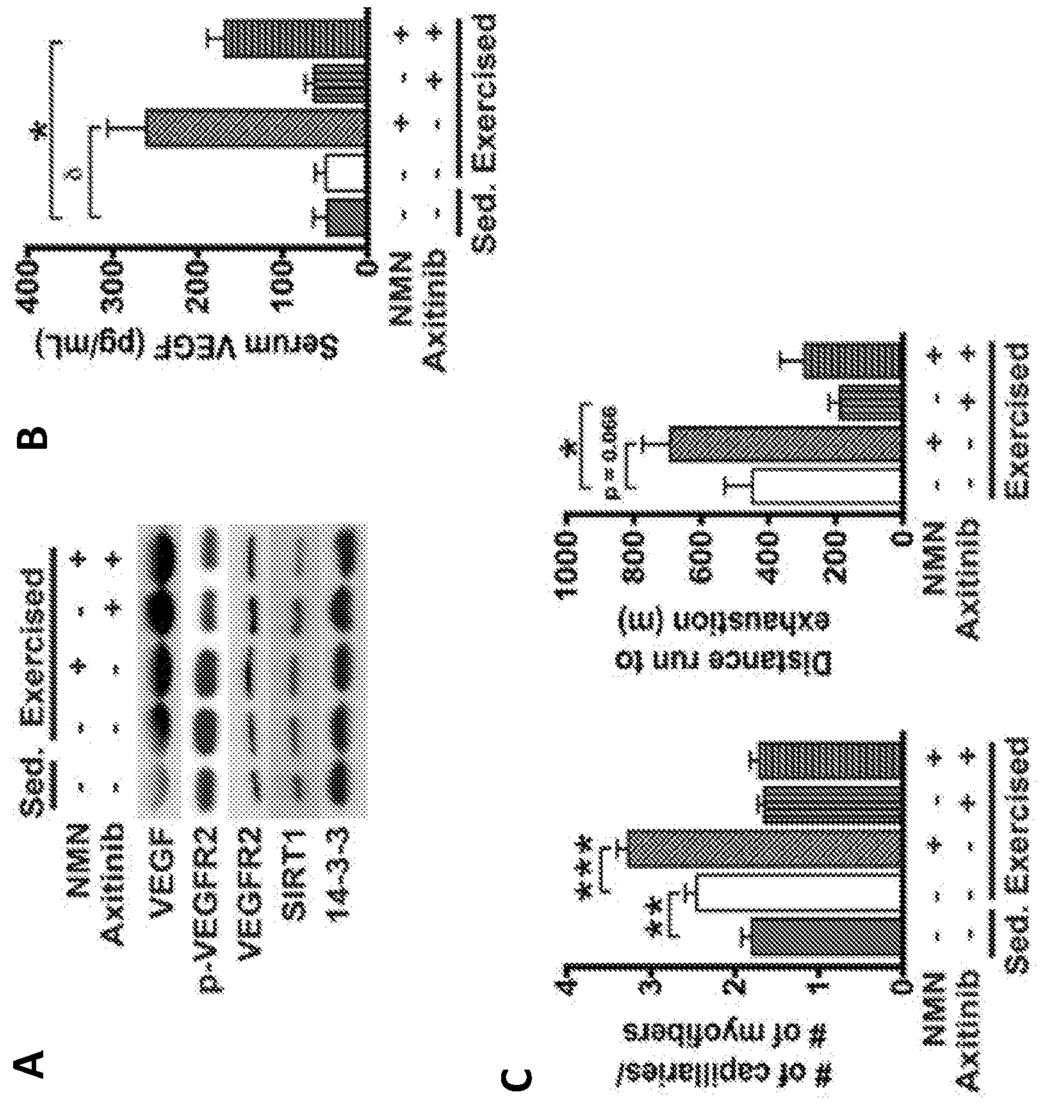

FIG. 49 is (A) an image of Western blots for VEGF, VEGFR1, phosphorylated VEGFR1 and SIRT1 in quadriceps tissue homogenates from WT C57BL/6J mice (5-month old) that were kept sedentary or trained for four weeks of treadmill exercise training+/−NMN (400 mg/kg/day) and +/−axitinib (30 mg/kg/day). 14-3-3 was used as loading control. (B) a graph showing quantification of VEGF protein levels in serum collected from the above mice referred to in (A) (n=5). (C) graphs showing the number of capillaries/number of myofiber ratio per HPF in quadriceps muscle of FIG. 6(J) WT C57BL/6J mice (5-month old) kept sedentary or trained for four weeks of treadmill exercise training+/−NMN (400 mg/kg/day) and +/−axitinib (30 mg/kg/day) (n=5). At the end of the training exercised mice were assessed for the exhaustive endurance in a high intensity treadmill test. The average distance run until exhaustion is shown on the right (n=5). Data are expressed as mean±SEM. *p<0.05, p<0.005, *p<0.0005, $^{\delta}$p<0.00005 by one-way ANOVA with Bonferroni's Multiple Comparisons Test.

Figure 50:
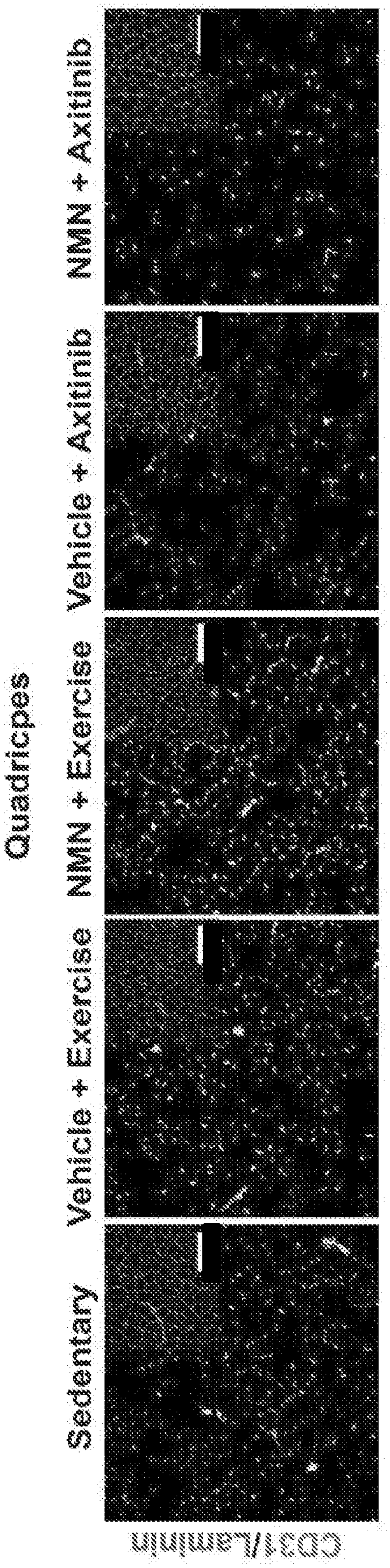

FIG. 50 is (A) representative images of capillaries (CD31) and muscle stroma (laminin, inset) in quadriceps muscle cross-sections (20× magnification) from C57BL/6J mice (5-month old) that were kept sedentary or exercise trained+/−NMN and +/−axitinib. (white bar=200 μm).

Figure 51:
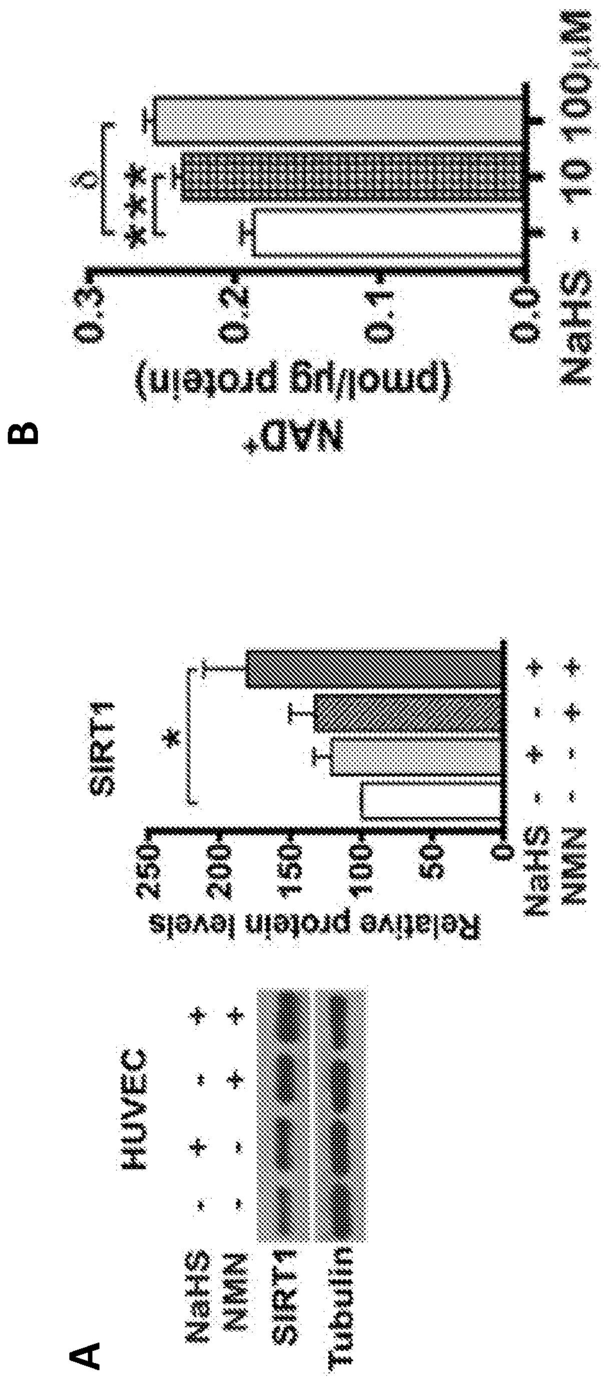

FIG. 51 is (A) Western blots (left) showing SIRT1 protein levels in HUVECs treated with NaHS (0.1 mM) and/or NMN (0.5 mM), and (right) relative SIRT1 protein levels in HUVECs treated with NaHS (0.1 mM) and/or NMN (0.5 mM) (n=4). (B) a graph showing relative NAD+ levels in HUVECs treated with increasing doses of NaHS for 24 hrs (n=6). Data are expressed as mean±SEM. *p<0.05, p<0.005, *p<0.0005, $^{\delta}$p<0.00005 by one-way ANOVA with Bonferroni's Multiple Comparisons Test.

Figure 52:
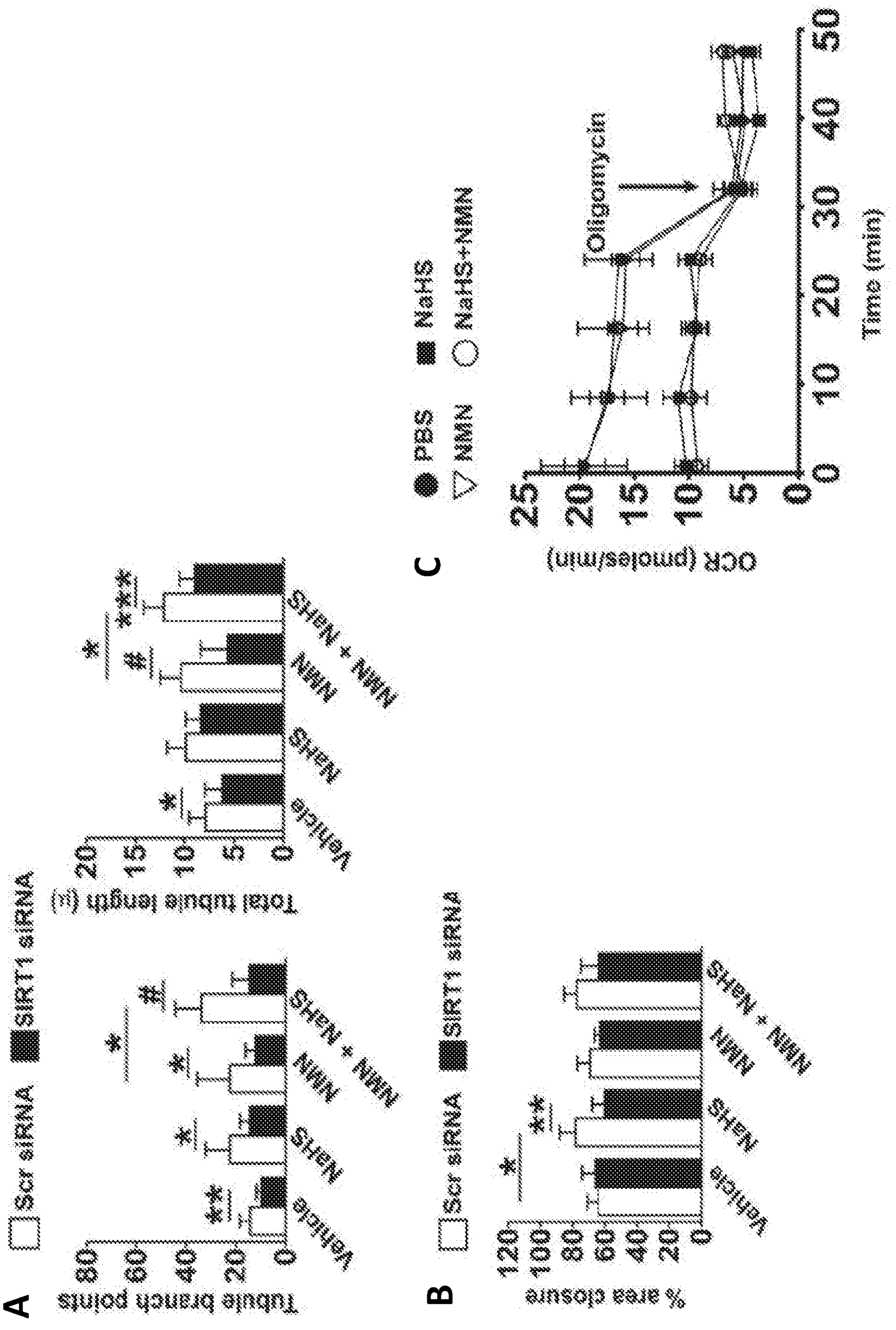

FIG. 52 is (A) graphs showing Scr or SIRT1 siRNA-transduced HUVECs treated with $H_2O_2$ (150 μM) for 1 h and then subjected to VEGF-mediated tube formation with vehicle, NaHS (100 μM), NMN (500 μM) or NaHS+NMN combination for 10 h. Quantification of tube branch points and total tube length per field of view are shown (n=12). (B) a graph showing cell migration when confluent monolayers of Scr or SIRT1 siRNA-transduced HUVECs were exposed to $H_2O_2$ (150 μM) for 1 h, a scratch made and cells allowed to migrate with vehicle, NaHS (100 μM) and/or NMN (500 μM) for 6 h. Bars represent the percentage of closed gaps (n=6). (C) a graph showing basal oxygen consumption rate (OCR) of HUVECs treated with vehicle, NaHS (100 μM), NMN (500 μM) or NMN+NaHS combination as measured using XF96 seahorse analyzer (n=6). Oligomycin (1 μM) was added to measure the OCR while inhibiting Complex V and blocking ATP synthesis.

Figure 53:
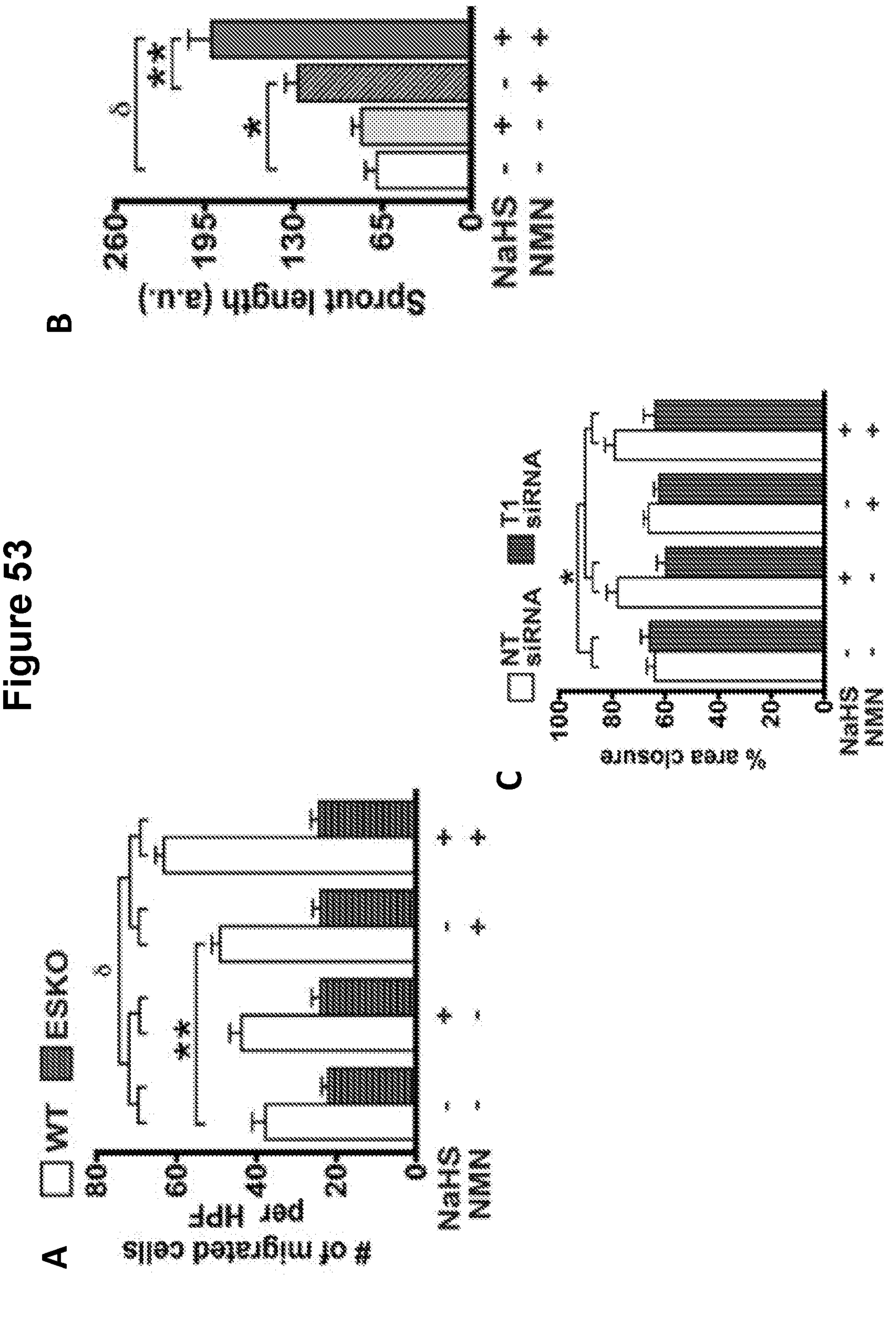

FIG. 53 is (A) a graph showing the number of migrated cells per field of view (n=15) in a transwell migration assay in which MLECs isolated from WT and ESKO mice was stimulated with C2C12 CM, +/−NaHS (0.1 mM) and +/−NMN (0.5 mM) for 12 hours. (B) a graph showing quantification of sprout length of spheroids from HUVECs stimulated with VEGF (50 ng/mL), +/−NaHS (0.1 mM) and +/−NMN (0.5 mM) (n=7). (C) a graph showing percentage of area closure in a scratch assay in which HUVECs were transduced with NT or T1 siRNAs, grown to confluent monolayer and a scratch made using a 200 μL pipette tip. ECs were allowed to migrate with +/−NaHS (0.1 mM) and +/−NMN (0.5 mM) for 6 h. Bars represent the percentage of closed gaps (n=6). Data are expressed as mean±SEM. *p<0.05, p<0.005, *p<0.0005, $^{\delta}$p<0.00005 by one-way (B and C) or two-way (A) ANOVA with Bonferroni's Multiple Comparisons Test.

Figure 54:
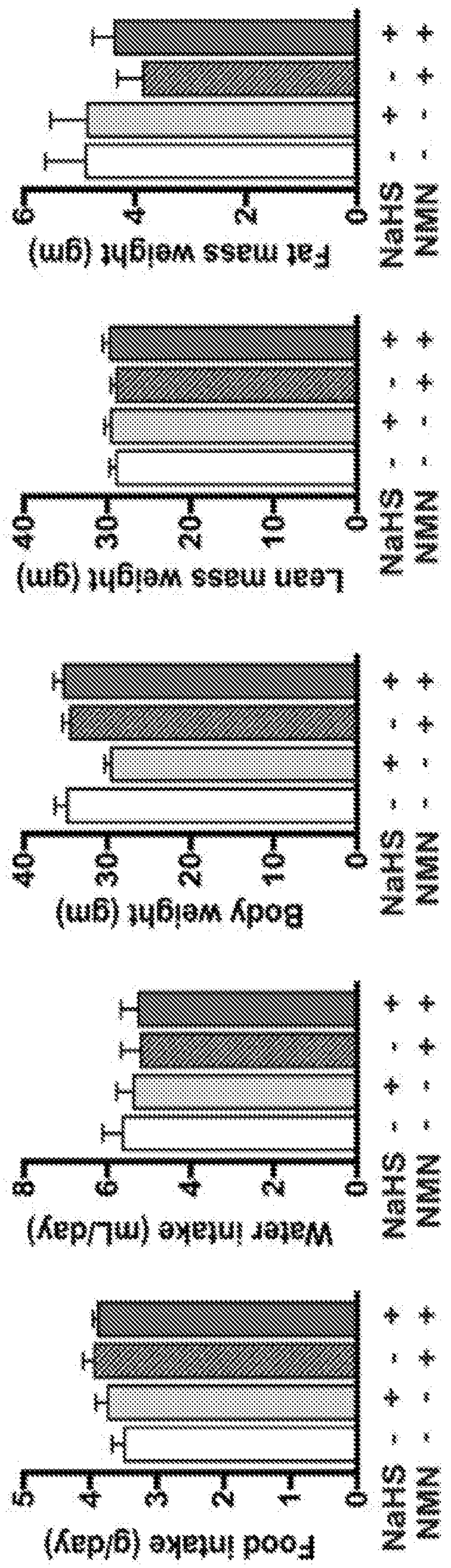

FIG. 54 are graphs showing quantifications of food intake, water consumption, body weights, lean mass and fat mass of 32-month old vehicle, NaHS, NMN and NMN+NaHS-treated mice (n=7).

Figure 55:
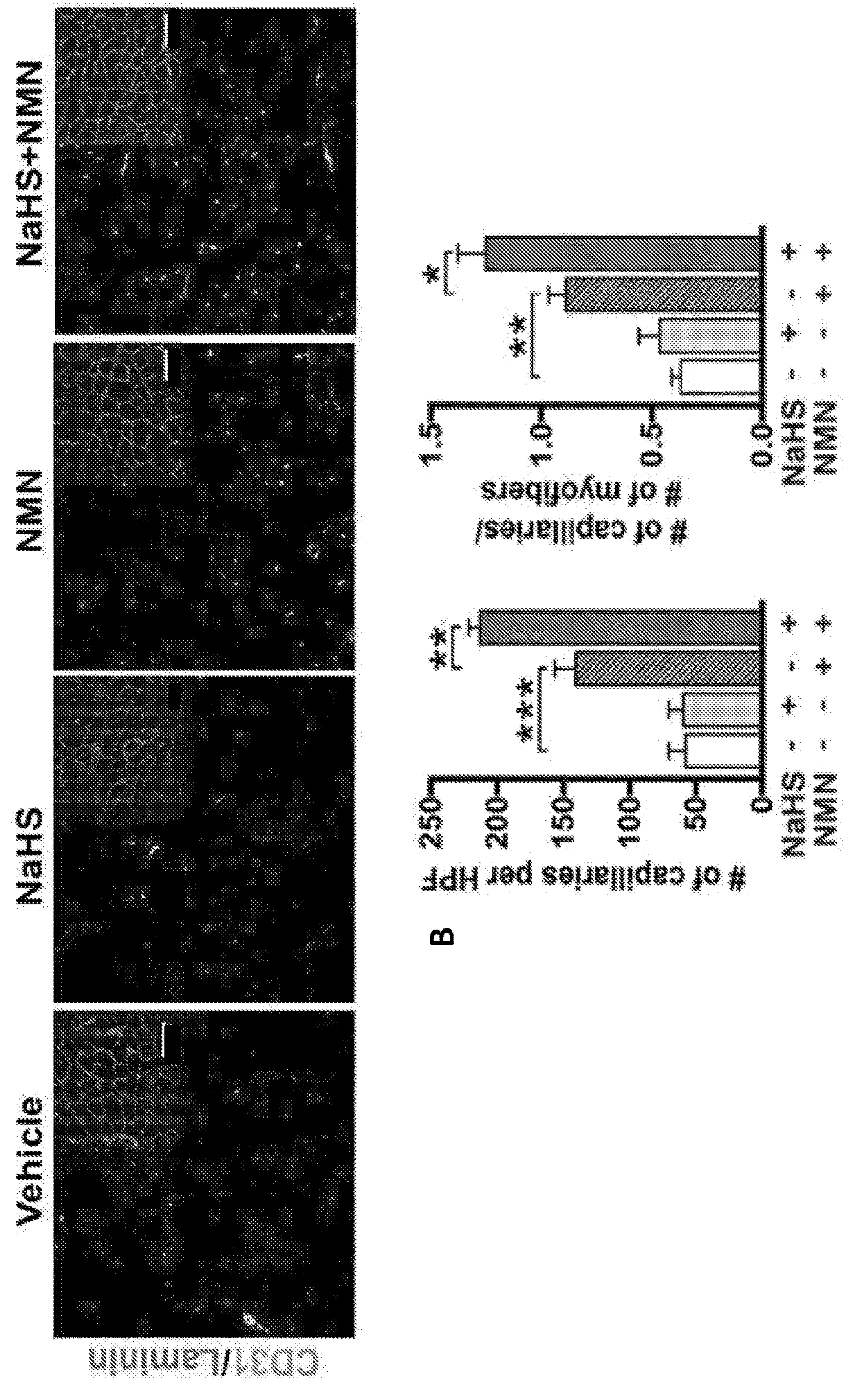

FIG. 55 is (A) representative images of capillaries (CD31) and muscle stroma (laminin, inset) (20× magnification) in quadriceps muscle cross-sections from 32-month old mice treated with +/−NaHS (20 mg/kg/day) and +/−NMN (400 mg/kg/day) for four weeks. (white bar=100 μm) (B) graphs showing the number of capillaries per HPF, and number of capillaries/number of myofiber ratio per HPF, in quadriceps referred to in (A) (n=7). Data are expressed as mean±SEM. *p<0.05, p<0.005, *p<0.0005, $^{\delta}$p<0.00005 by one-way ANOVA with Bonferroni's Multiple Comparisons Test.

Figure 56:
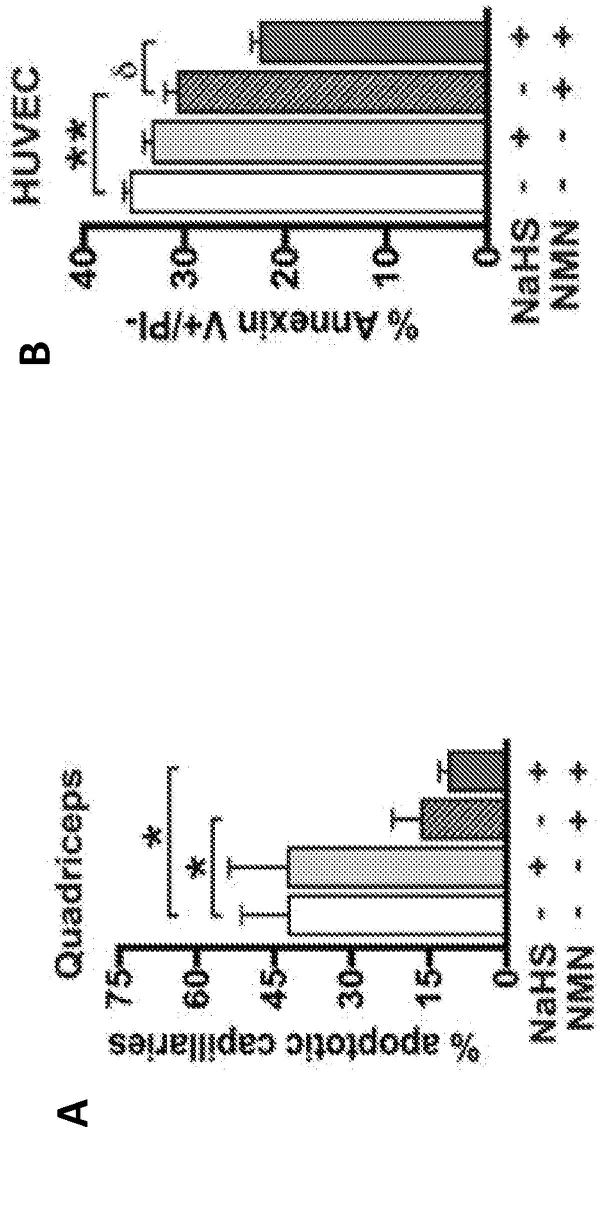

FIG. 56 is (A) a graph showing percentage apoptosis in capillaries in quadriceps muscle cross-sections from 32-month old mice treated with +/−NaHS and +/−NMN analyzed by TUNEL and CD31 immunostaining (n=5). (B) a graph showing percent apoptotic cells (annexin V+/PI−) in HUVECs pretreated with vehicle, NaHS (0.1 mM) and/or NMN (0.5 mM) for 6 hrs, followed by exposure to $H_2O_2$ (600 μM) for another 4 hrs. Apoptotic cells were detected by Annexin V and PI staining and analyzed using flow cytometry (n=12). Data are expressed as mean±SEM. *p<0.05, p<0.005, *p<0.0005, $^{\delta}$p<0.00005 by one-way ANOVA with Bonferroni's Multiple Comparisons Test.

Figure 57:
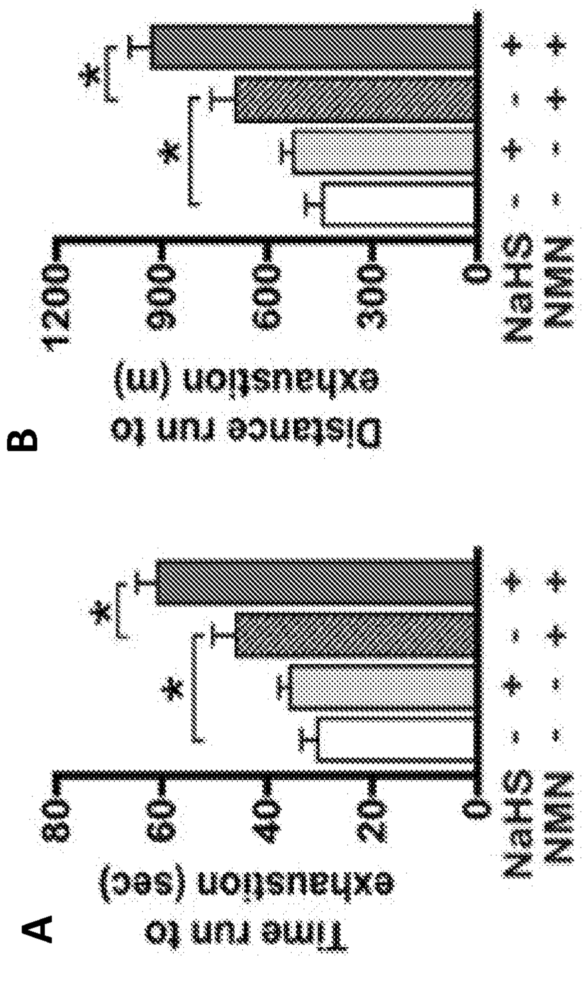

FIG. 57 are graphs showing (A) time spent and (B) distance run until exhaustion, by 31-month old vehicle, NaHS, NMN and NMN+NaHS-treated mice in a low intensity treadmill exercise test (n=7, *p<0.05 and #p<0.00005 versus vehicle). Data are expressed as mean±SEM. *p<0.05 by one-way ANOVA with Bonferroni's Multiple Comparisons Test.

Figure 58:
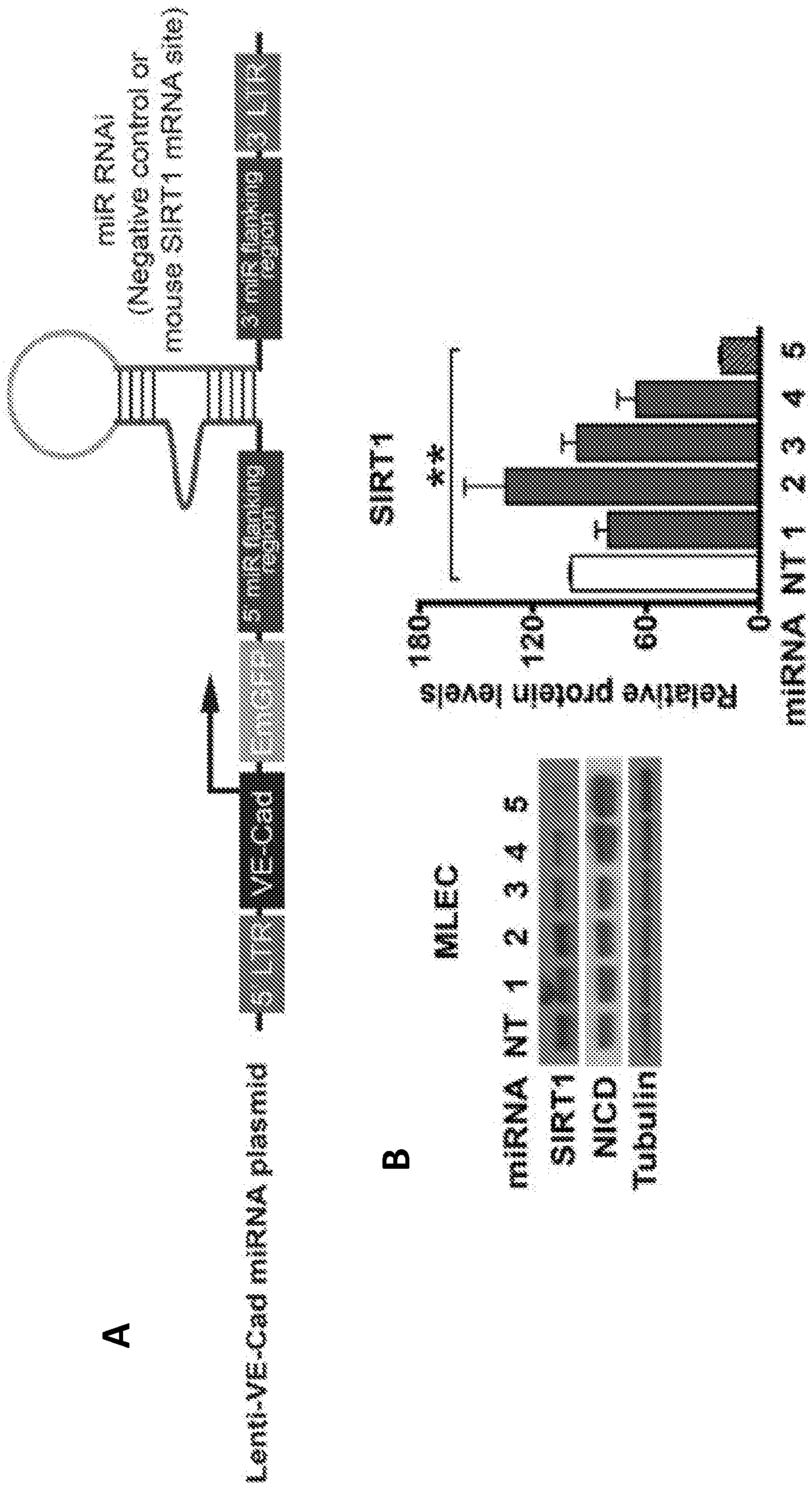

FIG. 58 is (A) a schematic diagram of a lentiviral construct based on FUW backbone, in which the EGFP transgene and SIRT1 miRNA are expressed from VE-cadherin promoter to target ECs only. (B) Western blots (left) of SIRT1 and NICD protein levels in WT MLECs transduced with lentiviruses expressing non-targeting (NT) or SIRT1 miRNAs (miRNA #1-5) under the control of the VE-cadherin promoter. A graph of relative SIRT1 protein levels of transduced MLECs is shown on the right (n=3). Transduction of SIRT1 miRNA #5 expressing lentivirus resulted in knockdown of SIRT1 by 80 with concomitant increase in NICD protein levels in the MLECs. Data are expressed as mean±SEM. **p<0.005 by Student's t Test.

Figure 59:
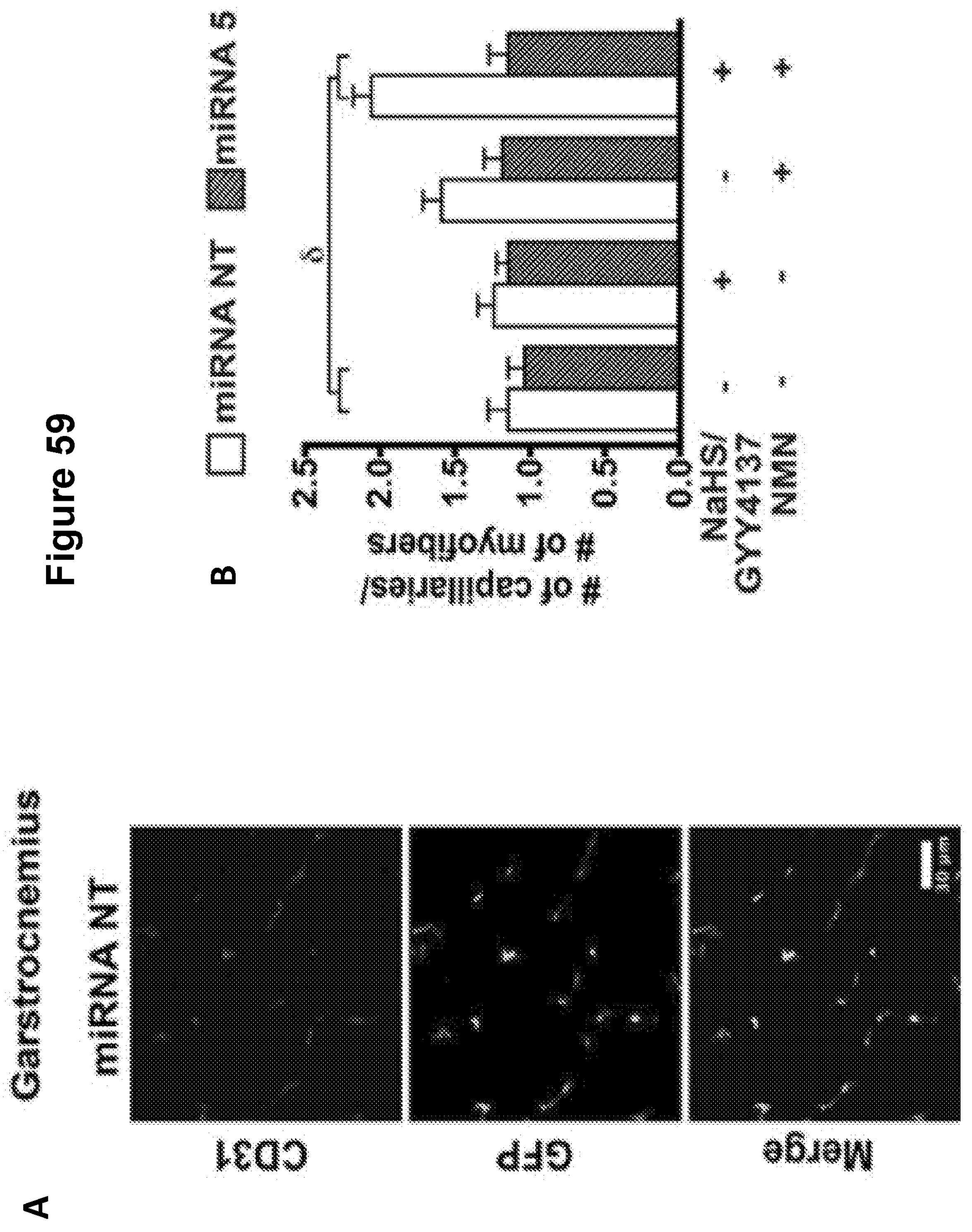

FIG. 59 is (A) representative image (40× magnification) showing distribution and EC-specificity of lentiviral delivery. WT C57BL/6J mice (20-month old) were administered lentiviral particles, which transduced EGFP and NT miRNA under the control of VE-cadherin promoter via retro-orbital injection. After 10 days, gastrocnemius cross-sections were immunostained for EGFP and CD31. (white bar=30 μm) (B) a graph showing number of capillaries/number of myofibers ratio in the gastrocnemius muscle cross-sections per HPF (40× magnification) (n=6) in WT C57BL/6J mice (20-month old) administered lentiviral particles transducing NT or SIRT1 #5 miRNA NT or miRNA 5 and treated with +/−NaHS (20 mg/kg/day), +/−GYY4137 (20 mg/kg/day) and +/−NMN (400 mg/kg/day) for four weeks, followed by analysis of muscle capillaries by immunostaining for CD31 (capillaries) and laminin (muscle stroma). Data expressed as mean±SEM. *p<0.05, p<0.005, *p<0.0005, $^{\delta}p<0.00005$ by two-way ANOVA with Bonferroni's Multiple Comparisons Test.

DETAILED DESCRIPTION

The present disclosure relates to a method of increasing vascular density and/or blood flow in tissue of a subject. The method comprises administering to the subject an effective amount of an agent which elevates SIRT1 activity or SIRT1 expression in endothelial cells of the tissue of the subject.

Sirtuin 1 (SIRT1) is a member of the sirtuin family of $NAD^+$-dependent deacylases that mediate the health benefits of dietary restriction.

As described in the Examples, the inventors have found that aged mice carrying a deletion of SIRT1 have reduced vascular density in skeletal muscle, and have reduced exercise capacity, compared to aged mice carrying wild-type SIRT1. The inventors have found that over-expression of SIRT1 in endothelial cells of aged mice from an exogenously supplied transgene results in increased vascular density in skeletal muscle tissue of the mice and increased exercise capacity of the mice compared to aged mice not expressing the transgene. The inventors have found that by administering an agent which increases SIRT1 activity and/or expression in endothelial cells, vascular density and exercise capacity can be increased.

The inventors have further found that $NAD^+$ levels decline with old age, and that restoration or elevation of $NAD^+$ levels through treatment with $NAD^+$ agonists during old age results in increased vascular density, increased muscle perfusion, and improved exercise capacity.

As used herein, "vascular density" is the number of blood vessels, typically capillaries, per portion of tissue. The portion of tissue may be, for example, a volume of tissue or area of tissue, such as a cross-sectional area of tissue. In some embodiments in which the tissue is muscle, vascular density may be expressed as the number of blood vessels, typically capillaries, per myofiber, or per cross-sectional area. The vascular density in muscle tissue may be calculated, for example, by determining the number of capillaries per high power field in a cross-section of muscle tissue. The area can be calculated based on the area viewed, and the density can be expressed as the number of capillaries per square micrometre. In one form, the capillary density in muscle may be expressed as a capillary per myofiber ratio. The capillary per myofiber ration may be calculated, for example, as the number of capillaries divided by the number of myofibers, per viewing field, typically per high power field, in cross-sections of muscle tissue.

In one aspect, the present invention provides a method of increasing vascular density in tissue of a subject, the method comprising administering to the subject an effective amount of an agent which elevates SIRT1 activity or SIRT1 expression in endothelial cells of the subject. The method increases vascular density in tissue of the subject, that is, vascular density in tissue of the subject is increased relative to the vascular density of the tissue prior to administration of the agent.

In one embodiment, the increase in vascular density is an increase in microvascular density. Typically, the increase in microvascular density is an increase in capillary density.

Another aspect provides a method of increasing blood flow in tissue of a subject, the method comprising administering to the subject an effective amount of an agent which elevates SIRT1 activity or SIRT1 expression in endothelial cells of the subject. The method increases blood flow in tissue of the subject, that is, blood flow in tissue of the subject is increased relative to the blood flow in the tissue prior to administration of the agent.

Another aspect provides a method of increasing vascular density and blood flow in tissue of a subject, the method comprising administering to the subject an effective amount of an agent which elevates SIRT1 activity or SIRT1 expression in endothelial cells of the subject.

The tissue may be any tissue which can benefit from an increase in vascular density and/or blood flow. In one embodiment, the tissue is selected from the group consisting of muscle, liver, brain, bone, eyes, skin and heart. In one embodiment, the tissue is muscle. In one embodiment, the muscle is skeletal muscle. In one embodiment, the tissue is heart. In one embodiment, the tissue is brain. In one embodiment, the tissue is liver. In one embodiment, the tissue is skin. In one embodiment, the tissue is eyes. In one embodiment, the tissue is bone.

In some embodiments, the tissue is healthy tissue. In some embodiments, the tissue is ischaemic tissue.

Typically, the agent elevates SIRT1 activation or expression in endothelial cells in all tissues of the subject. However, in some embodiments, the agent may be specific to one or more particular tissues (e.g. a particular organ) of the subject.

In another aspect, the present invention provides a method of increasing the exercise capacity of a subject, the method comprising administering to the subject an effective amount of an agent which elevates SIRT1 activity or SIRT1 expression in endothelial cells of the subject. The method increases the exercise capacity of the subject, that is, the exercise capacity of the subject is increased relative to the exercise capacity of the subject prior to administration of the agent.

As used herein, "exercise capacity" is the ability of a subject to resist fatigue during exercise, typically during continuous exercise, more typically during continuous strenuous exercise. The exercise may be aerobic or anaerobic exercise. Typically, an increase in the ability of the subject to resist fatigue during exercise is an increase in endurance of the subject. The increase in the exercise capacity of a subject may be due to one or more of the following:

(a) an increase in the elimination of lactate from muscle tissue of the subject during exercise;
(b) an increase in oxygen supply to muscle tissue during exercise;
(c) an increase in elimination of oxidative products from muscle tissue during exercise;
(d) an increase in supply of enzymes and co-factors for tissue function during exercise;
(e) an increase in reperfusion of muscle tissue during exercise; and/or
(f) a reduction in lactate levels during exercise.

As SIRT1 is an $NAD^+$-dependent cyclase, SIRT1 activity can be increased in a cell by raising $NAD^+$ levels, increasing the ratio of $NAD^+$ to NADH, and/or increasing production of $NAD^+$ in the cell.

In one embodiment, the agent which increases SIRT1 activity or SIRT1 expression in endothelial cells comprises an $NAD^+$ agonist.

In an aspect, the present invention provides a method of increasing vascular density and/or blood flow in tissue of a subject, comprising administering to the subject an effective amount of an $NAD^+$ agonist.

In another aspect, the present invention provides a method of increasing exercise capacity in a subject, comprising administering to the subject an effective amount of an $NAD^+$ agonist.

As used herein, an "$NAD^+$ agonist" is an agent which raises $NAD^+$ levels in an endothelial cell, and/or increases the ratio of $NAD^+$ to NADH in an endothelial cell, and/or increases production of $NAD^+$ in an endothelial cell.

In one embodiment, the $NAD^+$ agonist is an agent which raises $NAD^+$ levels in an endothelial cell. An agent which raises $NAD^+$ levels in an endothelial cell increases the amount of $NAD^+$ in the endothelial cell relative to the amount of $NAD^+$ in the endothelial cell prior to contact with the agent.

In one embodiment, the $NAD^+$ agonist is an agent which increases the ratio of $NAD^+$ to NADH in an endothelial cell. An agent which raises the ratio of $NAD^+$ to NADH in an endothelial cell increases the ratio of $NAD^+$ to NADH in the endothelial cell relative to the ratio of $NAD^+$ to NADH in the endothelial cell prior to contact with the agent.

In one embodiment, the $NAD^+$ agonist is an agent which increases production of $NAD^+$ in an endothelial cell. An agent which increases production of $NAD^+$ in an endothelial cell increases the production of $NAD^+$ in the endothelial cell relative to the production of $NAD^+$ in the endothelial cell prior to contact with the agent.

In one embodiment, the $NAD^+$ agonist raises $NAD^+$ levels in an endothelial cell and increases the ratio of $NAD^+$ to NADH in an endothelial cell. In one embodiment, the $NAD^+$ agonist raises $NAD^+$ levels in an endothelial cell, increases the ratio of $NAD^+$ to NADH in an endothelial cell and increases the rate of production of $NAD^+$ in the endothelial cell. In one embodiment, the $NAD^+$ agonist raises $NAD^+$ levels in an endothelial cell and increases production of $NAD^+$ in the endothelial cell.

Methods for determining the amount of $NAD^+$ in a cell, the ratio of $NAD^+$ to NADH in a cell, and the production of $NAD^+$ in a cell, are known in the art and are described in, for example, Schwartz et al. (1974) J. Biol. Chem. 249: 4138-4143; Sauve and Schramm (2003) Biochemistry 42(31):9249-9256; Yamada et al. (2006) Analytical Biochemistry 352:282-285, or can be determined using commercially available kits such as, for example, NAD/NADH-Glo Assay (Promega Inc.) or NAD/NADH Quantitation Colorimetric Kit (BioVision Inc.).

In one form, the $NAD^+$ agonist reduces breakdown of $NAD^+$ in the endothelial cell thereby raising the $NAD^+$ levels in the cell. An example of an agent which reduces the breakdown of $NAD^+$ in cells, including endothelial cells, is a CD38 inhibitor. CD38 is an enzyme which catalyzes the synthesis and hydrolysis of cyclic ADP-ribose from $NAD^+$ and ADP-ribose. CD38 reduces $NAD^+$ levels in the cell by converting $NAD^+$ to cyclic ADP-ribose. Thus, in one embodiment, the $NAD^+$ agonist is a CD38 inhibitor.

As used herein, a "CD38 inhibitor" is an agent which reduces or eliminates the biological activity of CD38. The biological activity of CD38 may be reduced or eliminated by inhibiting enzyme function, or by inhibiting expression of CD38 at the level of gene expression and enzyme production. "Inhibiting" is intended to refer to reducing or eliminating, and contemplates both partial and complete reduction or elimination.

In one embodiment, the CD38 inhibitor is an inhibitor of CD38 enzyme function. An inhibitor of CD38 enzyme function is an agent that blocks or reduces the enzymatic activity of CD38.

In one embodiment, the inhibitor of CD38 enzyme function is a compound of formula I:

Formula I

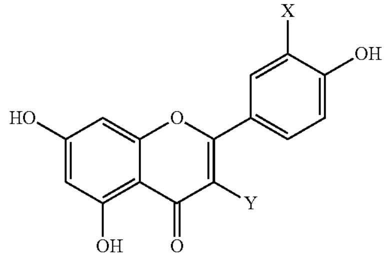

wherein:

X is H or OH; and

Y is H or OH;

or a pharmaceutically acceptable salt, derivative or prodrug thereof.

In one embodiment, X and Y are both H.

An example of an inhibitor of CD38 enzyme function is apigenin, or a pharmaceutically acceptable salt, derivative or prodrug thereof. Apigenin (5,7-dihydroxy-2-(4-hydroxyphenyl)-4H-1-benzopyran-4-one), also known as 4',5,7-trihydroxyflavone, is an isoflavone found in plants, including fruits and vegetables, such as parsley, celery and chamomile. Apigenin has the following structure:

Formula II

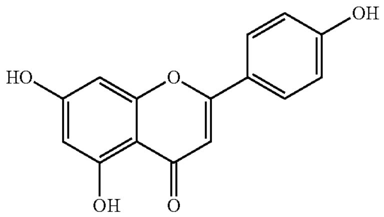

Another example of an inhibitor of CD38 enzyme function is quercetin, or a pharmaceutically acceptable salt, derivative or prodrug thereof. Quercetin [2-(3,4-dihydroxyphenyl)-3,5,7-trihydroxy-4H-chromen-4-one]) is an isoflavone found in plants, including fruits, vegetables, leaves and grains. Quercetin has the following structure:

Formula III

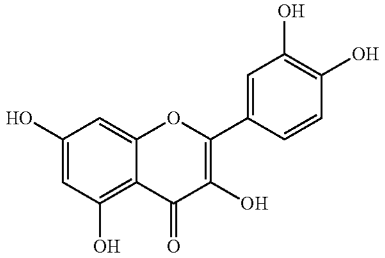

Both apigenin and quercetin have been shown to be inhibitors of CD38 activity in vitro (Esande et al. (2013) Diabetes, 1084-1093).

Isoflavones (such as apigenin or quercetin) are typically administered in isolated form. By "isolated" it is meant that the isoflavone has undergone at least one purification step. When the inhibitor of CD38 enzyme function is an isoflavone, the inhibitor is conveniently administered in a composition comprising at least 10% w/v inhibitor, at least 20% w/v inhibitor, at least 30% w/v inhibitor, at least 40% w/v inhibitor, at least 50% w/v inhibitor, at least 60% w/v inhibitor, at least 70% w/v inhibitor, at least 80% w/v inhibitor, at least 90% w/v inhibitor, at least 95% w/v inhibitor, at least 98% w/v inhibitor. In one embodiment, the inhibitor is in a biologically pure form (i.e. substantially free of other biologically active compounds). Methods for isolation of biologically pure forms of isoflavones such as apigenin and quercetin are known in the art. Biologically pure apigenin and quercetin is also commercially available from, for example, Sigma Chemical Company (St. Louis) (Cat. No. A3145 and Cat. No. Q4951), or Indofine Chemical Company (Cat. No. A-002).

In some embodiments, the CD38 inhibitor is a pharmaceutically acceptable salt or pro-drug form of the inhibitor of CD38 enzyme function, such as a pharmaceutically acceptable salt or prodrug of apigenin or quercetin. The term "prodrug" is used herein in its broadest sense to include those compounds which are converted in vivo to the active form of the drug. Use of the prodrug strategy may optimise the delivery of the $NAD^+$ agonist to its site of action.

In one embodiment, the pro-drug of the inhibitor of CD38 enzyme function is an ester or an imine of the inhibitor.

In one embodiment, the $NAD^+$ agonist is apigenin, or a pharmaceutically acceptable salt, derivative or prodrug thereof.

In another embodiment, the CD38 inhibitor is an inhibitor of CD38 gene expression or enzyme production. An inhibitor of CD38 gene expression or enzyme production is an agent that blocks or reduces transcription or translation of the CD38 gene. Inhibition of CD38 gene expression or enzyme production may be, for example, by RNA interference (RNAi) (e.g. siRNA, shRNA), antisense nucleic acid, locked nucleic acid (LNA), DNAzymes, or ribozymes, which target CD38 mRNA transcripts, by genome editing technologies such as Zinc finger nucleases (ZFN), Transcription Activator-Like effector Nucleases (TALENS), Clustered regular Interspaced Short Palindromic Repeats (CRISPR), or engineered meganuclease reengineered homing nuclease, which target the CD38 gene. "RNAi" refers to a nucleic acid that forms a double stranded RNA, which double stranded RNA has the ability to reduce or inhibit expression of a target gene when the siRNA is present in the same cell as the gene or target gene. "shRNA" or "short hairpin RNA" refers to a nucleic acid that forms a double stranded RNA with a tight hairpin loop, which has the ability to reduce or inhibit expression of a gene or target gene. An "antisense" polynucleotide is a polynucleotide that is substantially complementary to a target polynucleotide and has the ability to specifically hybridize to the target polynucleotide to decrease expression of a target gene. Ribozymes and DNAzymes are catalytic RNA and DNA molecules, respectively, which hybridise to and cleave a target sequence to thereby reduce or inhibit expression of the target gene. General methods of using antisense, ribozyme, DNAzyme and RNAi technology, to control gene expression, are known in the art. Genome editing uses artificially engineered nucleases to create specific double strand breaks at desired locations in the genome, and harnesses the cells endogenous mechanisms to repair the breaks. Methods for silencing genes using genome editing technologies are described in, for example, Tan et al. (2012) Precision editing of large animal genomes, Adv. Genet. 80: 37-97; de Souza (2011) Primer: Genome editing with engineered nucleases, Nat. Meth. 9(1) 27-27; Smith et al. (2006) A combinatorial approach to create artificial homing endonucleases cleaving chosen sequences, Nucleic Acids Research 34: 22, e149; Umov et al. (2010) Nat. Rev. Genet. 11(9): 636-646. Inhibition of CD38 expression using iRNA is described in, for example, Escande et al. (2013) Diabetes, 62: 1084-1093.

In another embodiment, the $NAD^+$ agonist is an agent which promotes synthesis of $NAD^+$ in the endothelial cell thereby raising $NAD^+$ levels in the endothelial cell. An example of an agent which promotes synthesis of $NAD^+$ is an $NAD^+$ precursor.

In one aspect, there is provided a method of increasing vascular density and/or blood flow in tissue of a subject, comprising administering to the subject an effective amount of an $NAD^+$ precursor.

In one aspect, there is provided a method of increasing exercise capacity of a subject, comprising administering to the subject an effective amount of an $NAD^+$ precursor.

In one aspect, there is provided a method of increasing angiogenesis and/or neovascularization in tissue of a subject, comprising administering to the subject an effective amount of an $NAD^+$ precursor.

As used herein, an "$NAD^+$ precursor" is an intermediate of $NAD^+$ synthesis which does not inhibit sirtuin activity. Examples of $NAD^+$ precursors include nicotinamide mononucleotide (NMN), nicotinamide riboside (NR), nicotinic acid riboside (NaR), ester derivatives of nicotinic acid riboside, nicotinic acid (niacin), ester derivatives of nicotinic acid, nicotinic acid mononucleotide (NaMN), nicotinic acid adenine dinucleotide (NAAD), 5-phospho-α-D-ribosyl-1-pyrophosphate (PPRP), or a pharmaceutically acceptable salt, derivative or prodrug thereof.

In one embodiment, the $NAD^+$ agonist is NMN or a pharmaceutically acceptable salt, derivative or prodrug thereof, NR or a pharmaceutically acceptable salt, derivative or prodrug thereof, or NAAD or a pharmaceutically acceptable salt, derivative or prodrug thereof.

In one embodiment, the $NAD^+$ agonist is NMN or a pharmaceutically acceptable salt, derivative or prodrug thereof.

In one embodiment, the $NAD^+$ agonist is NR or a pharmaceutically acceptable salt, derivative or prodrug thereof. Examples of derivatives of NR and methods for their production, are described in, for example, U.S. Pat. No. 8,106,184.

In one embodiment, the $NAD^+$ agonist is NAAD or a pharmaceutically acceptable salt, derivative or prodrug thereof.

In one embodiment, the $NAD^+$ agonist is NaR or a pharmaceutically acceptable salt, derivative or prodrug thereof.

In another embodiment, the $NAD^+$ agonist is a cell permeable form of $NAD^+$, derivative or prodrug thereof.

In another embodiment, $NAD^+$ levels may be raised by reducing inhibition of translation of the $NAD^+$ biosynthetic enzymes NAMPT, NMNAT1, NMNAT2, and NMNAT3. Inhibition of translation of the $NAD^+$ biosynthetic enzymes NAMPT, NMNAT1, NMNAT2, and NMNAT3 is mediated by endogenous micro RNA (miRNA) that target NAMPT, NMNAT1, NMNAT2, and NMNAT3. Thus, $NAD^+$ levels may be raised in the endothelial cell by inhibiting the activity of endogenous miRNA which targets NAMPT, NMNAT1, NMNAT2, and NMNAT3. Accordingly, in one embodiment, the $NAD^+$ agonist is an NAMPT, NMNAT1, NMNAT2, and/or NMNAT3 miRNA antagonist. As used herein, a "NAMPT, NMNAT1, NMNAT2, and/or NMNAT3 miRNA antagonist" is an agent which inhibits the activity of miRNA that inhibits translation of any one or more of NAMPT, NMNAT1, NMNAT2, and NMNAT3. The NAMPT, NMNAT1, NMNAT2, and/or NMNAT3 miRNA antagonist may act by inhibiting NAMPT, NMNAT1, NMNAT2, and/or NMNAT3 miRNA through, for example, RNA interference (RNAi) (e.g. siRNA, shRNA), antisense nucleic acid, locked nucleic acid (LNA), DNAzymes, or ribozymes, which target miRNAs that target NAMPT, NMNAT1, NMNAT2, and/or NMNAT3, or by genome editing technologies such as Zinc finger nucleases (ZFN), Transcription Activator-Like effector Nucleases (TALENS), Clustered regular Interspaced Short Palindromic Repeats (CRISPR), or engineered meganuclease reengineered homing nuclease, which target the DNA sequences which encode the miRNAs that target NAMPT, NMNAT1, NMNAT2, and/or NMNAT3. Activation domains may be targeted to the genes of NAD biosynthetic genes (e.g. NAMPT, NMNAT1, NMNAT2, and/or NMNAT3) to increase gene expression using CRISPR-directed heterologous regulatory domains (e.g. VP16 or VP64).

In another embodiment, $NAD^+$ levels may be raised by contacting the cell with an $NAD^+$ agonist which enhances the enzymatic activity of $NAD^+$ biosynthetic enzymes, such as the $NAD^+$ biosynthetic enzymes NAMPT, NMNAT1, NMNAT2, and/or NMNAT3 or PNC1 from other species such as yeast, flies or plants. For example, P7C3 enhances activity of NAMPT in vitro, thereby increasing the level of intracellular $NAD^+$ (Wang et al. (2014) Cell, 158(6):1324-1334). P7C3 has the following structure:

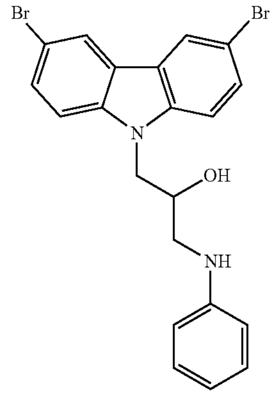 [SMILES: OC(CNc1ccccc1)Cn1c2ccc(Br)cc2c2cc(Br)ccc21]

The enzymatic activity of $NAD^+$ biosynthetic enzymes, such as NAMPT, NMNAT1, NMNAT2, and/or NMNAT3, may be enhanced by introducing into cells of the subject nucleic acid which expresses one or more of the $NAD^+$ biosynthetic enzymes in endothelial cells of the subject.

In one embodiment, the $NAD^+$ agonist is an agent which increases the ratio of $NAD^+$ to NADH in the cell relative to the ratio of $NAD^+$ to NADH in the cell prior to contact with the $NAD^+$ agonist. For example, the ratio of the amount of $NAD^+$ to NADH may be increased by contacting the cell with an $NAD^+$ agonist which activates an enzyme that converts NADH to $NAD^+$. For example, β-lapachone (3,4-dihydro-2,2-dimethyl-2H-napthol[1,2-b]pyran-5,6-dione) activates the enzyme NADH:quinone oxidoreductase (NQ01) which catalyses the reduction of quinones to hydroquinones by utilizing NADH as an electron donor, with a consequent increase in the ratio of $NAD^+$ to NADH.

Accordingly, in one embodiment, the $NAD^+$ agonist is an activator of NQ01, such as lapachone, or a pharmaceutically acceptable salt, derivative or prodrug thereof.

As described in the examples, the inventors have found that administration of the $NAD^+$ precursor NMN:

- increases NAD+ levels in cell including endothelial cells;
- increases vascular density, and increases blood flow, in skeletal muscles when administered to aged mice;
- increases vascular density in skeletal muscles of young and old when administered to mice that are undergoing exercise training;
- reduces blood lactate levels following intense exercise;
- increases exercise capacity;
- promotes proliferation of endothelial cells and stimulates angiogenesis;
- increases vascular density and blood flow in ischaemic tissue.

In one embodiment, there is provided a method of increasing vascular density and/or blood flow in tissue of a subject, and/or increasing exercise capacity of the subject, comprising administering to the subject an effective amount of NMN, or a pharmaceutically acceptable salt, derivative, or prodrug thereof.

In one embodiment, there is provided a method of increasing vascular density and/or blood flow in tissue of a subject, comprising administering to the subject an effective amount of NMN, or a pharmaceutically acceptable salt, derivative, or prodrug thereof.

In one embodiment, there is provided a method of increasing exercise capacity of a subject, comprising administering an effective amount of NMN, or a pharmaceutically acceptable salt, derivative, or prodrug thereof.

In one embodiment, there is provided a method of increasing angiogenesis and/or neovascularization in tissue of a subject, comprising administering to the subject an effective amount of NMN, or a pharmaceutically acceptable salt, derivative, or prodrug thereof.

As described in the Examples, the inventors have further found that aged mice administered the $NAD^+$ agonist, NMN, and the $H_2S$ precursor, sodium hydrosulfide, have a skeletal muscle vascular density and exercise capacity that is greater than that of mice treated with NMN or sodium hydrosulfide alone.

Thus, in one embodiment, the method of the present invention comprises administering an $NAD^+$ agonist in combination with a compound which raises $H_2S$ levels in endothelial cells of the subject.

In one embodiment, the compound which raises $H_2S$ levels in endothelial cells of the subject is a $H_2S$ precursor. Thus, in one embodiment, there is provided a method of increasing vascular density and/or blood flow in tissue of a subject, comprising administering to the subject an effective amount of an $NAD^+$ agonist in combination with an $H_2S$ precursor.

In one embodiment, there is provided a method of increasing exercise capacity of a subject, comprising administering to the subject an effective amount of an $NAD^+$ agonist in combination with an $H_2S$ precursor.

In one embodiment, the $H_2S$ precursor is sodium hydrosulfide or morpholin-4-ium 4-methoxyphenyl(morpholino) phosphinodithioate (GYY4137).

In one embodiment, the $H_2S$ precursor is sodium hydrosulfide.

In one embodiment, the $H_2S$ precursor is GYY4137.

As described in the Examples, the inventors have also found that expression of a SIRT1 transgene in endothelial cells of a subject results in increased vascular density and increased exercise capacity.

Accordingly, in one embodiment, the agent which elevates activity and/or expression of SIRT1 in endothelial cells of the subject elevates expression of SIRT1 in the endothelial cells of the subject. In one embodiment, an agent which elevates expression of SIRT 1 in the endothelial cells of tissue of the subject comprises a nucleic acid that is capable of expressing SIRT1 in endothelial cells of a subject. A nucleic acid that is capable of expressing SIRT1 in endothelial cells of tissue of a subject may comprise the coding sequence of SIRT1 operably linked to regulatory sequence which operate together to express a protein encoded by the coding sequence in endothelial cells. “Coding sequence” refers to a DNA or RNA sequence that codes for a specific amino acid sequence. It may constitute an “uninterrupted coding sequence”, i.e., lacking an intron, such as in a cDNA, or it may include one or more introns bounded by appropriate splice junctions. An example of human SIRT1 coding sequence is the nucleotide sequence from nucleotide 210 to 1877 of Genbank accession no. BC012499 (SEQ ID NO: 1). A “regulatory sequence” is a nucleotide sequence located upstream (5' non-coding sequences), within, or downstream (3' non-coding sequences) of a coding sequence, and which influences the transcription, RNA processing or stability, or translation of the associated coding sequence. Regulatory sequences are known in the art and may include, for example, transcriptional regulatory sequences such as promoters, enhancers translation leader sequences, introns, and polyadenylation signal sequences. The coding sequence is typically operably linked to a promoter. A promoter is a DNA region capable under certain conditions of binding RNA polymerase and initiating transcription of a coding sequence usually located downstream (in the 3' direction) from the promoter. The coding sequence may also be operably linked to termination signals. The expression cassette may also include sequences required for proper translation of the coding sequence. The coding sequence may be under the control of a constitutive promoter or of a regulatable promoter that initiates transcription in endothelial cells of the tissue. For example, the SIRT1 coding sequence may be operably linked to a promoter which is not native to the SIRT1 gene, such as a promoter that expresses the coding sequence in, or is inducible in, endothelial cells. Examples of suitable promoters include Tie-1, Tie-2, CD34, eNOS, Flt-1, VE-cadherin, vWF, PDGFB, PECAM-1, VCAM-1.

A nucleic acid encoding a protein (coding sequence) is operably linked to a regulatory sequence when it is arranged relative to the regulatory sequence to permit expression of the protein in a cell. For instance, a promoter is operatively linked to a coding region if the promoter helps initiate transcription of the coding sequence.

As used herein, “expression” of a nucleic acid sequence refers to the transcription and translation of a nucleic acid sequence comprising a coding sequence to produce the polypeptide encoded by the coding sequence.

The nucleic acid sequence encoding SIRT1 may be inserted into an appropriate vector sequence. The term “vector” refers to a nucleic acid sequence suitable for transferring genes into a host cell. The term “vector” includes plasmids, cosmids, naked DNA, viral vectors, etc. In one embodiment, the vector is a plasmid vector. A plasmid vector is a double stranded circular DNA molecule into which additional sequence may be inserted. The plasmid may be an expression vector. Plasmids and expression vectors are known in the art and described in, for example, Sambrook et al. Molecular Cloning: A Laboratory Manual, $4^{th}$ Ed. Vol. 1-3, Cold Spring Harbor, N.Y. (2012).

In some embodiments, the vector is a viral vector. Viral vectors comprise viral sequence which permits, depending on the viral vector, viral particle production and/or integration into the host cell genome and/or viral replication. Viral vectors which can be utilized with the methods and compositions described herein include any viral vector which is capable of introducing a nucleic acid into endothelial cells, such as endothelial cells of skeletal muscle. Examples of viral vectors include adenovirus vectors; lentiviral vectors; adeno-associated viral vectors; Rabiesvirus vectors; Herpes Simplex viral vectors; SV40; polyoma viral vectors; poxvirus vector.

In one aspect, there is provided a nucleic acid for increasing vascular density and/or blood flow in tissue of a subject, and/or exercise capacity of a subject, wherein the nucleic acid comprises a coding sequence which encodes a protein or RNA which causes the activity of SIRT1 or expression of SIRT1 to be increased in endothelial cells of the subject. In various embodiments, the coding sequence encodes:

(a) SIRT1 protein;

(b) one or more $NAD^+$ biosynthetic enzymes, or (c) an NAMPT, NMNAT1, NMNAT2, and/or NMNAT3 miRNA antagonist.

In one embodiment, the coding sequence encodes SIRT1. Examples of SIRT1 amino acid sequence include Genbank accession numbers AAI52315.1 (mouse) (SEQ ID NO:3), AAH12499.1, (human) (SEQ ID NO: 2), NP_001277175.1 (cat) (SEQ ID NO: 4), XP_005619990.1 (dog) (SEQ ID NO: 5).

In one embodiment, the coding sequence encodes a protein or RNA which causes $NAD^+$ levels to be increased in endothelial cells of a subject. In one embodiment, the coding sequence encodes one or more $NAD^+$ biosynthetic enzymes selected from the group consisting of NAMPT, NMNAT1, NMNAT2, and NMNAT3. Examples of the amino acid sequence of NAMPT is Genbank accession numbers NP_005737.1 (human) (SEQ ID NO: 6), NP_067499.2 (mouse) (SEQ ID NO: 7), XP_022261566.1 (dog) (SEQ ID NO: 8); examples of the amino acid sequence of NMNAT1 is Genbank accession numbers AAH14943.1 (human) (SEQ ID NO: 9), NP_597679.1 (mouse) (SEQ ID NO: 10), XP_005620579.1 (dog) (SEQ ID NO: 11); examples of the amino acid sequence of NMNAT2 is Genbank accession numbers NP_055854.1 (human) (SEQ ID NO: 12), NP_780669.1 (mouse) (SEQ ID NO: 13), XP_022276670.1 (dog) (SEQ ID NO: 14); examples of the amino acid sequence of NMNAT3 is AAH36218.1 (human) (SEQ ID NO: 15), NP_001344374.1 (mouse) (SEQ ID NO: 16), (XP_022264401.1) (dog) (SEQ ID NO: 17).

In one embodiment, the coding sequence encodes a NAMPT, NMNAT1, NMNAT2, and/or NMNAT3 miRNA antagonist.

In one embodiment, the coding sequence which encodes: SIRT1 protein; one or more $NAD^+$ biosynthetic enzymes, or the NAMPT, NMNAT1, NMNAT2, and/or NMNAT3 miRNA antagonist, is operably linked to a promoter which expresses the coding sequence in, or is inducible in, endothelial cells. In one embodiment, the promoter is selected from the group consisting of Tie-1, Tie-2, CD34, eNOS, Flt-1, VE-cadherin, vWF, PDGFB, PECAM-1, VCAM-1. In one embodiment, the promoter is Tie-2.

The nucleic acid for increasing vascular density and/or blood flow in tissue of a subject, and/or exercise capacity of a subject, may be incorporated into a viral vector for administering to the subject. Accordingly, in one aspect, there is provided a viral vector, wherein the viral vector comprises nucleic acid for increasing vascular density and/or blood flow in tissue of a subject, and/or exercise capacity of a subject, wherein the nucleic acid comprises coding sequence which encodes a protein or RNA which causes the activity of SIRT1 or expression of SIRT1 to be increased in endothelial cells of the subject. In various embodiments, the coding sequence encodes:

(a) SIRT1 protein;
(b) one or more $NAD^+$ biosynthetic enzymes, or
(c) an NAMPT, NMNAT1, NMNAT2, and/or NMNAT3 miRNA antagonist.

Typically, the coding sequence is operably linked to promoter which expresses the coding sequence in, or is inducible in, endothelial cells. In one embodiment, the promoter is selected from the group consisting of Tie-1, Tie-2, CD34, eNOS, Flt-1, VE-cadherin, vWF, PDGFB, PECAM-1, VCAM-1. In one embodiment, the promoter is Tie-2. Typical viral vectors are as mentioned above, and include adenovirus vectors; lentiviral vectors; adeno-associated viral vectors; Rabiesvirus vectors; Herpes Simplex viral vectors; SV40; polyoma viral vectors; poxvirus vector.

In one embodiment, the viral vector is an adeno-associated viral (AAV) vector. In one embodiment, the AAV vector is a serotype selected from the group consisting of AAV1, AAV2, AAV3, AAV4, AAV5, AAV6, AAV6.2, AAV7, AAV8, and AAV9 vector or variants thereof. The use of recombinant AAV vectors for introducing nucleic acids into cells is known in the art and described in, for example, US20160038613; Grieger and Samulski (2005) Adeno-associated virus as a gene therapy vector: vector development, production and clinical applications, Advances in Biochemical Engineering/Biotechnology 99: 119-145; Methods for the production of recombinant AAV are known in the art and described in, for example, Harasta et al (2015) Neuropsychopharmacology 40: 1969-1978.

Viral vectors are typically packaged into viral particles using methods known in the art. The viral particles may then be used to transfer the nucleic acid for increasing vascular density and/or blood flow in tissue of a subject, and/or exercise capacity of a subject, to a subject. Thus, another aspect provides a virus comprising a vial vector, wherein the viral vector comprises nucleic acid for increasing vascular density and/or blood flow in tissue of a subject, and/or exercise capacity of a subject, wherein the nucleic acid comprises a coding sequence which encodes a protein or RNA which causes the activity of SIRT1 or expression of SIRT1 to be increased in endothelial cells of the subject. In various embodiments, the coding sequence encodes:

(a) SIRT1;
(b) one or more $NAD^+$ biosynthetic enzymes, or
(c) an NAMPT, NMNAT1, NMNAT2, and/or NMNAT3 miRNA antagonist.

In one aspect, there is a method of increasing vascular density and/or blood flow in tissue of an aged subject, and/or increasing exercise capacity in an aged subject, comprising administering an effective amount of the virus described herein.

As used herein, the term "subject" refers to a mammal. The mammal may, for example, be a human, primate, or other animal (e.g. sheep, cow, horse, donkey, pig, dog, cat, mouse, rabbit, rat, guinea pig, hamster, fox, deer, monkey).

In one embodiment, the mammal is a human.

In one embodiment, the mammal is a non-human.

In one embodiment, the mammal is a racing animal (e.g. racehorse, greyhound).

In one embodiment, the mammal is a companion animal (e.g. dog, cat).

Although the present invention is exemplified using a murine model, the method of the present invention may be applied to other species.

In some embodiments the subject is a middle-aged or an aged subject. In some embodiments, the middle-aged or aged subject is a human. In some embodiments, the subject is a middle-aged human. A middle-aged human has an age in the range of from 35 to 65 years. In some embodiments, the subject is aged. In some embodiments, the subject is an aged human. An aged human has an age in the range of from 66 to 110 years. It will be appreciated that what is considered middle aged and aged will depend on the species of the subject and can be readily determined by those skilled in the art.

In some embodiments, the subject may be any age.

In one embodiment, there is provided a method of increasing vascular density and/or blood flow in tissue of a middle aged or aged subject, typically an aged subject, the method comprising administering to the subject an effective amount of an agent which elevates SIRT1 activity or SIRT1 expression in endothelial cells of the subject, optionally in combination with a $H_2S$ precursor.

In one embodiment, there is provided a method of increasing vascular density and/or blood flow in tissue of a middle aged or aged subject, typically an aged subject, the method comprising administering to the subject an effective amount of an $NAD^+$ agonist, optionally in combination with a $H_2S$ precursor.

In one embodiment, there is provided a method of increasing vascular density and/or blood flow in tissue of a middle aged or aged subject, typically an aged subject, the method comprising administering to the subject an effective amount of an $NAD^+$ precursor, optionally in combination with a $H_2S$ precursor.

In one embodiment, there is provided a method of increasing exercise capacity of a middle aged or aged subject, typically an aged subject, the method comprising administering to the subject an effective amount of an agent which elevates SIRT1 activity or SIRT1 expression in endothelial cells of the subject, optionally in combination with a $H_2S$ precursor.

In one embodiment, there is provided a method of increasing exercise capacity of a middle aged or aged subject, typically an aged subject, the method comprising administering to the subject an effective amount of an $NAD^+$ agonist, optionally in combination with a $H_2S$ precursor.

In one embodiment, there is provided a method of increasing exercise capacity of a middle aged or aged subject, typically an aged subject, the method comprising administering to the subject an effective amount of an $NAD^+$ precursor, optionally in combination with a $H_2S$ precursor.

The inventors envisage the method may be used to treat, prevent or improve any disease or condition that is treated, prevented or improved by an increase in vascular density and/or blood flow and/or an increase in exercise capacity. For example, the inventors envisage that: the ability to promote vascular density in heart tissue will be useful for the treatment or prevention of heart disease, such as ischaemic heart disease and heart failure; the ability to promote vascular density in peripheral tissue will be useful for the treatment of diabetic vascular disease, peripheral arterial disease and ulcers; the ability to promote vascular density in heart tissue will be useful for the treatment of coronary arterial disease and heart disease; the ability to promote vascular density in brain tissue will be useful for the treatment of vascular dementia; the ability to promote vascular density in lung tissue will be useful for the treatment of lung conditions such as COPD and pulmonary hypertension; the ability to promote vascular density in skeletal muscle will be useful for the treatment of sarcopenia and frailty; the ability to promote vascular density and/or blood flow in the brain will be useful for the treatment of neurodegenerative diseases such as vascular dementia, as well as other brain conditions such as stroke, and haemorrhage; the ability to promote vascular density and/or blood flow in bone will be useful for the treatment of osteoporosis.

In one aspect, there is provided a method of treating or preventing coronary and/or peripheral arterial disease comprising administering to the subject an effective amount of an agent which increases SIRT1 activity or SIRT1 expression in endothelial cells of the subject.

In one aspect, there is provided a method of treating or preventing coronary and/or peripheral arterial disease comprising administering to the subject an effective amount of an NAD+ precursor.

In one aspect, there is provided a method of treating or preventing ischaemia comprising administering to the subject an effective amount of an agent which increases SIRT1 activity or SIRT1 expression in endothelial cells of the subject.

In one aspect, there is provided a method of treating or preventing ischaemia in a subject, comprising administering to the subject an effective amount of an NAD+ precursor.

In one aspect, there is provided a method of treating or preventing ulcers comprising administering to the subject an effective amount of an agent which increases SIRT1 activity or SIRT1 expression in endothelial cells of the subject.

In one aspect, there is provided a method of treating or preventing ulcers in a subject, comprising administering to the subject an effective amount of an $NAD^+$ precursor.

In one aspect, there is provided a method of treating or preventing a lung condition in a subject, comprising administering to the subject an effective amount of an agent which increases SIRT1 activity or SIRT1 expression in endothelial cells of the subject.

In one aspect, there is provided a method of treating or preventing a lung condition in a subject, comprising administering to the subject an effective amount of an NAD+ precursor.

In one embodiment, the lung condition is a lung disease, such as COPD.

In one embodiment, the lung condition is pulmonary hypertension.

In one aspect, there is provided a method of treating or preventing frailty comprising administering to the subject an effective amount of an agent which increases SIRT1 activity or SIRT1 expression in endothelial cells of the subject.

In one aspect, there is provided a method of treating or preventing frailty comprising administering to the subject an effective amount of an $NAD^+$ precursor.

Frailty is a condition, typically associated with ageing, associated with an increased risk of poor health outcomes. Components of frailty include sarcopenia and muscle weakness.

In one aspect, there is provided a method of treating or preventing sarcopenia comprising administering to the subject an effective amount of an agent which increases SIRT1 activity or SIRT1 expression in endothelial cells of the subject.

In one aspect, there is provided a method of treating or preventing in a subject, comprising administering to the subject an effective amount of an $NAD^+$ precursor.

In one embodiment, the sarcopenia is zero gravity sarcopenia, typically resulting from space travel.

In one embodiment, the sarcopenia is age related sarcopenia.

In one aspect, there is provided a method of increasing vascular density or exercise capacity in a subject having reduced mobility comprising administering to the subject an effective amount of an agent which increases SIRT1 activity or SIRT1 expression in endothelial cells of the subject.

In one aspect, there is provided a method of increasing vascular density or exercise capacity in a subject having reduced mobility, comprising administering to the subject an effective amount of an $NAD^+$ precursor.

A subject having reduced mobility may have reduced mobility of one or more body parts. Subjects having reduced mobility are susceptible to sarcopenia, frailty and/or a reduction in exercise capacity due to the reduced mobility of one or more body parts. Examples of subjects having reduced mobility include quadraplegics, paraplegics, amyotrophic lateral sclerosis patients, subjects requiring extended bedrest, subjects with immobilised limbs following injuries such as broken bones, aged subjects and subjects having sedentary lifestyles.

In one aspect, there is provided a method of treating or preventing neurodegenerative disease, comprising administering to the subject an effective amount of an agent which increases SIRT1 activity or SIRT1 expression in endothelial cells of the subject.

In one aspect, there is provided a method of treating or preventing neurodegenerative disease, comprising administering to the subject an effective amount of an $NAD^+$ precursor.

In one embodiment, the neurodegenerative disease is vascular dementia.

In one aspect, there is provided a method of treating or preventing stroke, comprising administering to the subject an effective amount of an agent which increases SIRT1 activity or SIRT1 expression in endothelial cells of the subject.

In one aspect, there is provided a method of treating or preventing stroke, comprising administering to the subject an effective amount of an $NAD^+$ precursor.

In one aspect, there is provided a method of treating or preventing hemorrhage, comprising administering to the subject an effective amount of an agent which increases SIRT1 activity or SIRT1 expression in endothelial cells of the subject.

In one aspect, there is provided a method of treating or preventing hemorrhage, comprising administering to the subject an effective amount of an $NAD^+$ precursor.

In one aspect, there is provided a method of treating or preventing heart disease comprising administering to the subject an effective amount of an agent which increases SIRT1 activity or SIRT1 expression in endothelial cells of the subject.

In one aspect, there is provided a method of treating or preventing heart disease comprising administering to the subject an effective amount of an $NAD^+$ precursor.

In one aspect, there is provided a method of treating or preventing vascular disease comprising administering to the subject an effective amount of an agent which increases SIRT1 activity or SIRT1 expression in endothelial cells of the subject.

In one aspect, there is provided a method of treating or preventing vascular disease comprising administering to the subject an effective amount of an $NAD^+$ precursor.

In one embodiment, the vascular disease is diabetic vascular disease.

In one aspect, there is provided a method of enhancing the physical performance of a subject, such as athletes, recreational sports people, military personnel, or law enforcement personnel, comprising administering to the subject an effective amount of an agent which increases SIRT1 activity or SIRT1 expression in endothelial cells of the subject.

In one aspect, there is provided a method of enhancing the physical performance of a subject, such as athletes, recreational sports people, military personnel, or law enforcement personnel, comprising administering to the subject an effective amount of an $NAD^+$ precursor.

In one aspect, there is provided a method of enhancing the benefits of physiotherapy, comprising administering to the subject an effective amount of an agent which increases SIRT1 activity or SIRT1 expression in endothelial cells of the subject.

In one aspect, there is provided a method of enhancing the benefits of physiotherapy, comprising administering to the subject an effective amount of an $NAD^+$ precursor.

In one aspect, there is provided a method of improving meat production, such as meat production in animals kept under immobile conditions, comprising administering to the animal an effective amount of an agent which increases SIRT1 activity or SIRT1 expression in endothelial cells of the animal.

In one aspect, there is provided a method of improving meat production, such as meat production in animals kept under immobile conditions, comprising administering to the animal an effective amount of an $NAD^+$ precursor.

In one aspect, there is provided a method of enhancing blood flow to the skin of a subject, e.g. to enhance skin appearance for cosmetic uses, comprising administering to the subject an effective amount of an agent which increases SIRT1 activity or SIRT1 expression in endothelial cells of the subject.

In one aspect, there is provided a method of enhancing blood flow to the skin of a subject, e.g. to enhance skin appearance for cosmetic uses, comprising administering to the subject an effective amount of an $NAD^+$ precursor.

Typically, the enhanced blood flow to the skin is enhanced cutaneous and subcutaneous blood flow.

In one aspect, there is provided a method of enhancing the effects of exercise in a subject, comprising administering to the subject an effective amount of an agent which increases SIRT1 activity or SIRT1 expression in endothelial cells of the subject.

In one aspect, there is provided a method of enhancing the effects of exercise in a subject, comprising administering to the subject an effective amount of an $NAD^+$ precursor.

As described in the Examples, administration of the $NAD^+$ precursor NMN promotes growth of blood vessels and blood flow in ischemic tissue.

Accordingly, in one aspect, there is provided a method of increasing vascular density and/or blood flow in ischaemic tissue of a subject, comprising administering an effective amount of an agent which elevates SIRT1 activity or SIRT1 expression in endothelial cells. Typically, the agent is an $NAD^+$ agonist. Typically, the agent is an $NAD^+$ precursor.

In one aspect, there is provided a method of increasing vascular density and/or blood flow in ischaemic tissue of a subject, comprising administering an effective amount of an $NAD^+$ precursor.

In one aspect, there is provided a method of improving vascular recovery in a subject following injury or immobilisation, comprising administering to the subject an effective amount of an agent which elevates SIRT1 activity or SIRT1 expression in endothelial cells of the subject.

In one aspect, there is provided a method of improving vascular recovery in a subject following injury or immobilisation, comprising administering to the subject an effective amount of an $NAD^+$ precursor.

In one aspect, there is provided a method of improving physical performance in a subject following an extended period of zero gravity, for example following space travel, comprising administering to the subject an effective amount of an agent which increases SIRT1 activity or SIRT1 expression in endothelial cells of the subject.

In one aspect, there is provided a method of improving physical performance in a subject following an extended period of zero gravity, for example following space travel, comprising administering to the subject an effective amount of an $NAD^+$ precursor.

As the agents described herein promote vascular density and blood flow, the inventors envisage that administration of the agents described herein will assist in enhancing exchange of metabolic by-products and toxins in the liver. Thus, in one aspect, there is provided a method of enhancing liver sinusoidal endothelial cell function comprising administering to the subject an effective amount of an agent which increases SIRT1 activity or SIRT1 expression in endothelial cells of the subject.

In one aspect there is provided a method of enhancing liver sinusoidal endothelial cell function comprising administering to the subject an effective amount of an NAD+ precursor.

The inventors envisage that as more blood is provided to tissues, the vitality or activity levels of a subject will be increased. The inventors envisage therefore that increasing vascular density, blood flow and/or exercise capacity of a subject will increase their vitality. Such an increase in vitality would be important for not only aged humans, but also aged pets, such as dogs, cats, horses etc.

Accordingly, in one aspect, there is provided a method of increasing vitality of an aged subject, comprising administering to the subject an effective amount of an agent which elevates SIRT1 activity or SIRT1 expression in endothelial cells of the subject.

In one aspect, there is provided a method of increasing vitality of an aged subject, comprising administering to the subject an effective amount of an $NAD^+$ agonist.

In one aspect, there is provided a method of increasing vitality of an aged subject, comprising administering to the subject an effective amount of an $NAD^+$ precursor.

In one embodiment, the subject is an animal. In one embodiment, the animal is a companion animal, such as a pet.

As used herein, vitality refers to willingness and ability to engage in activity, including physical activity, mental activity and eating.

An increase in vitality can assist in reducing the following symptoms in an animal: lack of coordination, extreme fatigue and lethargy, loss of appetite, decline or worsening of an existing condition, such as a terminal illness, slow healing of wounds, and the onset of age-related disease, in aged animals. Accordingly, in various aspects, there is provided a method of reducing:

(a) lack of coordination;
(b) extreme fatigue and lethargy;
(c) loss of appetite;

(d) decline or worsening of an existing condition;
(e) slow healing of wounds; or
(f) the onset of age-related diseases, in an aged subject, comprising administering to the subject an effective amount of an agent which elevates SIRT1 activity or SIRT1 expression in endothelial cells of the subject. In one embodiment, the aged subject is a companion animal. In one embodiment, the companion animal is a dog.

In various embodiments, there is provided a method of reducing:

(a) lack of coordination;
(b) extreme fatigue and lethargy;
(c) loss of appetite;
(d) decline or worsening of an existing condition;
(e) slow healing of wounds; or
(f) the onset of age-related diseases, in an aged subject, comprising administering to the subject an effective amount of an $NAD^+$ agonist. In one embodiment, the aged subject is a companion animal. In one embodiment, the companion animal is a dog.

In various embodiments, there is provided a method of reducing:

(a) lack of coordination;
(b) extreme fatigue and lethargy;
(c) loss of appetite;
(d) decline or worsening of an existing condition;
(e) slow healing of wounds; or
(f) the onset of age-related diseases, in an aged subject, comprising administering to the subject an effective amount of an $NAD^+$ precursor. In one embodiment, the aged subject is a companion animal. In one embodiment, the companion animal is a dog.

As described in the Examples, when NMN alone, or NMN and sodium hydrosulfide, or NMN and GYY4137, were administered to mice in conjunction with exercise, the mice exhibited an increase in vascular density and exercise capacity that was greater than the increase in vascular density and exercise capacity of mice administered NMN alone, or NMN and sodium hydrosulfide, without exercise. The inventors therefore envisage that the administration of an agent which elevates SIRT1 activity or expression may enhance physical performance in subjects which are in training and/or which require enhanced physical performance, such as athletes, military or law enforcement personnel, astronauts, and racing animals.

Accordingly, in one aspect, there is provided a method of enhancing the physical performance of a subject (e.g. a racing animal, an athlete, military or law enforcement personnel, or astronaut), comprising administering to the subject an effective amount of an agent which increases SIRT1 activity or SIRT1 expression in endothelial cells of tissue of the subject.

In one aspect, there is provided a method of enhancing the physical performance of a subject (e.g. a racing animal, an athlete, military or law enforcement personnel, or astronaut), comprising administering to the subject an effective amount of an $NAD^+$ precursor. The subject may be any animal for which an enhanced exercise capacity is sought. In one embodiment, the subject is a human for which an enhanced exercise capacity is sought. In one embodiment, the subject is an athlete, or recreational sports person. In another embodiment, the subject is a member of the military or law enforcement, who will have improved physical performance. In another embodiment, the subject is an astronaut, who will be susceptible to decreased physical performance following an extended period of zero gravity space travel.

In one embodiment, the subject is a racing animal. The racing animal may be any animal for which an enhanced exercise capacity is sought. In one embodiment, the racing animal is selected from the group consisting of horse and dog. Examples of racing animals include an a racehorse, a greyhound.

In one aspect, there is provided a method of increasing vascular density and/or blood flow in tissue of a subject, comprising: (a) subjecting the subject to exercise training over an exercise training period; and (b) administering to the subject an effective amount of an agent which increases SIRT1 activity or SIRT1 expression in endothelial cells of the subject, before and/or during the exercise training period.

In one aspect, there is provided a method of increasing vascular density and/or blood flow in tissue of a subject, comprising: (a) subjecting the subject to exercise training over an exercise training period; and (b) administering to the subject an effective amount of an $NAD^+$ precursor before and/or during the exercise training period.

The method increases vascular density and/or blood flow in tissue of the subject relative to the vascular density and blood flow of tissue following the exercise training without administration of the $NAD^+$ precursor.

The exercise training is carried out over an exercise training period. The exercise training period is a length of time sufficient to permit an increase in vascular density and/or blood flow with exercise training at regular intervals over the exercise training period. It will be appreciated that the exercise training period will vary depending on various factors including the species of the subject, diet, sex, and the condition of the subject. For example, the exercise training period for a healthy human may be in the range of 1 week to 1 year, 1 week to 6 months, or 1 month to 6 months, or 2 week to 5 months, or 1 week to 4 months, or 1 week to 3 months, or 1 week to 2 months, or 1 week to 1 month. Exercise training during the exercise training period may be any exercise that is conducted at regular intervals over the exercise training period. Typically, the type of exercise training is the training that would increase vascular density and blood flow to a tissue in a healthy young subject (e.g. endurance training).

The agent is administered prior to, and/or during the exercise training period. In this regard, the agent may be administered immediately before the exercise training period begins, and/or may be administered in one or more doses over the course of the exercise training period.

In some embodiments, the agent is administered in conjunction with exercise training to treat a condition which requires vascularisation of the muscles worked in the exercise training. For example, the agent may be administered to subjects in conjunction with exercise training to treat vascular disease.

Accordingly, one aspect provides a method of treating vascular disease in a subject, comprising (a) subjecting the subject to exercise training over an exercise period; and (b) administering to the subject an effective amount of an agent which increases SIRT1 activity or SIRT1 expression in endothelial cells of the subject, before and/or during the exercise training period.

In one aspect, there is provided a method of treating vascular disease in a subject, comprising (a) subjecting the subject to exercise training over an exercise period; and (b) administering to the subject an effective amount of an NAD+ precursor before and/or during the exercise training period.

As described in the Examples, treatment of mice with NMN alone, or NMN and sodium hydrosulfide, or NMN and GYY4137, resulted in increased exercise capacity, including increased endurance. Accordingly, in one aspect, there is provided a method of increasing endurance in a subject, comprising administering to the subject an effective amount of an agent which increases SIRT1 activity or SIRT1 expression in endothelial cells of the subject.

In one aspect, there is provided a method of increasing endurance in a subject, comprising administering to the subject an effective amount of an NAD+ precursor.

In various embodiments, there is provided a method of:

(a) increasing vascular density in muscle tissue of a subject;
(b) increasing exercise capacity of a subject;
(c) promoting angiogenesis and/or neovascularisation in tissue of a subject;
(d) treating or preventing coronary and/or peripheral arterial disease in a subject;
(e) treating or preventing ischaemia in a subject;
(f) treating or preventing ulcers in a subject;
(g) treating or preventing lung disease in a subject;
(h) treating or preventing pulmonary hypertension in a subject;
(i) treating or preventing frailty in a subject;
(j) treating or preventing sarcopenia in a subject;
(k) increasing vascular density or exercise capacity in subjects having reduced mobility in a subject;
(l) treating or preventing heart disease in a subject;
(m) treating or preventing diabetic vascular disease in a subject;
(n) enhancing liver sinusoidal endothelial cell function in a subject;
(o) enhancing the physical performance of a subject in a subject;
(p) increasing endurance in a subject in a subject;
(q) enhancing the performance of a racing animal;
(r) enhancing the effects of exercise in a subject in a subject;
(s) improving vascular recovery in a subject following injury or immobilisation in a subject;
(t) enhancing benefits of physiotherapy in a subject in a subject;
(u) enhancing blood flow to eyes of a subject;
(v) enhancing skin appearance in a subject;
(w) enhancing meat production in an animal;
(x) treating or preventing neurodegenerative disease (such as vascular dementia);
(y) treating or preventing stroke;
(z) treating or preventing hemorrhage;
(aa) treating or preventing osteoporosis;
(bb) increasing vitality;

in a subject, comprising administering to the subject an effective amount of an $NAD^+$ agonist and a $H_2S$ precursor.

In various embodiments, there is provided a method of:

(a) increasing vascular density in muscle tissue of a subject;
(b) increasing exercise capacity of a subject;
(c) promoting angiogenesis and/or neovascularisation in tissue of a subject;
(d) treating or preventing coronary and/or peripheral arterial disease in a subject;
(e) treating or preventing ischaemia in a subject;
(f) treating or preventing ulcers in a subject;
(g) treating or preventing lung disease in a subject;
(h) treating or preventing pulmonary hypertension in a subject;
(i) treating or preventing frailty in a subject;
(j) treating or preventing sarcopenia in a subject;
(k) increasing vascular density or exercise capacity in subjects having reduced mobility in a subject;
(l) treating or preventing heart disease in a subject;
(m) treating or preventing diabetic vascular disease in a subject;
(n) enhancing liver sinusoidal endothelial cell function in a subject;
(o) enhancing the physical performance of a subject in a subject;
(p) increasing endurance in a subject in a subject;
(q) enhancing the performance of a racing animal;
(r) enhancing the effects of exercise in a subject in a subject;
(s) improving vascular recovery in a subject following injury or immobilisation in a subject;
(t) enhancing benefits of physiotherapy in a subject in a subject;
(u) enhancing blood flow to eyes of a subject;
(v) enhancing skin appearance in a subject;
(w) enhancing meat production in an animal;
(x) treating or preventing neurodegenerative disease (such as vascular dementia);
(y) treating or preventing stroke;
(z) treating or preventing hemorrhage;
(aa) treating or preventing osteoporosis;
(bb) increasing vitality;

in a subject, comprising administering to the subject an effective amount of an $NAD^+$ precursor and a $H_2S$ precursor.

In various embodiments, the $NAD^+$ precursor is:

(a) NMN or a pharmaceutically acceptable salt, derivative or prodrug thereof;
(b) NR or a pharmaceutically acceptable salt, derivative or prodrug thereof;
(c) NAAD or a pharmaceutically acceptable salt, derivative or prodrug thereof;
(d) NaR or a pharmaceutically acceptable salt, derivative or prodrug thereof;
(e) nicotinic acid (niacin), an ester derivative of nicotinic acid, or a pharmaceutically acceptable salt, derivative or prodrug thereof;
(f) NaMN or a pharmaceutically acceptable salt, derivative or prodrug thereof; or
(g) PPRP or a pharmaceutically acceptable salt, derivative or prodrug thereof.

As used herein, "treating" means affecting a subject, tissue or cell to obtain a desired pharmacological and/or physiological effect and includes inhibiting the condition, i.e. arresting its development; or relieving or ameliorating the effects of the condition i.e., cause reversal or regression of the effects of the condition. As used herein, "preventing" means preventing a condition from occurring in a cell or subject that may be at risk of having the condition, but does not necessarily mean that condition will not eventually develop, or that a subject will not eventually develop a condition. Preventing includes delaying the onset of a condition in a cell or subject.

The term "effective amount" refers to the amount of the compound that will elicit the biological or medical response of a tissue, system, animal or human that is being sought by the researcher, veterinarian, medical doctor or other clinician. Accordingly, a reference to the administration of an effective amount of an agent which elevates SIRT1 activity or SIRT1 expression in endothelial cells of a subject refers to an amount of the agent effective to elevate SIRT1 activity or SIRT1 expression in endothelial cells of the subject.

The agent which elevates SIRT1 activity or expression, such as an $NAD^+$ agonist, may be administered as a pharmaceutical composition comprising the agent, and a pharmaceutically acceptable carrier. A "pharmaceutically acceptable carrier" is a carrier that it is compatible with the other ingredients of the composition and is not deleterious to a subject. The compositions may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: The Science and Practice of Pharmacy, 21st Ed., 2005, Lippincott Williams & Wilkins).

In some embodiments, the carrier is a synthetic (non-naturally occurring) carrier.

The agent which elevates SIRT1 activity or expression may be administered by any means which permits the agent to elevate SIRT1 activity or expression in endothelial cells of tissue of the subject. In embodiments in which the agent is an $NAD^+$ agonist, the agent may be administered orally, such as in the form of tablets, capsules, granules or powders; sublingually; buccally; parenterally, such as by subcutaneous, intravenous, intramuscular, intra(trans)dermal, intraperitoneal, or intracisternal injection or infusion techniques (e.g., as sterile injectable aqueous or non-aqueous solutions or suspensions); nasally such as by inhalation spray or insufflation; in dosage unit formulations containing non-toxic, pharmaceutically acceptable vehicles or diluents. The agent may, for example, be administered in a form suitable for immediate release or extended release. Immediate release or extended release may be achieved by the use of suitable pharmaceutical compositions comprising the agent. Typically, the agent which elevates SIRT1 activity or expression is administered orally.

The pharmaceutical compositions for administration may conveniently be presented in dosage unit form and may be prepared by any of the methods well known in the art of pharmacy. These methods generally include the step of bringing the agent into association with the carrier which constitutes one or more accessory ingredients. In general, the pharmaceutical compositions are prepared by uniformly and intimately bringing the compound into association with a liquid carrier or a finely divided solid carrier or both, and then, if necessary, shaping the product into the desired formulation. In the pharmaceutical composition the active compound is included in an amount sufficient to produce the desired effect. As used herein, the term "composition" is intended to encompass a product comprising the specified ingredients in the specified amounts, as well as any product which results, directly or indirectly, from combination of the specified ingredients in the specified amounts.

The pharmaceutical compositions may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents such as sweetening agents, flavouring agents, colouring agents and preserving agents, e.g. to provide pharmaceutically stable and palatable preparations. Tablets containing one or more $NAD^+$ agonist, may be prepared in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the agent which elevates SIRT1 activity or expression is mixed with an inert solid diluent, for example, calcium carbonate, calcium phosphate or kaolin, or as soft gelatin capsules wherein the agent is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the agent which elevates SIRT1 activity or expression in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavouring and colouring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

The agent which elevates SIRT1 activity or expression can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilizers, preservatives, excipients and the like. The preferred lipids are the phospholipids and phosphatidyl cholines, both natural and synthetic. Methods to form liposomes are known in the art.

The agent which elevates SIRT1 activity or expression can also be administered in the form of a crystalline $NAD^+$ precursor for superior stabilization and purity.

In various embodiments, there is provided a pharmaceutical composition comprising:

(a) NMN or a pharmaceutically acceptable salt thereof;
(b) NR or a pharmaceutically acceptable salt thereof;
(c) NAAD or a pharmaceutically acceptable salt thereof;
(d) NaMN or a pharmaceutically acceptable salt thereof;
(e) NaR or a pharmaceutically acceptable salt thereof;
(f) NMN or a pharmaceutically acceptable salt thereof and sodium hydrosulfide or a pharmaceutically acceptable salt thereof;
(g) NMN or a pharmaceutically acceptable salt thereof and GYY4137 or a pharmaceutically acceptable salt thereof;
(h) NR or a pharmaceutically acceptable salt thereof and sodium hydrosulfide or a pharmaceutically acceptable salt thereof;
(i) NR or a pharmaceutically acceptable salt thereof and GYY4137 or a pharmaceutically acceptable salt thereof;
(j) NAAD or a pharmaceutically acceptable salt thereof and sodium hydrosulfide or a pharmaceutically acceptable salt thereof;
(k) NAAD or a pharmaceutically acceptable salt thereof and GYY4137 or a pharmaceutically acceptable salt thereof;
(l) NaMN or a pharmaceutically acceptable salt thereof and sodium hydrosulfide or a pharmaceutically acceptable salt thereof;
(m) NaMN or a pharmaceutically acceptable salt thereof and GYY4137 or a pharmaceutically acceptable salt thereof;
(n) NaR or a pharmaceutically acceptable salt thereof and sodium hydrosulfide or a pharmaceutically acceptable salt thereof; or
(o) NaR or a pharmaceutically acceptable salt thereof and GYY4137 or a pharmaceutically acceptable salt thereof.

A further aspect provides an exercise mimetic comprising an $NAD^+$ agonist, and optionally a $H_2S$ precursor.

Another aspect provides an exercise mimetic comprising an $NAD^+$ precursor, and optionally a $H_2S$ precursor.

As used herein, an "exercise mimetic" is an agent which mimics one or more physiological effects associated with exercise.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, the rate of excretion, drug combinations, and the severity of the particular condition.

Also provided is an article of manufacture and a kit, comprising a container comprising an $NAD^+$ agonist. The container may be simply be a bottle comprising the $NAD^+$ agonist in oral dosage form, each dosage form comprising a unit dose of the $NAD^+$ agonist. For example, apigenin in an amount for instance from about 100 mg to 750 mg, or NMN in an amount from about 100 mg to 750 mg and NaHS in an amount of from about 100 mg to 750 mg. The kit will further comprise printed instructions. The article of manufacture will comprise a label or the like, indicating treatment of a subject according to the present method. In one form, the article of manufacture may be a container comprising the $NAD^+$ agonist in a form for topical dosage. For example, the $NAD^+$ agonist may be in the form of a cream in a disposable container such as a tube or bottle.

The inventors also envisage that in some circumstances, reducing the vascular density can be advantageous, such as in meats in which white-ness is desirable, such as veal.

Accordingly, in one aspect, there is provided a method of enhancing veal white-ness, comprising administration to an animal an effective amount of an agent which reduces $NAD^+$ or SIRT1 activity or SIRT1 protein levels.

As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

All publications mentioned in this specification are herein incorporated by reference. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In order to exemplify the nature of the present invention such that it may be more clearly understood, the following non-limiting examples are provided.

EXAMPLES

In this study, we tested whether a decline in SIRT1 in endothelial cells is a major reason why blood flow in muscle and endurance are reduced with age, and whether such effects of aging can be reversed.

Experimental Procedures

Mice and Drinking Water Supplementation

SIRT1-iKO, SIRT1-Tg and SIRT1$^{STOP}$ mice were described previously (Firestein et al., 2008, PLoS One 3, e2020; Price et al., 2012, Cell Metab 15, 675-690). Tie2Cre and Sirt1$^{flox/flox}$ mice were purchased from Jackson Laboratory (Bar Harbor, ME). MCK-PGC-1α and MyogCre mice were gifts from Dr. Bruce Spiegelman (Dana Farber Cancer Center, MA) and Dr. Eric N. Olson (UT Southwestern, Dallas, TX), respectively. mT-STOP$^{flox/flox}$, Gfp mouse was generated in house by E.O.W., which consists of an allele driven by ubiquitous actin B promoter, which has loxP sites flanking membrane-targeted tandem dimer Tomato (mT) and transcriptional STOP cassette, followed by a GFP coding sequence. Wild-type C57Bl/6J mice for the NMN and NaHS experiments were purchased from Australian BioResources (Moss Vale, NSW). SIRT1-iKO mice were fed tamoxifen (360 mg/kg) diet for five weeks to elicit whole-body SIRT1 exon 4 excision as described previously (Price et al., 2012). NMN (400 mg/kg, Bontac Bio-Engineering, China) and NaHS (20 mg/kg, Sigma) and/or GYY4137 (20 mg/kg/day, Cayman Chemical) were administered in drinking water. NMN stock was changed twice per week and NaHS/GYY4137 was supplemented daily. Axitinib (30 mg/kg/day) was given via food and changed daily.

Mice were fed standard rodent chow and housed under a 12 h light/12 h dark cycle, with lights on at 7 a.m., and lights off at 7 p.m. All experiments were performed according to procedures approved by UNSW Animal Care and Ethics Committee (University of New South Wales, Sydney, Australia), MIT's Committee on Animal Care (Massachusetts Institute of Technology, Cambridge, MA) and Institutional Animal Care and Use Committees (Beth Israel Deaconess Medical Center and Harvard Center for Comparative Medicine, Boston, MA).

Retro-Orbital Administration of Lentivirus

Lentiviral particles were concentrated by ultracentrifugation (cite) and viral titer was determined by (cite kit) and injected at 1×10$^{10}$ TU/mouse carrying SIRT1 or NT miRNAs to 20-mo old WT C57BL/6J mice (NIA) via retro-orbital injection. Mice received two consecutive injections behind alternate eyes two days apart. 10 days post final injection, mice were assigned to different treatment groups.

Glucose, Lactate, VEGF and Creatinine Measurements

Mice were fasted for 6 h and blood glucose levels were measured by tail bleed (Accu Check Performa, Roche). Blood lactate was measured before and immediately after treadmill exercise training for 20 minutes at 15 meters/minute by tail bleed (Accutrend Plus, Roche). For VEGF analysis, whole blood was drawn from the retroorbital sinus under brief isoflurane anesthesia. The serum was collected and assayed for VEGF expression by ELISA (Eve Technologies, Canada). Urine was collected after a 2 h fast and analyzed for creatinine levels using a colorimetric assay kit (Cayman chemical, US) as per manufacturer's protocol.

Treadmill and Rotarod Tests

Endurance testing. Treadmill tests were carried out on a 1050-RM Exer 3/6 Open Treadmill (Columbus Instruments, OH). Mice were acclimatized to the treadmill system for 3 days prior to endurance testing by running at 10-15 m/min for 20 min. In low intensity endurance testing, the speed started at 5 m/min for 5 min (warm up), and then the speed was increased by 1 every minute until 21 m/min and kept constant. In high intensity endurance testing, the speed started at 13 m/min for 5 min (warm up) at 5° inclination, and then the speed was increased by 1 every minute until 20 m/min and kept constant for 20 min. Every 20 min, the speed was increased by 5 m/min and held constant for 20 min. Mice were considered exhausted when they sat on the shocker plate for more than 10 sec without attempting to reinitiate running.

Exercise Training

Mice were acclimatized to the treadmill system for 3 days prior to the start of exercise training by running at 10 m/min for 20 min. The animals that were successfully acclimatized were then subjected to running at 15-20 m/min at 5° inclination for 30 minutes once daily for one month.

Rotarod Test

Motor coordination was assessed using the rotarod test as previously described (Mersmann et al., 2011, Plos One 6, e20336). In short, mice were acclimatized with the apparatus (Ugo Basile, Comerio, Italy) for 3 days in three trials lasting 2 min each at a constant speed of 5 rpm. On the 4$^{th}$ day, the animals were subjected to three trials on the accelerating roller (4-40 rpm in 4 min) and the time that the mice remained was recorded.

Hindlimb Ischemia

The effect of NMN in ischemia-induced vessel formation was assessed in a murine model of hindlimb ischemia using SIRT1-iKO and WT mice according to the published protocol (Limbourg et al., 2009, Nat Protoc 4, 1737-1746). Treatment of animals with NMN (500 mg/kg/day) via drinking water started one week prior to femoral ligation and was continued until the end of the experiment. The blood flow in the ischemic limb was measured using contrast-enhanced ultrasound imaging, 20 days after the surgery.

In Vivo Imaging

Optoacoustic imaging. An MSOT inVision 256-TF small animal imaging system (iThera Medical GmbH, Munich, Germany) was used (Morscher et al., 2014, Photoacoustics 2, 103-110). Mice were anesthetized with isoflurane (1.5-2%, 500 ml $O_2$/min), and body portion below chest area was shaved using depilatory cream. The animals were then placed horizontally in the imaging chamber and three-dimensional scanning of the lower portion was performed as per manufacture's protocol. Briefly, a tunable optical parametric oscillator (OPO) pumped by an Nd:YAG laser provided excitation pulses with a duration of 9 ns at wavelengths from 680 nm to 980 nm at a repetition rate of 10 Hz with a wavelength tuning speed of 10 ms and a peak pulse energy of 100 mJ at 730 nm. Ten arms of a fiber bundle provided even illumination of a ring-shaped light strip of approx. 8 mm width. For ultrasound detection, 256 toroidally focused ultrasound transducers with a center frequency of 5 MHz (60% bandwidth), organized in a concave array of 270° angular coverage and a radius of curvature of 4 cm, were used.

Contrast-Enhanced Ultrasound

Mice were anesthetized with isoflurane (1.5-2%, 500 ml 02/min), hindlimbs were shaved using depilatory cream and a 27-gauge catheter was placed into each mouse's tail and kept in place with surgical tape. Each mouse was placed in a supine position on a platform heated to 38° C. with each paw taped to a surface electrode to monitor ECG, heart rate, and respiratory rate. Contrast-enhanced ultrasound (CEU) (Vevo 2100, Visualsonics, Canada) was performed at an imaging frequency of 18 MHz. The probe was placed on the medial side of the leg to image the lower hindlimb in a sagittal plane. A bolus injection of microbubbles (Vevo MicroMarker, Canada) were injected through the tail vein catheter according to the manufacturer's instructions. A cine loop was recorded at a frame rate of 20 frames/s for a total of 1,000 frames. Curve fit analysis was used to measure echo power over time. The difference in maximum and minimum video intensity was determined as the peak enhancement and was the variable used to determine muscle perfusion.

Cardiac ultrasound. Parasternal short-axis M-mode images were acquired using the Vevo 2100 system (Visualsonics) as previously described (Respress and Wehrens, 2010). Mice were anesthetized with 1-2% isoflurane, and heart rate was maintained between 450 and 500 beats/min for all measurements.

Metabolic Measurements and Body Composition

Metabolic chambers (CLAMS™, Columbus Instruments, Columbus, OH) were used to perform whole-body measurements of metabolic function. Following acclimatization to the metabolic chambers, individually housed mice were monitored continuously over 48 h to determine oxygen consumption, carbon dioxide production, respiratory exchange ratio, energy expenditure, food intake, water intake and activity. Body composition (fat mass, lean mass, and total body water) was measured by EchoMRI (Echo MRI™ 900).

Analysis of CD31+ cells in muscle: Skeletal muscle was dissected, then digested with collagenase/dispase and filtered through 40-micron filter. The cell suspension was incubated with APC-conjugated anti-mouse CD31 antibody (Biolegend) and analyzed by flow cytometry (BD LSR II, BD Biosciences).

Permeabilized Fiber Respiration

Permeabilized fibres were prepared according to published protocols with some modifications (Kuznetsov et al., 2008, Nat Protoc 3, 965-976). Briefly, soleus and extensor digitorum longus (EDL) muscles were dissected tendon-to-tendon into ice-cold isolation buffer A (Kuznetsov et al., 2008, Nat Protoc 3, 965-976) and fibers were prepared immediately for high resolution respirometry. Fiber bundles (~3 mg wet weight) were treated with saponin 50 μg/ml for 20 min at 4° C. and subsequently washed in cold respiration medium B (0.5 mM EGTA, 3 mM MgCl2.6H2O, 20 mM taurine, 10 mM KH2PO4, 20 mM HEPES, 0.1% BSA, 15 mM potassium-lactobionate, 110 mM mannitol, 0.3 mM dithiothreitol, pH 7.1). Mitochondrial respiratory chain function was analyzed on a clark-type electrode (Rank Brothers Ltd, Cambridge, UK) in situ in respiration medium B at 37° C. according to published protocols (Kuznetsov et al., 2008, Nat Protoc 3, 965-976) with the sequential addition of 10 mM glutamate and 5 mM malate, 2 mM ADP, 0.5 μM rotenone, 10 mM succinate, 5 μM antimycin A, 0.5 mM N,N,N',N'-tetramethyl-pphenylenediamine dihydrochloride (TMPD) and 2 mM ascorbate, 10 μM cytochrome c. Fibers were recovered after polarography and results were expressed as nanomoles of oxygen per minute per milligram of wet weight. Mitochondrial membrane integrity was verified by cytochrome c release test.

Enzyme Activity Assays

Quadriceps muscle was homogenized 1:19 (w/v) in 50 mM Tris-HCl, 1 mM EDTA, 0.1% Triton X-100, pH 7.4. The homogenates were subjected to three freeze-thaw cycles and centrifuged for 10 min at 7,000 g at 4° C. Supernatants were used to determine the activity for citrate synthase (CS) and succinate dehydrogenase (SDH) as described previously (Turner et al., 2009, Diabetes 58, 2547-2554). Cytochrome c oxidase staining of muscle sections was performed according to the published protocol (Ross, 2011, J Vis Exp, e3266). Briefly, 20 μm cryostat sections of quadriceps muscle were incubated with Cytochrome c (0.1 mM, Sigma), catalase (2 μg/mL, Sigma) and 3,3'-diaminobenzidine (DAB, 0.05%, Sigma) in PBS for 40 min at 37° C. The slides were dehydrated through alcohol, cleared in xylene and then mounted with DPX (Grale HDS).

$NAD^+$ Measurements

Levels of $NAD^+$ and NADH levels were measured in EC and muscle homogenates using commercially available kit (NAD-NADH Glo, Promega) according to manufacturer's instructions. Alternatively, $NAD^+$ levels in muscle and liver were measured by assay in-house developed method (Uddin et al., 2016, Front Pharmacol 7, 258). In brief, liver and gastrocnemius samples were homogenized in extraction buffer (10 mM Tris-HCl, 0.5% TritonX-100, 10 mM Nicotinamide, pH7.4) and then centrifuged (12,000×g for 5 min at 4° C.), after which an aliquot of supernatant was taken for protein quantification. After phenol:chloroform:isoamylalcohol (25:24:1) and chloroform extractions the supernatant was separated in two aliquots. One was used to measure total NAD. The other aliquot was acidified with HCl, and then neutralized with NaOH on ice to quantify $NAD^+$. Samples were mixed in a 96-well plate samples were mixed with alcohol dehydrogenase (ADH) at room temperature. Total NADH and $NAD^+$ were quantified using a Bio-Rad Imark microplate reader.

Cell Cultures, RNAi Knockdown and Adenoviral Infection

Pooled human umbilical vein endothelial cells (HUVECs) and human aortic endothelial cells (HAECs) were purchased from Lonza, Australia and grown in EGM-2 (Lonza, Australia) containing vascular endothelial growth factor (VEGF), basic fibroblast growth factor (bFGF), insulin-like growth factor-1 (IGF-1), epidermal growth factor (EGF), hydrocortisone, heparin, gentamicin sulfate amphotericin, 1% ascorbic acid and 2% fetal bovine serum (FBS) at 37° C. in a humidified atmosphere with 5% $CO_2$. MS1 cells (ATCC) were grown in high glucose DMEM supplemented with 10% FBS, 100 IU/mL penicillin, and 100 mg/mL streptomycin at 37° C. in a humidified incubator with 5% $CO_2$. Primary mouse ECs from lung (MLECs) and muscle were isolated and purified according to published protocol (van Beijnum et al., 2008, Nat Protoc 3, 1085-1091) with modifications and using EasySep selection kit (Stem Cell Technologies). ECs were cultured in EGM-2 media (Lonza) at 37° C. with 3% $O_2$ and 5% $CO_2$. C2C12 and HEK293T cells were grown in DMEM (Life Technologies) supplemented with 10% FBS at 37° C. with 5% $CO_2$. C2C12 myoblasts transfected with adenovirus expressing PGC-1α were differentiated into myotubes and then conditioned media (CM) was collected for 48 hrs.

HUVECs and HAECs were transfected with SIRT1 siRNA (L-003540-00-0005, GE Dharmacon) and non-targeting scrambled (Scr) siRNA (D-001810-01-05, GE Dharmacon) using Dharmafect 4 (GE Dharmacon) as per manufacturer's protocol. MS1 cells were transfected with esiRNA targeting murine SIRT1 (000411, Sigma-Aldrich) using Lipofectamine 2000 (Life Technologies). HUVECs were infected with SIRT1 or GFP adenovirus (ABM Inc., Canada) as per manufacturer's protocol. Cells were used in the assays 48 h after transfection.

To silence SIRT1, SIRT3 and SIRT6 expression, ECs were transfected with a validated pool of siRNA duplexes (ON-Targetplus SMART pool, Dharmacon) using Dharmafect 4 transfection reagent as per manufacturer's protocol. ON-TARGETplus Non-Targeting control (NT) siRNA was used as a negative control. SIRT1 silencing was achieved using pLKO.1 shRNAs as described before (Gomes et al., 2013, Cell 155, 1624-1638). pLKO.1 endoding a scrambled shRNA was used as a negative control. Adenoviruses expressing human SIRT1 or GFP were purchased from Abmgood Inc. and ECs were transduced according to manufacturer's protocol.

Dll4 and VEGF stimulation of ECs. The ECs to be stimulated were serum-starved overnight and transferred to media containing VEGF (50 ng/mL) or to Dll4-coated plates, and then incubated for indicated time. Dll4 coating was performed as described before (Guarani et al., 2011, Nature 473, 234-238). Lyophilized recombinant Dll4 (R&D Systems) were reconstituted in PBS containing 0.1% bovine serum albumin. The culture dishes were coated with Dll4 (0.5 μg/mL) in 0.1 gelatin solution for 1 hr at 37° C.

Construction of Lentiviral miRNA Vectors

The lentiviruses expressing NT or SIRT1 miRNAs were constructed as described (Zhang et al., 2013, FASEB J 27, 4041-4058). Lenti-VE-Cad miRNA plasmid was a generous gift from Dr. Patty J. Lee (Yale University). Pre-miRNA sequences targeting mouse SIRT1 open reading frame (GenBank accession no. NM 019812.3) were designed using the BLOCK-iT RNAi designer tool (Invitrogen). Oligos corresponding to miRNAs were annealed and ligated into pcDNA6.2-GW/EmGFP-miR vector (Invitrogen) according to manufacturer's instructions. pcDNA6.2-GW/EmGFP-miR-neg control plasmid was used as a control. The fragments carrying EmGFP and miRNA sequences were amplified by polymerase chain reaction (PCR) using the primers: sense, 5'-AGGCGCGCCTGGCTAACTAGAGAAC-3', and antisense, 5'-GAATTCTATCTCGAGTGCGGC-3'. The amplified fragments were digested with AscI and EcoRI, and then inserted into the AscI and EcoRI sites of Lenti-VE-Cad miRNA plasmid to generate lentiviral plasmids expressing NT or SIRT1 miRNAs. All restriction endonucleases were purchased from New England Biolabs.

Lentivirus Production

The lentiviral particles were produced according to the protocol described by Addgene. Briefly, psPAX2 (gift from Didier Trono, Addgene plasmid #12260), pMD2.G (gift from Didier Trono, Addgene plasmid #12259) and vector plasmids were cotransfected into 293T cells using FuGENE HD transfection reagent (Promega). At 48 hrs post-transfection, virus was harvested and concentrated in PBS by ultracentrifugation to ~$1\times10^{12}$ transducing units (TU)/mL. The lentiviral titration kit was purchased from Takara Bio Inc. and used according to the manufacturer's instructions.

Cell Proliferation Assay

ECs (0.1×105 cells) were seeded in a 48-well plate and incubated with PBS (vehicle) or NMN (500 μM) in complete growth medium for 48 h. At the end of the incubation time, the cells were harvested and resuspended in Opti-MEM medium. Cell number was determined using flow cytometry (FACSCanto II Analyzer, BD Biosciences, USA).

Tube Formation Assay

Formation of tube networks was assessed as described before (Borradaile and Pickering, 2009, Aging Cell 8, 100-112). ECs were seeded at 10,000 cells per well in a 24-well plate (Corning) coated with 150 μL Cultrex reduced growth factor basement membrane extract (Trevigen). The cells were supplemented with C2C12 CM or EBM-2 medium containing VEGF (30 ng/mL) or FGF (30 ng/mL). NMN (0.5 mM) and NaHS (0.1 mM) were added to the media wherever mentioned. Following an 18 h-incubation, resulting tube networks were analyzed by light microscopy (Nikon Eclipse TiE). For tube formation assays with $H_2O_2$ treatment, cells were incubated with 150 μM $H_2O_2$ for 1 h before seeding and imaged after 10 h-incubation. The number of branch points and total length of tubule networks were quantified by ImageJ software.

Spheroid Assay

ECs spheroids were generated as described previously (Korff and Augustin, 1998, J Cell Biol 143, 1341-1352). ECs (1000 cells per spheroid) were suspended in EGM-2 medium containing 20% methocel (viscosity: 4000 cps, Sigma) and seeded in non-adherent round-bottom 96-well plates (Sigma). Under these conditions all suspended cells contributed to the formation of a single spheroid. The spheroids were harvested after 24 h embedded into collagen gels. Sprouting was initiated by adding C2C12 CM or EBM-2 medium containing VEGF (50 ng/mL). NMN (0.5 mM), NaHS (0.1 mM), DAPT (20 μM, Cayman Chemical) or SU5416 (10 μM, Sigma) were added to the media wherever mentioned. Angiogenic activity was quantified by measuring the sprout length that had grown out of each spheroid analyzing 8-10 spheroids per group.

Aortic Ring Assay

Aortic ring assay was performed according to the published protocol (Baker et al., 2012, Nat Protoc 7, 89-104). Briefly, thoracic aortas from mice were excised and transferred to Opti-MEM media. All extraneous fat, tissue and branching vessels were removed with forceps and a scalpel under a dissection microscope. The aortas were cut into ~0.5 mm wide rings and serum starved overnight by incubating in Opti-MEM at 37° C./5% $CO_2$. Next day, each aortic ring was embedded in 50 μL collagen matrix in a 96-well plate and incubated at 37° C./5% $CO_2$ for 1 h. After embedding, the vessel sprouting was stimulated by supplementing the rings with 150 μL of Opti-MEM culture containing FBS (2.5%), with or without VEGF (30 ng/mL), or FGF (30 ng/mL) and incubating at 37° C./5% $CO_2$ for 7 days. NMN (500 μM) was added to the media wherever mentioned and replaced every 3 days. The resulting sprouts were stained with BS1 lectin-FITC (Sigma) and imaged using fluorescence microscope. The number and total area of sprouts originating from aortic rings were quantified by ImageJ software.

Cell Apoptosis Assay

HUVECs were treated with PBS (vehicle), NaHS (100 μM), NMN (500 μM) or NMN+NaHS for 6 h, followed by exposure to $H_2O_2$ (600 μM) for another 4 h. After treatments, the number of apoptotic cells was determined using Annexin V-FITC apoptosis detection kit (eBioscience) as per manufacturer's instructions. Briefly, cells were collected by trypsinization and centrifugation at 1500 rpm for 5 minutes, followed by washing cell pellet twice with cold PBS and resuspending cell pellet in 1× Annexin-binding buffer. Then, 5 μL of Annexin-V FITC was added to 195 μL of cell suspension and incubated at room temperature for 15 min in the dark. After the incubation, cells were centrifuged, resuspended in 195 μL of 1× Annexin-binding buffer and then 5 μL of propidium iodide working solution was added. After mixing gently, the fluorescence intensity was detected with a flow cytometry (FACSCanto II Analyzer, BD Biosciences) at emission at 530 nm and 575 nm and excitation at 488 nm. Annexin-V and PI staining were detected with a flow cytometry (FACSCanto II Analyzer, BD Biosciences) at emission at 530 nm and 575 nm and excitation at 488 run.

Wound Scratch Assay

ECs were cultured until forming a confluent monolayer and a scratch was made using a 200 μL pipette tip. Then the cells were allowed to migrate+/−NaHS (0.1 mM) and +/−NMN (0.5 mM) in EGM-2 medium for 6 hrs. Images were taken at the same location using a brightfield inverted microscope (Olympus 2467) every 2 h. The area of gap closure was calculated using ImageJ software. In some experiments, HUVECs were transduced with Scr or SIRT1 siRNA and cultured until forming a confluent monolayer. The cells were exposed to $H_2O_2$ (150 μM) for 1 h and a scratch was made using a 200 μL pipette tip. Then the cells were allowed to migrate with PBS (vehicle), NaHS (100 μM) and/or NMN (500 μM) in EGM-2 medium for 6 h. Images were taken at the same location using a brightfield inverted microscope (Olympus 2467) every 2 h. The area of gap closure was calculated using ImageJ software.

Transwell Migration Assay

Chemotaxis assays were performed as described previously (Oommen et al., 2011). ECs were serum-starved in DMEM supplemented with 0.2% FBS overnight, and then plated at a density of 25,000-50,000 cells per insert in the upper compartment of Transwell inserts (8.0 μm pore size) (Corning Life Sciences) which had been pre-warmed with DMEM with 0.2% FBS at 37° C. for 2 h. At 30 min after plating the cells, media in the lower compartment was replaced with chemoattractant media (either DMEM containing 10 ng/mL VEGF and 0.2% FBS, or DMEM with 1% FBS or conditioned media collected from differentiated C2C12 myotubes transfected with adenoviral expression constructs for PGC-1α). HUEVCs and HAECs were stimulated with EBM-2 media (Lonza) with 0.2% FBS containing VEGF (50 ng/mL, Invitrogen) or FGF (50 ng/mL, Invitrogen). NMN (0.5 mM, Bontac Bio-Engineering, China) and NaHS (0.1 mM, Sigma) were added to the chemo-attractant media wherever mentioned. Migration of ECs to the lower compartment of the Transwell inserts was measured after 18 h-24 hrs. Migrated ECs were fixed with 4% paraformaldehyde in PBS for 20 min at room temperature, and cells remaining in the upper compartment were removed using cotton swabs. Transwell membranes were blocked with 5% BSA in TBST and then stained with phallioidin-FITC (eBioscience) in TBST for 4 h to visualize filamentous actin. Transwell inserts were washed 3× in PBST and mounted onto slides with DAPI mounting medium (Vector Labs). Images were acquired using a fluorescence microscope (Olympus, Waltham, MA). Quantification of the number of migrated cells was performed using ImageJ software on 4 random fields of each Transwell membrane.

HUVECs were plated at a density of 50,000 cells per insert in the upper compartment of Transwell inserts (8.0 μm pore size) (Corning Life Sciences) which had been prewarmed with EBM-2 with 0.2% FBS at 37° C. for 1 h. After 30 min, media in the lower compartment was replaced with EBM-2 media containing NMN (500 μM) and/or VEGF (30 ng/mL). Migration of cells was measured after 6 h. The migrated cells were processed and analyzed as described above.

Seahorse Analysis

Oxygen consumption rates were measured in accordance with manufacturer instructions using Seahorse XF96 analyzer (Seahorse Bioscience). Briefly, 40,000 HUVECs were plated onto XF96 plates and incubated overnight at 37° C./5% $CO_2$. Next day, the media was replaced with XF assay media (DMEM), supplemented with glucose (1 g/L), glutamate (2 mM) and pyruvate (1 mM) and the pH was adjusted to 7.4. NaHS (100 μM) and/or NMN (500 μM) were added at the start of the experiment. Oxygen consumption measurements were made approximately every 8 minutes under basal conditions, and after the addition of oligomycin (1 μM). Experiments were replicated in six wells and averaged for each experimental condition.

Immunofluorescence

Freshly isolated whole quadriceps and gastrocnemius muscle samples were mounted in OCT compound (Tissue-Tek), placed in an isopentane bath and slowly cooled in liquid nitrogen. Transverse sections at 20 μm-thickness were sectioned on a cryostat (Leica). The sections were fixed in pre-cooled acetone (−20° C.) for 10 min and washed with PBS. Slides were then blocked in normal goat serum and 5% Blocking Reagent (PerkinElmer) in PBST (PBS with 0.1% Triton-X) for 1 h at room temperature, and then incubated with anti-CD31 (ab56299, Abcam) and anti-Laminin (L9393, Sigma), GFP (ab6556, Abcam) or SIRT1 (HPA006295, Sigma) antibodies diluted in blocking buffer overnight at 4° C. Slides were washed with PBST and then incubated with anti-rat Alexa Fluor 488-conjugated (Life Technologies) and anti-rabbit Alexa Fluor 594-conjugated (Life Technologies) antibodies diluted to 1:500 in blocking buffer for 2 h at room temperature. Slides were washed again with PBST and mounted with Fluoroshield with DAPI mounting medium (Sigma). Images were acquired using a confocal fluorescence microscope (Nikon A1). Quantification of capillaries and capillary density were performed using ImageJ software. TUNEL staining was performed in muscle sections using in situ BrdU-Red DNA fragmentation (TUNEL) assay kit (Abcam) as per manufacturer's protocol.

H&E (Hematoxylin and Eosin) Staining

After fixation of frozen sections, samples were stained with 0.1% Hematoxylin (Sigma) for 10 min, rinsed with $dH_2O$, stained with Scott's blue solution for 1 min and then washed with $dH_2O$. The sections were then dipped in Eosin for 3 min, dehydrated through alcohol and cleared in xylene. The slides were mounted with DPX (Grale HDS).

PCR Analysis

A small piece of tail or tissue was obtained from SIRT1-iKO and control mice and 50 μL of alkaline lysis reagent (25 mM NaOH, 0.2 mM EDTA, pH 12) was added to each. The samples were incubated at 100° C. for 1 h. After cooling, 50 μL of neutralizing reagent (40 mM Tris-HCl, pH 5) was added to each and mixed. About 2 μL of the supernatant was used for PCR to detect the excision of SIRT1 gene using the primers Sir2A6860 (CATGTAATCTCAACCTTGAG) and Sir2A6171 (GCCCATTAAAGCAGTATGTG).

RNA Analysis

Total mRNA was isolated from cells and tissues using TRIzol (Life Technologies). cDNAs were synthesized from 1 μg of total RNA using M-MLV reverse transcriptase (Biorad). qPCR was performed with LightCycler 48 SYBR Green I Mastermix (Roche) using the LightCycler 480 System (Roche) according to the manufacturer's instructions. Relative mRNA expression levels were calculated using the ΔΔCt method. The forward and reverse primer sequences used in qPCR amplification reactions are displayed in Table 1.

TABLE 1

Primer sequences used in qPCR amplification reactions

| Gene | Forward primer | Reverse primer |
|---|---|---|
| Human SIRT1 | TAGCCTT GTCAGAT AAGGAAG GA (SEQ ID NO: 18) | ACAGCTT CACAGTC AACTTTG T (SEQ ID NO: 19) |

TABLE 1-continued

Primer sequences used in qPCR amplification reactions

| Gene | Forward primer | Reverse primer |
|---|---|---|
| Murine SIRT1 | TGTGACA GAGAGAT GGCTGG (SEQ ID NO: 20) | ATCTTCC AGATCCT CAAGCG (SEQ ID NO: 21) |
| Human VEGF | AGCTGCG CTGATAG ACATCC (SEQ ID NO: 22) | CTACCTC CACCATG CCAAGT (SEQ ID NO: 23) |
| Murine VEGF | CTGTAAC GATGAAG CCCTGGA G (SEQ ID NO: 24) | TGGTGAG GTTTGAT CCGCAT (SEQ ID NO: 25) |
| Murine MHC-I | GCCAACT ATGCTGG AGCTGAT GCCC (SEQ ID NO: 26) | GGTGCGT GGAGCGC AAGTTTG TCATAAG (SEQ ID NO: 27) |
| Murine MHC-IIa | GGCACAA ACTGCTG AAGCAGA GGC (SEQ ID NO: 28) | GGTGCTC CTGAGGT TGGTCAT CAGC (SEQ ID NO: 29) |
| Murine MHC-IIb | GAGCTAC TGGATGC CAGTGAG CGC (SEQ ID NO: 30) | CTGGACG ATGTCTT CCATCTC TCC (SEQ ID NO: 31) |
| Murine MHC-IIx | GGCAGCA GCAGCTG CGGAAGC AGAGT CTGG (SEQ ID NO: 32) | GAGTGCT CCTCAGA TTGGTCA TTAGC (SEQ ID NO: 33) |
| Murine HPRT | GTTAAGC AGTACAG CCCCAAA (SEQ ID NO: 34) | AGGGCAT ATCCAAC AACAAAC TT (SEQ ID NO: 35) |
| Murine GAPDH | AGGTCGG TGTGAAC GGATTTG (SEQ ID NO: 36) | TGTAGAC CATGTAG TTGAGGT CA (SEQ ID NO: 37) |
| Human HEY1 | AACTGTT GGTGGCC TGAATC (SEQ ID NO: 38) | AATTCTT TGTGTTG CTGGGG (SEQ ID NO: 39) |
| Human HEY2 | TTCAAGG CAGCTCG GTAACT (SEQ ID NO: 40) | GGGCATT TTACTTC CCCAAT (SEQ ID NO: 41) |
| Human HES1 | TCAACAC GACACCG GATAAAC (SEQ ID NO: 42) | GCCGCGA GCTATCT TTCTTCA (SEQ ID NO: 43) |
| Human NRARP | TCAACGT GAACTCG TTCGGG (SEQ ID NO: 44) | ACTTCGC CTTGGTG ATGAGAT (SEQ ID NO: 45) |
| Human NOTCH1 | GCAACAG CTCCTTC CACTTC (SEQ ID NO: 46) | GCCTCAG ACACTTT GAAGCC (SEQ ID NO: 47) |
| Human Actin | GTTGTCG ACGACGA GCG (SEQ ID NO: 48) | GCACAGA GCCTCGC CTT (SEQ ID NO: 49) |
| Human HPRT | ACCCTTT CCAAATC CTCAGC (SEQ ID NO: 50) | GTTATGG CGACCCG CAG (SEQ ID NO: 51) |

Western Blotting

SDS-PAGE and Western blot analysis were performed according to standard procedures and detected with the ECL detection kit (Bio-rad, Australia). For Western blot analysis antibodies directed against SIRT1 (Sigma), SIRT3 (CST), SIRT6 (SantaCruz), eNOS (Cell Signaling Technology or CST), cleaved Notch1 (CST), total OXPHOS cocktail (Abcam), PGC-1α (Millipore), VEGF (Abcam), VEGFR2 (Abcam), phospho-VEGFR2 (Millipore), Actin (Cell Signaling Technology), Tubulin (Sigma), 14-3-3 (Cell Signaling Technology), GAPDH (SantaCruz) were used. Quantification of band intensities by densitometry was carried out using ImageJ software.

Statistical Analysis

Data are presented as means±standard deviations. Statistical significance was performed using twotailed Student's t test, One-way or two-way ANOVA with Bonferroni's Multiple Comparisons Test. Statistical test was performed using GraphPad Prism software. P values of less than 0.05 were considered statistically significant.

Results

Figure 1:
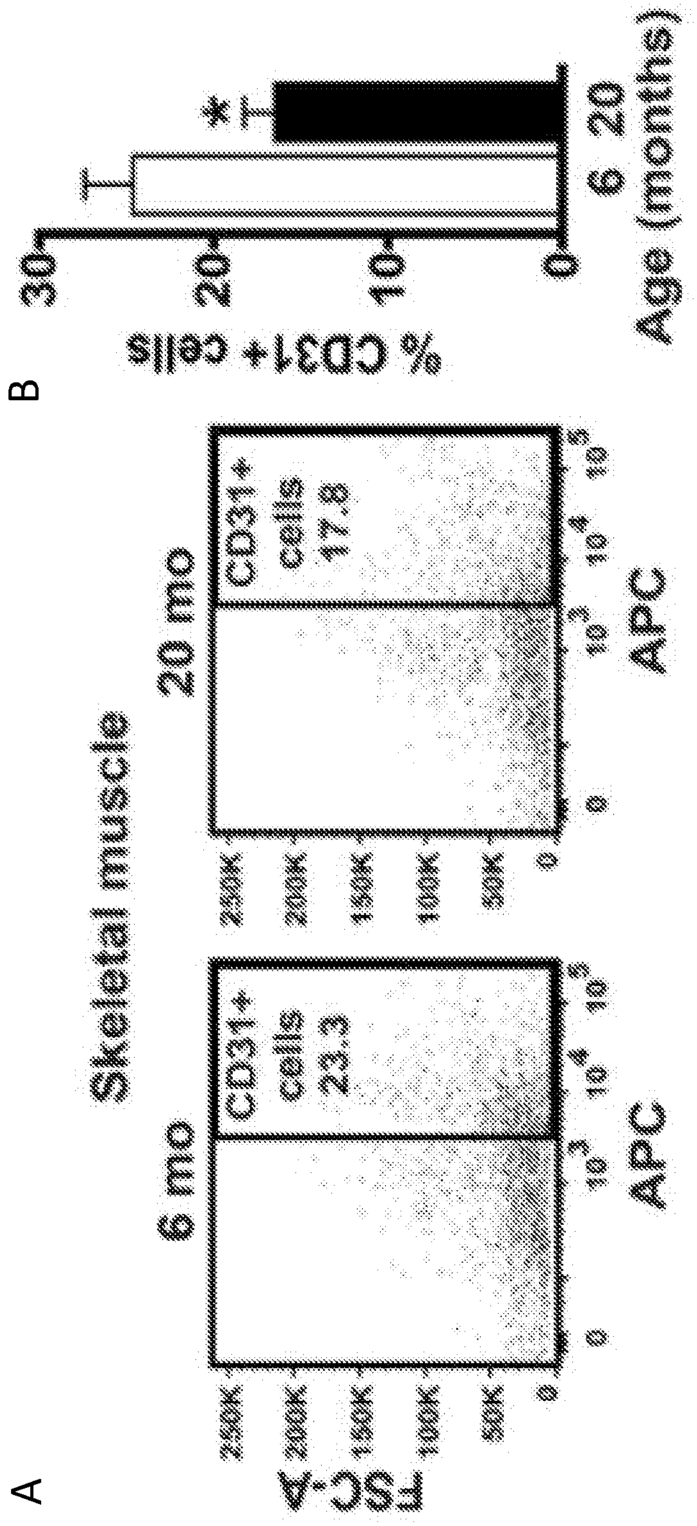
FIG. 1 shows (A) a representative scatter plot of CD31+ endothelial cells in skeletal muscle following collagenase/dispase digestion of skeletal muscle from 6 and 20-month old C57BL/6J wild-type mice and detection of the endothelial cells (ECs) by flow cytometry using APC-conjugated CD31 antibody; and (B) a graph showing the percentage of CD31 positive ECs in skeletal muscle (n=7). Data is expressed as mean±SEM. *p<0.05 by Student's t test.
Figure 2:
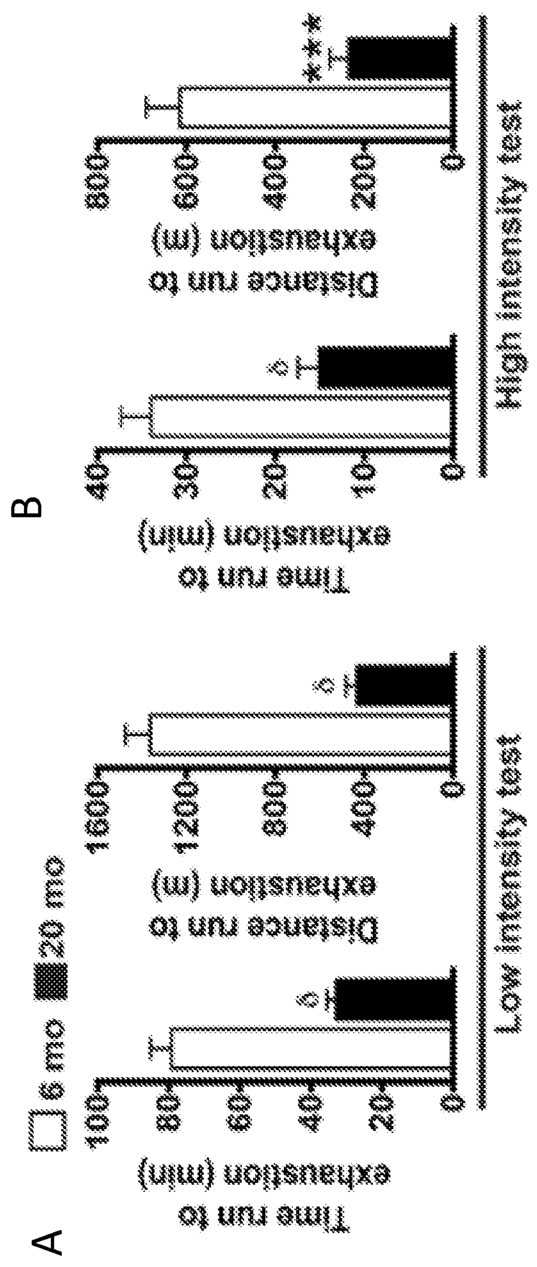
FIG. 2 is a graph showing (A) time run to exhaustion, and (B) distance run to exhaustion, by 6-month and 20-month old mice in low and high intensity treadmill tests (n=11). The mice were trained in a treadmill and their exercise capacity was measured in the two different treadmill tests. Data are expressed as mean±SEM. ***p<0.0005, $^{\delta}$p<0.00005 by Student's t test.
Figure 3:
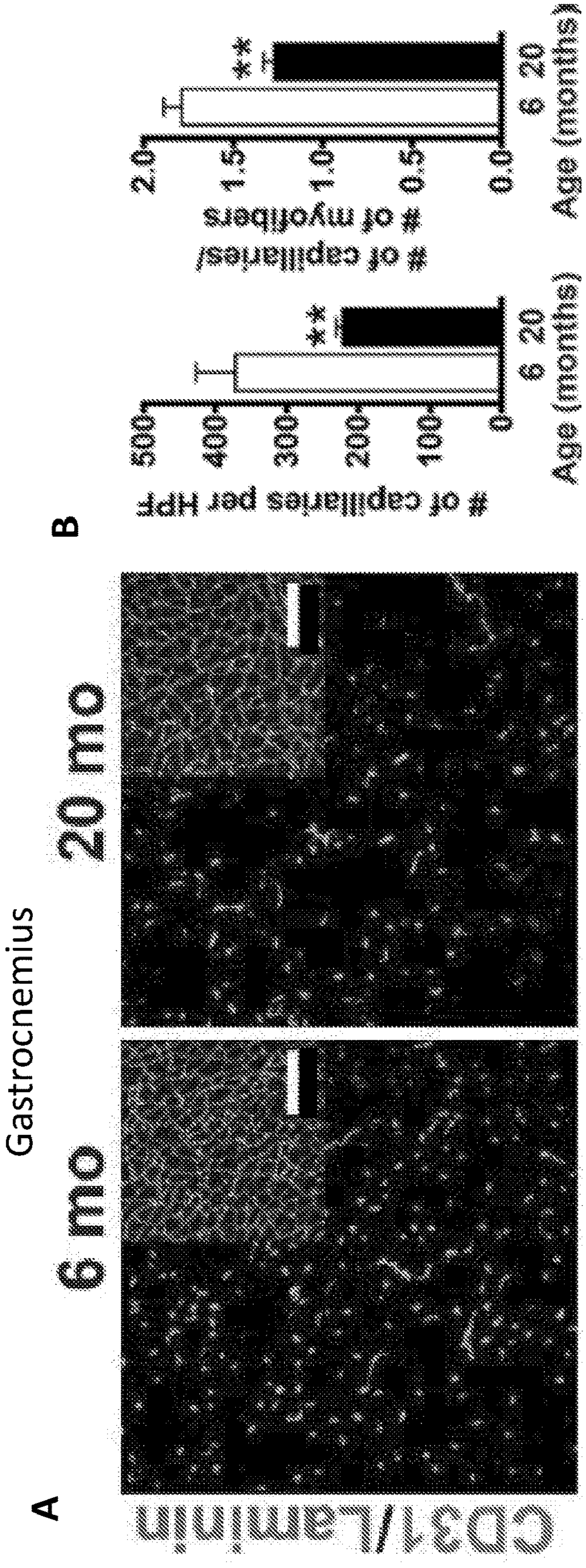
FIG. 3 is (A) is a representative image of traverse cross-sections of gastrocnemius muscle from 6 and 20-month old mice immunostained with CD31 and laminin (inset) antibodies to visualize capillaries and stroma respectively (20× magnification) (white bar=200 μm); (B) is a graph of the number of capillaries per high power field (HPF), and the number of capillaries per number of myofibers ratio (capillary density) (n=7) in the gastrocnemius muscle; (C) is representative images of quadriceps sections (20× magnification) from 6 and 20-month old mice immunostained with CD31 and laminin (inset) antibodies to visualize capillaries and stroma respectively; (D) is a graph of the number of capillaries per high power field (HPF), and the number of capillaries per number of myofibers ratio (capillary density) (n=5) in the quadriceps muscle. Data are expressed as mean±SEM. *$p<0.05$, **$p<0.005$, by Student's t test.
Figure 3:
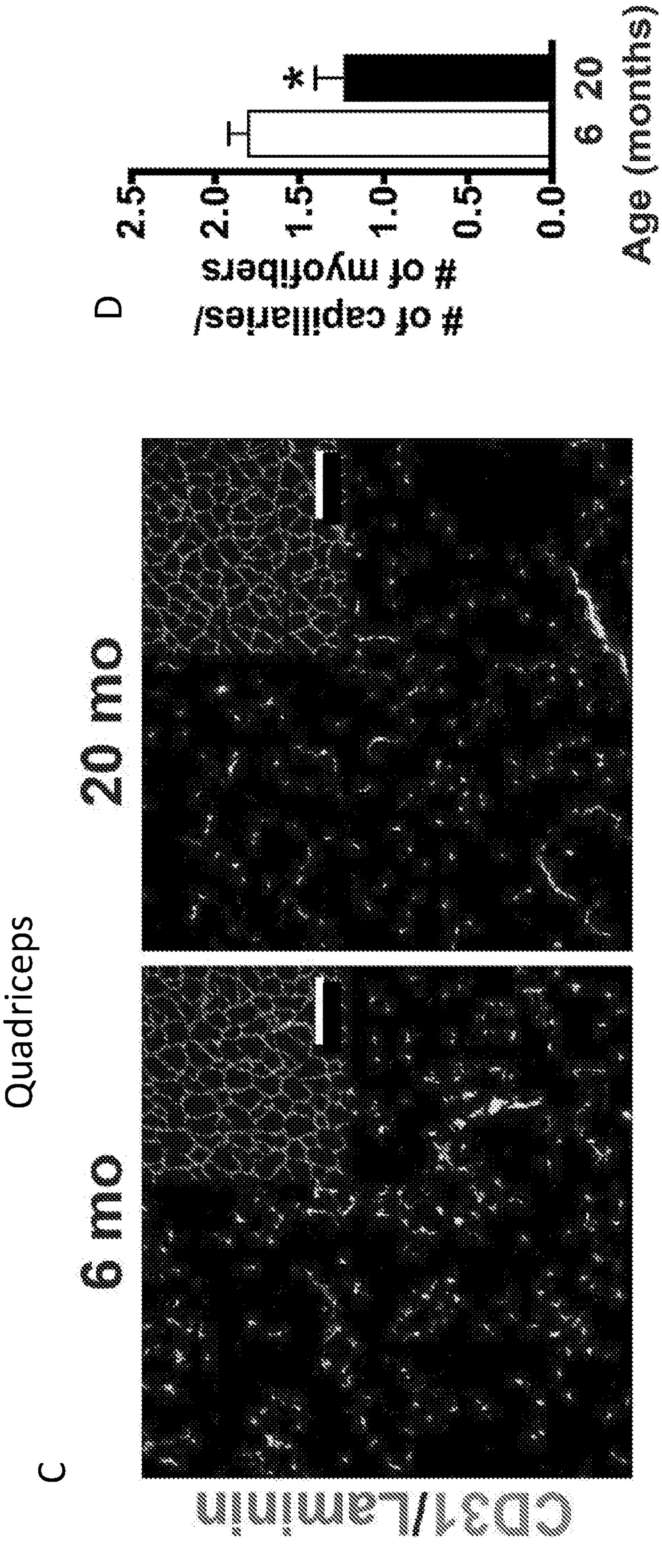

One of the most reliable, yet pernicious aspects of mammalian aging is a decrease in blood flow to skeletal muscle. Consistent with this, the abundance of endothelial cells (ECs) and capillaries in skeletal muscle of 20-month old C57BL/6J mice was significantly lower compared to 6-month olds (FIGS. 1A and 1B) and their exercise capacity, as determined by the time spent and distance covered until exhaustion in treadmill tests, was also lower (FIGS. 2A and 2B). Moreover, capillary numbers and capillary density in gastrocnemius muscle tissue and quadriceps muscle tissue of 20 month old mice was significantly reduced compared to that of 6 month old mice (FIG. 3A-3D)

Figure 5:
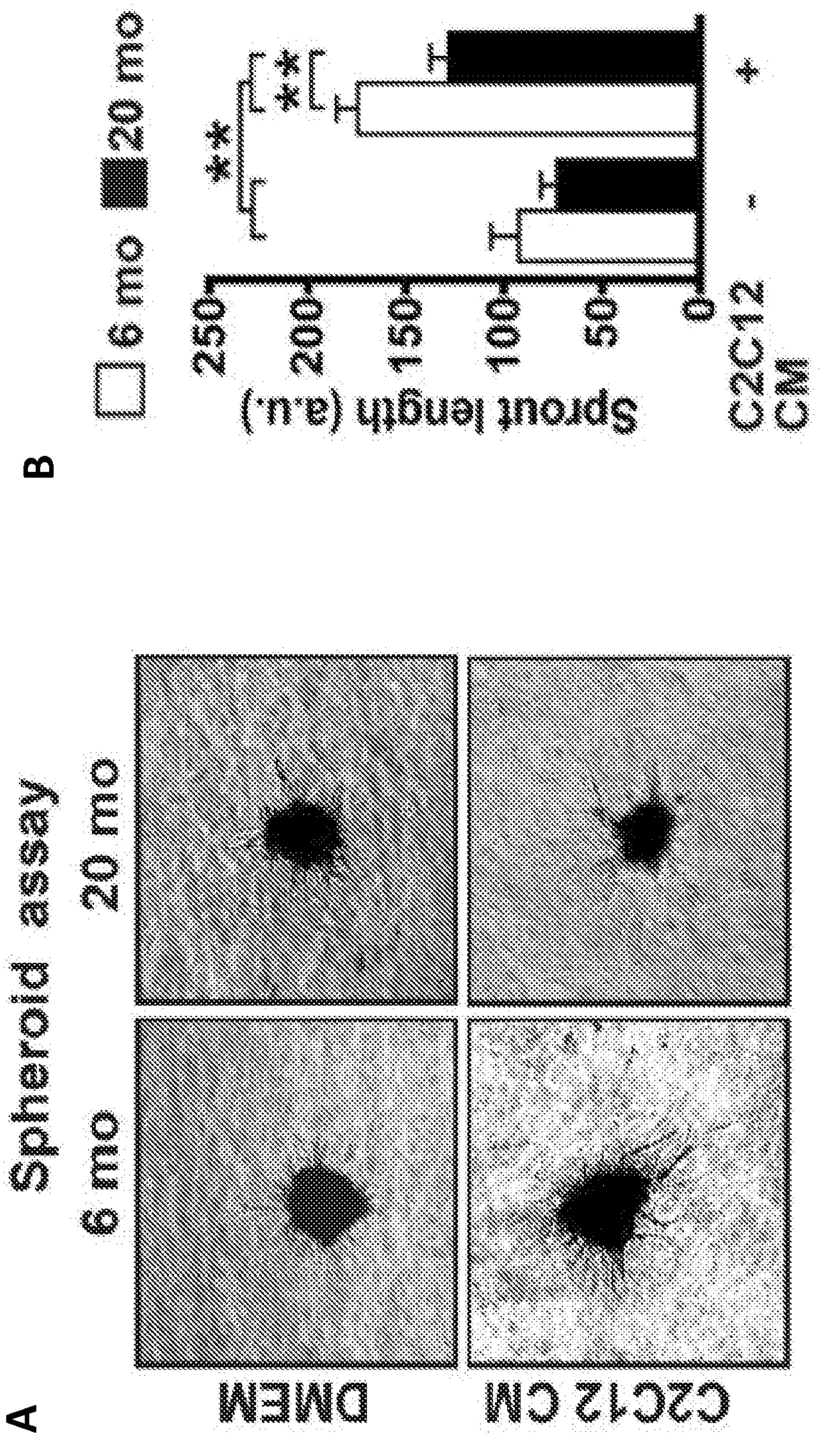
FIG. 5 is (A) representative phase-contrast micrographs (10× magnification) of EC spheroids, and (B) quantification of sprout length of the spheroids+/−C2C12 CM (n=10), in a spheroid assay, in which EC spheroids (1000 cells/spheroid) of MLECs from 6 and 20-month old mice were embedded in a type I collagen matrix and treated with C2C12 CM for 24 hours. Data is expressed as mean±SEM. *$p<0.05$, $p<0.005$, *$p<0.0005$, $^{\delta}p<0.00005$ by two-way ANOVA with Bonferroni's Multiple Comparisons Test.

A possible explanation for the reduced capillary density was impaired angiogenic potential. To test this, a series of in vitro angiogenesis assays were performed on mouse lung endothelial cells (MLECs) from young and old mice. MLECs were cultured in the presence of conditioned media (CM) with angiogenic factors provided by PGC-1α-overexpressing C2C12 myotubes (Arany et al., 2008, Nature 451, 1008-1012). Compared to those from young mice, MLECs from 20-month old mice had reduced migratory capacity (FIG. 4A) and decreased ability to form capillary-like structures, as measured by the number of branch points and tube lengths (FIG. 4B-4D). Similarly, when embedded in collagen gel and stimulated with angiogenic factors, EC spheroids from old MLECs had shorter sprout-like outgrowths invading the gel matrix than those from the young mice (FIGS. 5A and 5B).

Specific Deletion of Endothelial SIRT1 in Mice Mimics the Effect of Aging on Capillary Density and Endurance SIRT1 is an important regulator of angiogenesis during post-natal growth, but whether it is required for vascular maintenance and angiogenesis late in life is not known. To test this, we knocked out and overexpressed SIRT1 in the endothelial cells of mice and allowed them to grow old. Specifically, we used a Tie2 promoter-driven Cre strain (Tie2-Cre) to knock out or overexpress SIRT1 specifically in the ECs of mice before allowing the mice to grow old.

Figure 6:
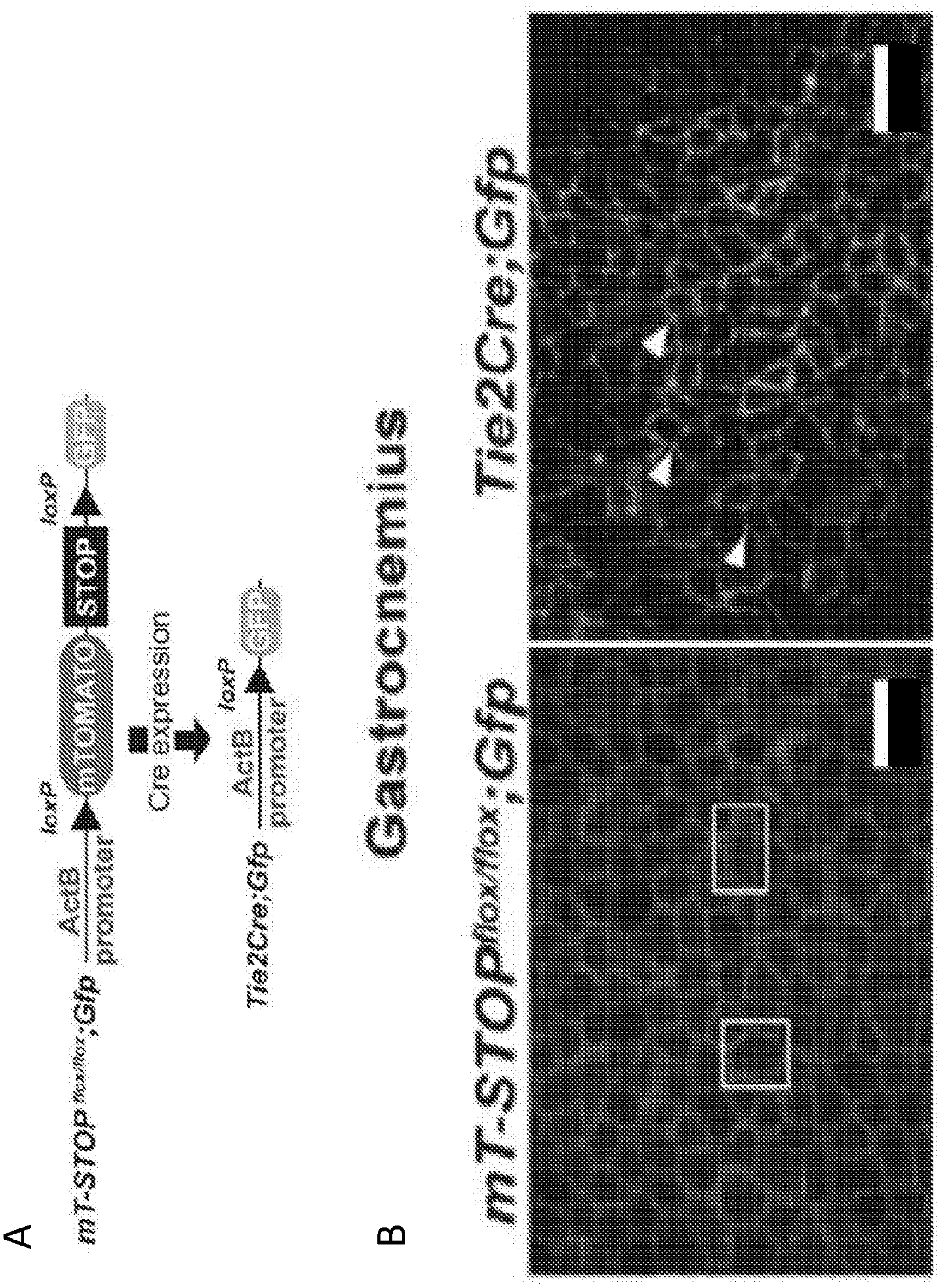
FIG. 6 is (A) a schematic representation of the strategy to generate endothelial cell-specific GFP reporter mouse (Tie2Cre;Gfp). mTSTOP$^{flox/flox}$, Gfp mouse expresses membrane-targeted tandem dimer Tomato (mT) and when crossed to Tie2Cre mouse (Tie2Cre;Gfp) expresses green fluorescent protein (GFP), and (B) representative images (20× magnification) of gastrocnemius muscle traverse cross-sections from mT-STOP$^{flox/flox}$, Gfp and Tie2Cre;Gfp mice showing the expression of mT and GFP. Tie2 promoter-mediated Cre protein results in GFP expression in the muscle capillaries. The boundaries of myofibers surrounded by extracellular matrix are highlighted with white boxes. White arrowheads indicate muscle capillaries expressing GFP. White bar=100 μm.
Figure 7:
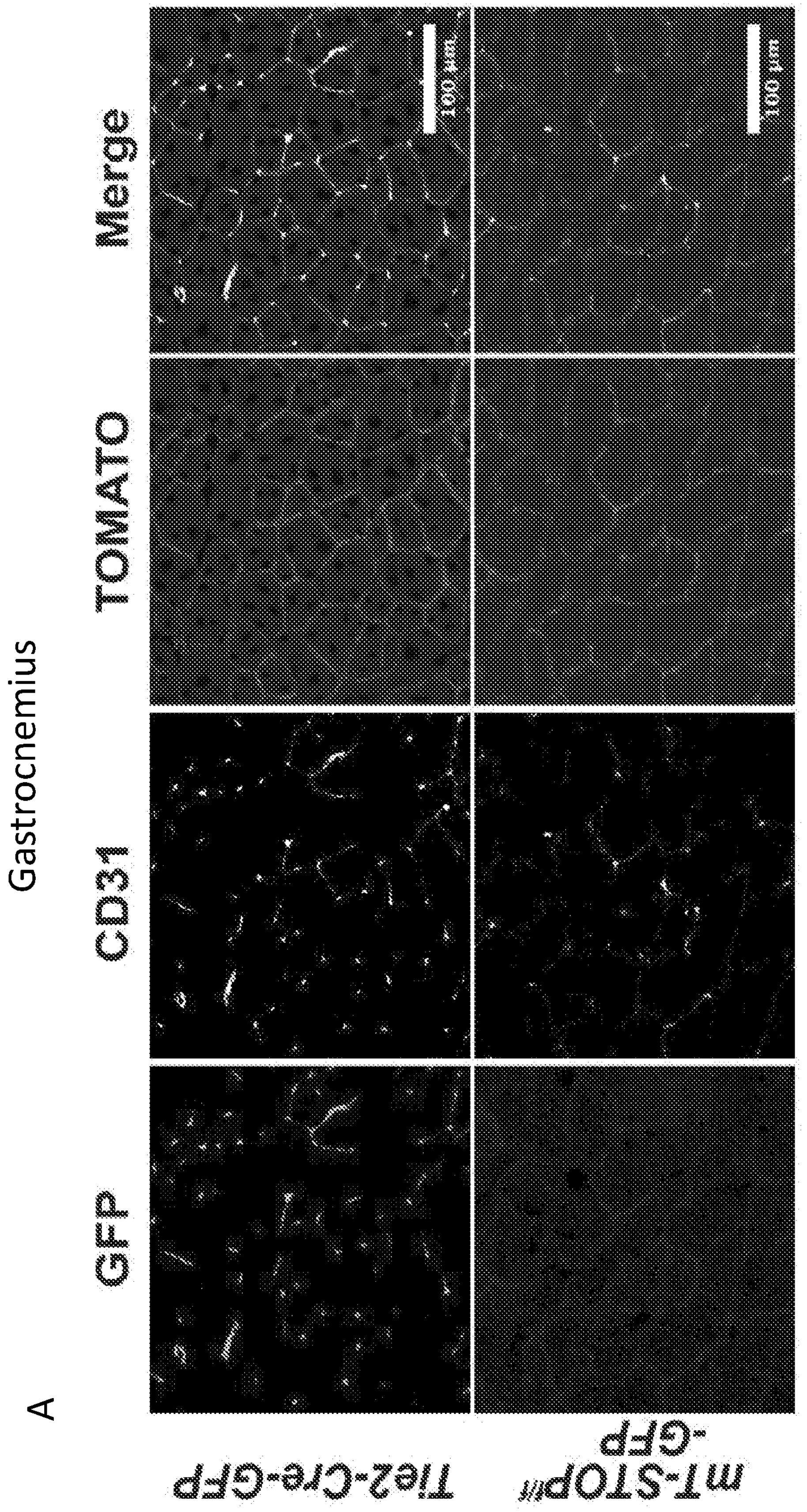
FIG. 7 is (A) representative images of gastrocnemius muscle cross-sections (40× magnification) from mT-STOPf/f-GFP and Tie2-Cre-GFP mice, immunostained with GFP and CD31 antibodies, showing that Tie2 promoter-mediated Cre protein results in GFP expression specifically in the muscle capillaries (CD31 positive), and the TOMATO protein is expressed in myofibers and surrounding stroma (White bar=100 μm); and (B) representative images of quadriceps muscle cross-sections (40× magnification) from mT-STOPf/f-GFP (white bar=100 μm) and Tie2-Cre-GFP mice (white bar=150 μm), immunostained using GFP and CD31 antibodies.
Figure 7:
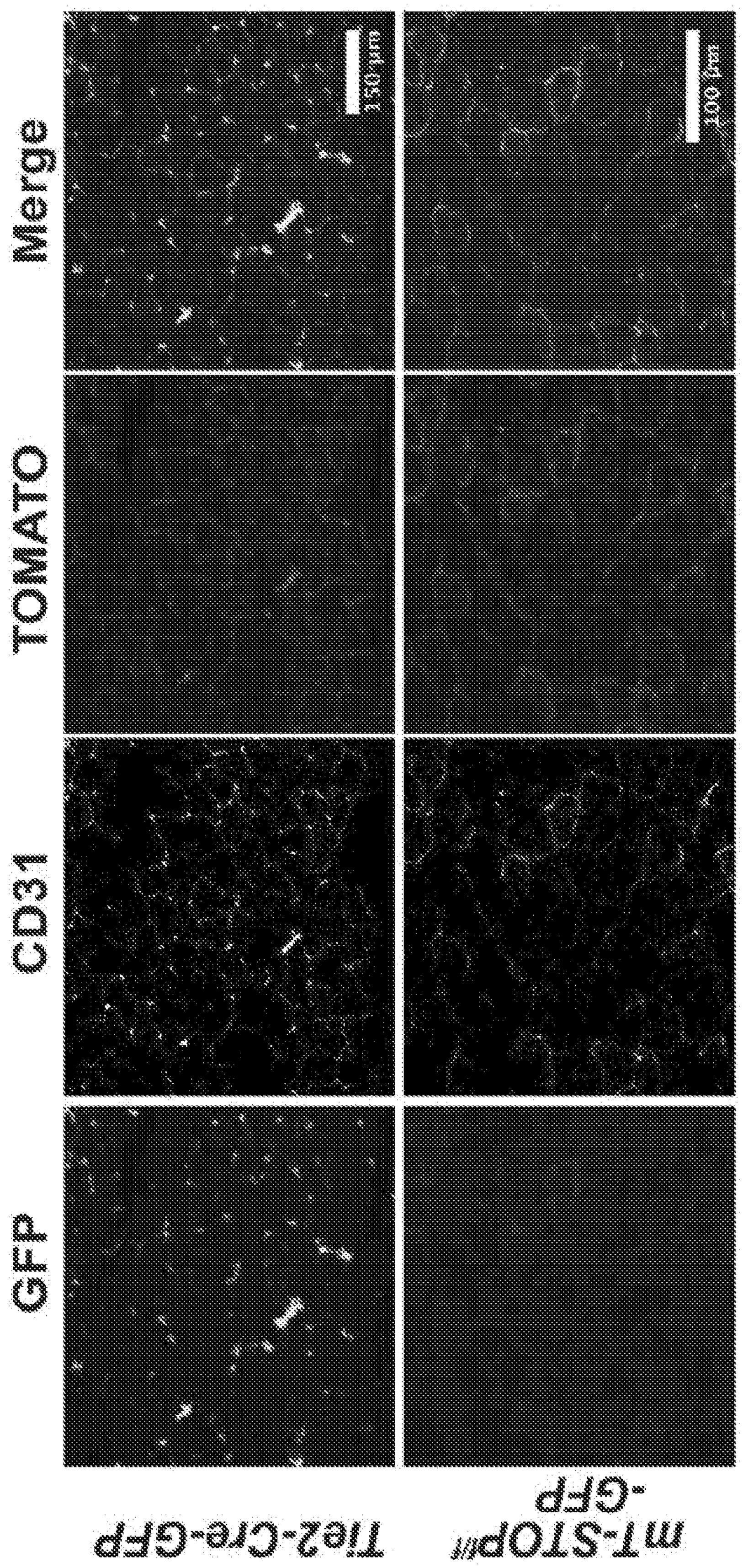
Figure 8:
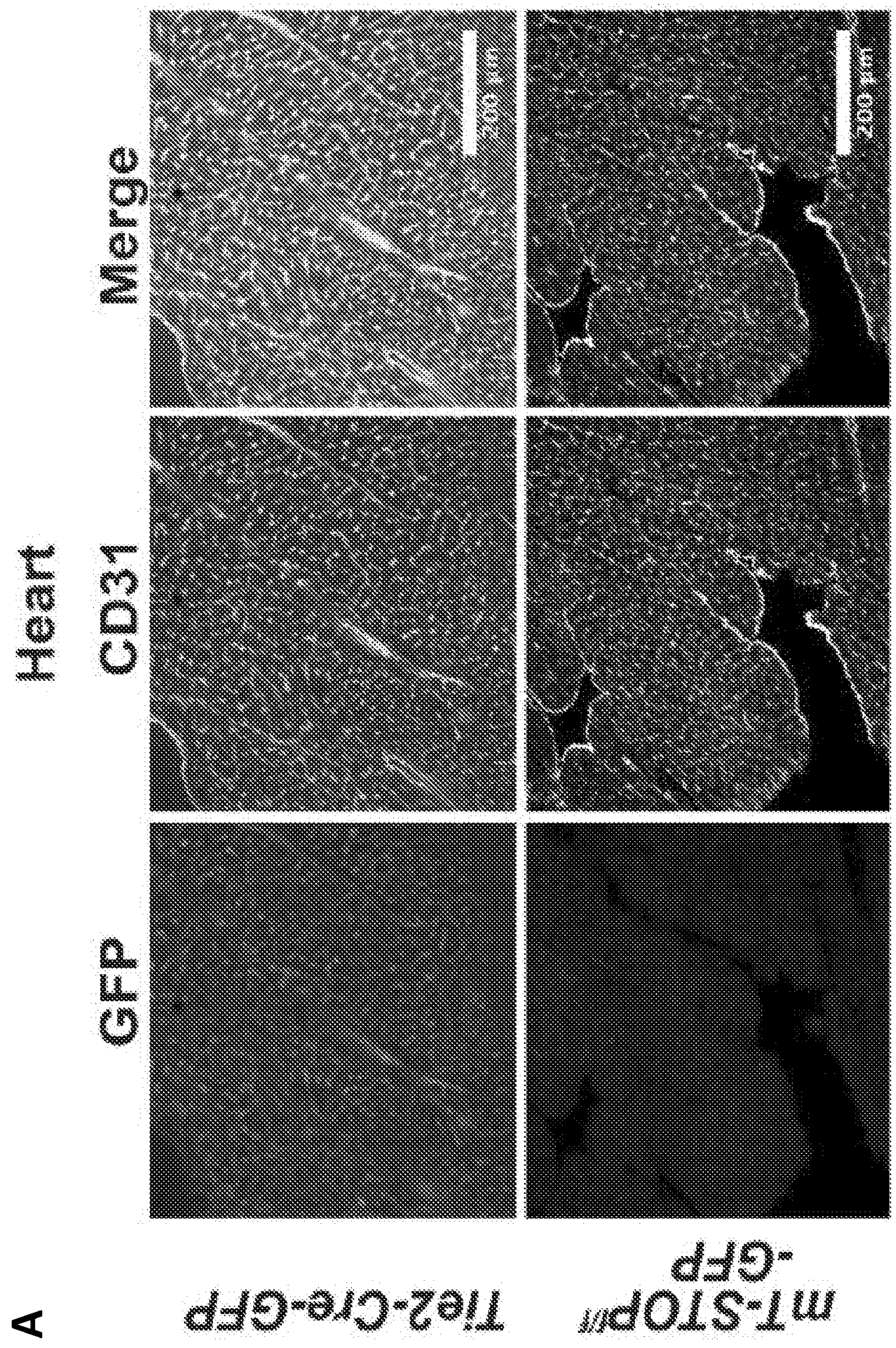
FIG. 8 is (A) representative images of heart sections (40× magnification) from mT-STOPf/f-GFP and Tie2-Cre-GFP mice, immunostained using GFP and CD31 antibodies; and (B) representative images of lung sections (40× magnification) from mT-STOPf/f-GFP and Tie2-Cre-GFP mice, immunostained using GFP and CD31 antibodies (white bar=200 μm).
Figure 8:
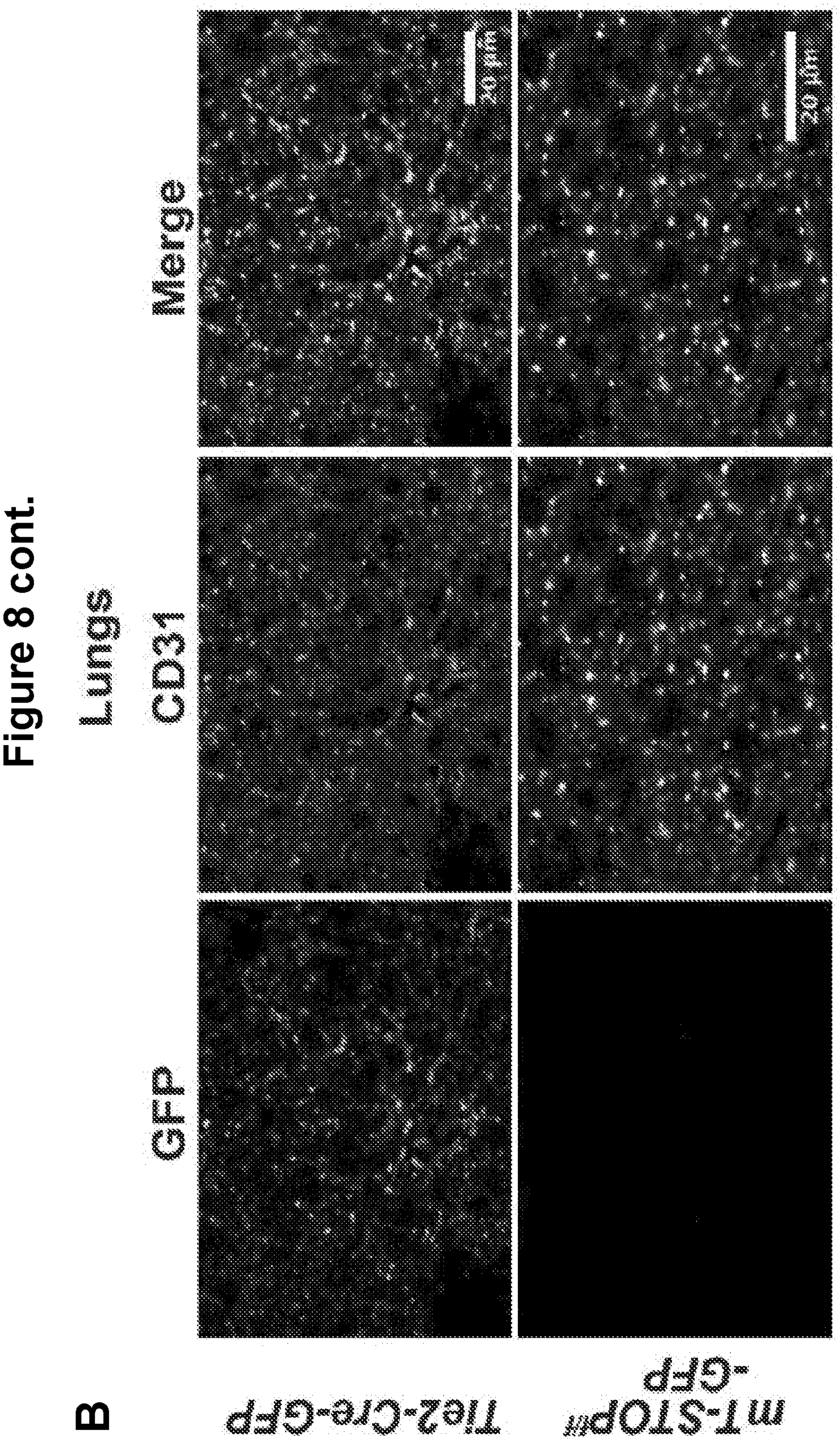

To test if the Tie2 promoter was endothelial cell specific, we crossed a C57BL/6J mouse strain to a floxed Tomato florescence protein (mT) EGFP mouse strain (mT-STOP$^{flox/flox}$, Gfp) (Koni et al., 2001) (FIG. 6A). This mouse is specifically designed to express a membrane-targeted Tomato fluorescent protein (mT) ubiquitously and express green fluorescent protein (EGFP) wherever Cre is present (Muzumdar et al., 2007). In mT-STOP$^{flox/flox}$, Gfp control mice, mT was expressed at the periphery of adjoining myofibers and in the surrounding stromal cells of transverse cross-sections of gastrocnemius and quadriceps muscles with no evidence of EGFP (FIGS. 6B, 7A and 7B). In the Tie2Cre;Gfp mice, EGFP was apparent only in the extracellular matrix of adjoining myofibers where capillaries lie, coincident with CD31 staining (FIGS. 7A and 7B). Similar expression was also observed in tibialis and soleus muscle cross-sections, confirming capillary-specific expression in skeletal muscle. Overlap between GFP and CD31 in heart and lung cross-sections (FIGS. 8A and 8B) confirmed that Tie2-driven Cre was expressed specifically in the capillaries of skeletal muscle, heart and lung tissues.

Endothelial SIRT1 knockout mice (genotype Tie2-Cre; SIRT1$^{flox/flox}$) or "ESKO mice" were generated by crossing a Tie2-Cre mice with a floxed SIRT1 strain in which loxP sites flanked the exon 4 of SIRT1 (FIG. 9A) (Potente et al., 2007, Genes Dev 21, 2644-2658; Vasko et al., 2014, J Am Soc Nephrol 25, 276-291; Wen et al., 2013, Proc Natl Acad Sci USA 110, E2420-2427; Pearson et al., 2008, Cell Metab 8, 157-168).

Figure 9:
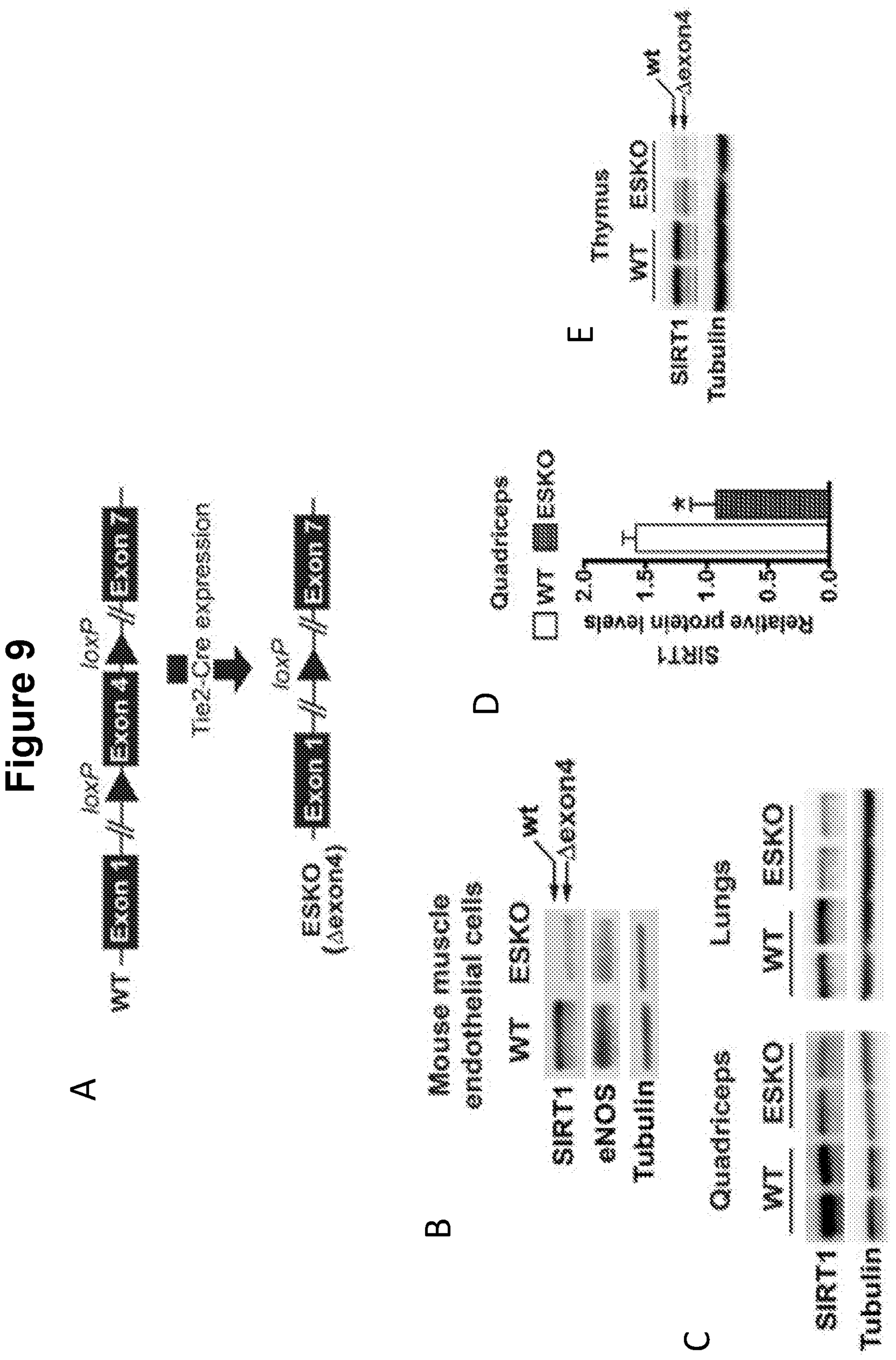
FIG. 9 is (A) a schematic diagram showing the strategy to generate EC-specific SIRT1 knockout mouse (ESKO) by crossing a transgenic mouse that expresses Cre protein under the direction of EC-specific Tie2 promoter (Tie2-Cre) and a mouse containing loxP sites flanking exon 4 (catalytic domain) of SIRT1 (SIRT1f/f or WT); (B) images of Western blots for SIRT1 and eNOS in ECs isolated from skeletal muscle of wild-type (WT) and endothelial-specific SIRT1 knock-out (ESKO) mice. EC-specific SIRT1 exon 4 excision in ESKO results in SIRT1 band (Δexon4) running slightly below the wild-type (wt) SIRT1 band (white bar=20 μm); (C) images of Western blots for SIRT1 in lung and quadriceps tissue protein homogenates from WT and ESKO mice showing an overall reduction in SIRT1 protein level; (D) a graph showing relative quantification of SIRT1 levels in the quadriceps muscles from WT and ESKO mice for the Western blot shown in (C) (n=3) *$p<0.05$, by Student's t test.; and (E) is an image of Western blots for SIRT1 in thymic tissue protein homogenates from WT and ESKO mice, in which the exon 4-excised SIRT1 band (Δexon4) runs slightly below the wild-type (wt) SIRT1 band. Tubulin was used as loading control.
Figure 10:
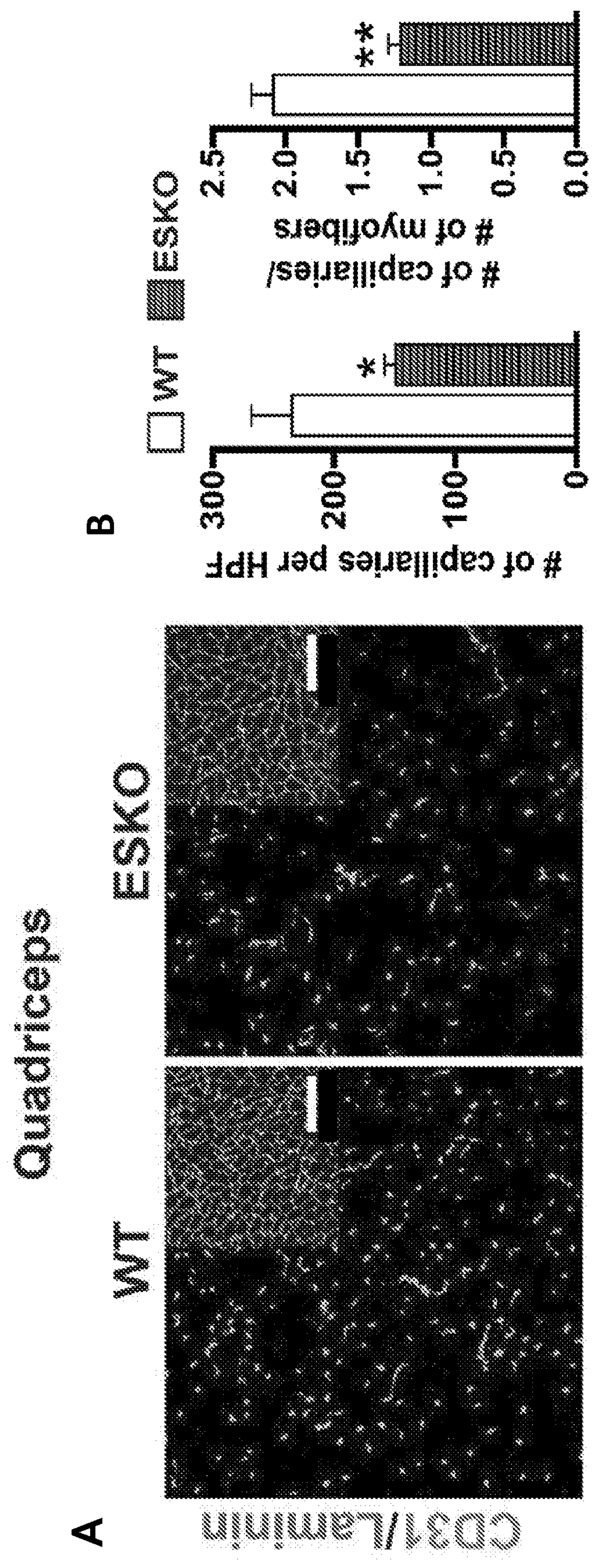
FIG. 10 is (A) representative images of capillaries (CD31) and muscle stroma (laminin, inset) in quadriceps muscle cross-sections (20× magnification) from 6-month old WT and ESKO mice immunostained with CD31 and laminin (inset) antibodies to visualize capillaries and stroma respectively (20× magnification) (white bar=200 μm); (B) a graph showing number of capillaries per HPF, and number of capillaries/number of myofibers per HPF (n=8) in quadriceps muscle cross-sections; (C) representative images of capillaries (CD31) and muscle stroma (laminin, inset) in gastrocnemius muscle cross-sections (20× magnification) from 6-month old WT and ESKO mice immunostained with CD31 and laminin (inset) antibodies (white bar=200 μm); and (D) a graph showing number of capillaries per HPF, and number of capillaries/number of myofibers per HPF (n=8) in gastrocnemius muscle cross-sections of 6-month old WT and ESKO mice. Data are expressed as mean±s. dev. *$p<0.05$, **$p<0.005$, by Student's t test.
Figure 10:
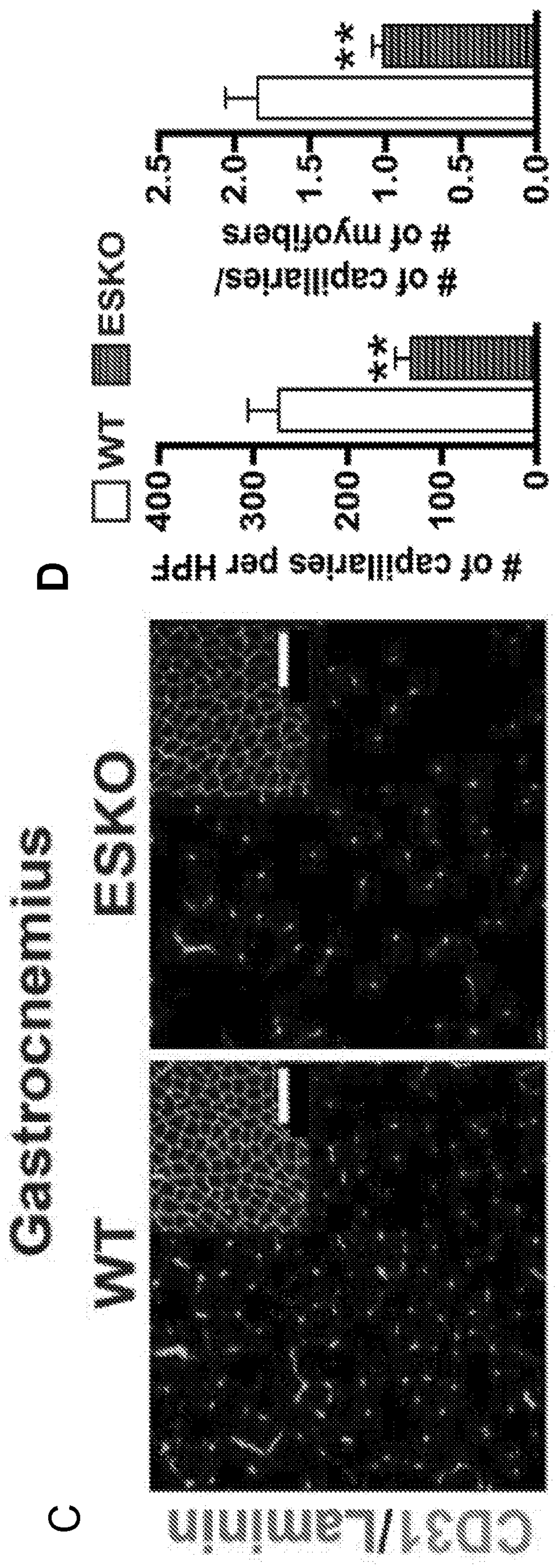

ESKO mice were born in expected Mendelian ratios with no overt developmental or physical abnormalities. The EC-specific deletion of SIRT1 exon 4 was confirmed in ECs isolated from skeletal muscle (FIG. 9B) and in quadriceps, lung, and thymus tissues (FIGS. 9C, 9D and 9E). Transverse cross-sections of quadriceps were then immunostained to visualize capillaries and basal lamina surrounding the fibers using anti-CD31 and anti-laminin antibodies, respectively (Cebasek et al., 2004, Eur J Histochem 48, 151-158). We restricted our examination to the midportion of the muscles because of its high capillary density and well-known adaptations to exercise (Chinsomboon et al., 2009 Proc Natl Acad Sci USA 106, 21401-21406). Interestingly, the density and number of capillaries in 6-month old ESKO mice was significantly lower compared to age-matched control wild-type (WT) control mice (FIGS. 10A and 10B). A similar analysis of gastrocnemius muscles also revealed a reduction in capillary density and number in the mid-portion of the gastrocnemius muscle in ESKO mice compared to control littermates (FIGS. 10C and 10D).

Figure 11:
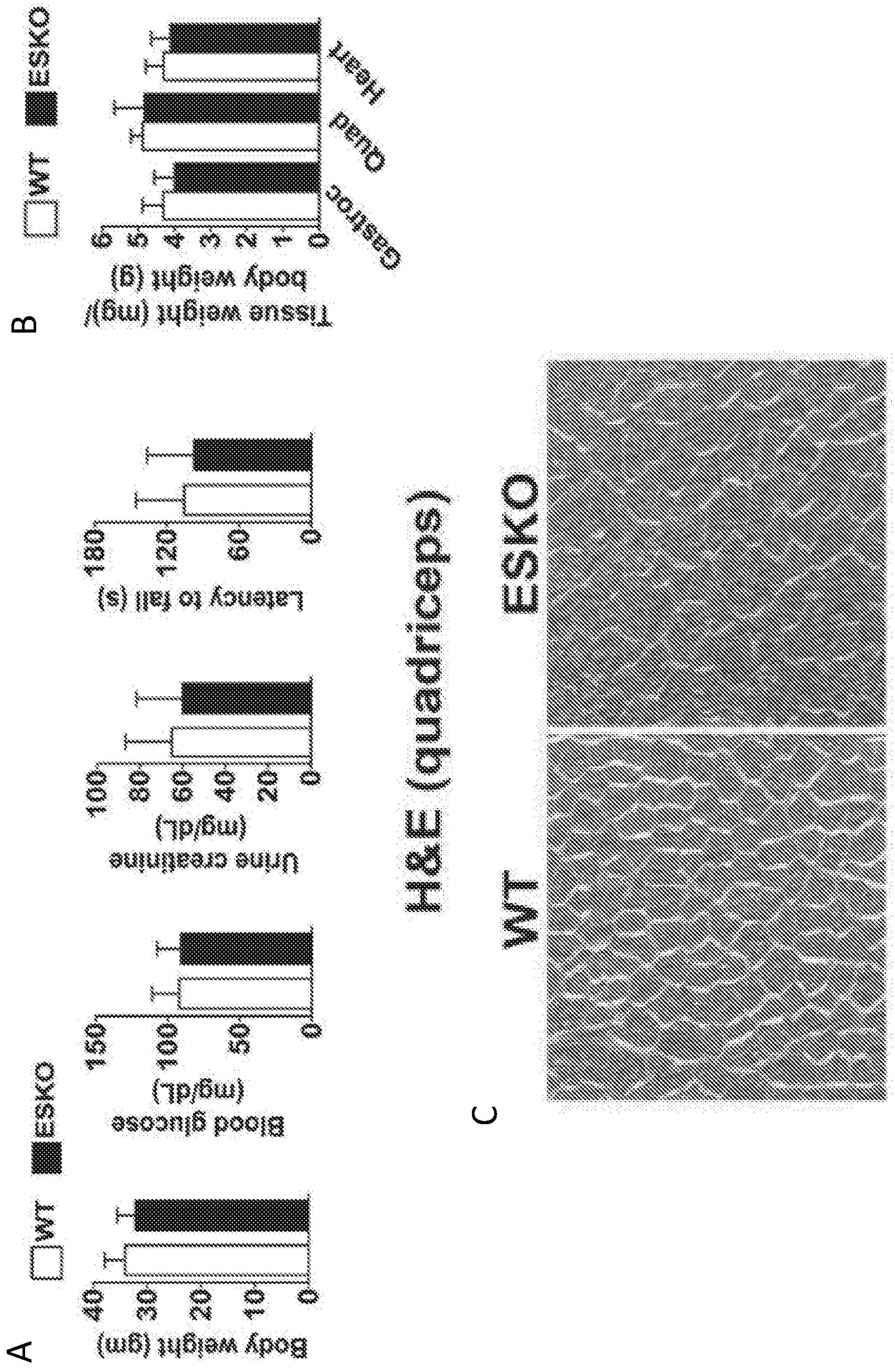
FIG. 11 is (A) graphs showing body weight, fasting blood glucose levels, urine creatinine levels and rotarod performance showing time of latency to fall of 6-month old WT and ESKO mice (n=7); (B) a graph showing gastrocnemius (Gastroc), quadriceps (Quad) and heart tissue/body weight ratios in 6-month old WT and ESKO mice (n=7); and (C) is representative H&E staining (10× magnification) images of quadriceps muscles from 6-month old WT and ESKO mice.
Figure 12:
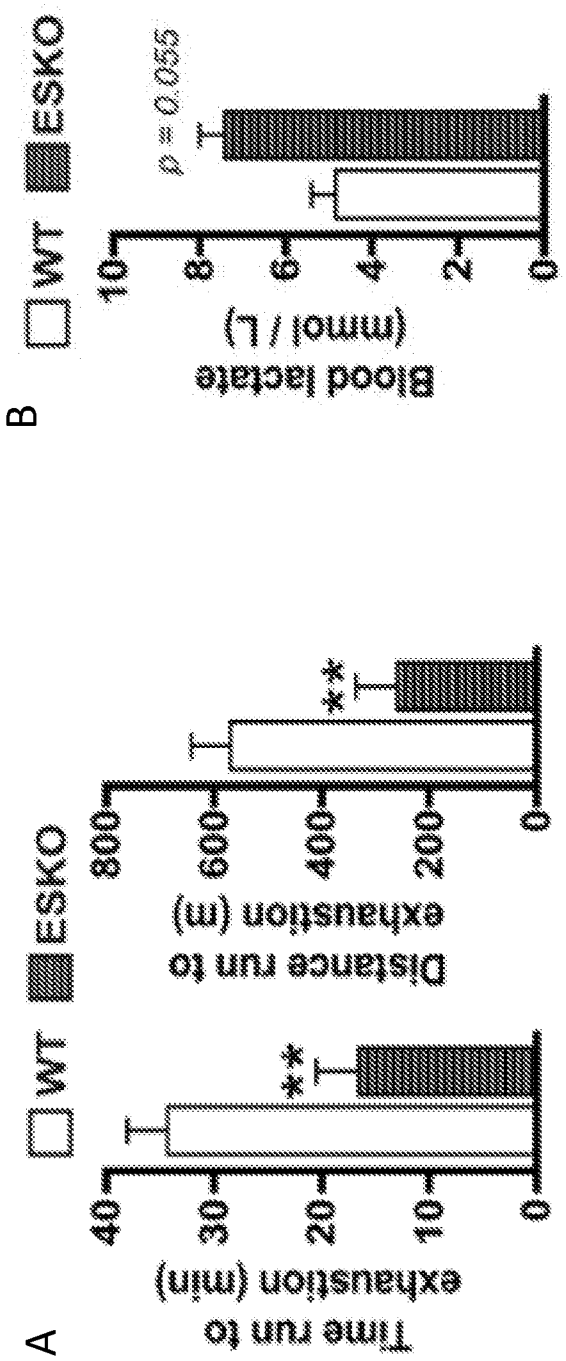
FIG. 12 is (A) a graph showing time run to exhaustion, and distance run until exhaustion, by 6-month old WT and ESKO mice in a high intensity treadmill exercise test (n=8) in which mice were run on treadmill at 15 m/min (5° elevation) for 20 min and; and (B) a graph showing post-exercise serum lactate levels in 6-month old WT and ESKO mice following high intensity treadmill exercise test. Blood lactate levels was measured by tail bleed (n=5). Data are expressed as mean±s. dev. **$p<0.005$, by Student's t test.

A gross analysis of ESKO mice compared to WT mice revealed no differences in total body weight, fasting blood glucose, urine creatinine, muscle weights, cardiac weight, muscle morphology, and motor coordination between the genotypes (FIG. 11A to 11C). Given that capillary number was lower in the ESKO mice, we hypothesized that exercise capacity might be lower. After an initial acclimatization phase, WT and ESKO mice were subjected to high intensity endurance testing with incremental increases in speed ranging from 13-30 m/min. ESKO mice had considerably lower exercise capacity compared to WT mice, running half as long and running half the distance on the treadmill as WT littermates (FIG. 12A). A trend towards higher post-exercise serum lactate levels was also noted (FIG. 12B) (p=0.055).

Figure 13:
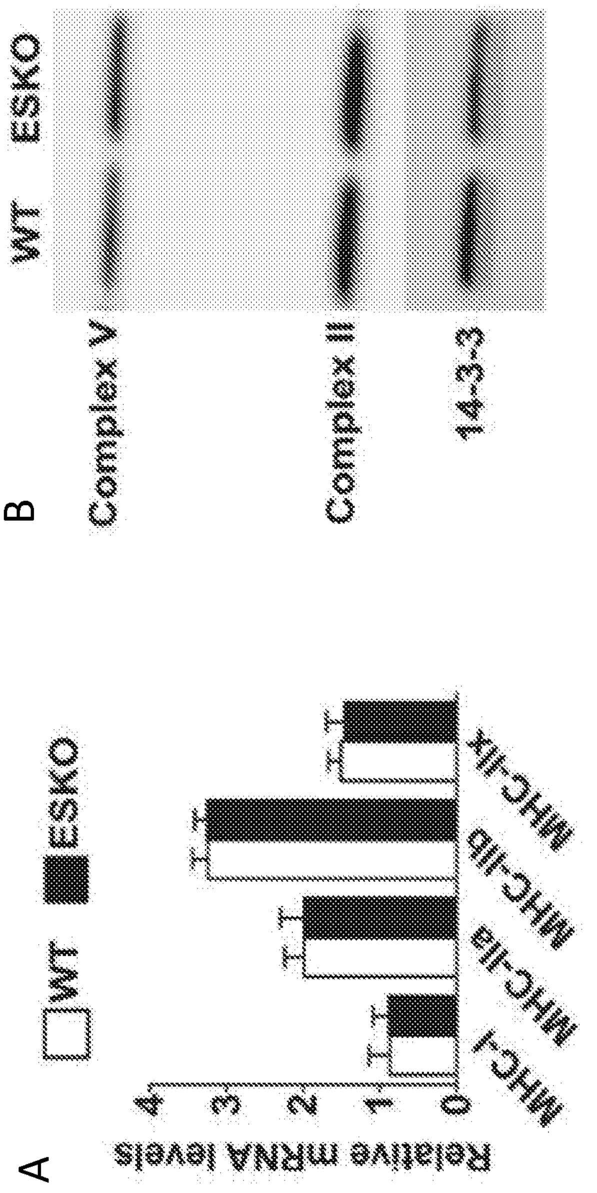
FIG. 13 is (A) a graph showing relative mRNA levels of myosin heavy chain I, IIA, IIB and IIX in gastrocnemius muscles from 6-month old WT and ESKO mice (n=10); and (B) an image of Western blots for mitochondrial protein complexes in quadriceps tissue homogenates from 6-month old WT and ESKO mice. 14-3-3 was used as loading control.

Differences in exercise capacity are commonly attributable to changes in muscle fiber type (Pette and Staron, 2000, Microsc Res Tech 50, 500-509) or mitochondrial content (Lin et al., 2002, Nature 418, 797-801). A comparison of gastrocnemius and quadriceps muscles from ESKO mice and WT mice showed no significant differences in fiber type (FIG. 13A) mitochondrial activity (FIG. 13B), indicating that the reduced exercise capacity of ESKO mice was due to reduced capillary density.

Endothelial SIRT1 is Required for Exercise-Induced Neovascularization

Figure 14:
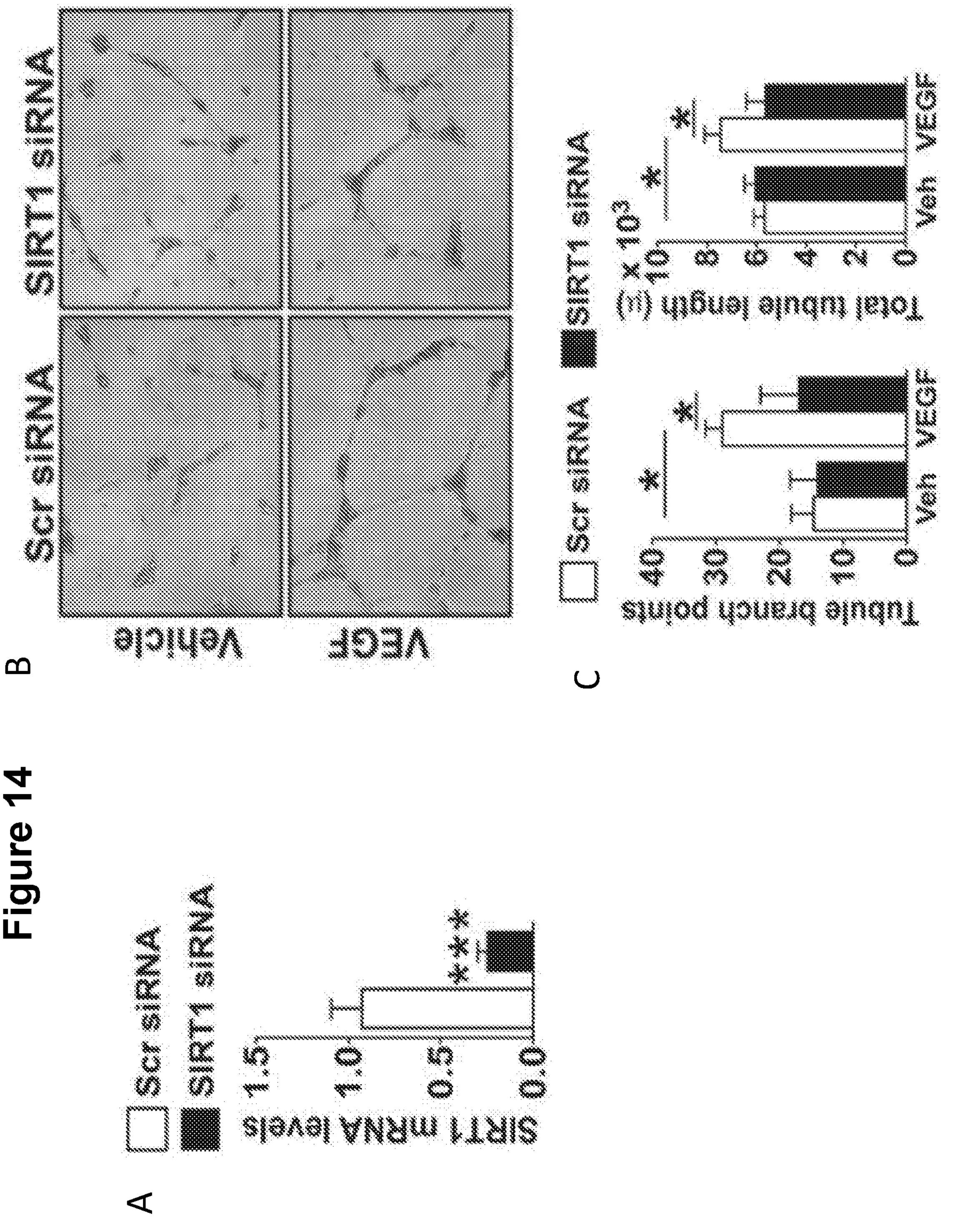
FIG. 14 is (A) a graph showing relative SIRT1 mRNA levels in HUVECs transduced with Scr or SIRT1 siRNA (n=3); (B) representative images of Human vein endothelial cells (HUVECs) transduced with scrambled (Scr) or SIRT1 siRNA and subjected to tube formation assay with or without VEGF (30 ng/mL). Representative bright field images (20× magnification) of resulting tube networks are shown; (C) a graph showing quantification of tube branch points and total tube length per field of view (n=12). Data are expressed as mean±s. dev. *p<0.05, **p<0.005, by Student's t test.
Figure 15:
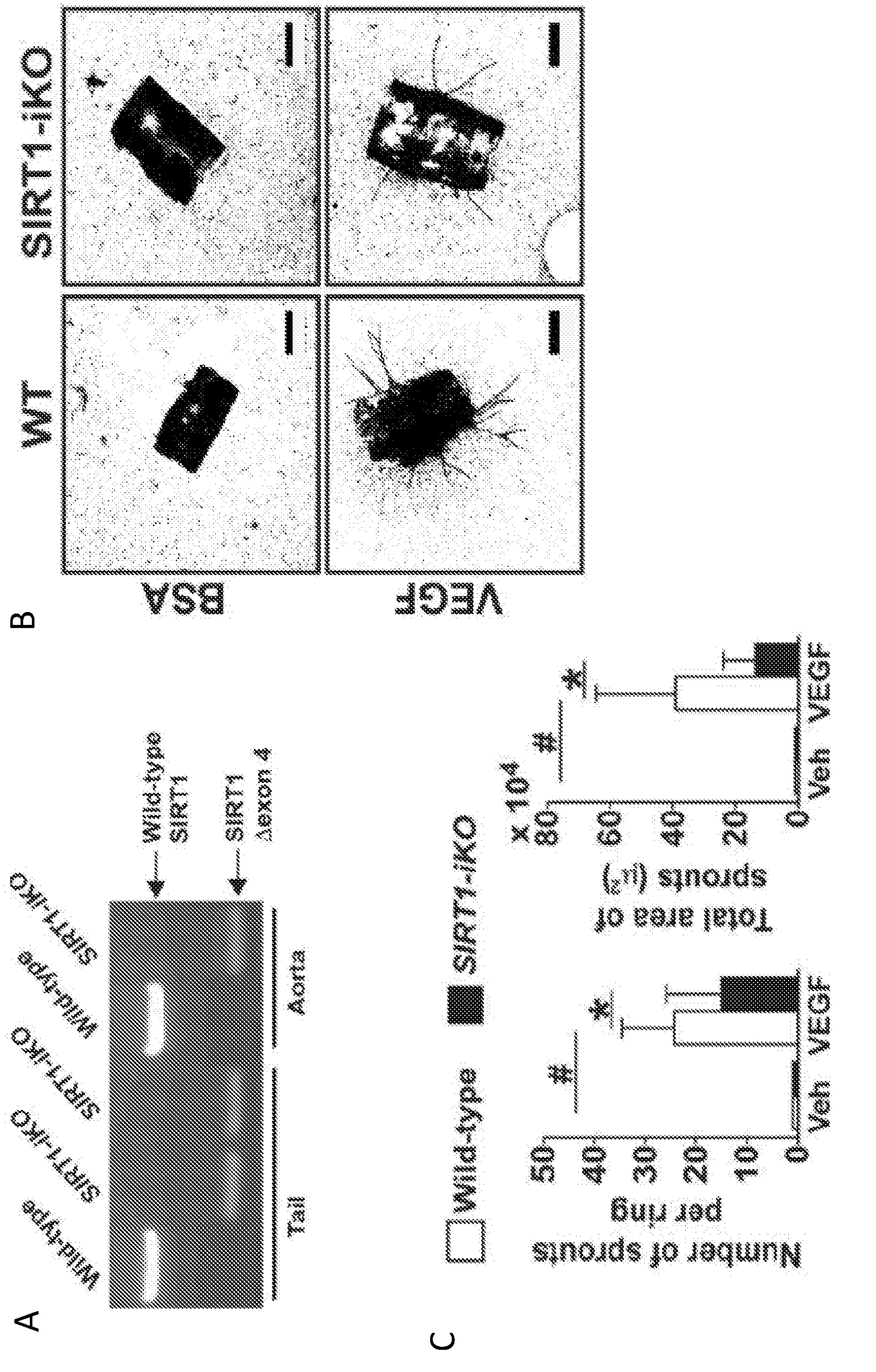
FIG. 15 is (A) the result of PCR analysis showing the excision of SIRT1 in the tail and aorta from SIRT1-iKO and wild-type control mice. This mouse expresses floxed allele of exon 4 (catalytic domain) of SIRT1 and ubiquitous CAG promoter driven Cre-esr1 fusion protein. Cre protein was activated upon treatment with 4-hydroxytamoxifen, resulting in deletion of exon 4. Full-length wild-type SIRT1 (top band) is evident in wild-type mice, while a smaller band corresponds to a loss of exon 4; (B) representative images (4× magnification) of microvessel sprouts in aortic rings embedded in collagen matrix. Aortic rings were prepared from whole-body SIRT1 inducible knock-out (SIRT1-iKO) mice and littermate control (Wild-type) mice and then treated with VEGF (30 ng/mL) or vehicle for 7 days. The resulting sprouts were stained with BS1 lectin-FITC (black bar=500 μm); (C) a graph showing quantification of the number and total area of sprouts originating from aortic rings (n=15 per treatment) referred to in (B). Data are expressed as mean±s. dev. *p<0.05, **p<0.005, #p<0.00005 by two-tailed Student's t test.
Figure 16:
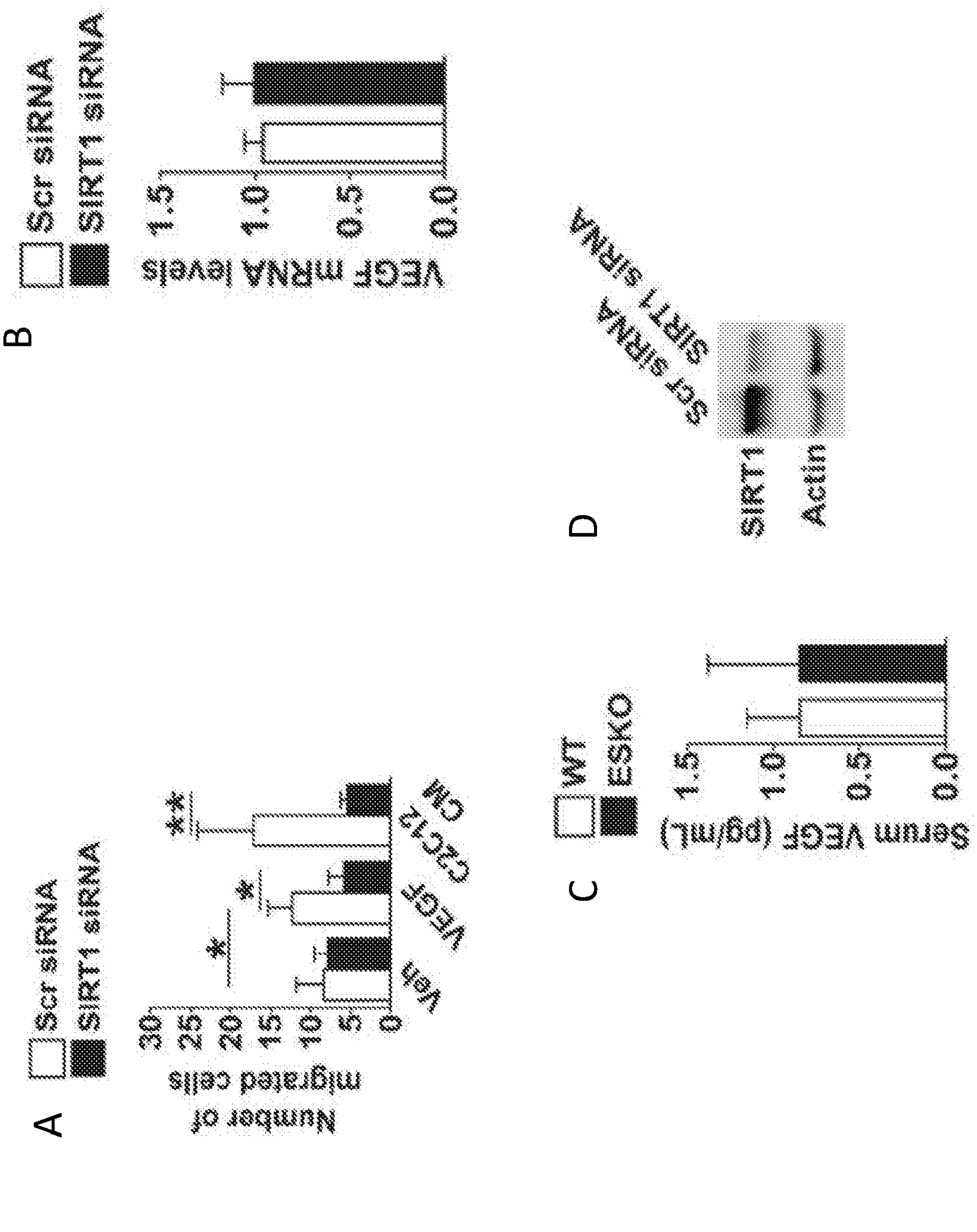
FIG. 16 is (A) a graph of the number of migrated MS1 cells in a transwell migration assay. MS1 cells were transfected with Scr or SIRT1 siRNA and then subjected to a transwell migration assay using 10 ng/mL VEGF or conditioned media from C2C12 cells transduced with Adeno-PGC-1α. The number of migrated cells per HPF was then quantified (n=16); (B) a graph showing relative VEGF mRNA levels in HUVECs transduced with Scr or SIRT1 siRNA (n=3); (C) a graph showing VEGF protein levels in serum collected from 6-month old ESKO and WT control mice (n=5); (D) Western blots showing SIRT1 protein levels in MS1 cells transfected with Scr or SIRT1 siRNA. Actin was used as a loading control. Data are expressed as mean±s. dev. *p<0.05, **p<0.005 by two-tailed Student's t test.

In young individuals exercise is a potent stimulator of angiogenesis but this effect wanes considerably with advancing age for reasons that are not known. Vascular endothelial growth factor (VEGF) is a critical regulator of angiogenesis that stimulates skeletal muscle neovascularization (Arany et al., 2008, Nature 451, 1008-1012). To determine if SIRT1 is required for VEGF to stimulate angiogenesis, we performed a series of in vitro and ex vivo assays. First, SIRT1 was knocked down in human umbilical vein ECs (HUVECs) using RNAi (FIG. 14A), then treated with vehicle or VEGF (30 ng/mL) and tested for an ability to form a tube-like network on growth factor reduced matrigel (FIGS. 14B and 14C). As shown in FIGS. 14B and 14C, knockdown of SIRT1 significantly reduced the ability of VEGF to stimulate tube formation in HUVECs, as indicated by a reduction in the number of branching points and the total length of tubules. An ex vivo angiogenesis assay in a three-dimensional (3D) collagen matrix was also performed in the absence or presence of VEGF by growing explant cultures of aortic rings collected from the thoracic aortae of 18-month old WT and SIRT1 knockout mice (SIRT1-iKO) (FIG. 15A) (Gomes et al., 2013, Cell 155, 1624-1638; Price et al., 2012, Cell Metab 15, 675-690). VEGF treatment increased sprouting in aortic rings compared to vehicle treatment alone (FIGS. 15B and 15C), an effect that was reduced two-fold by the SIRT1 deletion (FIG. 15C). SIRT1 had no apparent effect on the levels of VEGF mRNA in HUVECs (FIG. 16B) or VEGF protein in serum (FIG. 16C). Together, these results showed that SIRT1 is necessary for VEGF to efficiently promote angiogenesis.

After exercise, myofibers send a pro-angiogenic signal to ECs by secreting VEGF (Booth and Thomason, 1991, Physiol Rev 71, 541-585; Rowe et al., 2014, Circulation 129, 798-810). To test if endothelial SIRT1 is required for myoblast-EC communication, we performed an in vitro transwell migration assay in which VEGF or conditioned media from murine C2C12 myotubes was added to murine-derived immortalized MS1 ECs (Arbiser et al., 2000, Am J Pathol 156, 1469-1476). Surprisingly, knockdown of SIRT1 (FIG. 16D) almost completely abolished the chemotactic response of MS1 cells to VEGF and to C2C12 conditioned media (FIG. 16A). These data suggested that endothelial SIRT1 may be a key mediator of myofiber-EC communication that promotes muscle microvasculature remodeling after exercise.

Figure 17:
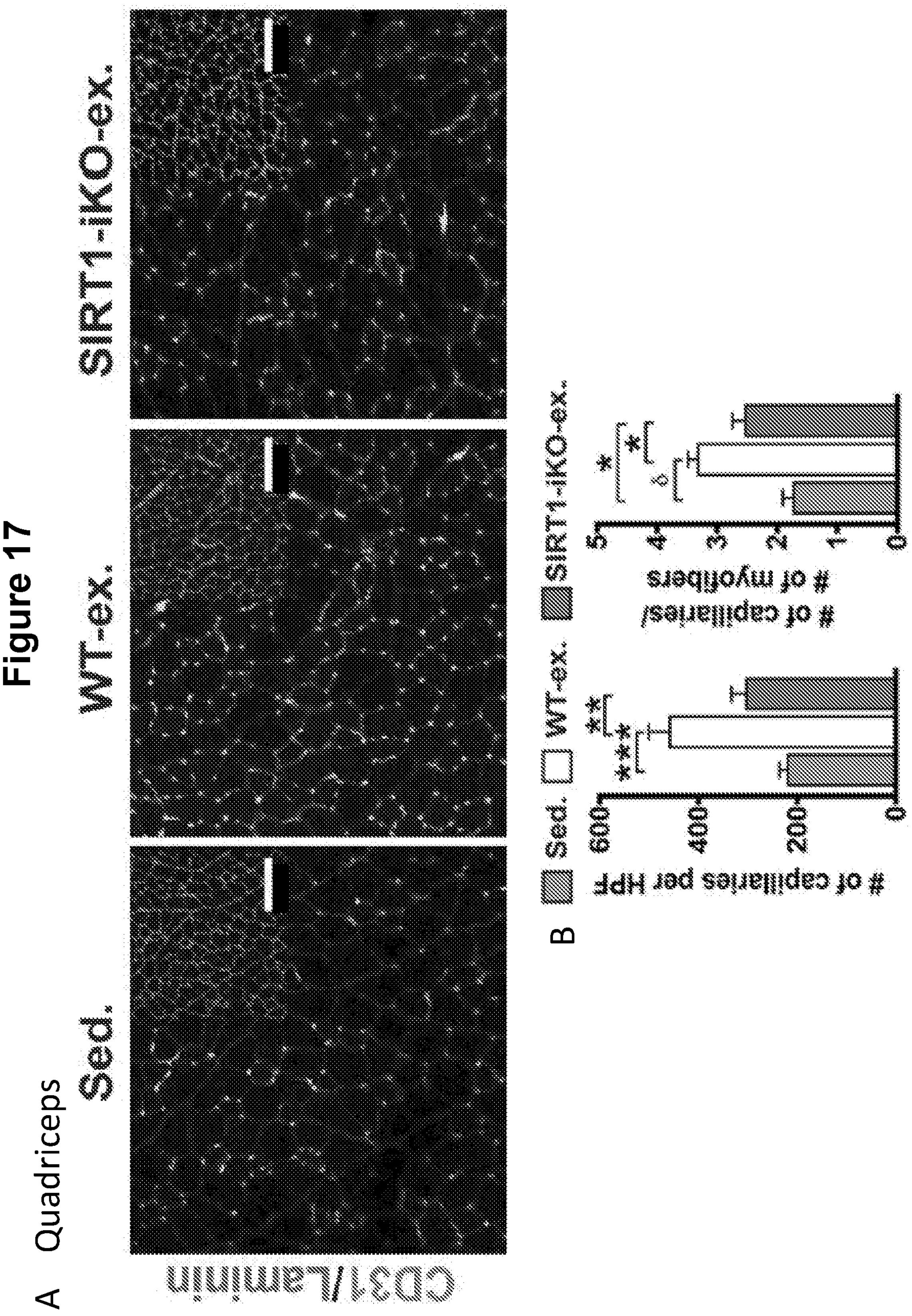
FIG. 17 is (A) representative images of capillaries (CD31) and stroma (laminin, inset) in quadriceps muscle cross-sections (20× magnification) from sedentary (SIRT1-iKO+WT)(Sed.), and exercised WT (WT-ex.) and SIRT1-iKO (SIRT1-iKO-ex) mice, showing SIRT1 is required for exercise induced skeletal muscle vascular remodeling. Whole-body SIRT1 inducible knock-out (SIRT1-iKO) and WT (control) mice (5-month old) were fed tamoxifen diet (360 mg/kg) for 5 weeks, after which the animals were trained for four weeks of treadmill exercise training (15 m/min for 30 min @5° inclination) (white bar=200 μm). (B) a graph showing quantification of the number of capillaries per HPF, and the number of capillaries/the number of myofiber ratio per HPF (n=6) in quadriceps of mice referred to in (A). Data are expressed as mean±SEM. *p<0.05, p<0.005, *p<0.0005, $^{\delta}$p<0.00005 by one-way ANOVA with Bonferroni's Multiple Comparisons Test.

We subjected young inducible SIRT1 knockout mice (SIRT1-iKO) (Price et al., 2012) to a four week treadmill training paradigm. Immediately after SIRT1 deletion, there was no difference in capillary number or density. After four weeks of exercise training, however, the number of capillaries and capillary density in the quadriceps muscle of SIRT1-iKO mice was only 1.4-fold higher than that of sedentary mice compared to WT mice, which were 2-fold higher than sedentary mice (FIGS. 17A and 17B), indicating that SIRT1 is required for exercise-induced muscle neovascularization.

Peroxisome proliferator-activated receptor gamma coactivator 1 (PGC-1α) is known for its role in boosting mitochondrial function in myocytes but it appears to have an equally important role in angiogenesis by inducing the secretion of VEGF to induce EC remodelling and neovascularization (Booth and Thomasen 1991, Physiol Rev 71, 541-585; Rowe et al. 2014; Arany et al., 2008). Indeed, mice lacking PGC-1α in skeletal muscle lack the capacity for exercise-induced angiogenesis (Chinsomboon et al., 2009) whereas mice overexpressing PGC-1α in muscle (MCK-PGC-1α) have increased mitochondria and capillary content in muscle and greater whole animal endurance capacity (Zin et al. 2002).

Figure 18:
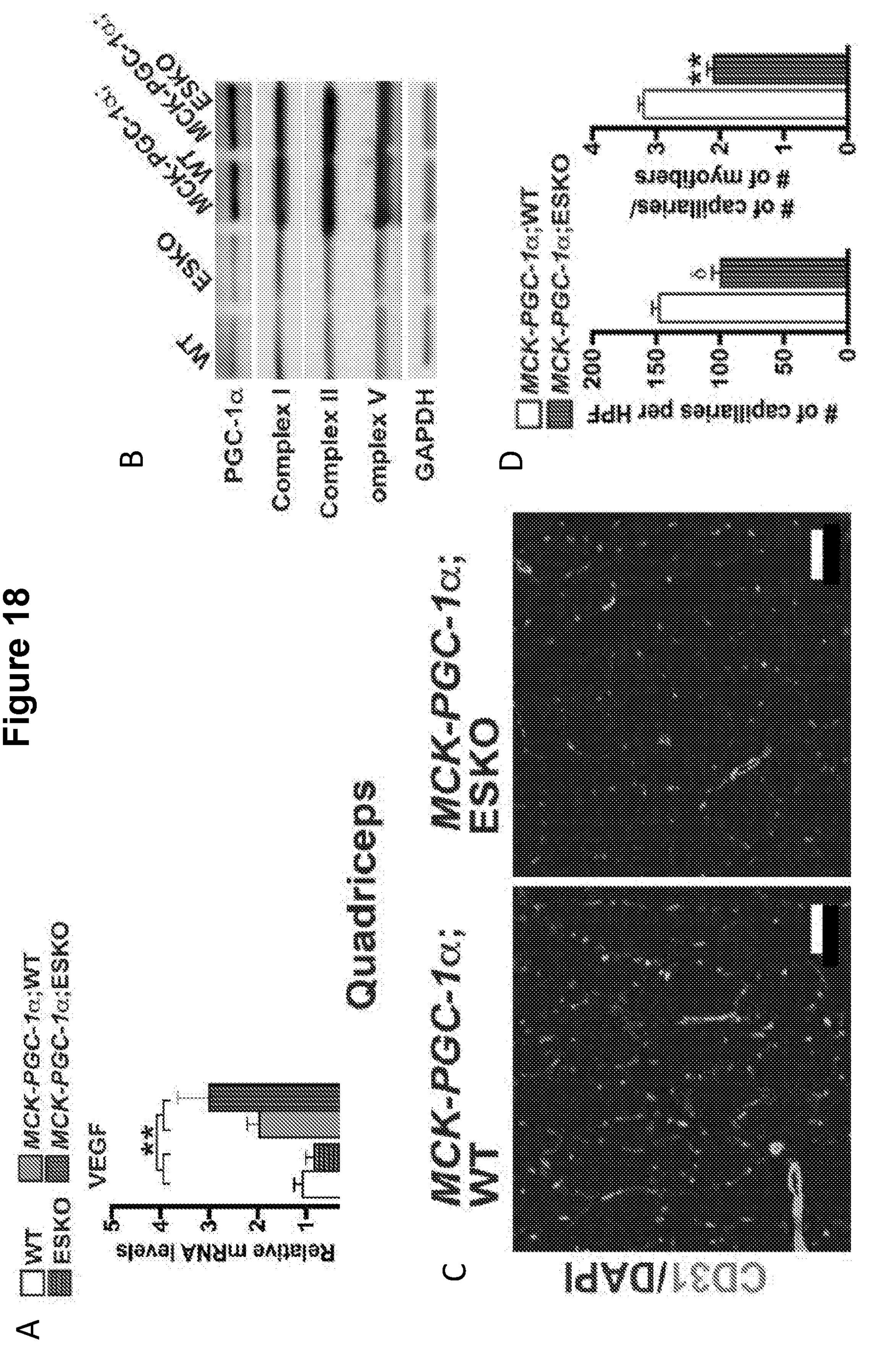
FIG. 18 is (A) a graph showing relative mRNA levels of VEGF in quadriceps muscles from 4-month old WT, ESKO, MCK-PGC-1α;WT and MCK-PGC-1α;ESKO mice (n=5). WT and ESKO mice were crossed to muscle-specific PGC1-α overexpressing (MCK-PGC-1α); (B) images of Western blots showing protein levels of PGC-1α, NDUFB5 (Complex I), SDH8 (Complex II) and ATP5a (Complex V) in quadriceps muscles from 4-month old WT, ESKO, MCK-PGC-1α;WT and MCK-PGC-1α;ESKO mice. GAPDH was used as a loading control. (C) representative images of nuclei (DAPI) and capillaries (CD31) in quadriceps muscle cross-sections (40× magnification) from MCK-PGC-1α;WT and MCK-PGC-1α;ESKO mice (4-month old) (white bar=100 μm); (D) graphs showing the number of capillaries per HPF, and the number of capillaries/the number of myofiber ratio per HPF (n=6), in quadriceps of mice referred to in (C). Data are expressed as mean±SEM. *p<0.05, $^{\delta}$p<0.00005 by Student's t test (D) or two-way ANOVA with Bonferroni's Multiple Comparisons Test (A).

To test if SIRT1 plays a role in this pathway, we deleted SIRT1 either in the ECs or myocytes of a PGC-1α overexpressing mouse strain (MCK-PGC-1α) that is considered to be an exercise mimetic on account of increased mitochondrial, capillary content in muscle and greater endurance capacity (FIG. 18A) (Lin et al., 2002). Despite there being no effect on mitochondrial protein levels (FIG. 18B) MCK-PGC-1α;ESKO mice had significantly reduced capillary numbers and capillary density compared to MCK-PGC-1α; WT mice (FIGS. 18C and 18D), indicating that endothelial SIRT1 is a key mediator of PGC-1α-induced angiogenesis.

Figure 19:
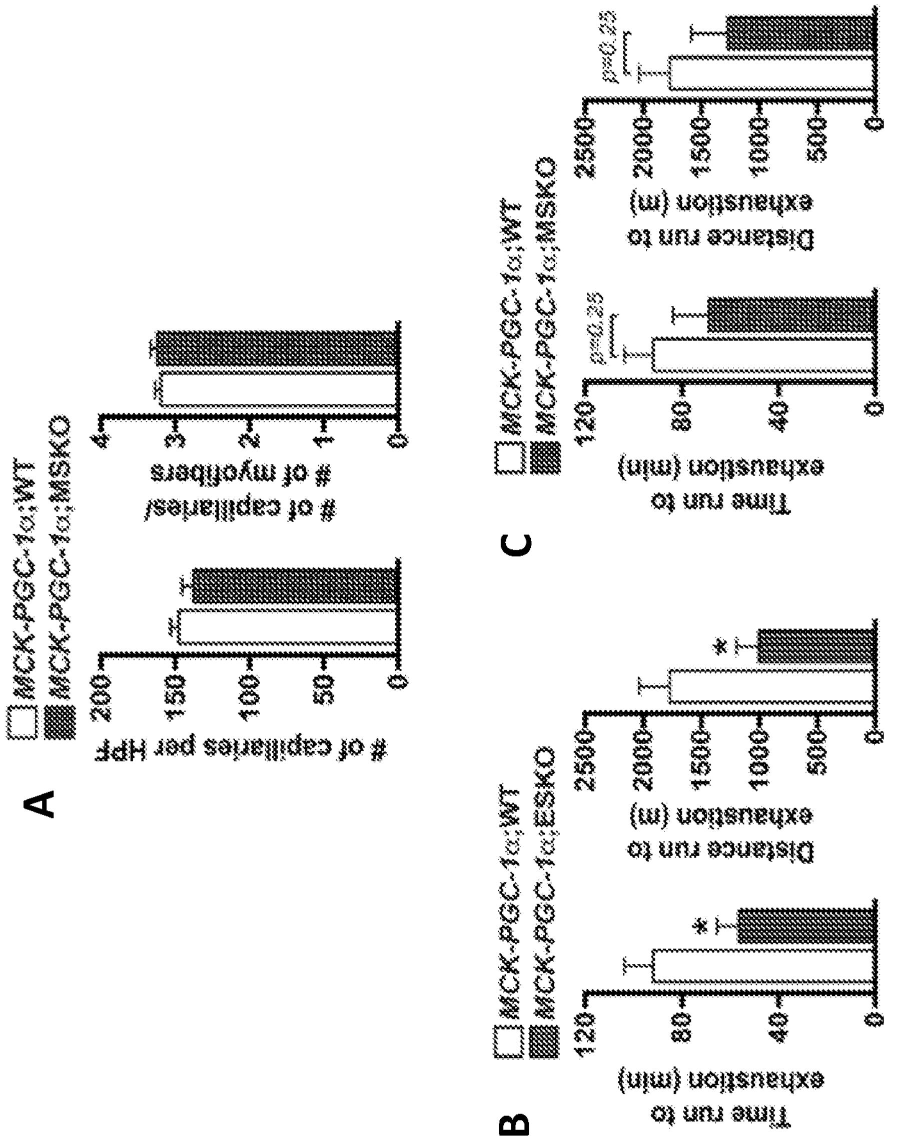
FIG. 19 is (A) a graph showing the number of capillaries per HPF, and the number of capillaries/the number of myofiber ratio per HPF, in quadriceps muscle cross-sections from MCK-PGC-1α;WT and MCK-PGC-1α;MSKO mice (4-month old) (n=6). The MCK-PGC-1α mouse was crossed to a muscle-specific SIRT1 KO (MSKO) mouse and muscle capillarity of littermates was assessed (40× magnification) following immunostaining with CD31 and laminin antibodies; (B) a graph showing time run to exhaustion and distance run until exhaustion by MCK-PGC-1α;WT and MCK-PGC-1α;ESKO mice (4-month old) in a high intensity treadmill exercise test (n=7). (C) a graph showing time run to exhaustion and distance run until exhaustion by MCK-PGC-1α;WT and MCK-PGC-1α;MSKO mice (4-month old) in a high intensity treadmill exercise test (n=7). Data are expressed as mean±SEM. *p<0.05, p<0.005, *p<0.0005, $^{\delta}$p<0.00005 by Student's t test.

To test if it was an endothelial-specific effect, we created a myocyte-specific SIRT1 knock-out mouse (MSKO) strain in which SIRT1 was deleted in skeletal muscle myocytes by crossing the SIRT1$^{flox/flox}$ mouse to a Myog-Cre mouse (Chalkiadaki et al., 2014, PLoS Genet 10, e1004490). Interestingly, there was no difference in the number of capillaries between muscle-specific SIRT1 knockout and control mice. We then crossed the MSKO strain with MCK-PGC-1α mice. As shown in FIG. 19A, the presence or absence of SIRT1 in myocytes made no difference in the number of capillaries induced in PGC-1α. Together, these data indicate that SIRT1 in endothelial cells, but not myocytes, of skeletal muscle is a critical downstream mediator of PGC-1α-induced pro-angiogenic signals originating from myofibers.

At the physiological level, the effects of deleting endothelial SIRT1 but not myocyte SIRT1 were clearly evident. In endurance tests, MCK-PGC-1α;ESKO mice ran only half a long and half as far compared to MCK-PGC-1α mice (FIG. 19B), whereas a statistically non-significant decrease in exercise capacity was observed in the MCK-PGC-1α-SIRT1 myocyte-specific knockout mice (FIG. 19C). Thus, SIRT1 in endothelial cells is required for PGC-1α to improve exercise tolerance in a mouse, even if mitochondrial function is already higher, underscoring the critical role of the vasculature SIRT1 in endurance. Together, these data support a model in which SIRT1 is necessary for ECs to receive vascular remodeling signals from myofibers to increase the capillary density and the endurance capacity of muscle.

Thus, an increase in muscle capillaries can further improve exercise tolerance in a mouse with increased mitochondrial function, underscoring the critical role of the vasculature in endurance. In conclusion, both the in vitro and in vivo data support a model in which SIRT1 is necessary for endothelial cells to receive vascular remodeling signals from myofibers to increase the capillary density and endurance capacity of muscle.

Figure 20:
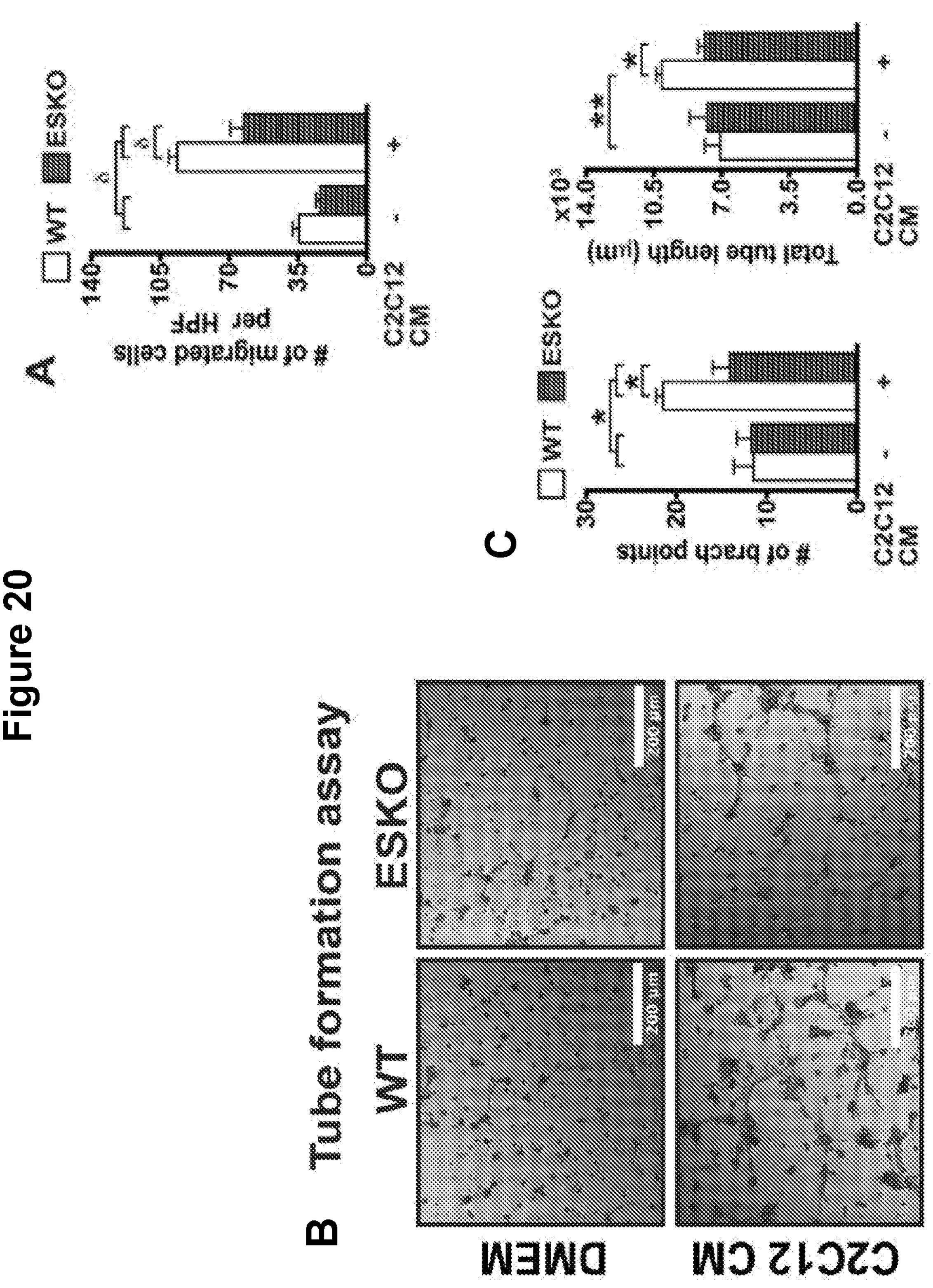
FIG. 20 is (A) a graph showing quantification of the number of migrated MLECs isolated from WT and ESKO mice+/−C2C12 CM per field of view (n=12) in a Transwell migration assay; (B) representative phase-contrast micrographs of tube networks (10× magnification) formed by WT and ESKO MLECs on matrigel matrix (white bar=200 μm); (C) a graph showing quantification of the tube branch points and tube length+/−C2C12 CM per field of view (n=5) from the tube formation assay referred to in (B); (D) representative phase-contrast micrographs (10× magnification) of spheroids from WT and ESKO MLECs treated with C2C12 CM (n=8) in a spheroid assay; and (E) a graph showing quantification of sprout length of the spheroids from WT and ESKO MLECs treated with C2C12 CM (n=8) in the spheroid assay referred to in (D). Data are expressed as mean±SEM. *p<0.05, p<0.005, *p<0.0005, $^{\delta}$p<0.00005 by Student's t test (E) or two-way ANOVA with Bonferroni's Multiple Comparison's test (A and C).
Figure 20:
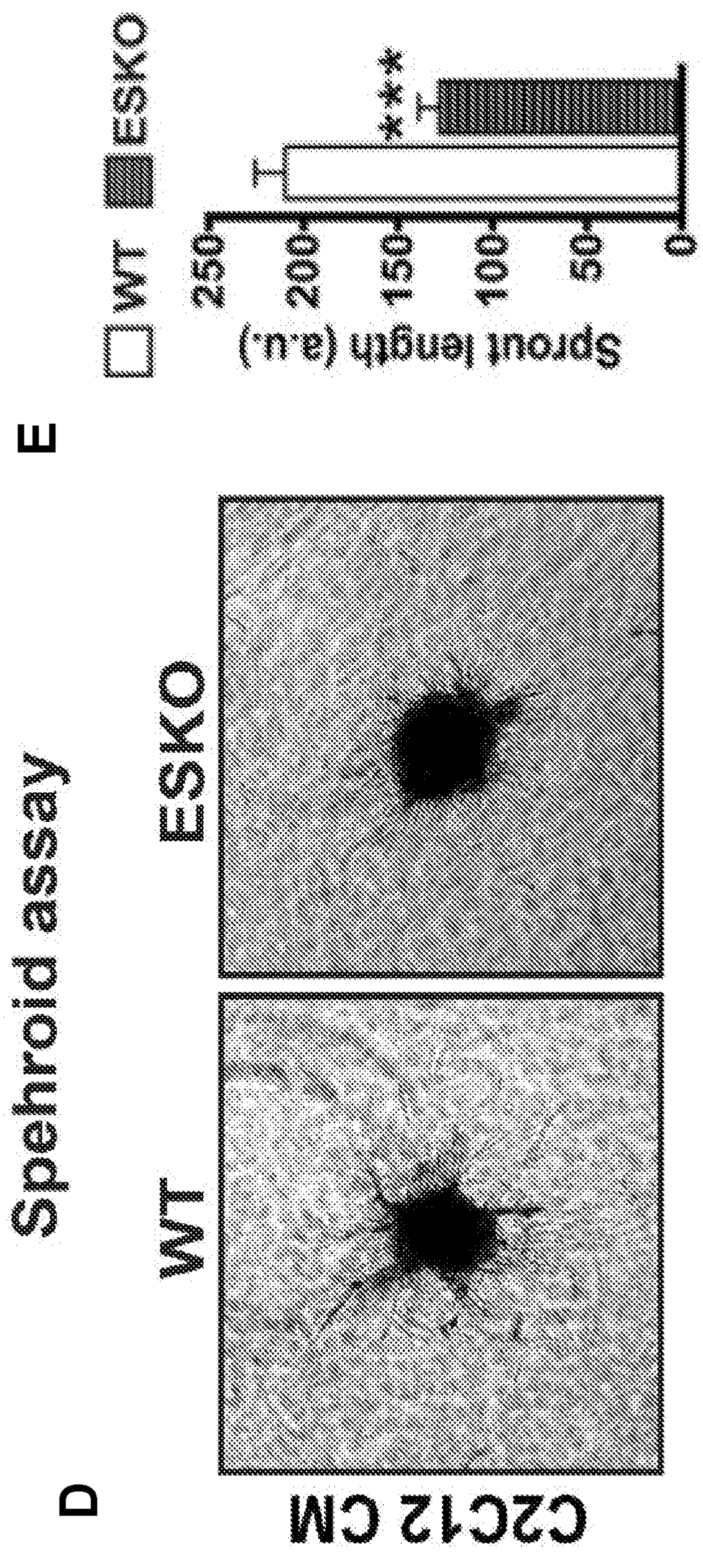
Figure 21:
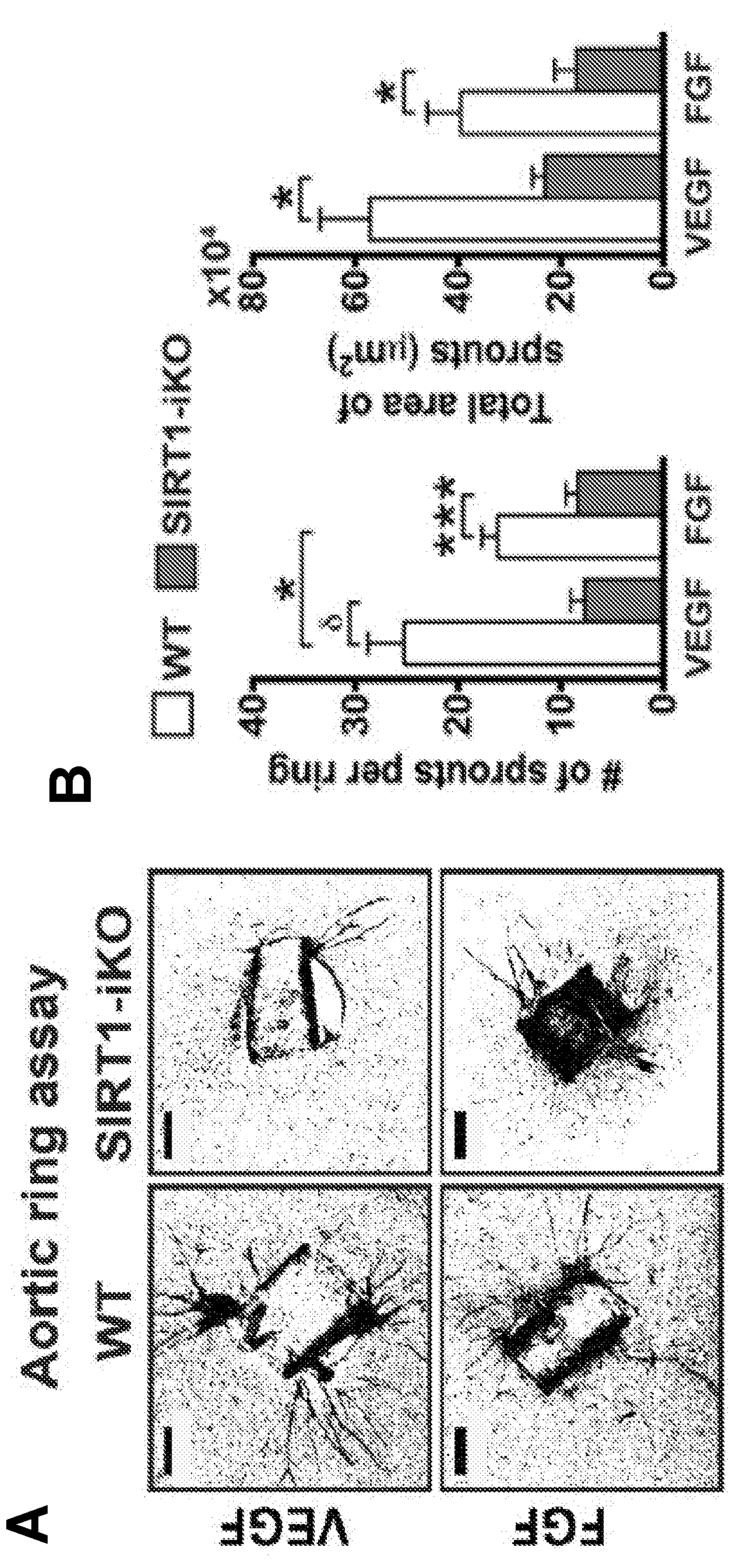
FIG. 21 is (A) representative images of microvessel sprouts in aortic rings (4× magnification) from WT and SIRT1-iKO mice (n=10), in which the aortic rings were prepared from tamoxifen-treated SIRT1-iKO and WT control mice and starved overnight, then embedded in a type I collagen matrix and stimulated with VEGF (50 ng/mL) or FGF (50 ng/mL) for 7 days. The fixed sprouts were stained with FITC-conjugated BS1 lectin. (black bar=500 μm) (B) graphs showing quantification of the number of sprouts per aortic ring, and the total area of sprouts originating from aortic rings (n=10) in aortic rings as prepared in (A). (C)
Figure 21:
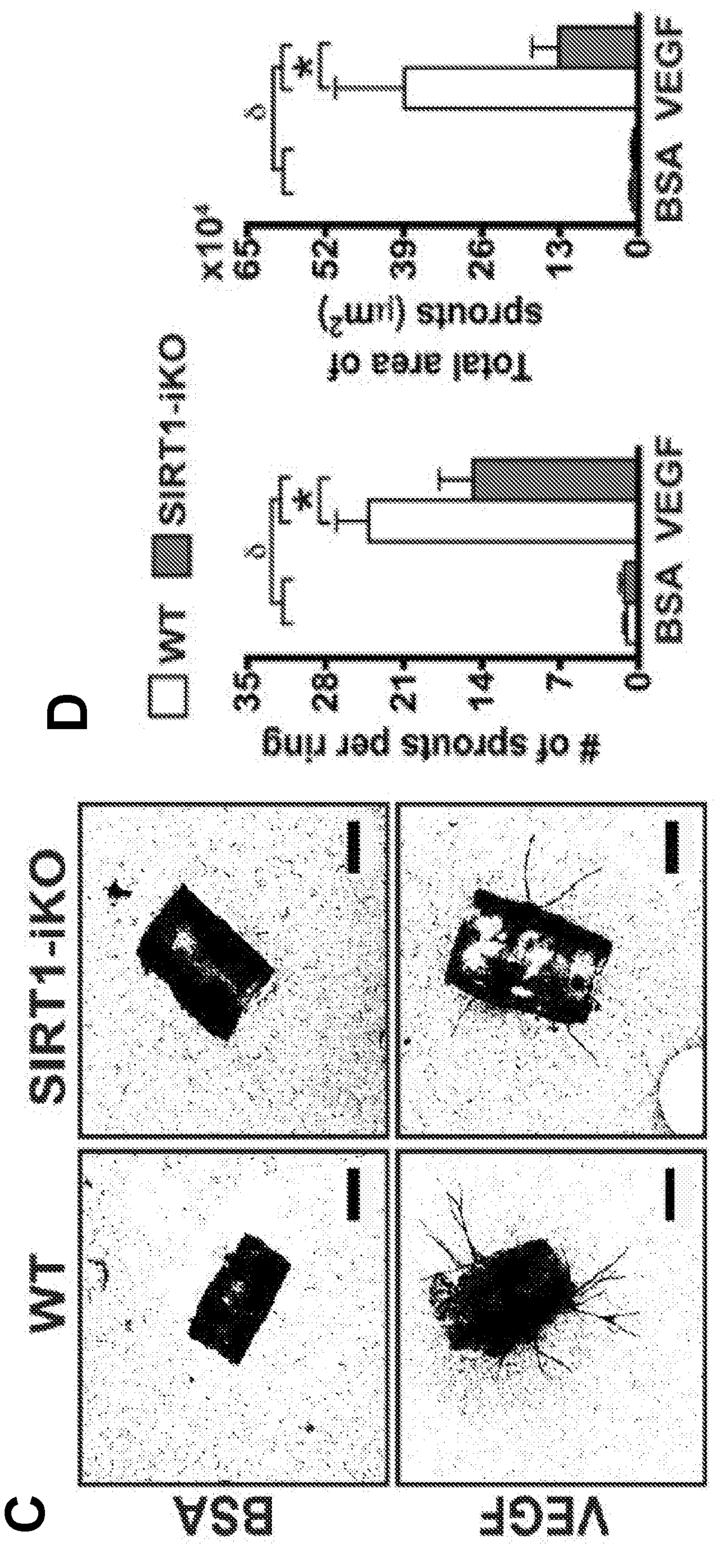

SIRT1 is Required for Pro-Angiogenic Growth Factor Signaling from Myocytes to ECs To investigate the specific signals that EC SIRT1 responds to, we performed in vitro transwell migration and spheroid assays using MLECs derived from WT and ESKO mice. MLECs without SIRT1 had a blunted chemotactic response (FIG. 20A), reduced tube formation (FIGS. 20B and 20C), and shorter EC spheroid sprout length (FIGS. 20D and 20E). Stimulation of EC replication and migration after exercise involves several pro-angiogenic factors including VEGF and basic fibroblast growth factor (FGF) (Arany et al., 2008). To determine if growth factors require EC SIRT1 activity, we utilized an ex vivo angiogenesis assay in a three-dimensional (3D) collagen matrix. Explant thoracic aortic ring cultures from wildtype and SIRT1-iKO mice were exposed to either VEGF or FGF (FIGS. 21A to 21D). The extent of sprouting by VEGF is greater than that by FGF at these doses (FIGS. 21A and 21B). Both VEGF and FGF treatment increased sprouting but this effect was reduced in the aortic rings lacking SIRT1 (FIG. 21A to 21D). As an additional test for SIRT1's role in downstream signaling, human aortic ECs (HAECs) in which SIRT1 was knocked down using lentiviral-mediated RNAi were tested for the ability to form a tube-like network on growth factor-reduced matrigel. Knockdown of SIRT1 reduced the abilities of VEGF and FGF to stimulate tube formation, as indicated by a reduction in the number of branch points and length of tubules (FIGS. 22A and 22B). SIRT1 knockdown also abolished growth factor induced migration of HAECs (FIG. 22C). In both cases, the effect of VEGF was significantly greater than that of FGF. SIRT1 had no apparent effect on the levels of VEGF mRNA in ECs (FIG. 22D) or VEGF protein in serum (FIG. 22E). These data support a model in which endothelial SIRT1 is a key downstream mediator of exercise-induced PCG-1α-VEGF signaling between myofibers and ECs.

SIRT1 Overexpression in the Endothelium Increases Skeletal Muscle Capillary Density and Exercise Capacity Having shown that endothelial SIRT1 is necessary for vascular remodeling and increased endurance in mice, we wondered if increasing its abundance or activity would be sufficient to induce these changes. We established a line of endothelial cell-specific SIRT1 overexpressing or "ESTO" mice by crossing Tie2Cre mice to a floxed SIRT1 transgenic mouse strain (SIRT1$^{STOP}$) that we had previously generated (Firestein et al., 2008, PLoS One 3, e2020) (FIG. 23A). Western blot analyses of quadriceps and tissues rich in capillaries, such as lung and thymus, confirmed that SIRT1 was overexpressed in ESTO mice compared to littermate controls (FIG. 23B). Immunohistochemistry of skeletal muscle confirmed that SIRT1 overexpression was specific to capillaries (FIG. 23C). As with the ESKO mice, ESTO mice were born in the expected Mendelian ratio with no apparent abnormalities. No significant differences between ESTO and SIRT1$^{STOP}$ mice were observed with respect to body weight, urine creatinine levels, and in a rotarod test (FIG. 23D). Muscle weight (FIG. 24A), muscle morphology (FIG. 24B), fiber composition (FIG. 24C) and oxidative metabolism (FIG. 24D) were also similar between the strains. Interestingly, blood glucose levels in ESTO mice were markedly lower compared to SIRT1$^{STOP}$ mice (FIG. 24E), indicating that endothelial SIRT1 may also promote glucose uptake or suppress gluconeogenesis.

Examination of the quadriceps of ESTO mice revealed a 1.5-fold higher density and 2-fold increase in the number of capillaries compared to the littermate controls (FIGS. 25A and 25B), with a similar increases in gastrocnemius muscle (FIGS. 25C and 25D). To test if there were physiological effects of these changes, 6 month-old mice were subjected to a high intensity treadmill protocol. We established that 6-month old ESTO mice and littermate controls have a substantially higher exercise capacity compared to WT controls, running 1.8 times longer on a treadmill and covering 1.9 times the distance before exhaustion (FIG. 26A). Even though ESTO mice ran further and longer, post-exercise serum lactate levels in ESTO mice were also significantly lower than the control mice (FIG. 26B). Thus, increasing SIRT1 in ECs is sufficient to increase not only the capillary density of skeletal muscle but also the animal's exercise tolerance.

The loss- and gain-of-function studies above indicated that endothelial SIRT1 is a downstream mediator of angiogenic signals from myocytes. If this was correct, then increasing the expression or activity of endothelial SIRT1 should augment these signals. Overexpression of SIRT1 in MLECs increased both cell motility towards a chemoattractant gradient (FIG. 27A), as well as tube formation and sprout length of EC spheroids in conditioned media (FIGS. 27B, 27C, 28A and 28B).

Our studies above indicated that endothelial SIRT1 is a downstream mediator of VEGF signaling from myocytes. If correct, then increasing the expression or activity of endothelial SIRT1 should augment the effect of VEGF. To test this, a tube formation assay was performed on HUVECs infected with adenovirus expressing SIRT1 cDNA (a.a. 194-747) or a GFP control in the presence or absence of VEGF (30 ng/mL) (FIG. 29A). Overexpression of SIRT1 in HUVECs increased the number of branching points by 33% and the total tubule length by 15% compared to the control cells (FIGS. 29B and 29C). In the spheroid sprouting assay, adeno-SIRT1 infected ECs resulted in 19% longer sprout length compared to the control cells upon VEGF stimulation (FIGS. 30A and 30B).

An ex vivo angiogenesis assay was then performed using aortic rings prepared from aortas of SIRT1 overexpressing mice (SIRT1-Tg) (Price et al., 2012) and their WT littermate controls (FIG. 31A). Compared to WT littermate controls (FIG. S4N), SIRT1 overexpression doubled sprout number and tripled total spout area when incubated in the presence of VEGF (FIGS. 31B and 31C). This result, combined with the fast that ESTO mice have higher VEGF serum protein levels (FIG. 31D), implies that SIRT1 activation may provide a positive feedback on myocyte VEGF. Either way, these results provided strong evidence that SIRT1 in endothelial cells is both necessary and sufficient for capillary formation in skeletal muscle in response to VEGF-mediated signal from the myocytes.

The $NAD^+$ Precursor, NMN, Promotes Angiogenesis by Inhibiting SIRT1-Mediated Notch Signaling Given the role of SIRT1 in aging, we hypothesized that the loss of exercise responsiveness in older mice and humans might be due to a decline in SIRT1 or the levels of its co-substrate $NAD^+$ (Gomes et al., 2013; Massudi et al., 2012). Treatment of mice with $NAD^+$ precursors is known to raise intracellular $NAD^+$ levels and stimulate SIRT1 activity (Bogan and Brenner, 2008, Annu Rev Nutr 28, 115-130; Gomes et al., 2013; Yoshino et al., 2011, Cell Metab 14, 528-536). First, we tested whether the $NAD^+$ precursor nicotinamide mononucleotide (NMN) could promote angiogenesis in a variety of cell-based assays, both in the presence and absence of SIRT1. NMN and VEGF cotreatment of HAECs resulted in 32% increase in number of branch points and 15% increase in tubule length compared to VEGF alone (FIGS. 32A and 32B). NMN itself increased the number of branch points by 25%, indicating that NMN could promote angiogenesis even without VEGF (FIGS. 32A and 32B). Moreover, NMN treatment of HAECs steadily increased the number of branch points and total length of tubes in a dose-dependent manner (FIG. 32C). Time-lapse videos of HAEC tube formation showed that NMN not only improved structured tubule formation but also prevented the disintegration of tubes over an extended 18 h period. Exposure of HUVECs to NMN also promoted cell growth (FIG. 32D) and motility in response to VEGF when treated with NMN in a transwell migration assay (FIG. 32E). In cell migration and sprouting angiogenesis assays with ESKO-derived MLECs (FIGS. 33A and 33B) or VEGF-treated HAECs (FIG. 33C), or in the tube formation assay (FIG. 33D), the ability of NMN to stimulate measures of angiogenesis was SIRT1-dependent. Interestingly, NMN treatment of HAECs not only improved structured tubule formation but also prevented the disintegration of tubes over an extended 18 h period.

To test the effects of NMN on angiogenesis in the context of old tissue, we performed an ex vivo VEGF-mediated angiogenesis assay using aortic rings from 18-month old mice (roughly equivalent to a 70-year old human). Measurement of VEGF-mediated outgrowths or sprouts from each aortic ring showed that NMN doubled the number of (FIG. 34C) endothelial sprouts compared to the PBS treated rings (FIG. 34C). The effects of NMN in HAEC cells was completely blocked by knockdown of SIRT1 (FIG. 34D). NMN doubled the number of outgrowths or sprouts from aortic rings from old WT mice but not from old SIRT1-iKO mice (FIGS. 34A and 34B).

In addition to SIRT1, SIRT3 and SIRT6 affect the angiogenic potential of ECs in culture (Cardus et al., 2013, Cardiovasc Res 97, 571-579; Wei et al., 2017, J Am Heart Assoc 6). Knockdown of SIRT3 and SIRT6 in HAECs using siRNAs (FIG. 35A) decreased VEGF-mediated tube formation and spheroid sprouting, and this was partially rescued by NMN treatment (FIGS. 35B and 35C), indicating that the angiogenic effects of NMN partially mediated by SIRT3 and SIRT6 but primarily by SIRT1.

The Notch signaling pathway is indispensible for blood vessel formation in vertebrates. During sprouting angiogenesis, the endothelial Notch signaling pathway governs tip and stalk cell behavior, downstream of VEGF signaling (Blanco and Gerhardt, 2013, Cold Spring Harb Perspect Med 3, a006569). Notch signaling in ECs is determined by the levels of the Notch1 intracellular domain (NICD) protein, which in turn is negatively regulated by SIRT1 (Guarani et al., 2011, Nature 473, 234-238). Consistent with this, after stimulation with VEGF or Notch ligand Dll4 (FIGS. 36A and 36B), NMN treatment significantly decreased Notch target gene expression and promoted NICD reduction (FIGS. 37A and 37B). Blocking NICD release with the γ-secretase inhibitor DAPT increased sprout length irrespective of SIRT1 levels (FIG. 37C) while treatment with the VEGF receptor (VEGFR) inhibitor SU5416 completely blocked sprouting and this was not rescued by NMN treatment (FIG. 37C). Consistent with Notch activation by NMN, treatment induced proliferation (FIG. 38A) and reduced apoptosis in ECs (Chang et al., 2013, Microvasc Res 89, 80-85; Noseda et al., 2004, Mol Cell Biol 24, 8813-8822) and these effects were SIRT1-dependent (FIG. 38B). Endothelial cell apoptosis counteracts neovascularization in the adult organism (Dimmeler and Zeiher, 2000). NMN reduced the percentage of cells undergoing early apoptosis and promoted VEGF mediated angiogenesis after treatment with $H_2O_2$(FIGS. 39A and 39B).

Together, these results showed that VEGF-induced angiogenesis is stimulated by the $NAD^+$ precursor NMN in a SIRT1-dependent manner.

These findings support a model in which VEGF and Notch signaling from myocytes to ECs depends on the $NAD^+$ levels of ECs and the concomitant activity of SIRT1 (FIG. 38C).

$NAD^+$ Reverses the Loss of Microvasculature and Exercise Capacity in Aged Mice During aging, the level of $NAD^+$ declines in many tissues, potentially due to increased activity of CD38, an NAD glycohydrolase and PARP1 (Braidy et al., 2011; Canto et al., 2012, Cell Metab 15, 838-847; Gomes et al., 2013; Massudi et al., 2012; Mouchiroud et al., 2013b, Cell 154, 430-441; Yoshino et al., 2011). We hypothesized that decreasing $NAD^+$ levels in ECs might explain why older individuals have fewer capillaries and decreased blood flow during aging. Consistent with our hypothesis, gastrocnemius muscle and ECs isolated from 20-month old mice had significantly lower $NAD^+$ levels compared to those from 6-month old mice (FIGS. 40A and 40B). We reasoned, therefore, that restoring $NAD^+$ levels in ECs of old mice to youthful levels might also restore capillary density, blood flow, and endurance. To test this, we administered NMN to 18-month old mice via drinking water for two months at 400 mg/kg/day. NMN raised $NAD^+$ levels in several tissues including muscle (FIG. 40B) and had no effect on food intake, water consumption, body weights, body composition, motor learning skills and cardiac function (FIGS. 41A and 41B).

Strikingly, NMN administration restored the number of capillaries and capillary density of the old mice to that of a young mouse (FIG. 42A to 42D) or compared to age-matched untreated mice (FIGS. 42A to 42D). Contrast-enhanced ultrasound imaging of the lower limb (Baltgalvis et al., 2014, Am J Physiol Heart Circ Physiol 306, H1128-1145) to assess peak enhancement (FIG. 43A), a measure of relative blood volume at steady state, also showed that NMN increased resting muscle perfusion (FIGS. 43C and 43D). Soluble oxygen ($sO_2$) levels in resting muscle as measured by photoacoustic tomography were 15% greater in NMN-treated mice compared to vehicle-treated age-matched controls (FIG. 43B).

NMN did not significantly alter mitochondrial protein levels (FIG. 44A), mitochondrial activity (FIGS. 44B and 44C), the respiratory capacity of individual fibers (FIG. 45A), tissue weights (FIG. 45B), muscle morphology (FIG. 45C), fiber type (FIG. 45D) or home cage activity. Compared to non-treated control mice, oxygen consumption in NMN-treated mice was 30% higher in the light cycle and 23% higher in the dark cycle FIG. 45E. NMN supplementation dramatically improved low-intensity endurance with a 56% improvement over the untreated mice (441 versus 686 meters) FIGS. 46A and 46B. When tested under a high-endurance exercise regimen, NMN-treated mice ran 80% further and had a lower blood lactate buildup compared to untreated mice (4.9 mmol/L vs. 3.9 mmol/L) FIGS. 46B and 46C.

Next, we sought to test if SIRT1 is necessary for neovascularization in vivo. SIRT1 was deleted from EC cells by treating 20-month old SIRT1-iKO mice with tamoxifen before placing them on NMN (400 mg/kg/day) for two months. NMN increased gastrocnemius capillarity in WT mice, whereas no change was observed in the SIRT1-iKO mice ((FIG. 47A). Vascular plasticity is not only an important component of normal physiology that declines with aging, but it is also essential in response to ischemia. Femoral ligations in 8-month old SIRT1-iKO and WT mice and the mice were treated with NMN (400 mg/kg/day) for 20 days. Consistent with our previous observations, NMN restored relative blood volume (peak enhancement) and capillary density and this effect was SIRT1-dependent (FIGS. 47B and 47C).

We hypothesized that NMN might further enhance the response to exercise training, even in younger mice. To test this, young mice were subjected to endurance training for one month with our without NMN (400 mg/kg/day). As expected, mice that were exercised had twice the number of capillaries compared to the sedentary mice (FIG. 48A). Interestingly, if NMN was added to the same training regimen, there was a 3.2-fold increase in capillary density was observed, but if kept sedentary, NMN supplementation did not increase capillary density or exercise capacity. The gastrocnemii of mice that received exercise alone had 33% more capillaries than those from sedentary mice, while those from exercised and NMN-treated mice had 70% more. Thus, NMN supplementation can be effective in skeletal muscle capillary formation not only in elderly but also in younger individuals, but only when coupled with exercise. These intriguing results indicate either that exercise relieves an inhibitor that limits neovascularization or that there are increased demands for $NAD^+$ during exercise.

To test if the effect of NMN required VEGF, we repeated the above exercise training regimen in mice treated with axitinib (30 mg/kg/day). Axitinib blocks VEGF signaling by inhibiting phosphorylation of VEGFR and by increasing serum VEGF levels (FIG. 49A) (Escudier and Gore, 2011). Axitinib treatment not only blocked NMN-mediated increases in capillary density but also any improvement in exercise capacity (FIGS. 49B, 49C and 50), confirming that NMN acts downstream of VEGF and that muscle capillarity is a key determinant of whether exercise increases endurance.

Together, these data show that short-term NMN treatment restores the number of capillaries in skeletal muscle and the endurance capacity of old mice back to youthful levels and that increased blood flow, rather than improved mitochondrial function, may be the explanation for the increased endurance of mice treated with STACs.

Exogenous Hydrogen Sulfide Activates SIRT1 and Augments the Effects of NMN $H_2S$ shares many similarities with $NAD^+$ as a signaling molecule. $H_2S$ increases SIRT1 activity, and protects against oxidative stress. We were thus interested in testing the potential overlap between $NAD^+$ and $H_2S$ signaling. We first tested the potential additive effects of NMN and NaHS on apoptosis of HUVEC cells. Treatment of HUVECs with NaHS or NMN alone increased SIRT1 protein levels and a combination of the two increased SIRT1 levels two-fold (FIG. 51A). NaHS also raised intracellular $NAD^+$ levels in ECs in a dose dependent manner (FIG. 51B).

Next, we sought to determine if this combination could improve the angiogenic potential of HUVEC cells under oxidative stress and whether this was mediated by SIRT1. Both treatments increased tube formation compared to untreated controls but the greatest effect was the combination of treatments, which significantly raised the number of branch points and total tube length (FIG. 52A). $H_2S$ increased cell migration in a SIRT1-dependent manner (FIG. 52B) and lowered the basal OCR of HUVECs (FIG. 52C), while NMN had no effect on these parameters.

There was an additive effect of the treatments on the motility of MLECs (FIG. 53A) and in the EC spheroid sprouting assay (FIG. 53B), an effect that was SIRT1-dependent (FIG. 53A). Consistent with Alban et al., $H_2S$ increased cell migration in a scratch assay independent of VEGF but dependent on SIRT1 (FIG. 53C). $H_2S$ also lowered the basal OCR of HUVECs while NMN did not. These findings indicate that $NAD^+$ and $H_2S$ have overlapping and distinct functions in ECs.

To test the effect of the combination of NMN and NaHS, we co-treated of mice with NMN and NaHS to see if they had an even greater effect on capillary formation and endurance than either treatment alone. A combination of NMN (400 mg/kg/day) and NaHS (20 mg/kg/day) was supplied in the drinking water of 30-month old mice for four weeks. The treatments had no effect on water consumption, food consumption, body weight, lean mass or fat mass (FIGS. 55A and 55B). As shown in FIGS. 55A and 55B, mice treated with the combination of NaHS and NMN had a higher capillary density and capillary number compared to all other groups.

Neovascularization in aged individuals declines, in part, because of an increase in oxidative stress and endothelial cell apoptosis, an effect that can be mimicked by $H_2O_2$ in cell culture (Dimmeler and Zeiher, 2000; Pearson et al., 2008). Co-staining of aged quadriceps tissue for CD31 and for DNA fragmentation using the TUNEL assay showed that NMN reduced the number of capillaries with apoptotic cells from 42% to 17% and the combination of NMN and NaHS reduced it to 11% (FIG. 56A). In response to $H_2O_2$, NMN reduced apoptosis in HUVECS by 13% and the combination reduced it by 36% (FIG. 56B).

To test if these structural changes in skeletal muscle were functional, the treated mice were subjected to treadmill tests. Mice treated with NMN showed a significant trend towards increased time and distance to exhaustion (FIGS. 57A and 57B) but it was the combination with NaHS that was most impressive, with a doubling of endurance, the largest increase yet reported for any treatment or exercise regime.

To test if the effect of the NMN and $H_2S$ combination was mediated by SIRT1, we generated an EC-specific SIRT1 KO in old adult mice using a lentiviral vector expressing an EGFP transgene and SIRT1 microRNA (miRNA) downstream of the vascular endothelium cadherin (VE-cad) promoter (FIG. 58A) (Zhang et al., 2013). After testing a variety of miRNAs constructs, number 5 was deemed the most efficient, knocking down SIRT1 protein levels by 80% (FIG. 58B). SIRT1 was then knocked down in 20-month old mice via retro-orbital injection. Immunostaining indicated that EGFP was expressed in cells which also stained positive with CD31, confirming efficiency and specificity of the knockdown (FIG. 59A). After confirming the lentiviral integration into ECs, mice were treated with NMN and $H_2S$ precursors, NaHS and GYY4137 (Rose et al., 2015), for four weeks. As shown in FIG. 59B, ability of NMN alone or in combination with $H_2S$ precursors to increase vascularization was blocked in the SIRT1 knockdown mice. Together, these data show that endothelial SIRT1 is a key mediator of the angiogenic response and that stimulating SIRT1 activity with NMN is an effective way to increase capillary formation and blood flow in skeletal muscle to improve exercise endurance, a pathway that can be further enhanced by co-treatment with $H_2S$.

Together, these data show that endothelial SIRT1 is a key mediator of the angiogenic response to exercise and that stimulating SIRT1 activity is an effective way to increase capillary formation and blood flow in skeletal muscle, a pathway that can be further enhanced by cotreatment with NaHS (FIG. 6G).

DISCUSSION

From the age of 35 onward in humans, the perfusion of tissues declines steadily and seemingly inexorably. This decline is a major determinant of the health and longevity of almost all people who live beyond middle-age, contributing to frailty, sarcopenia and most age-related diseases. Exercise is recommended, but it only delays the decline, initially because the angiogenic response to exercise becomes muted in middle age, and eventually because frailty prohibits exercise.

In this study, we set out to test if endothelial SIRT1 is involved in the regulation of muscle vasculature and if it could it be targeted to restore capillary density and endurance in old mice. Our experiments indicate that SIRT1 in endothelial cells is a critical regulator of vascular remodeling that is necessary for the response to PGC-1α-VEGF-stimulated angiogenesis.

We also show that the $NAD^+$ precursor nicotinamide mononucleotide (NMN) acts as an exercise-mimetic drug that can rapidly reverse the effects of aging on capillary formation, an effect that synergizes with $H_2S$ signaling, another SIRT1-dependent pathway. Surprisingly, even at 32-months of age in a mouse, approximately equivalent of a 90 year old human in percent of lifespan exhausted, the effects of aging on the microvasculature can be rapidly reversed. These findings point to the potential health benefits of $NAD^+$ and $H_2S$ precursors as a way to reverse the age-associated decline in exercise capacity and the body's ability to respond to exercise, thereby reestablishing a beneficial cycle of mobility.

Further, we show that the NAD+ precursor NMN, can increase vascular density and blood flow and increases exercise capacity in both young and old subjects when coupled with exercise training.

We also show that the NAD+ precursor NMN can promote increased vascular density and blood flow in ischaemic tissue.

CONCLUSION

We show that loss of endothelial SIRT1 activity results in a phenotype of early decline in skeletal muscle vascular density and exercise capacity, while overexpression of endothelial SIRT1 has the opposite, protective effect. Pharmacologically raising $NAD^+$ levels to stimulate SIRT1 activity restores the capillary density and treadmill endurance of elderly mice back to youthful levels, an effect that is further augmented by $H_2S$. Pharmacologically raising $NAD^+$ levels to stimulate SIRT1 activity, when combined with exercise, increases capillary density and treadmill endurance of both young and old mice. Pharmacologically raising $NAD^+$ levels increases capillary density in ischaemic tissue.

REFERENCES

Arany, Z., Foo, S. Y., Ma, Y., Ruas, J. L., Bommi-Reddy, A., Girnun, G., Cooper, M., Laznik, D., Chinsomboon, J., Rangwala, S. M., et al. (2008). HIF-independent regulation of VEGF and angiogenesis by the transcriptional coactivator PGC-1alpha. Nature 451, 1008-1012.

Arbiser, J. L., Larsson, H., Claesson-Welsh, L., Bai, X., LaMontagne, K., Weiss, S. W., Soker, S., Flynn, E., and Brown, L. F. (2000). Overexpression of VEGF 121 in immortalized endothelial cells causes conversion to slowly growing angiosarcoma and high level expression of the VEGF receptors VEGFR-1 and VEGFR-2 in vivo. Am J Pathol 156, 1469-1476.

Askew, C. D., Green, S., Walker, P. J., Kerr, G. K., Green, A. A., Williams, A. D., and Febbraio, M. A. (2005). Skeletal muscle phenotype is associated with exercise tolerance in patients with peripheral arterial disease. J Vasc Surg 41, 802-807.

Baker, M., Robinson, S. D., Lechertier, T., Barber, P. R., Tavora, B., D'Amico, G., Jones, D. T., Vojnovic, B., and Hodivala-Dilke, K. (2012). Use of the mouse aortic ring assay to study angiogenesis. Nat Protoc 7, 89-104.

Baltgalvis, K. A., White, K., Li, W., Claypool, M. D., Lang, W., Alcantara, R., Singh, B. K., Friera, A. M., McLaughlin, J., Hansen, D., et al. (2014). Exercise performance and peripheral vascular insufficiency improve with AMPK activation in high-fat diet-fed mice. Am J Physiol Heart Circ Physiol 306, H1128-1145.

Bassel-Duby, R., and Olson, E. N. (2006). Signaling pathways in skeletal muscle remodeling. Annu Rev Biochem 75, 19-37.

Bogan, K. L., and Brenner, C. (2008). Nicotinic acid, nicotinamide, and nicotinamide riboside: a molecular evaluation of $NAD^+$ precursor vitamins in human nutrition. Annu Rev Nutr 28, 115-130.

Booth, F. W., and Thomason, D. B. (1991). Molecular and cellular adaptation of muscle in response to exercise: perspectives of various models. Physiol Rev 71, 541-585.

Borradaile, N. M., and Pickering, J. G. (2009). Nicotinamide phosphoribosyltransferase imparts human endothelial cells with extended replicative lifespan and enhanced angiogenic capacity in a high glucose environment. Aging Cell 8, 100-112.

Braidy, N., Guillemin, G. J., Mansour, H., Chan-Ling, T., Poljak, A., and Grant, R. (2011). Age related changes in $NAD^+$ metabolism oxidative stress and Sirt1 activity in wistar rats. PLoS One 6, e19194.

Canto, C., Houtkooper, R. H., Pirinen, E., Youn, D. Y., Oosterveer, M. H., Cen, Y., Fernandez-Marcos, P. J., Yamamoto, H., Andreux, P. A., Cettour-Rose, P., et al. (2012). The $NAD(^+)$ precursor nicotinamide riboside enhances oxidative metabolism and protects against high-fat diet-induced obesity. Cell Metab 15, 838-847.

Cebasek, V., Kubinova, L., Ribaric, S., and Erzen, I. (2004). A novel staining method for quantification and 3D visualisation of capillaries and muscle fibres. Eur J Histochem 48, 151-158.

Chalkiadaki, A., Igarashi, M., Nasamu, A. S., Knezevic, J., and Guarente, L. (2014). Muscle-specific SIRT1 gain-of-function increases slow-twitch fibers and ameliorates pathophysiology in a mouse model of duchenne muscular dystrophy. PLoS Genet 10, e1004490.

Chinsomboon, J., Ruas, J., Gupta, R. K., Thom, R., Shoag, J., Rowe, G. C., Sawada, N., Raghuram, S., and Arany, Z. (2009). The transcriptional coactivator PGC-1alpha mediates exercise-induced angiogenesis in skeletal muscle. Proc Natl Acad Sci USA 106, 21401-21406.

Costa, C., and Virag, R. (2009). The endothelial-erectile dysfunction connection: an essential update. J Sex Med 6, 2390-2404.

Dimmeler, S., and Zeiher, A. M. (2000). Endothelial cell apoptosis in angiogenesis and vessel regression. Circ Res 87, 434-439.

Duscha, B. D., Kraus, W. E., Keteyian, S. J., Sullivan, M. J., Green, H. J., Schachat, F. H., Pippen, A. M., Brawner, C. A., Blank, J. M., and Annex, B. H. (1999). Capillary density of skeletal muscle: a contributing mechanism for exercise intolerance in class II-III chronic heart failure independent of other peripheral alterations. J Am Coll Cardiol 33, 1956-1963.

Firestein, R., Blander, G., Michan, S., Oberdoerffer, P., Ogino, S., Campbell, J., Bhimavarapu, A., Luikenhuis, S., de Cabo, R., Fuchs, C., et al. (2008). The SIRT1 deacetylase suppresses intestinal tumorigenesis and colon cancer growth. PLoS One 3, e2020.

Gomes, A. P., Price, N. L., Ling, A. J., Moslehi, J. J., Montgomery, M. K., Rajman, L., White, J. P., Teodoro, J. S., Wrann, C. D., Hubbard, B. P., et al. (2013). Declining $NAD(^+)$ induces a pseudohypoxic state disrupting nuclear-mitochondrial communication during aging. Cell 155, 1624-1638.

Hood, D. A. (2001). Invited Review: contractile activity-induced mitochondrial biogenesis in skeletal muscle. J Appl Physiol (1985) 90, 1137-1157.

Kolluru, G. K., Bir, S. C., and Kevil, C. G. (2012). Endothelial dysfunction and diabetes: effects on angiogenesis, vascular remodeling, and wound healing. Int J Vasc Med 2012, 918267.

Koni, P. A., Joshi, S. K., Temann, U. A., Olson, D., Burkly, L., and Flavell, R. A. (2001). Conditional vascular cell adhesion molecule 1 deletion in mice: impaired lymphocyte migration to bone marrow. J Exp Med 193, 741-754.

Kuznetsov, A. V., Veksler, V., Gellerich, F. N., Saks, V., Margreiter, R., and Kunz, W. S. (2008). Analysis of mitochondrial function in situ in permeabilized muscle fibers, tissues and cells. Nat Protoc 3, 965-976.

Lanza, G. A., and Crea, F. (2010). Primary coronary microvascular dysfunction: clinical presentation, pathophysiology, and management. Circulation 121, 2317-2325.

Lin, J., Wu, H., Tarr, P. T., Zhang, C. Y., Wu, Z., Boss, O., Michael, L. F., Puigserver, P., Isotani, E., Olson, E. N., et al. (2002). Transcriptional co-activator PGC-1 alpha drives the formation of slow-twitch muscle fibres. Nature 418, 797-801.

Massudi, H., Grant, R., Braidy, N., Guest, J., Farnsworth, B., and Guillemin, G. J. (2012). Ageassociated changes in oxidative stress and $NAD^+$ metabolism in human tissue. PLoS One 7, e42357.

McCormick, W. F. (1966). The pathology of vascular ("arteriovenous") malformations. J Neurosurg 24, 807-816.

Mersmann, N., Tkachev, D., Jelinek, R., Roth, P. T., Mobius, W., Ruhwedel, T., Ruhle, S., Weber-Fahr, W., Sartorius, A., and Klugmann, M. (2011). Aspartoacylase-lacZ knockin mice: an engineered model of Canavan disease. Plos One 6, e20336.

Morscher, S., Driessen, W. H., Claussen, J., and Burton, N.C. (2014). Semi-quantitative Multispectral Optoacoustic Tomography (MSOT) for volumetric PK imaging of gastric emptying. Photoacoustics 2, 103-110.

Mouchiroud, L., Houtkooper, R. H., and Auwerx, J. (2013a). NAD(+) metabolism: a therapeutic target for age-related metabolic disease. Crit Rev Biochem Mol Biol 48, 397-408.

Mouchiroud, L., Houtkooper, R. H., Moullan, N., Katsyuba, E., Ryu, D., Canto, C., Mottis, A., Jo, Y. S., Viswanathan, M., Schoonjans, K., et al. (2013b). The NAD(+)/Sirtuin Pathway Modulates Longevity through Activation of Mitochondrial UPR and FOXO Signaling. Cell 154, 430-441.

Muzumdar, M. D., Tasic, B., Miyamichi, K., Li, L., and Luo, L. (2007). A global double-fluorescent Cre reporter mouse. Genesis 45, 593-605.

Pette, D., and Staron, R. S. (2000). Myosin isoforms, muscle fiber types, and transitions. Microsc Res Tech 50, 500-509.

Potente, M., and Dimmeler, S. (2008). Emerging roles of SIRT1 in vascular endothelial homeostasis. Cell Cycle 7, 2117-2122.

Price, N. L., Gomes, A. P., Ling, A. J., Duarte, F. V., Martin-Montalvo, A., North, B. J., Agarwal, B., Ye, L., Ramadori, G., Teodoro, J. S., et al. (2012). SIRT1 is required for AMPK activation and the beneficial effects of resveratrol on mitochondrial function. Cell Metab 15, 675-690.

Prior, S. J., Ryan, A. S., Blumenthal, J. B., Watson, J. M., Katzel, L. I., and Goldberg, A. P. (2016). Sarcopenia Is Associated With Lower Skeletal Muscle Capillarization and Exercise Capacity in Older Adults. J Gerontol A Biol Sci Med Sci 71, 1096-1101.

Respress, J. L., and Wehrens, X. H. (2010). Transthoracic echocardiography in mice. J Vis Exp. Rowe, G. C., Safdar, A., and Arany, Z. (2014). Running forward: new frontiers in endurance exercise biology. Circulation 129, 798-810.

Uddin, G. M., Youngson, N. A., Sinclair, D. A., and Morris, M. J. (2016). Head to Head Comparison of Short-Term Treatment with the NAD(+) Precursor Nicotinamide Mononucleotide (NMN) and 6 Weeks of Exercise in Obese Female Mice. Front Pharmacol 7, 258.

Vasko, R., Xavier, S., Chen, J., Lin, C. H., Ratliff, B., Rabadi, M., Maizel, J., Tanokuchi, R., Zhang, F., Cao, J., et al. (2014). Endothelial sirtuin 1 deficiency perpetrates nephrosclerosis through downregulation of matrix metalloproteinase-14: relevance to fibrosis of vascular senescence. J Am Soc Nephrol 25, 276-291.

Wen, L., Chen, Z., Zhang, F., Cui, X., Sun, W., Geary, G. G., Wang, Y., Johnson, D. A., Zhu, Y., Chien, S., et al. (2013). Ca2+/calmodulin-dependent protein kinase kinase beta phosphorylation of Sirtuin 1 in endothelium is atheroprotective. Proc Natl Acad Sci USA 110, E2420-2427.

Yoshino, J., Mills, K. F., Yoon, M. J., and Imai, S. (2011). Nicotinamide mononucleotide, a key NAD(+) intermediate, treats the pathophysiology of diet- and age-induced diabetes in mice. Cell Metab 14, 528-536.

Zhu, C. T., and Rand, D. M. (2012). A hydrazine coupled cycling assay validates the decrease in redox ratio under starvation in Drosophila. PLoS One 7, e47584.

The invention claimed is:

1. A method of treating hemorrhage in a subject in need thereof, the method comprising administering to the subject an effective amount of a pharmaceutical composition comprising nicotinic acid mononucleotide (NaMN).

2. The method of claim 1, wherein the pharmaceutical composition is administered orally.

3. The method of claim 1, wherein the NaMN is in crystalline form.

4. The method of claim 1, wherein the pharmaceutical composition is in the form of a tablet, a troche, a lozenge, a dispersible powder or granule, a hard capsule.

5. The method of claim 1, wherein the pharmaceutical composition further comprises GYY4137, sodium hydrosulfide, or pharmaceutically acceptable salts thereof.

6. The method of claim 1, wherein the pharmaceutical composition is in the form of a tablet, a troche, a lozenge, an aqueous or oily suspension, a dispersible powder or granule, an emulsion, a hard or soft capsule, or a syrup or elixir.

7. The method of claim 1, wherein the pharmaceutical composition is in the form of a sterile injectable aqueous suspension, or a sterile injectable oleaginous suspension, or a sterile injectable aqueous solution, or a sterile injectable non-aqueous solution, or a sterile injectable non-aqueous suspension.

8. The method of claim 7, wherein the pharmaceutical composition further comprises a diluent or solvent selected from water, Ringer's solution, isotonic sodium chloride solution, oleic acid, and 1,3-butanediol.

9. The method of claim 7, wherein the pharmaceutical composition is administered in the form of a liposome.

10. The method of claim 9, wherein the liposome comprises phospholipid or phosphatidyl choline.

11. The method of claim 1, wherein said composition is adapted for administration by infusion.

12. The method of claim 1, wherein said composition is a sterile injectable aqueous solution.

13. A method of treating hemorrhage in a subject in need thereof, the method comprising administering to the subject an effective amount of nicotinic acid mononucleotide (NaMN) in a sterile injectable aqueous solution by infusion.

14. A method of treating ulcers in a subject in need thereof, the method comprising administering to the subject an effective amount of a pharmaceutical composition comprising nicotinic acid mononucleotide (NaMN).

15. The method of claim 14, wherein the pharmaceutical composition is administered orally.

16. The method of claim 14, wherein the NaMN is in crystalline form.

17. The method of claim 16, wherein the pharmaceutical composition is formulated as one or more tablets, a troches, a lozenges, a dispersible powder or granules, or hard capsules.

18. The method of claim 14, wherein the pharmaceutical composition further comprises GYY4137, sodium hydrosulfide, or pharmaceutically acceptable salts thereof.

19. The method of claim 14, wherein the pharmaceutical composition is formulated as an aqueous or oily suspension, an emulsion, a dispersible powder or granules, a syrup or elixir, or one or more tablets, troches, lozenges, or hard or soft capsules.

20. The method of claim 14, wherein the pharmaceutical composition is a sterile injectable aqueous suspension, a sterile injectable oleaginous suspension, a sterile injectable aqueous solution, a sterile injectable non-aqueous solution, or a sterile injectable non-aqueous suspension.

21. The method of claim 20, wherein the pharmaceutical composition further comprises a diluent or solvent selected from water, Ringer's solution, isotonic sodium chloride solution, oleic acid, and 1,3-butanediol.

22. The method of claim 20, wherein the pharmaceutical composition comprises a liposome.

23. The method of claim 22, wherein the liposome comprises a phospholipid or phosphatidyl choline.

24. The method of claim 14, wherein said composition is administered by infusion.

25. The method of claim 20, wherein said composition is a sterile injectable aqueous solution.

* * * * *